US010597364B2

(12) United States Patent
Long et al.

(10) Patent No.: US 10,597,364 B2
(45) Date of Patent: Mar. 24, 2020

(54) ANTHELMINTIC COMPOUNDS, COMPOSITIONS AND METHOD OF USING THEREOF

(71) Applicant: BOEHRINGER INGELHEIM ANIMAL HEALTH USA INC., Duluth, GA (US)

(72) Inventors: Alan Long, Flowery Branch, GA (US); Douglas Edward Wilkinson, Wake Forest, NC (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/544,837

(22) PCT Filed: Jan. 20, 2016

(86) PCT No.: PCT/US2016/014148
§ 371 (c)(1),
(2) Date: Jul. 19, 2017

(87) PCT Pub. No.: WO2016/118638
PCT Pub. Date: Jul. 28, 2016

(65) Prior Publication Data
US 2018/0009754 A1 Jan. 11, 2018

Related U.S. Application Data

(60) Provisional application No. 62/105,463, filed on Jan. 20, 2015.

(51) Int. Cl.
| | | |
|---|---|---|
| C07D 487/04 | (2006.01) | |
| C07D 213/74 | (2006.01) | |
| C07D 405/12 | (2006.01) | |
| C07D 401/12 | (2006.01) | |
| C07D 417/12 | (2006.01) | |
| C07D 409/12 | (2006.01) | |
| A61K 31/496 | (2006.01) | |
| A61K 45/06 | (2006.01) | |

(52) U.S. Cl.
CPC .......... *C07D 213/74* (2013.01); *A61K 31/496* (2013.01); *A61K 45/06* (2013.01); *C07D 401/12* (2013.01); *C07D 405/12* (2013.01); *C07D 409/12* (2013.01); *C07D 417/12* (2013.01); *C07D 487/04* (2013.01)

(58) Field of Classification Search
CPC ... C07D 401/12; C07D 405/12; C07D 487/04
See application file for complete search history.

(56) References Cited

U.S. PATENT DOCUMENTS

| | | | |
|---|---|---|---|
| 5,571,815 | A | 11/1996 | Schaper et al. |
| 9,249,102 | B2 | 2/2016 | Meng |
| 2014/0142114 | A1 | 5/2014 | Meng |
| 2016/0185726 | A1 | 6/2016 | Meng |

FOREIGN PATENT DOCUMENTS

| | | | |
|---|---|---|---|
| EP | 1403255 | A1 | 3/2004 |
| EP | 2468096 | A1 | 6/2012 |
| WO | 1999031072 | A1 | 6/1999 |
| WO | 2001054506 | A1 | 8/2001 |
| WO | 2009077527 | A1 | 6/2009 |
| WO | 2010115688 | A1 | 10/2010 |
| WO | 2010146083 | A1 | 12/2010 |
| WO | 2011143366 | A1 | 2/2014 |
| WO | 2014023723 | A1 | 2/2014 |
| WO | 2011044001 | A1 | 5/2014 |
| WO | 2014159690 | A1 | 10/2014 |
| WO | 2015071417 | A1 | 5/2015 |
| WO | 2015179414 | A1 | 11/2015 |

OTHER PUBLICATIONS

N'Guessan, et al. Bioorganic&Medicinal Chemistry 25 (2017) 6695-6706.*
CAS RN: 1350249-77-2; Entered STN Dec. 7, 2011; N-[cis-4-[[5-(4-methyl-1-piperazinyl)-1H-indazol-4-yl]oxy]cyclohexyl]-benzenamine.

* cited by examiner

*Primary Examiner* — Shawquia Jackson
(74) *Attorney, Agent, or Firm* — Judy Jarecki-Black; Katrina Bergbauer

(57) ABSTRACT

The present invention relates to novel anthelmintic compounds of formula (IA) below:

(IA)

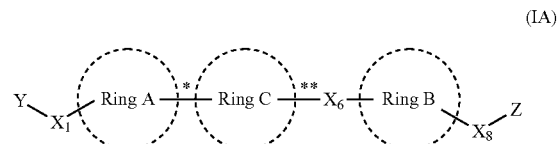

wherein, Y is selected from the group consisting of —H, aryl, cycloalkyl, cycloalkenyl, heteroaryl, heterocyclyl, alkyl, haloalkyl, and alkoxyalkyl; and Z is selected from the group consisting of aryl, cycloalkyl, cycloalkenyl, heteroaryl, heterocyclyl, alkyl, haloalkyl, and alkoxyalkyl. Variables Ring A, Ring B, Ring C, $X_1$, $X_6$, and $X_8$ are as defined herein. The invention also relates to parasiticidal compositions comprising the compounds, and methods and uses of the compounds for treating and preventing parasitic infections and infestations in animals.

4 Claims, No Drawings

ANTHELMINTIC COMPOUNDS, COMPOSITIONS AND METHOD OF USING THEREOF

CROSS REFERENCE TO RELATED APPLICATIONS

This application claims the benefit of priority to U.S. provisional application No. 62/105,463 filed Jan. 20, 2015, which is incorporated herein by reference in its entirety.

FIELD OF THE INVENTION

The present invention relates to novel anthelmintic compounds of formula (IA) and compositions containing the compounds:

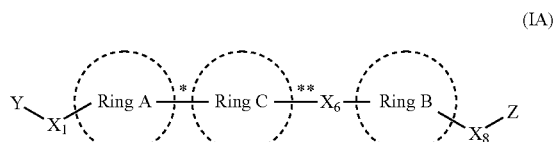

(IA)

wherein, Y is selected from the group consisting of —H, aryl, cycloalkyl, cycloalkenyl, heteroaryl, heterocyclyl, alkyl, haloalkyl, and alkoxyalkyl; and Z is selected from the group consisting of aryl, cycloalkyl, cycloalkenyl, heteroaryl, heterocyclyl, alkyl, haloalkyl, and alkoxyalkyl. Variables Ring A, Ring B, Ring C, $X_1$, $X_6$, and $X_8$ are as defined below. The invention also relates to parasiticidal compositions comprising the compounds, and methods and uses of the compounds for treating and preventing parasitic infections and infestations in animals.

BACKGROUND OF THE INVENTION

Animals such as mammals and birds are often susceptible to parasite infestations/infections. These parasites may be ectoparasites, such as insects, and endoparasites such as nematodes and other worms. Domesticated animals, such as cats and dogs, are often infested with one or more of the following ectoparasites:
fleas (e.g. *Ctenocephalides* spp., such as *Ctenocephalides* felts and the like);
ticks (e.g. *Rhipicephalus* spp., *Ixodes* spp., *Dermacentor* spp., *Amblyoma* spp., and the like);
mites (e.g. *Demodex* spp., *Sarcoptes* spp., *Otodectes* spp., and the like);
lice (e.g. *Trichodectes* spp., *Cheyletiella* spp., *Linognathus* spp. and the like);
mosquitoes (*Aedes* spp., *Culex* spp., *Anopheles* spp. and the like); and
flies (*Hematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals Major diseases which may be transmitted by ticks include borrelioses (Lyme disease caused by *Borrelia burgdorferi*), babesioses (or piroplasmoses caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. Parasites prevalent among cattle in some regions are ticks of the genus *Rhipicephalus*, especially those of the species *microplus* (cattle tick), *decoloratus* and *annulatus*. Ticks such as *Rhipicephalus microplus* (formerly *Boophilus microplus*) are difficult to control because they lay eggs in the pasture where farm animals graze. This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesioses ("cattle fever") and anaplasmosis.

Animals and humans also suffer from endoparasitic infections including, for example, helminthiasis which is caused by of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*.

Another endoparasite which seriously harms animals is *Dirofilaria immitis*, also known as Heartworm. The most common hosts are dogs and cats but other animals such as ferrets and raccoons may also be infected. The parasitic worm is transmitted by the mosquitoe bites, which carry the heartworm larvae. The adult worms live in the major blood vessels of the lung, causing inflammation of the blood vessels and potentially resulting in heart damage and early death. In advanced infections, the worms enter the heart as well.

Recently, anthelmintic compounds with activity against various endoparasitic species were reported in WO 2009/077527 A1, WO 2010/115688 A1, WO 2010/146083 A1, WO 2014/023723 A1 and EP 2 468 096 A1 (all incorporated herein by reference). Although many parasitic infections can be treated with known antiparasitic compounds and compositions, there is a need for new parasiticidal active agents and veterinary compositions and methods with improved efficacy, bioavailability, and spectrum of coverage to protect animals against endoparasites and/or ectoparasites. This invention addresses this need.

SUMMARY OF THE INVENTION

The present invention is directed to novel and inventive anthelmintic compounds of formulae (IA), (IA-1), (IA-2), and (IA-3):

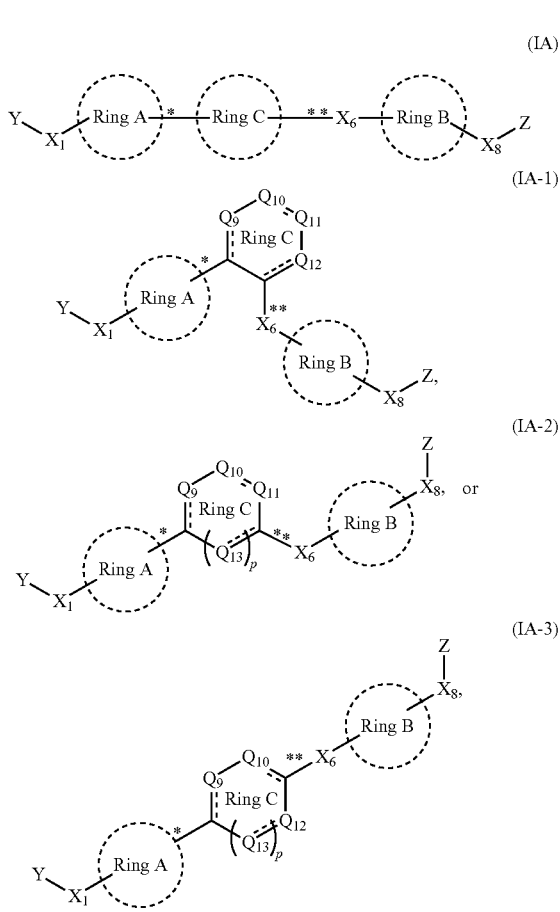

as described herein and compositions comprising the compounds in combination with a pharmaceutically acceptable carrier or diluent.

The present invention is also directed to methods for the treatment and prevention of a parasitic infection in an animal comprising administering at least one of the compounds of the invention to the animal. Also included in the present invention are uses of the compounds for the treatment and/or prevention of parasitic infections in animals and the use of the compounds in the preparation of a medicament for the treatment and/or prevention of a parasitic infection in an animal.

The compounds of the invention are intended to encompass racemic mixtures, specific stereoisomers and tautomeric forms of the compound. Another aspect of the invention is a salt form of the compound of the invention.

Another aspect of the invention are solid state forms of the compounds of the invention which consists of crystalline forms including single crystals, nanocrystals, co-crystals, molecular complexes, hydrates, anhydrates, solvates, desolvates, clathrates and inclusion complexes and non-crystalline forms including non-crystalline glass and non-crystalline amorphous forms.

It is noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is further noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

DETAILED DESCRIPTION OF THE INVENTION

The present invention provides novel and inventive anthelmintic compounds of formulae (IA), (IA-1), (IA-2), and (IA-3) as described herein, and compositions comprising the compounds together with a pharmaceutically acceptable carrier or diluent. The compounds of the invention have been found to be highly efficacious against internal parasites (endoparasites) that cause harm to animals. In certain embodiments, the compounds of the invention may also be used to combat external parasites (ectoparasites) that cause harm to animals.

The compounds may be combined with one or more additional active agents in compositions to broaden the scope of coverage against both endoparasites and ectoparasites.

Also provided are methods and uses of the compounds and compositions for the treatment and/or prophylaxis of parasitic infections and infestations of animals, comprising administering a therapeutically effective amount of a compound or composition of the invention to the animal.

Definitions

Terms used herein will have their customary meaning in the art unless specified otherwise.

The organic moieties mentioned in the definitions of the variables of formula (IA) are—like the term halogen—collective terms for individual listings of the individual group members. The prefix $C_n$-$C_m$ indicates in each case the possible number of carbon atoms in the group.

In the formulas set forth herein, the single asterisk (*) represents the portion of Ring C bound to Ring A, and double asterisk (**) represents the portion of Ring C bound to $X_6$. Further, it should be understood, when partial structures of the compounds are illustrated, the squiggle line "⌇" indicates the point of attachment of the partial structure to the rest of the molecule.

Unless otherwise specifically noted or apparent by context, "active agent" or "active ingredient" or "therapeutic agent" as used in this specification, means an anthelmintic compound of the invention. The term "acid halide" as used herein, refers to —C(=O)-halogen wherein the "halogen" is as defined herein.

The term "alkenyl" as used herein refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_4$, $C_2$-$C_8$, $C_2$-$C_6$, $C_2$-$C_{12}$, or $C_2$-$C_{10}$ r alkenyl groups. In one embodiment of alkenyl, the number of double bonds is one to three, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, and the like.

The term "alkenylamino" as used herein, refers to alkenyl-amino-, wherein "alkenyl" and "amino" are as defined herein.

The term "alkenylene" as used herein, refers to a divalent straight and branched carbon chains which have at least one carbon-carbon double bond. In some embodiments, alkenylene groups may include $C_2$-$C_{20}$ alkenylene groups. In other embodiments, alkenylene includes $C_2$-$C_4$, $C_2$-$C_8$, $C_2$-$C_6$, $C_2$-$C_{12}$, or $C_2$-$C_{10}$ alkenylene groups. In one embodiment of alkenylene, the number of double bonds is one to three, in another embodiment of alkenylene, the number of double bonds is one or two.

The term "alkenyloxy" as used herein, refers to alkenyl-O— wherein the "alkenyl" is as defined herein.

The term "alkenylsulfinyl" as used herein, refers to alkenyl-S(O)— wherein the "alkenyl" is as defined herein.

The term "alkenylsulfonyl" as used herein, refers to alkenyl-S(O)$_2$— wherein the "alkenyl" is as defined herein.

The term "alkoxy" as used herein, refers to alkyl-O—, wherein alkyl is as defined above. "Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—CH($CH_3$)O—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, and the like.

The term "alkoxyalkyl" as used herein, refers to alkyl-O-alkyl, wherein alkyl is as defined above.

The terms "alkoxycarbonyl," as used herein, refer to alkoxy-C(O)— wherein alkoxy, is as defined herein.

The term "alkyl" as used herein, refers to an aliphatic hydrocarbon group which may be straight or branched having about 1 to about 15 carbon atoms in the chain "Lower alkyl" as a group means, unless otherwise specified, an aliphatic hydro carbon group which may be straight or branched having about 1 to about 4 carbon atoms in the chain. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl, 1,1-dimethylethyl and the like. The alkyl group can be unsubstituted or substituted with one or more moieties selected from the group consisting of acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

The term "alkylamino" as used herein, refer to alkyl-amino- wherein alkyl and amino are as defined herein.

The terms "alkylaminocarbonyl" as used herein, refer to alkylamino-C(O)— where alkylamino is as defined herein.

The term "alkylaryl" as used herein refers to an -alkyl-aryl group, wherein the "alkyl" and "aryl" groups are as defined herein.

The terms "alkylcarbonyl," as used herein, refer to alkyl-C(O)— wherein alkyl is as defined herein.

The terms "alkylhaloalkyl" as used herein, refer to haloalkyl-alkyl- wherein haloalkyl and alkyl are as defined herein.

The term "alkylsulfinyl" as used herein, refers to alkyl-S(O)—, wherein alkyl is as defined above.

The term "alkylsulfonyl" as used herein, refers to alkyl-S(O)$_2$—, wherein alkyl is as defined above.

The term "alkylthio" as used herein refers to alkyl-S—, wherein alkyl is as defined herein.

The term "alkynyl" as used herein refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl, and the like.

The term "alkynylamino" as used herein, refers to alkynyl-amino- wherein alkynyl and amino are as defined herein.

The term "alkynyloxy" as used herein, refers to alkynyl-O— wherein alkynyl is as defined herein.

The term "alkynylsulfinyl" as used herein, refers to alkynyl-S(O)— wherein alkynyl is as defined herein.

The term "alkynylsulfonyl" as used herein, refers to alkynyl-S(O)$_2$— wherein alkynyl is as defined herein.

The term "amido" as used herein refers to —C(=O)NR'R" or —NR'C(=O)R" wherein R' and R" are independently hydrogen, alkyl, alkoxy, cycloalkyl, heterocycloalkyl, aryl or heteroaryl.

The term "amino," as used herein, refers to —NR$^a$R$^b$, wherein R$^a$ and R$^b$ are independently selected from the group consisting of hydrogen, alkyl, alkylcarbonyl, cycloalkyl, (cycloalkyl)alkyl, and unsubstituted phenyl.

The term "aminoalkyl" as used herein refers to amino-alkyl-, wherein amino and alkyl are as defined herein.

The term "aminocarbonyl" as used herein refers to amino-C(=O)— wherein amino is as defined herein.

The term "anhydride" as used herein refers to compounds of the general structure R$^a$C(=O)—O—C(=O)— wherein R$^a$ is hydrogen, aryl or alkyl as defined herein.

The term "animal" as used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

The term "aryl" as used herein, refers to a monovalent aromatic carbocyclic group of from 6 to 14 carbon atoms having a single ring or multiple condensed rings provided that the point of attachment is through an aryl ring atom. In some embodiments, aryl groups include $C_6$-$C_{10}$ aryl groups. Aryl groups include, but are not limited to, phenyl, biphenyl, naphthyl, tetrahydronaphthyl, phenylcyclopropyl, biphenyl, fluorenyl, anthracenyl, acenaphthenyl, phenanthrenyl, indanyl, and the like. Examples of bicyclic aryl groups include naphthyl and indanyl. Aryl groups may be unsubstituted or substituted by one or more moieties selected from the group consisting of acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

The term "arylalkoxy" as used herein, refers to aryl-alkoxy- where "aryl" and "alkoxy" are as defined herein.

The terms "aralkyl" or "arylalkyl" as used herein, refers to aryl-alkyl- where "aryl" and "akyl" are as defined herein.

The term "arylalkylsulfiny" as used herein, refers to aryl-alkylsulfinyl- where "aryl" and "alkylsulfinyl" are as defined herein.

The term "arylalkylsulfony" as used herein, refers to aryl-alkylsulfonyl- where "aryl" and "alkylsulfonyl" are as defined herein.

The term "arylalkylthio" as used herein, refers to aryl-alkylthio- where "aryl" and "alkylthio" are as defined herein.

The term "arylamino" as used herein, refers to aryl-amino- where "aryl" and "amino" are as defined herein.

The term "arylcarbonyl" as used herein, refers to aryl-C(=O)— where "aryl" is as defined herein.

The term "arylester," or "aryloxycarbonyl" as used herein, refers to the group aryl-O—C(=O)— wherein aryl is as defined herein.

The term "arylene" as used herein, means an aryl group as defined herein having two monovalent radical centers derived by the removal of two hydrogen atoms from two different carbon atoms of a parent aryl group. Examples of arylene include, but are not limited to, 1,4-benzylene, 1,3-benzylene, 1,2-benzylene, 1,8-naphthylene, 1,4-anthracenylene, and the like. Arylene groups may be unsubstituted or substituted by one or more moieties selected from the group consisting of acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

The term "aryloxy" as used herein refers to aryl-O—, wherein "aryl" is as defined herein.

The term "arylsulfinyl", as used herein, refers to aryl-S(O)— wherein "aryl" is as defined herein.

The term "arylsulfonyl", as used herein, refers to aryl-S(O)$_2$— wherein "aryl" is as defined herein.

The term "arylthio", as used herein, refers to aryl-S— wherein "aryl" is as defined herein.

"Azido" as used herein refers to an $N_3$— group.

The term "carbocyclyl" as used herein refers to carbon-containing ring systems, including both "cycloalkyl" and "aryl" groups as defined herein. The carbocyclyl may be unsubstituted or substituted by one or more moieties selected from the group consisting of acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

The term "carbocyclylene" as used herein refers to carbon-containing ring systems, including both "cycloalkyl" and "aryl" groups as defined herein, having two monovalent radical centers derived by the removal of two hydrogen atoms from two different carbon atoms of a parent aryl or cycloalkyl group. The carbocyclyene may be unsubstituted or substituted by one or more moieties selected from the group consisting of acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

The term "cyano" as used herein refers to a —CN group.

The term "carboxyl" as used herein refers to a carboxylic acid radical, —C(O)OH.

The term "cycloalkenyl" as used herein means a cycloalkyl group, as defined herein, containing at least one carbon-carbon double bond. Exemplary monocyclic cycloalkenyl groups include cyclopentenyl, cyclohexenyl or cycloheptenyl. Exemplary spirocyclic cycloalkenyl groups include spiro[4.5]deca-1,6-diene. Cycloalkenyl groups may be unsubstituted or substituted by one or more moieties unsubstituted or substituted by one or more moieties selected from the group consisting of oxo (=O), acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl. The term "cycloalkenylene" as used herein means a cycloalkenyl as defined herein having two monovalent radical centers derived by the removal of two hydrogen atoms from two different carbon atoms of a parent cycloalkenyl group. Exemplary cycloalkenylene groups include cyclopentenylene, cyclohexenylene, cycloheptenylene, cyclooctenylene, cyclononenylene, cyclodecenylene, norbornenylene, 3-cyclohexen-1,2-ylene group, 2,5-cyclohexadien-1,4-ylene, and the like.

The term "cycloalkenyloxy" as used herein refers to cycloalkenyl-O— wherein "cycloalkenyl is as defined herein.

The term "cycloalkyl" as used herein means a saturated monocyclic or bicyclic ring system of about 3 to about 10 carbon atoms in a mono- or bicyclic, fused, bridged or spirocyclic ring. Exemplary monocyclic cycloalkyl rings include C3-C8 cycloalkyl rings such as cyclopropyl, cyclopentyl, cyclohexyl, cycloheptyl, norbornyl and the like. Exemplary spiroyclic cycloalkyl rings include spiro[3.4]octane, spiro[5.5]undecane, spiro[4.5]decane and spiro[3.3]heptane. Exemplary bridged cycloalkyl rings include bicyclo[2.2.1]heptane, bicyclo[2,2,2]Octaine, bicyclo[3,3,1]nonane, and Bicyclo[4 3,1]decane. Cycloalkyl groups may be unsubstituted or substituted by one or more moieties unsubstituted or substituted by one or more moieties selected from the group consisting of oxo (=O), acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

The term "cycloalkylene" as used herein means a cycloalkyl as defined herein having two monovalent radical centers derived by the removal of two hydrogen atoms from two different carbon atoms of a parent cycloalkyl group Exemplary monocyclic cycloalkylene rings include $C_3$-$C_8$ cycloalkylene rings such as 1,2-cyclopentylene group, 1,2-cyclohexylene group, 1,3-cyclohexylene group, 1,4-cyclohexylene group, 1,3-cycloheptylene group, and the like. Cycloalkylene groups may be unsubstituted or substituted by one or more moieties unsubstituted or substituted by one or more moieties selected from the group consisting of oxo (=O), acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

The term "cycloalkylthio" as used herein refers to cycloalkyl-S— wherein cycloalkyl is as defined herein.

The term "cycloalkoxy" as used herein refers to cycloalkyl-O—, wherein cycloalkyl is as defined herein.

The term "dialkenylamino" as used herein, refer to (alkenyl)$_2$N— where alkenyl is as defined herein.

The term "dialkylamino" as used herein, refer to (alkyl)$_2$N— where alkyl is as defined herein.

The term "dialkylaminocarbonyl" as used herein, refer to dialkylamino-C(O)— where dialkylamino is as defined herein.

The term "dialkynylamino" as used herein, refer to (alkynyl)$_2$N— where alkynyl is as defined herein.

The term "dialkynylaminocarbonyl" as used herein, refer to dialkynylamino-C(O)— where dialkynylamino is as defined herein.

The terms "dihaloalkylaminocarbonyl" as used herein, refer to (haloalkyl)$_2$amino-C(O)— wherein haloalkyl and amino are as defined herein.

The term "fatty acid" as used herein refers to carboxylic acids having from 4 to 26 carbon atoms.

The terms "fatty alcohol" or "long-chain aliphatic alcohol" as used herein refer to aliphatic alcohols containing from 6 to 20 carbon atoms.

The term "halo" or "halogen," as used herein, refers to F, Cl, Br, or I The term "haloalkenyl" as used herein, refers to an alkenyl group, as defined herein, which is substituted by one or more halogen atoms.

The term "haloalkenyloxy" as used herein refers to a haloalkenyl-O— group, wherein haloalkenyl is as defined herein.

The term "haloalkenylsulfinyl" as used herein refers to a haloalkenyl-S(O)— group, wherein haloalkenyl is as defined herein.

The term "haloalkenylsulfonyl" as used herein refers to a haloalkenyl-S(O)$_2$— group, wherein haloalkenyl is as defined herein.

The term "haloalkoxy" or "haloalkyloxy" as used herein refers to haloalkyl-O—, wherein haloalkyl is as defined herein.

The term "haloalkyl" as used herein, refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, and the like.

The term "haloalkylamino" as used herein refers to alkylamino as defined herein which is substituted with one or more halogen atoms.

The term "haloalkylaminocarbonyl" as used herein, refer haloalkylamino-C(O)— wherein haloalkylamino is as defined herein.

The term "haloalkylthio," refers to haloalkyl-S— wherein haloalkyl is as defined herein. The term "haloalkylcarbonyl" as used herein, refer to haloalkyl-C(O)— wherein haloalkyl is as defined herein.

The term "haloalkylsulfinyl" refers to haloalkyl-S(O)— where haloalkyl is as defined herein.

The term "haloalkylsulfonyl" refers to haloalkyl-S(O)$_2$— where haloalkyl is as defined herein.

The term "haloalkylthio" refers to haloalkyl-S— where haloalkyl is as defined herein.

The term "haloalkoxy" or "haloalkyloxy" as used herein, refers to an alkoxy group, as defined herein, which is substituted by one or more halogen atoms.

The term "haloalkoxycarbonyl," as used herein, refers to the group haloalkoxy-C(O)—, wherein haloalkoxy, is as defined herein.

The term "haloalkynyl" as used herein, refers to an alkynyl group, as defined herein, which is substituted by one or more halogen atoms.

The term "haloalkynyloxy" as used herein means haloalkynyl-O— wherein haloalkynyl is as defined herein.

The term "haloalkynylsulfinyl" as used herein means haloalkynyl-S(O)— wherein haloalkynyl is as defined herein.

The term "haloalkynylsulfonyl" as used herein means haloalkynyl-S(O)$_2$— wherein haloalkynyl is as defined herein.

The term "haloalkynylthio" as used herein means haloalkynyl-S— wherein haloalkynyl is as defined herein.

The term "halocycloalkenyl" as used herein, refers to an cycloalkenyl group, as defined herein, which is substituted by one or more halogen atoms.

The term "halocycloalkyl" as used herein, refers to an cycloalkyl group, as defined herein, which is substituted by one or more halogen atoms.

The term "halocycloalkylthio" as used herein, refers to halocycloalkyl-S—, wherein halocycloalkyl is as defined herein.

The term "halocycloalkoxy" as used herein, refers to halocycloalkyl-O— wherein halocycloalkyl is as defined herein. The term "halocycloalkenyl" as used herein, refers to an cycloalkenyl group, as defined herein, which is substituted by one or more halogen atoms.

The term "halocycloalkenyloxy" as used herein, refers to halocycloalkenyl-O— wherein halocycloalkenyl is as defined herein.

The term "halothio" as used herein refers to (halogen)$_5$-S—, wherein halogen is as defined above. An example of "halothio" is the group F$_5$S—.

The term "heteroaryl" as used herein, refers to a monovalent monocyclic or bicyclic aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include acridinyl, benzimidazolyl, benzothiazolyl, benzothiophenyl, benzofuranyl, benzoxazolyl, benz[d]isoxazolyl, benzotriazolyl, 1,2,3-benzotriazinyl, 1,2,4-benzotriazinyl, benzothienyl, benzimidazolyl, carbazolyl, cinnolinyl, furyl, furopyridinyl (such as furo[2,3c]pyridyl, furo[3,2b]pyridyl, or furo[2,3b]pyridyl) imidazolyl, indolyl, indolizinyl, indazolyl, isoindolyl, isoxazolyl, isoquinolinyl, isothiazolyl, isoquinolinyl, isoxazolyl, oxadiazolyl, oxazolyl, 2-oxazepinyl, phthalazinyl, phenanthrolinyl, phenanthridinyl, pyrazinyl, pyridazinyl, pyrazolyl, pyridyl, pyrimidinyl, pyrrolyl, pyrrolopyridyl, quinazolinyl, quinoxalinyl, quinolinyl, 1,3,4-thiadiazolyl, thiazolyl, thienyl, thiophenyl, triazinyl, triazolyl groups, and the like. Heteroaryl rings may be unsubstituted or substituted by one or more moieties as described for aryl above.

The term "heteroarylalkoxy" refers to heteroaryl-alkoxy-, wherein heteroaryl and alkoxy are as defined herein.

The term "heteroarylalkylsulfinyl" refers to heteroaryl-alkyl-S(O)—, wherein heteroaryl and alkyl are as defined herein.

The term "heteroarylalkylsulfonyl" refers to heteroaryl-alkyl-S(O)$_2$—, wherein heteroaryl and alkyl are as defined herein.

The term "heteroarylalkylthio" refers to heteroaryl-alkyl-S—, wherein heteroaryl and alkyl are as defined herein.

The term "heteroarylene" as used herein, refers to a "heteroaryl" as defined herein having two monovalent radical centers derived by the removal of two hydrogen atoms from two different carbon atoms of a parent heteroaryl group. Examples of such groups include benzofuran-4,7-diyl, benzofuran-4,6-diyl, benzofuran-5,7-diyl, benzothiophene-4,7-diyl, benzothiophene-4,6-diyl, benzothiophene-5,7-diyl, 1,3-benzoxazole-4,7-diyl, 1,3-benzoxazole-4,6-diyl, 1,3-benzoxazole-5,7-diyl, 1,2-benzoxazole-4,7-diyl, 1,2-benzoxazole-4,6-diyl, 1,2-benzoxazole-5,7-diyl, 1,3-benzthiazole-4,7-diyl, 1,3-benzthiazole-4,6-diyl, 1,3-benzthiazole-5,7-diyl, 1,2-benzthiazole-4,7-diyl, 1,2-benzthiazole-4,6-diyl, 1,2-benzthiazole-5,7-diyl, benzimidazole-4,7-diyl, benzimidazole-4,6-diyl, benzimidazole-5,7-diyl, furan-2,5-diyl, imidazole-4,5-diyl, imidazole-2,4-diyl, indazole-4,7-diyl, indazole-5,7-diyl, indazole-4,6-diyl, indole-4,7-diyl, indole-4,6-diyl, indole-4,5-diyl, isoxazolyl-3,4-diyl, isoxazolyl-3,5-diyl, 1,3,4-oxadiazole-2,5-diyl, pyrazole-3,5-diyl, pyridine-2,4-diyl, pyridine-2,3-diyl, pyridine-2,5-diyl, pyridine-3,5-diyl, pyridine-2,6-diyl, pyridazine-3,5-diyl, pyridazine-3,6-diyl, pyrazine-2,5-diyl, pyrimidine-2,4-diyl, pyrimidine-2,5-diyl, pyrimidine-4,6-diyl, quinoline-2,3-diyl, quinoxaline-5,8-diyl, quinoxaline-5,7-diyl, quinazoline-5,8-diyl, quinazoline-5,7-diyl, quinoline-5,8-diyl, quinoline-5,7-diyl, thiophene-2,4-diyl, 1,3,4-thiadiazole-2,5-diyl, 1,3-thiazole-2,4-diyl, 1,3-thiazole-2,5-diyl, 1,3,5-triazine-2,6-diyl, 1,2,4-triazine-3,6-diyl, 1,2,5-triazine-3,6-diyl, and the like. Heteroarylene groups may be unsubstituted or substituted by one or more moieties selected from the group consisting of acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

The term "heteroaryloxy" as used herein refers to heteroaryl-O— wherein heteroaryl is as defined herein.

The term "heteroarylsulfinyl" refers to heteroaryl-S(O)—, wherein heteroaryl is as defined herein.

The term "heteroarylsulfonyl" refers to heteroaryl-S(O)$_2$—, wherein heteroaryl is as defined herein.

The term "heteroarylthio" refers to heteroaryl-S—, wherein heteroaryl is as defined herein.

The term "heterocyclyl," as used herein refers to a 3 to 12-membered heterocyclic monocylic, bicyclic, tricyclic, fused, bridged or spirocyclic ring system, for example, 3 to 8 membered monocyclic or 4 to 7 membered monocyclic; 7 to 11 membered bicyclic, 10 to 15 membered tricyclic, or 7 to 11 spiro ring systems having one or more degrees of unsaturation and containing one or more heteroatoms selected from S, O, or N, preferably 1 to 4 or 1 to 3 heteroatoms. The nitrogen and sulfur heteroatoms may optionally be oxidized and the nitrogen heteroatoms may optionally be quaternized. The heterocyclyl group may be attached at any heteroatom or carbon atom of the ring or ring system and may be unsubstituted or substituted by one or more moieties selected the group consisting of oxo (=O), acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxy carbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl.

Exemplary monocyclic heterocyclyl groups include, but are not limited to, azetidinyl pyrrolidinyl, oxetanyl, pyrazolinyl, imidazolyl, imidazolinyl, imidazolidinyl, oxazolidinyl, isoxazolinyl, thiazolidinyl, isothiazolidinyl, tetrahydropyranyl, piperidinyl, piperazinyl, 2-oxopiperazinyl, 2-oxopiperidinyl, 2-oxopyrrolodinyl, 4-piperidonyl, tetrahydropyranyl, morpholinyl, thiomorpholinyl, thiomorpholine-1-oxide, thiomorpholine-1,1-dioxide, 1,3-dioxolane and tetrahydro-1,1-dioxothienyl, and the like.

Exemplary bicyclic heterocyclyl groups include, but are not limited to, benzodioxolyl, quinuclidinyl, benzopyranyl, dihydrobenzofuranyl, chromonyl, coumarinyl, indazolyl, dihydroisoindolyl, dihydroquinazolinyl (such as 3,4-dihydro-4-oxo-quinazolinyl), tetrahydroquinolinyl, tetrahydroisoquinolinyl, and the like.

Exemplary spiro heterocyclyl groups include, but are not limited to, 1,5-diazaspiro[3.3]heptane, 1,5-diazaspiro[3.4]octane, 1-oxaspiro[4.5]decane, and 1,4-dioxa-8-azaspiro[4.5]decane.

Exemplary tricyclic heterocyclyl groups include benzidolyl, xanthenyl, and the like.

The term "heterocyclylene" as used herein, refers to a "heterocyclyl" as defined herein having two monovalent radical centers derived by the removal of two hydrogen atoms from two different carbon atoms of a parent heterocycle, the removal of two hydrogen atoms from two nitrogen atoms of a parent heterocycle, or the removal of a hydrogen atom from a nitrogen and the removal of a hydrogen atom from a carbon atom of a parent heterocycle. The heterocylylene may be optionally substituted with substituents selected from the group consisting of oxo (=O), acid halide, alkenyl, alkenylamino, alkenyloxy, alkenylsulfinyl, alkenylsulfonyl, alkoxy, alkoxycarbonyl, alkyl, alkylamino, alkylaminocarbonyl, alkylcarbonyl, alkylhaloalkyl, alkylsulfinyl, alkylsulfonyl, alkylthio, alkynyl, alkynylamino, alkynyloxy, alkynylsulfinyl, alkynylsulfonyl, amido, amino, aminoalkyl, aminocarbonyl, anhydride, aryl, arylalkoxy, arylalkylsulfinyl, arylalkylsulfonyl, arylalkylthio, arylamino, arylcarbonyl, aryloxy, aryloxycarbonyl, arylsulfinyl, arylsulfonyl, arylthio, azido, carboxyl, cyano, cycloalkenyl, cycloalkenyloxy, cycloalkoxy, cycloalkyl, cycloalkylthio, dialkenylamino, dialkylamino, dialkylaminocarbonyl, dialkynylamino, haloalkenyl, haloalkenyloxy, haloalkenylsulfinyl, haloalkenylsulfonyl, haloalkoxy, haloalkyl, haloalkylsulfinyl, haloalkylsulfonyl haloalkylthio, haloalkynyl, haloalkynyloxy, haloalkynylsulfinyl, haloalkynylsulfonyl, halocycloalkenyl, halocycloalkyl, halocycloalkylthio, halocycloalkenyloxy, halocycloalkoxy, halogen, halothio, heteroaryl, heteroarylalkoxy, heteroarylalkylsulfinyl, heteroarylalkylsulfonyl, heteroarylalkylthio, heteroaryloxy, heteroarylsulfinyl, heteroarylsulfonyl, heteroarylthio, hydroxyl, hydroxyalkyl, imino, nitro, oxime, phosphinyl, phosphonate, phosphoric acid, phosphoryl, sulfamonyl, sulfonic acid, thioester, thiol, and trialkylsilyl. Examples of "heterocyclylene" include, but are not limited to, azetidin-1,3-diyl, tetrahydrofuran-2,5-diyl, morpholin-2,3-diyl, pyran-2,4-diyl, 1,4-dioxan-2,3-diyl, 1,3-dioxan-2,4-diyl, piperidin-2,4-diyl, piperidin-1,4-diyl, pyrrolidin-1,3-diyl, morpholin-2,4-diyl, piperazin-1,4-diyl, 1,5-diazaspiro[3.3]heptan-1,5-diyl, 1,5-diazaspiro[3.4]octan-1,5-diyl and the like.

The term "hydroxyl" as used herein refers to —OH.

The term "hydroxyalkyl" as used herein refers to HO-alkyl-, wherein alkyl is as defined herein.

The term "imino" as used herein refers to the radical —C(=N)—$R^b$, where $R^b$ can be, for example, alkyl, alkenyl, alkynyl, aryl, arylalkyl, or cycloalkyl.

The term "nitro" as used herein is represented by the formula —$NO_2$.

The term "oxime" as used herein refers to —C=NOH.

The term "pharmaceutically acceptable salt" as used herein includes acid addition salts, hydrates, alcolates and other salts which are physiologically compatible in animals, see for example, S. M. Berge, et al., "Pharmaceutical Salts," J. Pharm. Sci., 66:1-19 (1977), incorporated herein by reference. The salts can be prepared in situ during the final isolation and purification of the compounds of the invention, or separately by reacting the free base function with a suitable acid. These salts may be obtained from inorganic or organic acids. Examples of inorganic acids include hydrochloric acid, nitric acid, perchloric acid, hydrobromic acid, sulphuric acid or phosphoric acid. Examples of organic acids include acetic acid, propionic acid, oxalic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulphonic acid, p-toluene sulphonic acid, salicyclic acid and the like. Also, included are the salts with various amino acids such as alanine, arginine, asparagine, aspartic acid, cysteine, glutamine, glutamic acid, glycine, histidine, isoleucine, leucine, lysine; methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, glucoheptonate, glycerophosphate, gluconate, hemisulfate, heptanoate, hexanoate, hydroiodide, 2-hydtoxy-ethanesulfonate, lactobionate, lactate, laurate, lauryl sulfate, malonate, 2-naphthalenesulfonate, nicotinate, oleate, palmitate, pamoate, pectinate, persulfate, 3-phenyl-propionate, phosphate, picrate, pivalate, propionate, stearate, sulfate, tartrate, thiocyanate, p-toluenesulfonate, undecanoate, valerate salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "phosphinyl" as used herein includes —PH$_3$.

The term "phosphonate", as used herein, refers to —C—PO(OR$^c$)$_2$ wherein R$^c$ is independently alkyl or aryl.

The term phosphoric acid, as used herein refers to —C—PO(OH)$_2$.

The term "phosphoryl" as used herein refers to —P(=O)OR$^d_2$ wherein each R$^d$ is independently selected from the group consisting of alkyl, alkenyl, alkynyl, carbocyclyl, heterocyclyl, aryl, and aralkyl.

The term "sulfamoyl" as used herein refers to —SONH$_2$.

The term "sulfonic acid" as used herein refers to —S(O)(O)OH.

The term "thioester" as used herein, refers to the group —C(=O)SR$^f$, wherein R$^f$ is alkyl.

The term "thiol" as used herein refers to —SH.

The term "trialkylsilyl," as used herein, refers to —Si-alkyl, wherein alkyl is as defined herein.

The term "therapeutically effective amount", as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

The term "treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

Anthelmintic Compounds of the Invention

In a first aspect of the invention, an anthelmintic compound of Formula (IA) is provided

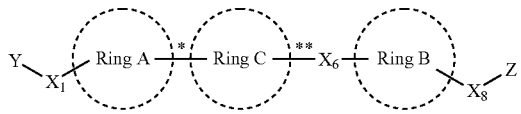

(IA)

wherein:

Y is —H or aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

Z is aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

$X_1$ is a bond, $C_2$-$C_4$ alkenylene, —O—, —C(O)—, —O—C(O)—, —C(O)—O—, —S—, —S(O)—, —S(O)$_2$—, —N(R$^1$)S(O)—, —S(O)—N(R$^1$)—, —N(R$^1$)—C(S)—, —C(S)—N(R$^1$)—, —N(R$^1$)SO$_2$—, —SO$_2$N(R$^1$)—, —N(R$^1$)—C(O)—, —C(O)—N(R$^1$)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, —C(O)—(CH$_2$)$_n$—O— where n is 1 to 3, —O—CH$_2$—, —CH$_2$—O—, —N(R$^1$)(CH$_2$)$_n$— where n is 1 to 3, —(CH$_2$)$_n$—N(R$^1$)— where n is 1 to 3, —S—CH$_2$—, —S(O)—CH$_2$—, —CH$_2$—S(O)—, —S(O)$_2$—CH$_2$—, or —CH$_2$—S(O)$_2$—;

Ring A is a diradical group selected from the group consisting of a 3-8 membered monocyclic carbocyclylene, a 3-8 membered heterocyclylene group, a 3-8 membered spirocyclic cycloalkylene group, a 3-8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is a diradical group selected from the group consisting of monocyclic arylene, monocyclic heteroarylene, monocyclic heterocyclylene, bicyclic arylene, bicyclic heteroarylene, and bicyclic heterocyclylene, optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_6$ is a bond, —(CH$_2$)$_n$— where n is 1 to 3, —O—, —C(O)—, —C(S)—, —S—, —S(O)—, —S(O)$_2$—, —N(R$^1$)(CH$_2$)$_n$— where n is 0 to 2, —(CH$_2$)$_n$—N(R$^1$)— where n is 0 to 2, —C(O)—N($R^1$)—, —C(S)—N($R^1$)—, —N($R^1$)—C(O)—, or —N($R^1$)—C(S)—;

Ring B is a diradical group selected from the group consisting of amonocyclic cycloalkylene group, a monocyclic heterocyclylene group, a 3-8 membered spirocyclic cycloalkylene group, a 3-8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$X_8$ is a bond, —(CH$_2$)$_n$— wherein n is 1 to 3, —(CH$_2$)$_n$—O— wherein n is 0 or 1, —O—(CH$_2$)$_n$— wherein n is 0 or 1, —C(O)—, —S—, —S(O)—, —S(O)$_2$—, —N(R1)S(O)—, —S(O)—N($R^1$)—, —N($R^1$)SO$_2$—, —SO$_2$NH—, —N($R^1$)(CH$_2$)$_n$— wherein n is 0 to 2, or —(CH$_2$)$_n$—N($R^1$)— wherein n is 0 to 2; and each $R^1$ is independently H, alkyl, or arylalkyl.

Another embodiment of the invention is an anthelmintic compound of Formula (IA) wherein:

Y is —H or aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

Z is aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

$X_1$ is a bond, $C_2$-$C_4$ alkenylene, —O—, —C(O)—, —O—C(O)—, —C(O)—O—, —S—, —S(O)—, —S(O)$_2$—, —N($R^1$)S(O)—, —S(O)—N($R^1$)—, —N($R^1$)—C(S)—, —C(S)—N($R^1$)—, —N($R^1$)SO$_2$—, —SO$_2$N($R^1$)—, —N($R^1$)—C(O)—, —C(O)—N($R^1$)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, —C(O)—(CH$_2$)$_n$—O— where n is 1 to 3, —O—CH$_2$—, —CH$_2$—O—, —N($R^1$)(CH$_2$)$_n$— where n is 1 to 3, —(CH$_2$)$_n$—N($R^1$)— where n is 1 to 3, —S—CH$_2$—, —S(O)—CH$_2$—, —CH$_2$—S(O)—, —S(O)$_2$—CH$_2$—, or —CH$_2$—S(O)$_2$—;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is selected from the group consisting of monocyclic arylene, monocyclic heteroarylene, monocyclic heterocyclylene, bicyclic arylene, bicyclic heteroarylene, and bicyclic heterocyclylene optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_6$ is —O—, —N($R^1$)—, —N($R^1$)CH$_2$—, or —CH$_2$N($R^1$)—;

Ring B is cycloalkylene or heterocyclylene, which may be optionally substituted with one or more halogen, hydroxy, hydroxyalkyl, alkoxy, haloalkoxy, amino, alkylamino, dialkylamino or aminoalkyl group;

$X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—; and each $R^1$ is independently H, alkyl, or arylalkyl.

Another embodiment of the invention is an anthelmintic compound of Formula (IA) wherein:

Z is aryl, or heteroaryl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is selected from the group consisting of monocyclic arylene, monocyclic heteroarylene, monocyclic heterocyclylene, bicyclic arylene, bicyclic heteroarylene, and bicyclic heterocyclylene optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_6$ is —O—, —N($R^1$)—, —N($R^1$)CH$_2$—, or —CH$_2$N($R^1$)—;

Ring B is cycloalkylene or heterocyclylene, which may be optionally substituted with one or more halogen, hydroxy, hydroxyalkyl, alkoxy, haloalkoxy, amino, alkylamino, dialkylamino or aminoalkyl group; and $X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—.

Another embodiment of the invention is an anthelmintic compound of Formula (IA) wherein:

Ring A is a diradical group selected from the group consisting of a 3-8 membered heterocyclylene group and a 3-8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is a diradical group selected from the group consisting of monocyclic arylene and monocyclic heteroarylene, optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

Y is —H or aryl, cycloalkyl, cycloalkenyl, heteroaryl, heterocyclyl, alkyl, or haloalkyl, optionally substituted by one or more of halogen, alkyl, haloalkyl, alkoxy, haloalkoxy, alkylthio, halothio, haloalkylthio, alkylsulfinyl, haloalkylsulfinyl, alkylsulfonyl, or haloalkylsulfonyl; and $X_1$ is a bond, $C_2$-$C_4$ alkenylene, —O—, —C(O)—, —O—C(O)—, —C(O)—O—, —N($R^1$)S(O)—, —S(O)—N($R^1$)—, —N($R^1$)—C(S)—, —C(S)—N($R^1$)—, —N($R^1$)SO$_2$—, —SO$_2$N($R^1$)—, —N($R^1$)—C(O)—, —C(O)—N($R^1$)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, or —C(O)—(CH$_2$)$_n$—O— where n is 1 to 3.

Another embodiment of the invention is an anthelmintic compound of Formula (IA) wherein:

Z is aryl, or heteroaryl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is a diradical group selected from the group consisting of monocyclic arylene and monocyclic heteroarylene, optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_6$ is —O—, —N($R^1$)—, —N($R^1$)CH$_2$—, or —CH$_2$N($R^1$)—;

Ring B is cycloalkylene or heterocyclylene, which may be optionally substituted with one or more halogen, hydroxy, hydroxyalkyl, alkoxy, haloalkoxy, amino, alkylamino, dialkylamino or aminoalkyl group; and $X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—.

Another embodiment of the invention is an anthelmintic compound of Formula (IA) wherein:

Ring A is a diradical group selected from the group consisting of a 6 membered heterocyclylene group and a 8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is a 6 membered monocyclic heteroarylene, optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

Y is —H or 5-6 membered aryl, 5-6 membered cycloalkyl, 5-6 membered cycloalkenyl, 5-6 membered heteroaryl, 5-6 membered heterocyclyl, $C_{1-4}$ alkyl, or $C_{1-4}$ haloalkyl, optionally substituted by one or more of halogen, alkyl, haloalkyl, alkoxy, haloalkoxy, alkylthio, halothio, haloalkylthio, alkylsulfinyl, haloalkylsulfinyl, alkylsulfonyl, or haloalkylsulfonyl; and $X_1$ is a bond, $C_2$-$C_4$ alkenylene, —O—, —C(O)—, —O—C(O)—, —C(O)—O—, —N($R^1$)S(O)—, —S(O)—N($R^1$)—, —N($R^1$)—C(S)—, —C(S)—N($R^1$)—, —N($R^1$)SO$_2$—, —SO$_2$N($R^1$)—, —N($R^1$)—C(O)—, —C(O)—N($R^1$)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, or —C(O)—(CH$_2$)$_n$—O— where n is 1 to 3.

Another embodiment of the invention is an anthelmintic compound of Formula (IA) wherein:

Z is a 6 membered aryl, or a 6 membered heteroaryl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is a diradical group selected from the group consisting of monocyclic arylene and monocyclic heteroarylene, optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_6$ is —O—, —N($R^1$)—, —N($R^1$)CH$_2$—, or —CH$_2$N($R^1$)—;

Ring B is 4-6 membered monocyclic cycloalkylene, 4-6 membered monocyclic heterocyclylene, 7-9 membered spirocyclic cycloalkylene, 7-9 membered spirocyclic heterocyclylene which may be optionally substituted with one or more halogen, hydroxy, hydroxyalkyl, alkoxy, haloalkoxy, amino, alkylamino, dialkylamino or aminoalkyl group; and $X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—.

Another embodiment of the invention is an anthelmintic compound of Formula (IA) wherein:

Ring A is a diradical group selected from the group consisting of a 6 membered heterocyclylene group and a 8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

Ring C is a 6 membered monocyclic heteroarylene, optionally substituted with one or two substituents independently selected from the group consisting of halogen, hydroxy, hydroxyalkyl, amino, alkylamino, dialkylamino, aminoalkyl, alkyl, haloalkyl, alkenyl, haloalkenyl, alkynyl, haloalkynyl, carbocyclyl and halocarbocyclyl;

$X_6$ is —O—, —N($R^1$)—, —N($R^1$)CH$_2$—, or —CH$_2$N($R^1$)—;

Ring B is 4-6 membered monocyclic cycloalkylene, 4-6 membered monocyclic heterocyclylene, 7-9 membered spirocyclic cycloalkylene, 7-9 membered spirocyclic heterocyclylene which may be optionally substituted with one or more halogen, hydroxy, hydroxyalkyl, alkoxy, haloalkoxy, amino, alkylamino, dialkylamino or aminoalkyl group;

$X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—;

Y is —H or 5-6 membered aryl, 5-6 membered cycloalkyl, 5-6 membered cycloalkenyl, 5-6 membered heteroaryl, 5-6 membered heterocyclyl, $C_1$-$C_4$ alkyl, or $C_1$-$C_4$ haloalkyl, optionally substituted by one or more of halogen, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Z is a 6 membered aryl, or a 6 membered heteroaryl, substituted by one or more of halogen, nitro, cyano, hydroxy, alkyl, halothio, haloalkylthio, alkylsulfinyl, haloalkylsulfinyl, alkylsulfonyl, or haloalkylsulfonyl;

$X_1$ is a bond, $C_2$-$C_4$ alkenylene, —O—, —C(O)—, —O—C(O)—, —C(O)—O—, —N($R^1$)S(O)—, —S(O)—N($R^1$)—, —N($R^1$)—C(S)—, —C(S)—N($R^1$)—, —N($R^1$)$SO_2$—, —$SO_2$N($R^1$)—, —N($R^1$)—C(O)—, —C(O)—N($R^1$)—, —($CH_2$)$_n$— where n is 1 to 3, —C(O)—($CH_2$)$_n$— where n is 1 to 3, —($CH_2$)$_n$—C(O)— where n is 1 to 3, —O—($CH_2$)$_n$—C(O)— where n is 1 to 3, or —C(O)—($CH_2$)$_n$—O— where n is 1 to 3; and each $R^1$ is independently H, or $C_1$-$C_3$ alkyl.

Another embodiment of the invention is an anthelmintic compound of Formula (IA) wherein the compound has the structure:

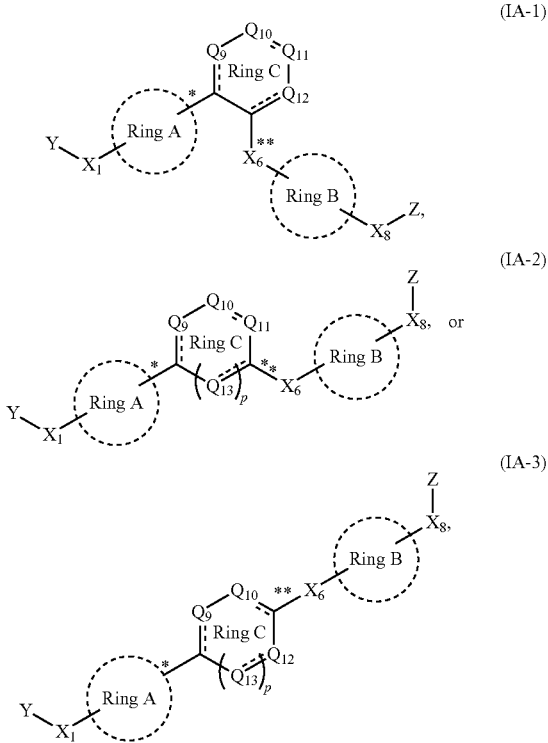

(IA-1)

(IA-2)

(IA-3)

wherein:

Y is —H or aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

Z is aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

$X_1$ is a bond, $C_2$-$C_4$ alkenylene, —O—, —C(O)—, —O—C(O)—, —C(O)—O—, —S—, —S(O)—, —S(O)$_2$—, —N($R^1$)S(O)—, —S(O)—N($R^1$)—, —N($R^1$)—C(S)—, —C(S)—N($R^1$)—, —N($R^1$)$SO_2$—, —$SO_2$N($R^1$)—, —N($R^1$)—C(O)—, —C(O)—N($R^1$)—, —($CH_2$)$_n$— where n is 1 to 3, —C(O)—($CH_2$)$_n$— where n is 1 to 3, —($CH_2$)$_n$—C(O)— where n is 1 to 3, —O—($CH_2$)$_n$—C(O)— where n is 1 to 3, —C(O)—($CH_2$)$_n$—O— where n is 1 to 3, —O—$CH_2$—, —$CH_2$—O—, —N($R^1$)($CH_2$)$_n$— where n is 1 to 3, —($CH_2$)$_n$—N($R^1$)— where n is 1 to 3, —S—$CH_2$—, —S(O)—$CH_2$—, —$CH_2$—S(O)—, —S(O)$_2$—$CH_2$—, or —$CH_2$—S(O)$_2$—;

Ring A is a diradical group selected from the group consisting of a 3-8 membered monocyclic carbocyclylene, a 3-8 membered heterocyclylene group, a 3-8 membered spirocyclic cycloalkylene group, a 3-8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH, —$CH_2$, —$CHR^9$, —$C(R^9)R^9$, or a heteroatom selected from N, —NH, —$NR^{9'}$, S or O;

the dotted lines in the ring represent single or double bonds;

each $R^9$ is each independently halogen, cyano, hydroxyl, amino, alkylamino, dialkylamino, alkyl, haloalkyl, carbocyclyl, heterocyclyl, alkenyl, haloalkenyl, alkynyl or haloalkynyl;

each $R^{9'}$ is each independently alkyl, or alklylaryl;

p is 0, 1 or 2;

$X_6$ is a bond, —($CH_2$)$_n$— where n is 1 to 3, —O—, —C(O)—, —C(S)—, —S—, —S(O)—, —S(O)$_2$—, —N($R^1$)($CH_2$)$_n$— where n is 0 to 2, —($CH_2$)$_n$—N($R^1$)— where n is 0 to 2, —C(O)—N($R^1$)—, —C(S)—N($R^1$)—C(O)—, or —N($R^1$)—C(S)—;

Ring B is a diradical group selected from the group consisting of amonocyclic cycloalkylene group, a monocyclic heterocyclylene group, a 3-8 membered spirocyclic cycloalkylene group, a 3-8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$X_8$ is a bond, —($CH_2$)$_n$— where n is 1 to 3, —($CH_2$)$_n$—O— where n is 0 or 1, —O—($CH_2$)$_n$— where n is 0 or 1, —C(O)—, —S—, —S(O)—, —S(O)$_2$—, —N(R1)S(O)—, —S(O)—N($R^1$)—, —N($R^1$)$SO_2$—, —$SO_2$NH—, —N($R^1$)($CH_2$)$_n$— where n is 0 to 2, or —($CH_2$)$_n$—N($R^1$)— where n is 0 to 2; and each $R^1$ is independently H, alkyl, or arylalkyl.

Another embodiment of the invention is an anthelmintic compound of Formula (IA) wherein:

Y is —H or aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

Z is aryl, cycloalkyl, cycloalkenyl, heteroaryl, heterocyclyl, alkyl, haloalkyl, or alkoxyalkyl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, haloalkylsulfonyl, aryl, aryloxy, arylalkoxy, arylthio, arylalkylthio, arylsulfinyl, arylsulfonyl, arylalkylsulfinyl, arylalkylsulfonyl, heteroaryl, heteroaryloxy, heteroarylalkoxy, heteroarylthio, heteroarylsulfinyl, heteroarylsulfonyl, heteroarylalkylthio, heteroarylalkylsulfinyl or heteroarylalkylsulfonyl;

$X_1$ is a bond, $C_2$-$C_4$ alkenylene, —O—, —C(O)—, —O—C(O)—, —C(O)—O—, —NR¹—, —S—, —S(O)—, —S(O)$_2$—, —N(R¹)S(O)—, —S(O)—N(R¹)—, —N(R¹)C(S)—, —C(S)—N(R¹)—, —N(R¹)SO$_2$—, —SO$_2$N(R¹)—, —N(R¹)—C(O)—, —C(O)—N(R¹)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, —C(O)—(CH$_2$)$_n$—O— where n is 1 to 3, —O—CH$_2$—, —CH$_2$—O—, —N(R¹)(CH$_2$)$_n$— where n is 1 to 3, —(CH$_2$)$_n$—N(R¹)— where n is 1 to 3, —S—CH$_2$—, —S(O)—CH$_2$—, —CH$_2$—S(O)—, —S(O)$_2$—CH$_2$—, or —CH$_2$—S(O)$_2$—;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH, —CH$_2$, —CHR⁹, —C(R⁹)R⁹, or a heteroatom selected from N, —NH, —NR⁹', S or O;

the dotted lines in the ring represent single or double bonds;

each R⁹ is each independently halogen, cyano, hydroxyl, amino, alkylamino, dialkylamino, alkyl, haloalkyl, carbocyclyl, heterocyclyl, alkenyl, haloalkenyl, alkynyl or haloalkynyl;

each R⁹' is each independently alkyl, or alklylaryl;

p is 0, 1 or 2;

$X_6$ is —O—, —N(R¹)—, —N(R¹)CH$_2$—, or —CH$_2$N(R¹)—,

Ring B is cycloalkylene or heterocyclylene, which may be optionally substituted with one or more halogen, hydroxy, hydroxyalkyl, alkoxy, haloalkoxy, amino, alkylamino, dialkylamino or aminoalkyl group;

$X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—; and each R¹ is independently H, alkyl, or arylalkyl.

Another embodiment of the invention is an anthelmintic compound of Formula (IA), wherein:

Z is aryl, or heteroaryl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH, —CH$_2$, —CHR⁹, —C(R⁹)R⁹, or a heteroatom selected from N, —NH, —NR⁹', S or O;

the dotted lines in the ring represent single or double bonds;

each R⁹ is each independently halogen, cyano, hydroxyl, amino, alkylamino, dialkylamino, alkyl, haloalkyl, carbocyclyl, heterocyclyl, alkenyl, haloalkenyl, alkynyl or haloalkynyl;

each R⁹' is each independently alkyl, or alklylaryl;

p is 0, 1 or 2;

$X_6$ is —O—, —N(R¹)—, —N(R¹)CH$_2$—, or —CH$_2$N(R¹)—,

Ring B is cycloalkylene or heterocyclylene, which may be optionally substituted with one or more halogen, hydroxy, hydroxyalkyl, alkoxy, haloalkoxy, amino, alkylamino, dialkylamino or aminoalkyl group; and $X_8$ is a bond, —(CH$_2$)$_n$ where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—.

Another embodiment of the invention is an anthelmintic compound of Formula (IA) wherein:

Ring A is a diradical group selected from the group consisting of a 3-8 membered heterocyclylene group and a 3-8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH, —CH$_2$, —CHR⁹, —C(R⁹)R⁹, or a heteroatom selected from N, —NH, —NR⁹', S or O;

the dotted lines in the ring represent single or double bonds;

each R⁹ is each independently halogen, cyano, hydroxyl, amino, alkylamino, dialkylamino, alkyl, haloalkyl, carbocyclyl, heterocyclyl, alkenyl, haloalkenyl, alkynyl or haloalkynyl;

each R⁹' is each independently alkyl, or alklylaryl;

p is 0, 1 or 2;

Y is —H or aryl, cycloalkyl, cycloalkenyl, heteroaryl, heterocyclyl, alkyl, or haloalkyl, optionally substituted by one or more of halogen, alkyl, haloalkyl, alkoxy, haloalkoxy, alkylthio, halothio, haloalkylthio, alkylsulfinyl, haloalkylsulfinyl, alkylsulfonyl, or haloalkylsulfonyl; and $X_1$ is a bond, $C_2$-$C_4$ alkenylene, —O—, —C(O)—, —O—C(O)—, —C(O)—O—, —N(R¹)S(O)—, —S(O)—N(R¹)—, —N(R¹)—C(S)—, —C(S)—N(R¹)—, —N(R¹)SO$_2$—, —SO$_2$N(R¹)—, —N(R¹)—C(O)—, —C(O)—N(R¹)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, or —C(O)—(CH$_2$)$_n$—O— where n is 1 to 3.

Another embodiment of the invention is an anthelmintic compound of Formula (IA) wherein:

Z is aryl, or heteroaryl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH, —CH$_2$, —CHR$^9$, —C(R$^9$)R$^9$, or a heteroatom selected from N, —NH, —NR$^{9'}$, S or O;

the dotted lines in the ring represent single or double bonds;

each R$^9$ is each independently halogen, cyano, hydroxyl, amino, alkylamino, dialkylamino, alkyl, haloalkyl, carbocyclyl, heterocyclyl, alkenyl, haloalkenyl, alkynyl or haloalkynyl;

each R$^{9'}$ is each independently alkyl, or alklylaryl;

p is 0, 1 or 2;

$X_6$ is —O—, —N(R$^1$)—, —N(R$^1$)CH$_2$—, or —CH$_2$N(R$^1$)—,

Ring B is cycloalkylene or heterocyclylene, which may be optionally substituted with one or more halogen, hydroxy, hydroxyalkyl, alkoxy, haloalkoxy, amino, alkylamino, dialkylamino or aminoalkyl group; and $X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—.

Another embodiment of the invention is an anthelmintic compound of Formula (IA) wherein:

Ring A is a diradical group selected from the group consisting of a 6 membered heterocyclylene group and a 8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH, —CH$_2$, —CHR$^9$, —C(R$^9$)R$^9$, or a heteroatom selected from N, —NH, —NR$^{9'}$, S or O;

the dotted lines in the ring represent single or double bonds;

each R$^9$ is each independently halogen, cyano, hydroxyl, amino, alkylamino, dialkylamino, alkyl, haloalkyl, carbocyclyl, heterocyclyl, alkenyl, haloalkenyl, alkynyl or haloalkynyl;

each R$^{9'}$ is each independently alkyl, or alklylaryl;

p is 0, 1 or 2;

Y is —H or 5-6 membered aryl, 5-6 membered cycloalkyl, 5-6 membered cycloalkenyl, 5-6 membered heteroaryl, 5-6 membered heterocyclyl, $C_{1-4}$ alkyl, or $C_{1-4}$ haloalkyl, optionally substituted by one or more of halogen, alkyl, haloalkyl, alkoxy, haloalkoxy, alkylthio, halothio, haloalkylthio, alkylsulfinyl, haloalkylsulfinyl, alkylsulfonyl, or haloalkylsulfonyl; and $X_1$ is a bond, $C_2$-$C_4$ alkenylene, —O—, —C(O)—, —O—C(O)—, —C(O)—O—, —N(R$^1$)S(O)—, —S(O)—N(R$^1$)—, —N(R$^1$)—C(S)—, —C(S)—N(R$^1$)—, —N(R$^1$)SO$_2$—, —SO$_2$N(R$^1$)—, —N(R$^1$)—C(O)—, —C(O)—N(R$^1$)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, or —C(O)—(CH$_2$)$_n$—O— where n is 1 to 3.

Another embodiment of the invention is an anthelmintic compound of Formula (IA) wherein:

Z is a 6 membered aryl, or a 6 membered heteroaryl, optionally substituted by one or more of halogen, nitro, cyano, hydroxy, hydroxyalkyl, amino, alkylamino, dialkylamino, aminoalkyl, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Ring A is a diradical group selected from the group consisting of a 3-8 membered monocyclic carbocyclylene and a 3-8 membered heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH, —CH$_2$, —CHR$^9$, —C(R$^9$)R$^9$, or a heteroatom selected from N, —NH, —NR$^{9'}$, S or O;

the dotted lines in the ring represent single or double bonds;

each R$^9$ is each independently halogen, cyano, hydroxyl, amino, alkylamino, dialkylamino, alkyl, haloalkyl, carbocyclyl, heterocyclyl, alkenyl, haloalkenyl, alkynyl or haloalkynyl;

each R$^{9'}$ is each independently alkyl, or alklylaryl;

p is 0, 1 or 2;

$X_6$ is —O—, —N(R$^1$)—, —N(R$^1$)CH$_2$—, or —CH$_2$N(R$^1$)—,

Ring B is 4-6 membered monocyclic cycloalkylene, 4-6 membered monocyclic heterocyclylene, 7-9 membered spirocyclic cycloalkylene, 7-9 membered spirocyclic heterocyclylene which may be optionally substituted with one or more halogen, hydroxy, hydroxyalkyl, alkoxy, haloalkoxy, amino, alkylamino, dialkylamino or aminoalkyl group; and $X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—.

Another embodiment of the invention is an anthelmintic compound of Formula (IA) wherein:

Ring A is a diradical group selected from the group consisting of a 6 membered heterocyclylene group and a 8 membered spirocyclic heterocyclylene group, optionally substituted with one or more substituents independently selected from halogen, alkyl, haloalkyl, alkoxy, haloalkoxy, hydroxy, hydroxyalkyl, amino, alkylamino, dialkylamino, aminoalkyl, and oxo (=O);

$Q_9$, $Q_{10}$, $Q_{11}$, $Q_{12}$ and $Q_{13}$ are each independently —CH or N;

the dotted lines in the ring represent double bonds;

$X_6$ is —O—, —N(R$^1$)—, —N(R$^1$)CH$_2$—, or —CH$_2$N(R$^1$)—;

Ring B is 4-6 membered monocyclic cycloalkylene, 4-6 membered monocyclic heterocyclylene, 7-9 membered spirocyclic cycloalkylene, 7-9 membered spirocyclic heterocyclylene which may be optionally substituted with one or more halogen, hydroxy, hydroxyalkyl, alkoxy, haloalkoxy, amino, alkylamino, dialkylamino or aminoalkyl group;

$X_8$ is a bond, —(CH$_2$)$_n$— where n is 1 to 3, —(CH$_2$)$_n$—O— where n is 0 or 1, —O—(CH$_2$)$_n$— where n is 0 or 1, —N(H)—, —N(H)CH$_2$—, or —CH$_2$N(H)—;

Y is —H or 5-6 membered aryl, 5-6 membered cycloalkyl, 5-6 membered cycloalkenyl, 5-6 membered heteroaryl, 5-6 membered heterocyclyl, $C_1$-$C_4$ alkyl, or $C_1$-$C_4$ haloalkyl, optionally substituted by one or more of halogen, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

Z is a 6 membered aryl, or a 6 membered heteroaryl, substituted by one or more of halogen, nitro, cyano, hydroxy, alkyl, halothio, haloalkylthio, alkylsulfinyl, haloalkylsulfinyl, alkylsulfonyl, or haloalkylsulfonyl;

$X_1$ is a bond, $C_2$-$C_4$ alkenylene, —O—, —C(O)—, —O—C(O)—, —C(O)—O—, —N($R^1$)S(O)—, —S(O)—N($R^1$)—, —N($R^1$)—C(S)—, —C(S)—N($R^1$)—, —N($R^1$)SO$_2$—, —SO$_2$N($R^1$)—, —N($R^1$)—C(O)—, —C(O)—N($R^1$)—, —(CH$_2$)$_n$— where n is 1 to 3, —C(O)—(CH$_2$)$_n$— where n is 1 to 3, —(CH$_2$)$_n$—C(O)— where n is 1 to 3, —O—(CH$_2$)$_n$—C(O)— where n is 1 to 3, or —C(O)—(CH$_2$)$_n$—O— where n is 1 to 3; and each $R^1$ is independently H, or $C_1$-$C_3$ alkyl.

Another embodiment of the invention is an anthelmintic compound of Formula (IA) wherein

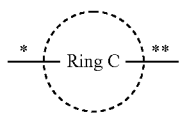

is optionally substituted and selected from the group consisting of

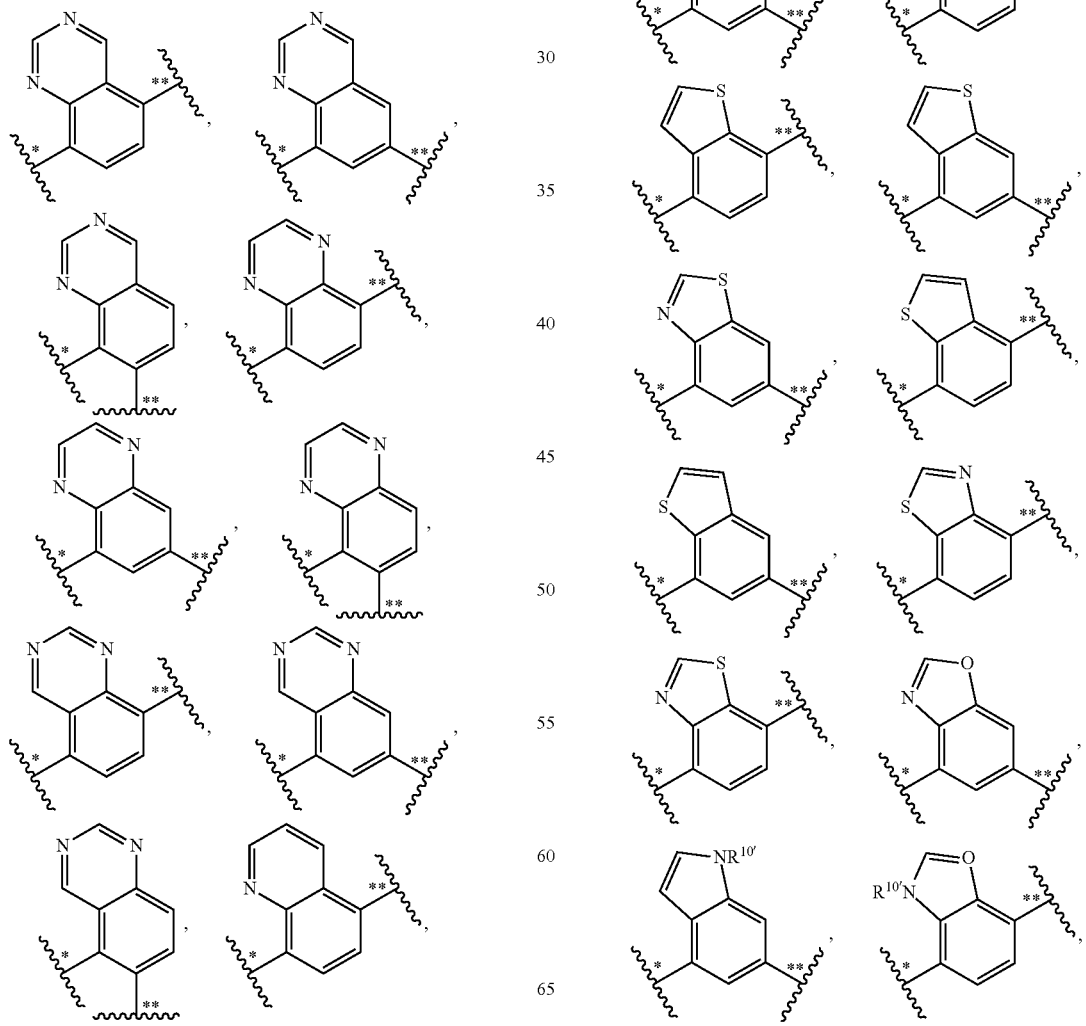

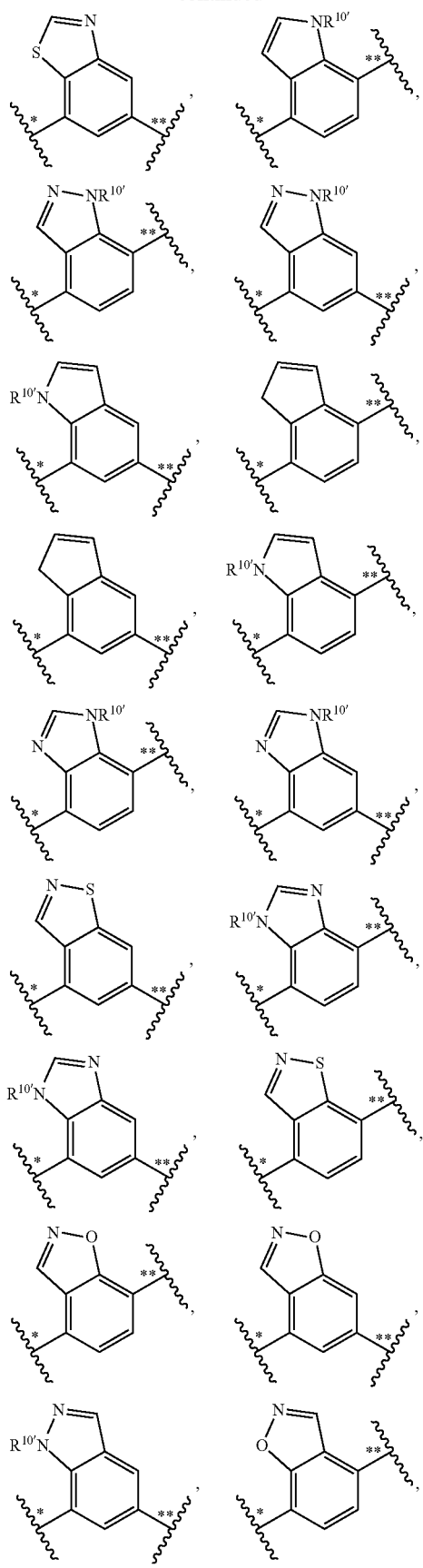
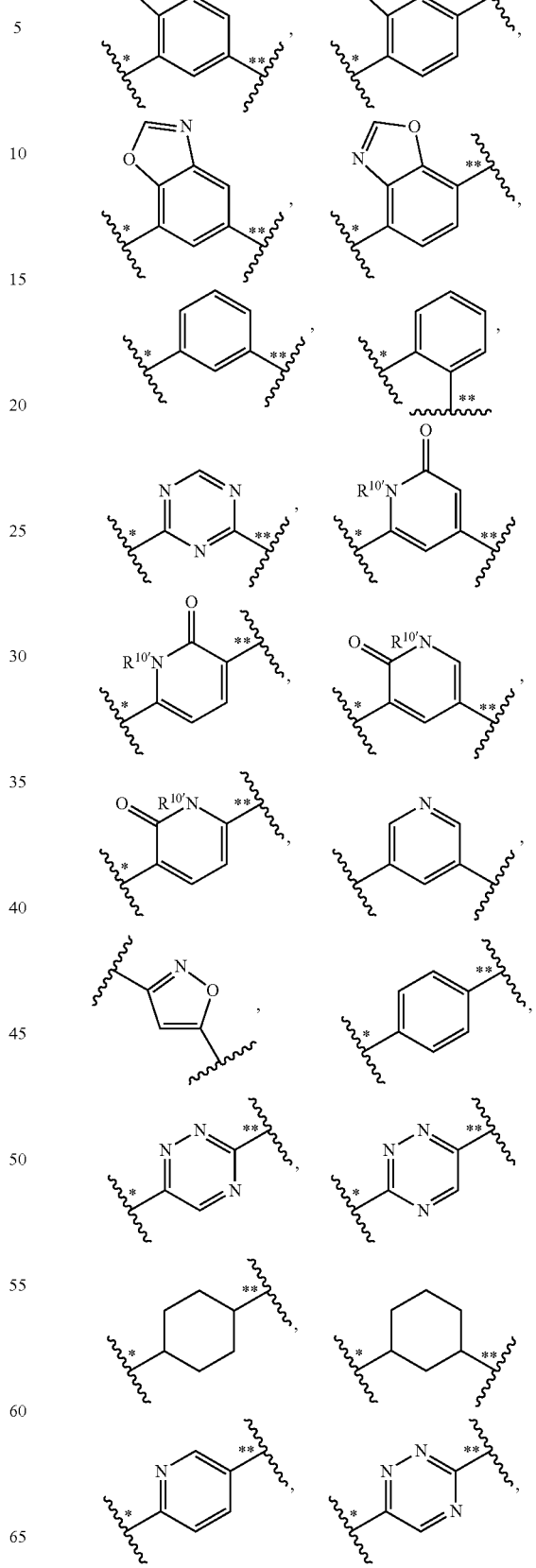

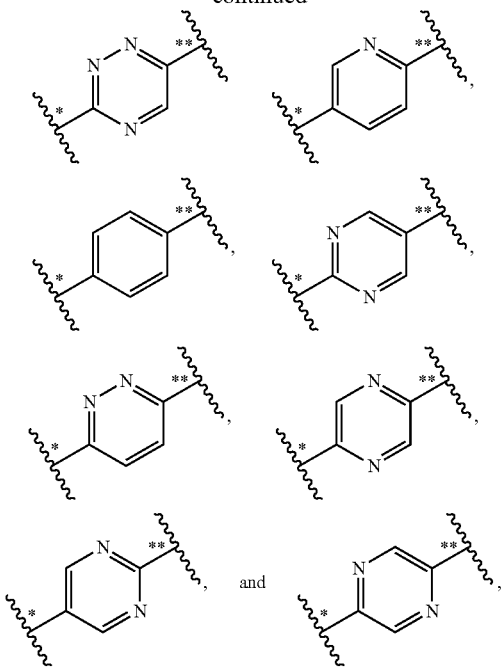

wherein the optional substituents are selected from the group consisting of halogen, cyano, hydroxyl, amino, alkylamino, dialkylamino, alkyl, haloalkyl, carbocyclyl, heterocyclyl, alkenyl, haloalkenyl, alkynyl and haloalkynyl; and R$^{10'}$ is alkyl or hydrogen.

Another embodiment of the invention is an anthelmintic compound of Formula (IA) wherein

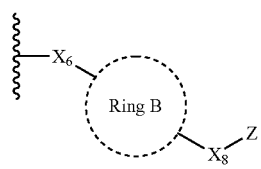

is selected from the group consisting of

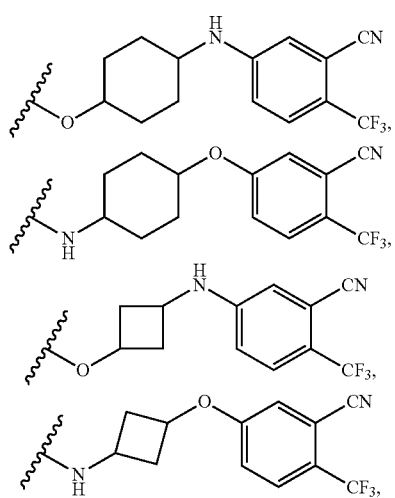

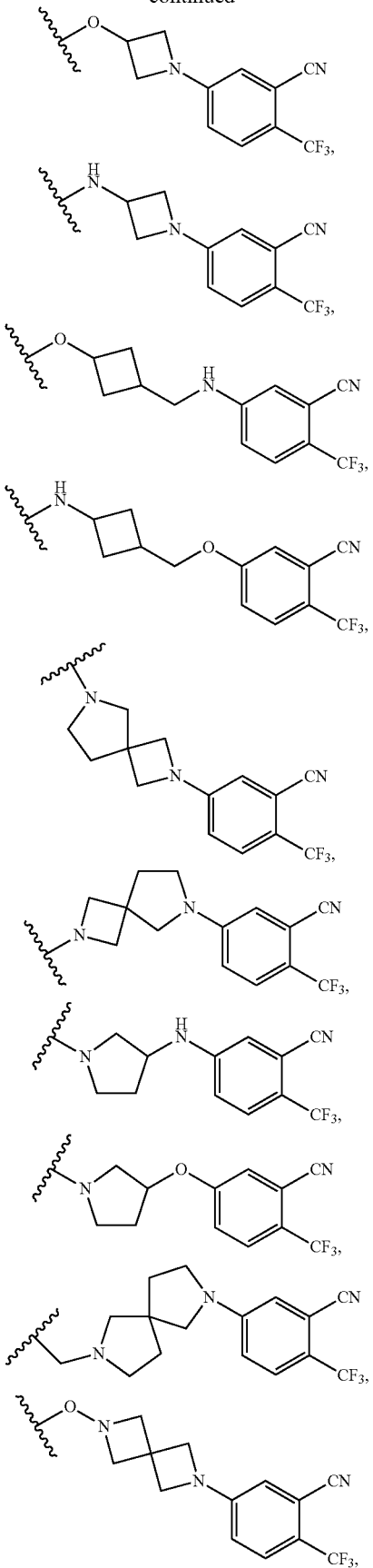

-continued
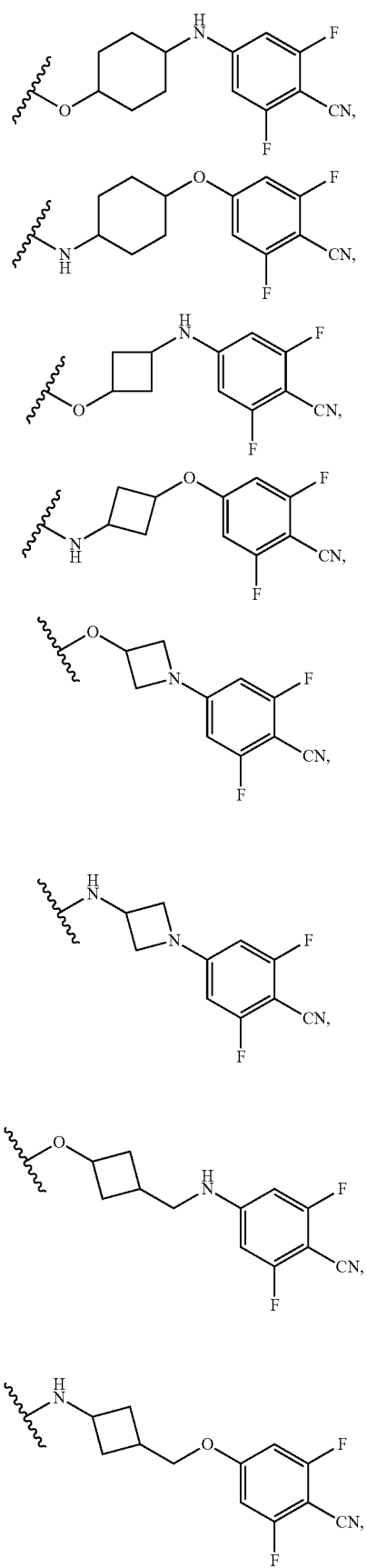
-continued
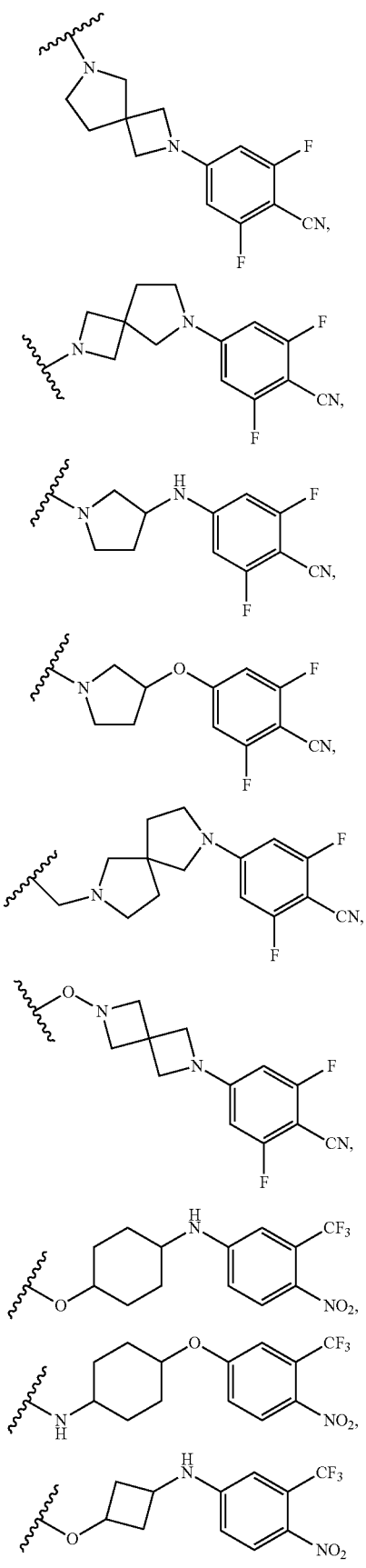

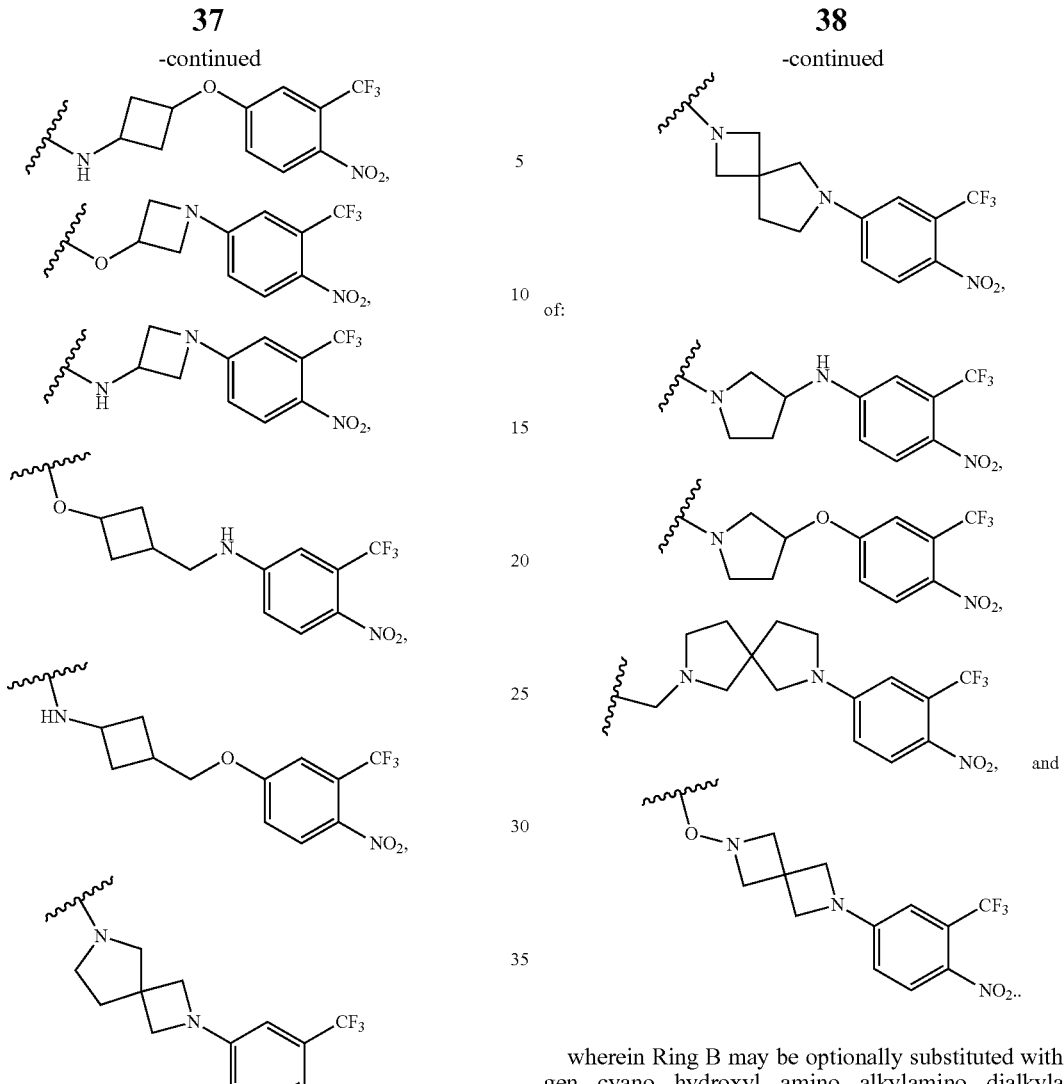
of:
wherein Ring B may be optionally substituted with halogen, cyano, hydroxyl, amino, alkylamino, dialkylamino, alkyl, haloalkyl, carbocyclyl, heterocyclyl, alkenyl, haloalkenyl, alkynyl and haloalkynyl.
Another embodiment of the invention is an anthelmintic compound of Formula (IA) as shown in the following table:
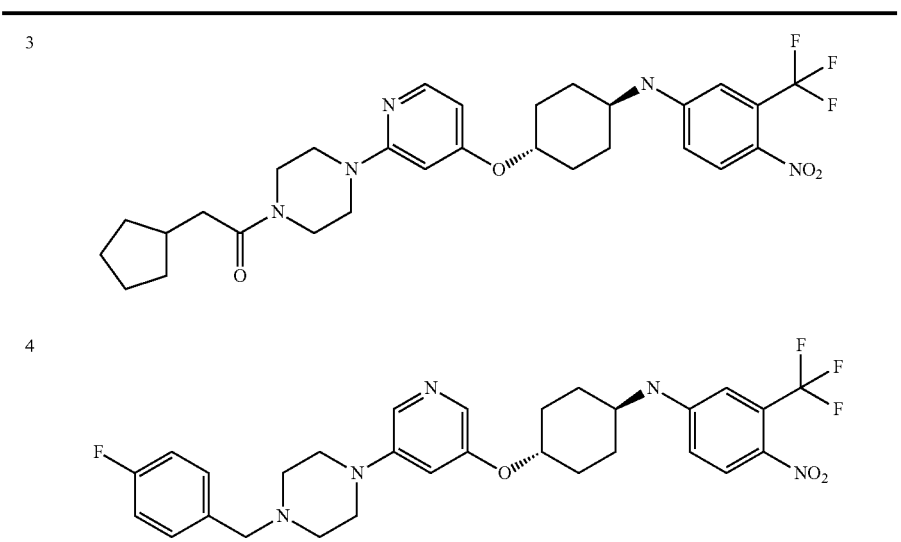

5
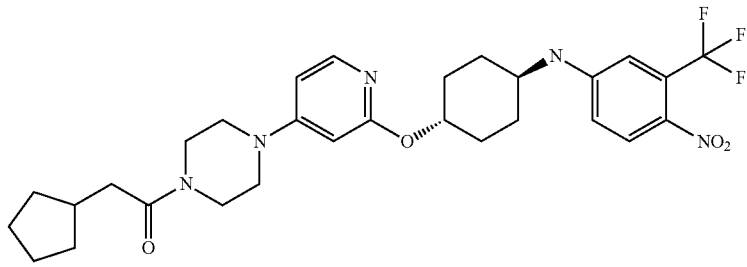
6
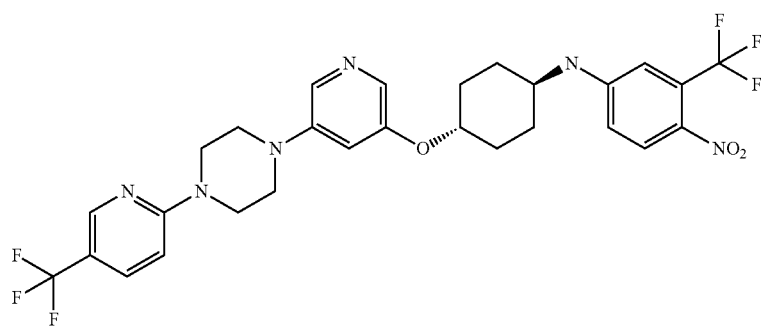 [SMILES: O=[N+]([O-])c1ccc(N[C@H]2CC[C@H](Oc3cncc(N4CCN(c5ccc(C(F)(F)F)cn5)CC4)c3)CC2)cc1C(F)(F)F]
7
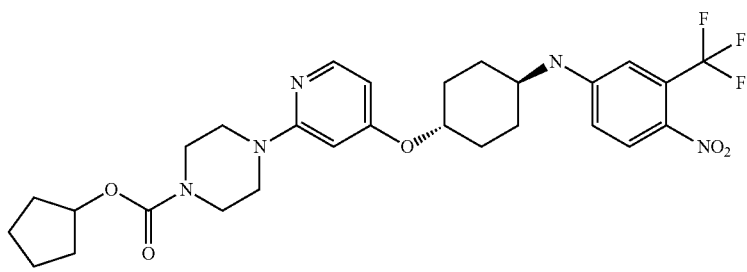
8
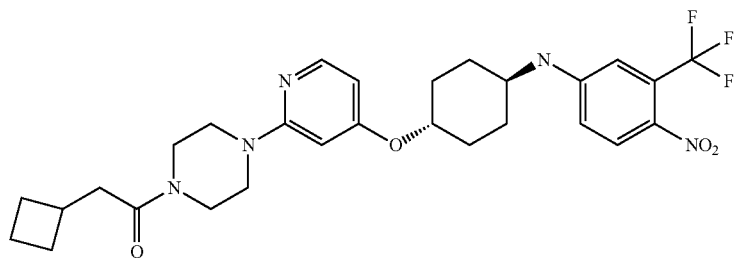 [SMILES: O=C(CC1CCC1)N1CCN(c2cc(O[C@H]3CC[C@H](Nc4ccc([N+](=O)[O-])c(C(F)(F)F)c4)CC3)ccn2)CC1]
9
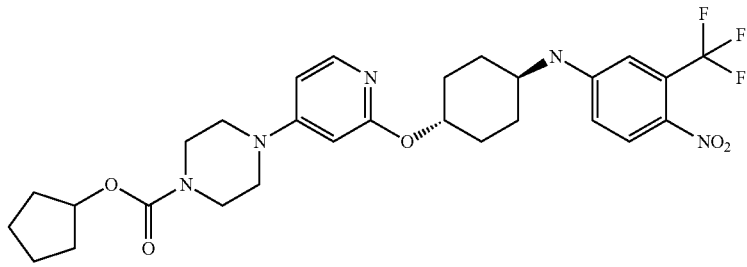

10
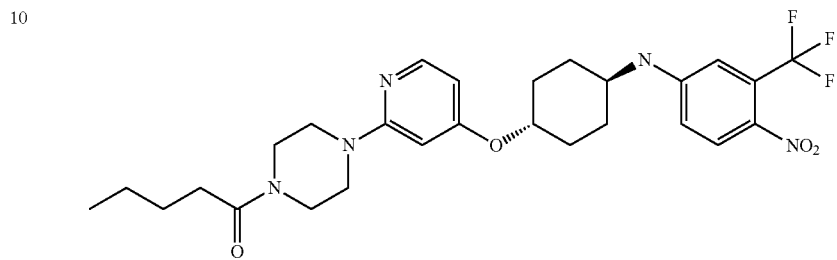
11
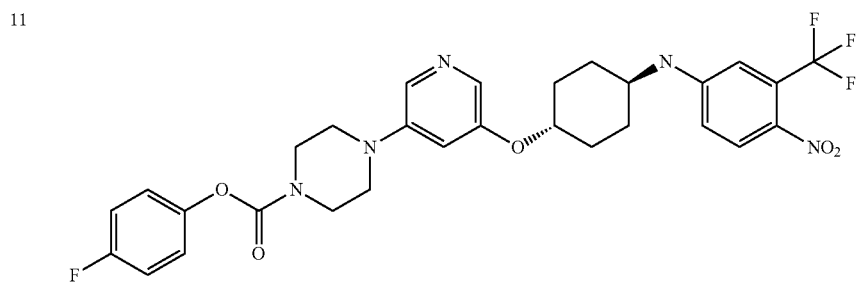
13
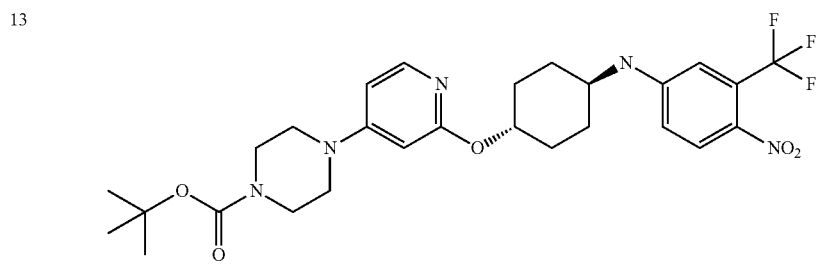
14
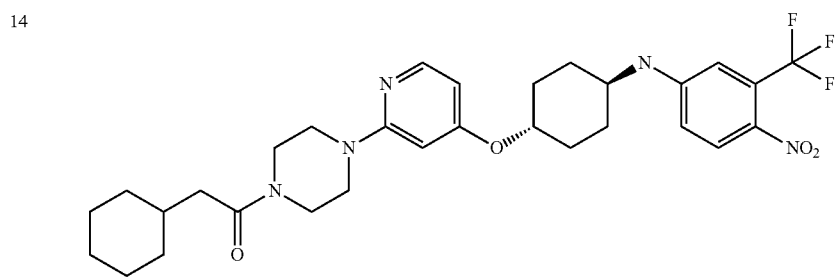
15
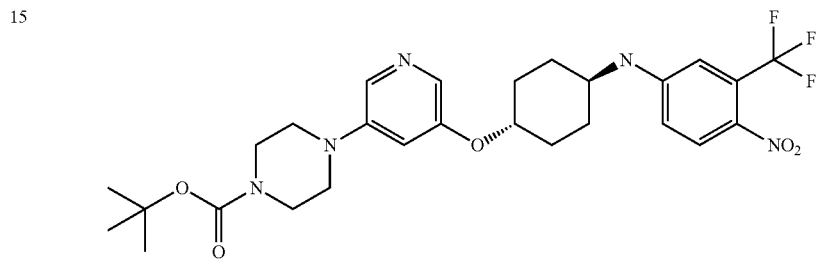
16
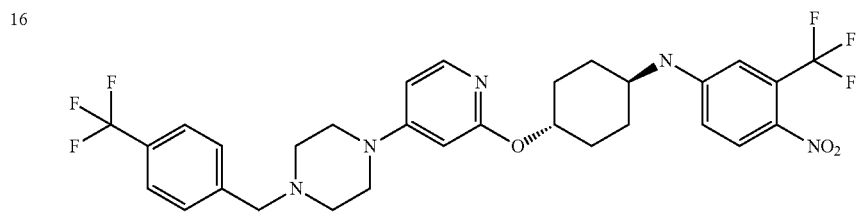

-continued
17 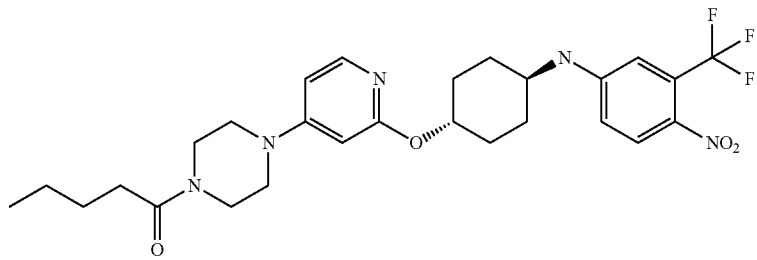
18 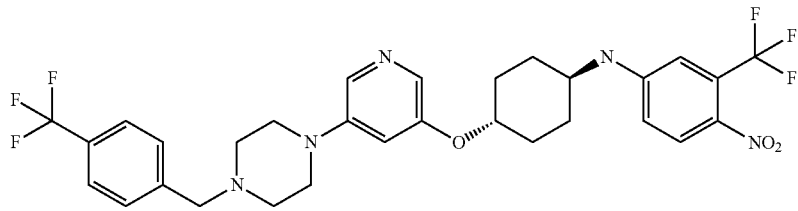 [SMILES: O=[N+]([O-])c1ccc(N[C@H]2CC[C@H](Oc3cncc(N4CCN(Cc5ccc(C(F)(F)F)cc5)CC4)c3)CC2)cc1C(F)(F)F]
19 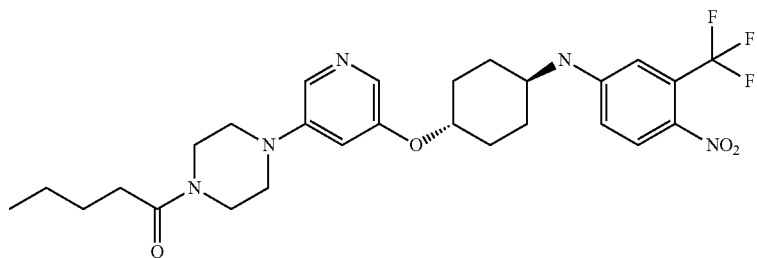
20 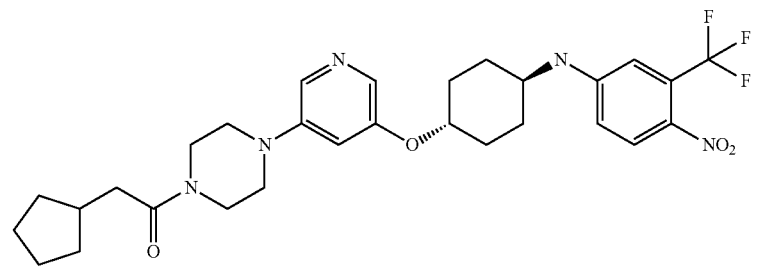
21 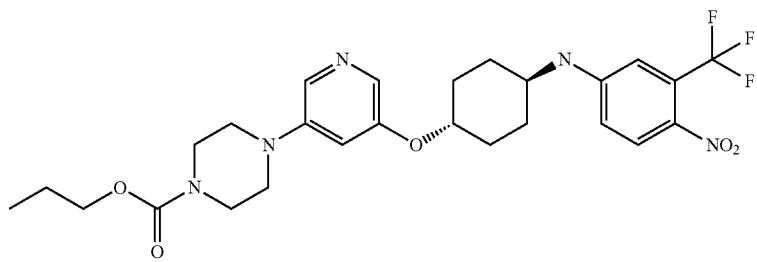 [SMILES: CCCOC(=O)N1CCN(c2cncc(O[C@H]3CC[C@H](Nc4ccc([N+](=O)[O-])c(C(F)(F)F)c4)CC3)c2)CC1]
22 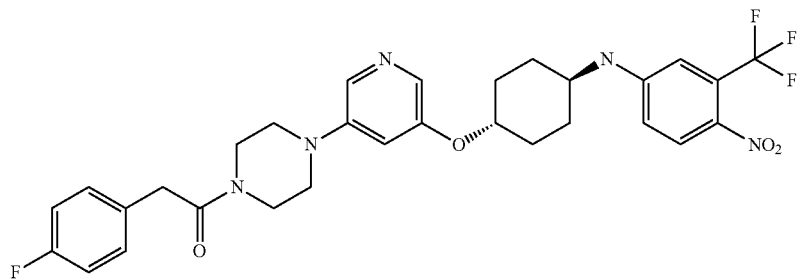

-continued
23
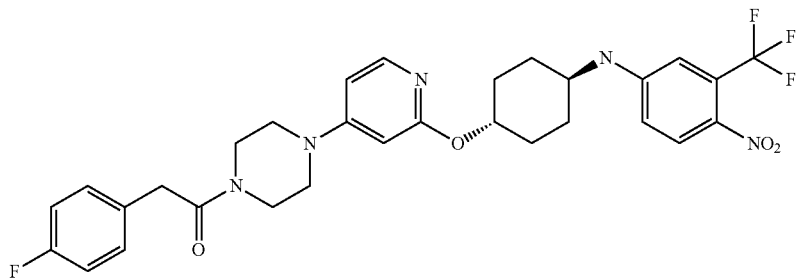
24
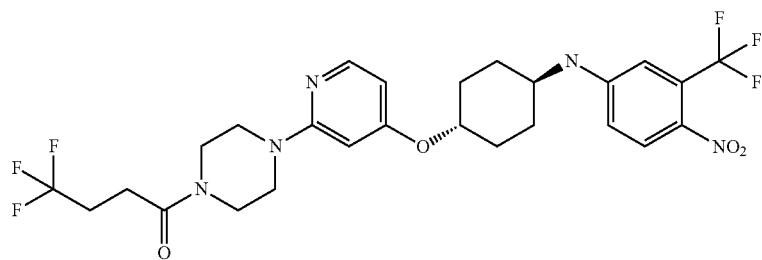 [SMILES: O=C(CCC(F)(F)F)N1CCN(c2cc(O[C@H]3CC[C@H](Nc4ccc([N+](=O)[O-])c(C(F)(F)F)c4)CC3)ccn2)CC1]
25
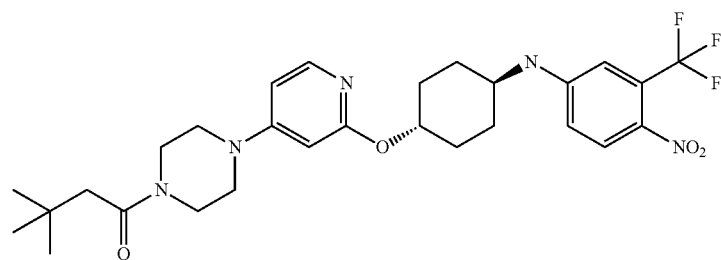 [SMILES: CC(C)(C)CC(=O)N1CCN(c2ccnc(O[C@H]3CC[C@H](Nc4ccc([N+](=O)[O-])c(C(F)(F)F)c4)CC3)c2)CC1]
26
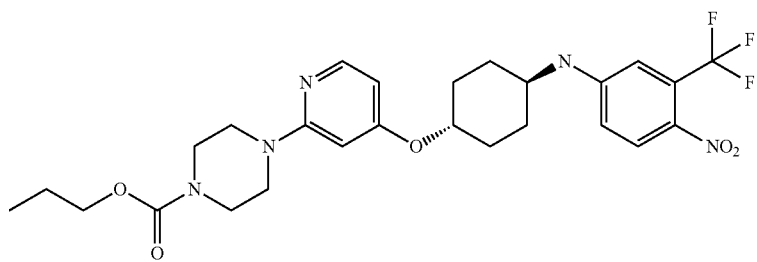 [SMILES: CCCOC(=O)N1CCN(c2cc(O[C@H]3CC[C@H](Nc4ccc([N+](=O)[O-])c(C(F)(F)F)c4)CC3)ccn2)CC1]
27
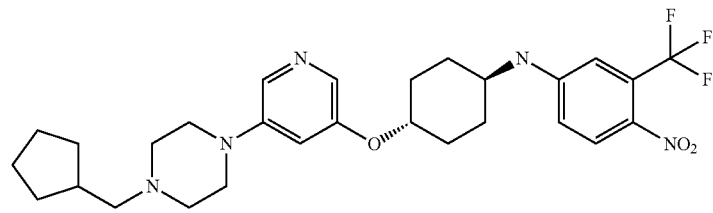 [SMILES: O=[N+]([O-])c1ccc(N[C@H]2CC[C@H](Oc3cncc(N4CCN(CC5CCCC5)CC4)c3)CC2)cc1C(F)(F)F]
28
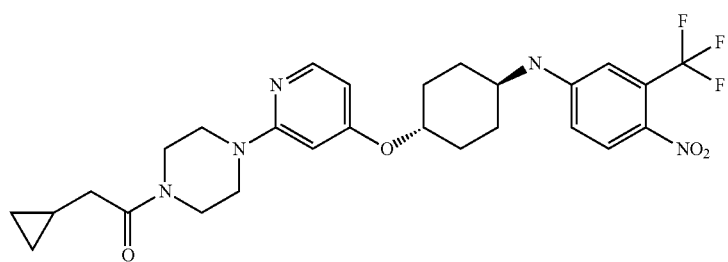 [SMILES: O=C(CC1CC1)N1CCN(c2cc(O[C@H]3CC[C@H](Nc4ccc([N+](=O)[O-])c(C(F)(F)F)c4)CC3)ccn2)CC1]

-continued
29
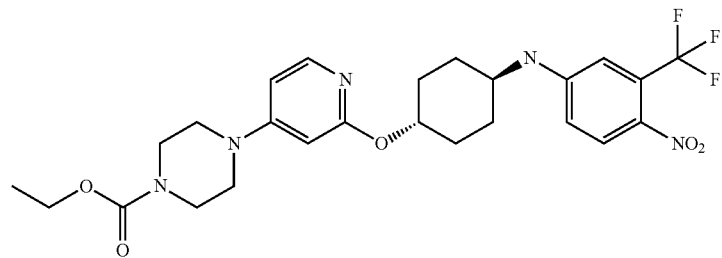
30
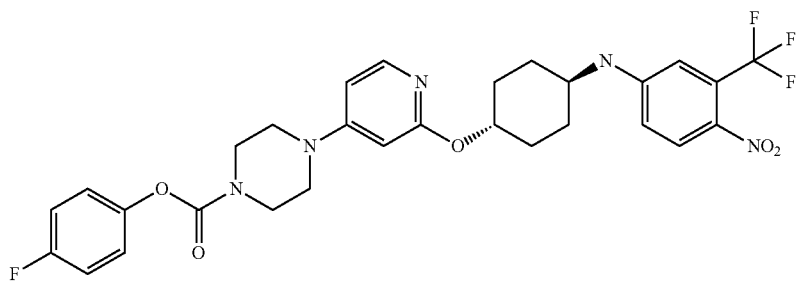
31
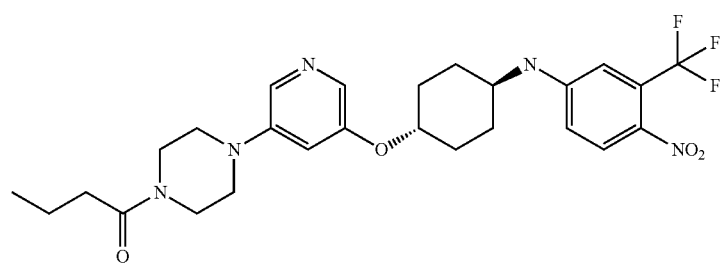
32
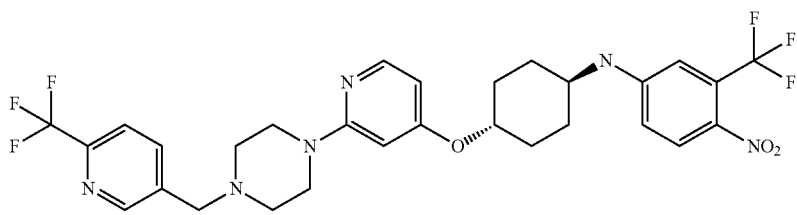 [SMILES: O=[N+]([O-])c1ccc(N[C@H]2CC[C@H](Oc3ccnc(N4CCN(Cc5ccc(C(F)(F)F)nc5)CC4)c3)CC2)cc1C(F)(F)F]
33
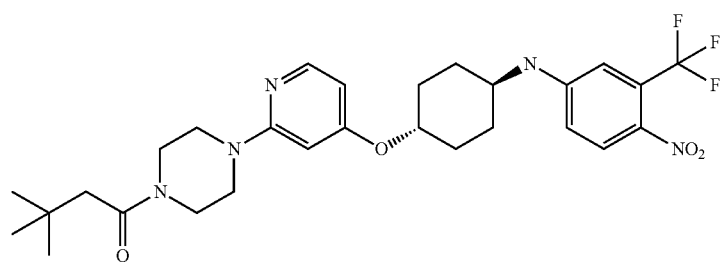
34
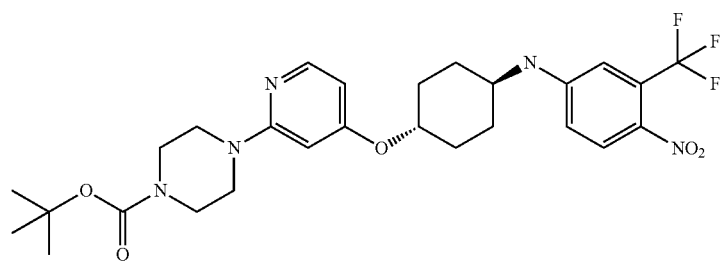 [SMILES: CC(C)(C)OC(=O)N1CCN(c2cc(O[C@H]3CC[C@H](Nc4ccc([N+](=O)[O-])c(C(F)(F)F)c4)CC3)ccn2)CC1]

| | |
|---|---|
| 35 | 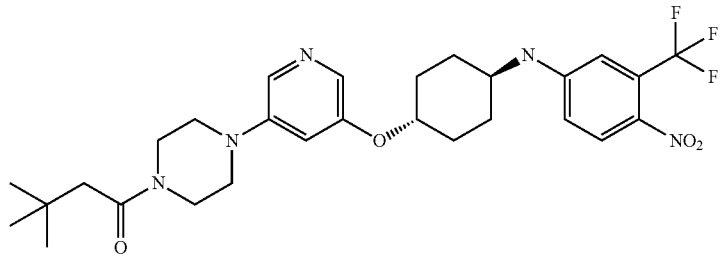 |
| 36 | 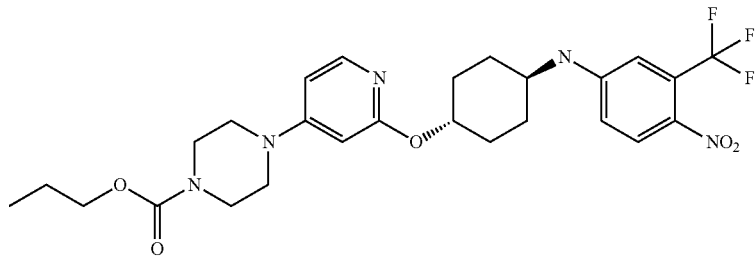 [SMILES: CCCOC(=O)N1CCN(c2ccnc(O[C@H]3CC[C@H](Nc4ccc([N+](=O)[O-])c(C(F)(F)F)c4)CC3)c2)CC1] |
| 37 | 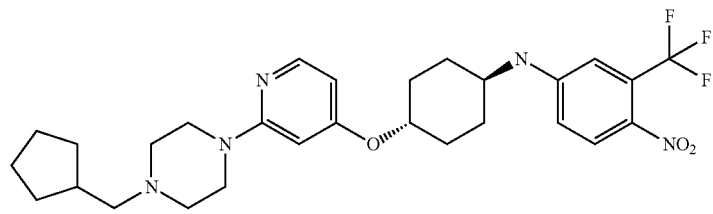 [SMILES: O=[N+]([O-])c1ccc(N[C@H]2CC[C@H](Oc3ccnc(N4CCN(CC5CCCC5)CC4)c3)CC2)cc1C(F)(F)F] |
| 38 | 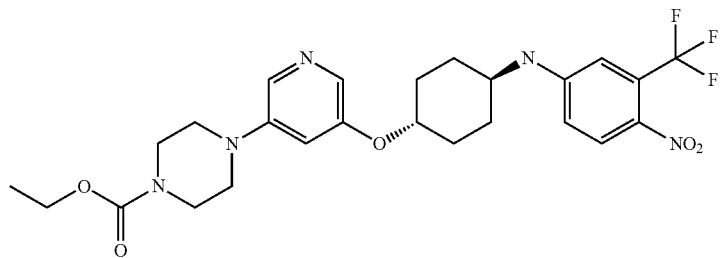 [SMILES: CCOC(=O)N1CCN(c2cncc(O[C@H]3CC[C@H](Nc4ccc([N+](=O)[O-])c(C(F)(F)F)c4)CC3)c2)CC1] |
| 39 | 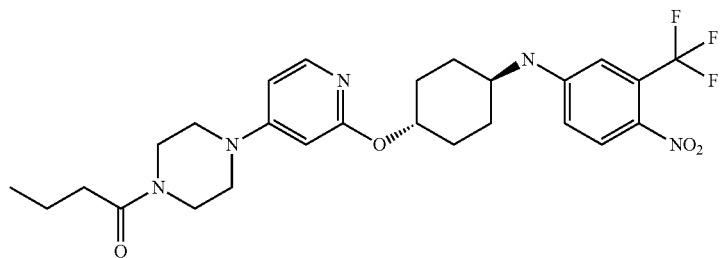 [SMILES: CCCC(=O)N1CCN(c2ccnc(O[C@H]3CC[C@H](Nc4ccc([N+](=O)[O-])c(C(F)(F)F)c4)CC3)c2)CC1] |
| 40 | 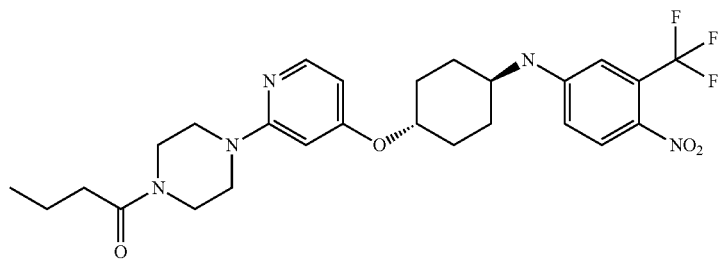 [SMILES: CCCC(=O)N1CCN(c2cc(O[C@H]3CC[C@H](Nc4ccc([N+](=O)[O-])c(C(F)(F)F)c4)CC3)ccn2)CC1] |

41
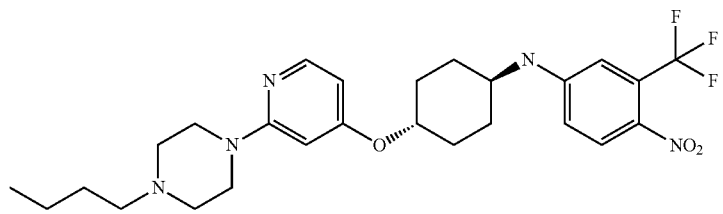 [SMILES: CCCCN1CCN(c2cc(O[C@H]3CC[C@H](Nc4ccc([N+](=O)[O-])c(C(F)(F)F)c4)CC3)ccn2)CC1]
42
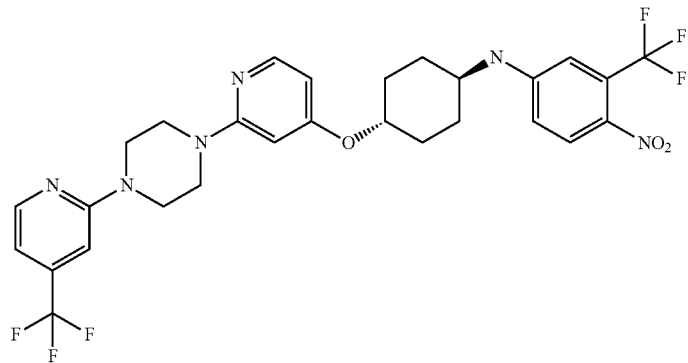 [SMILES: O=[N+]([O-])c1ccc(N[C@H]2CC[C@H](Oc3ccnc(N4CCN(c5cc(C(F)(F)F)ccn5)CC4)c3)CC2)cc1C(F)(F)F]
43
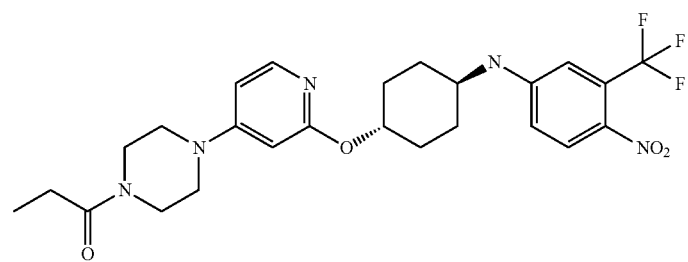 [SMILES: CCC(=O)N1CCN(c2ccnc(O[C@H]3CC[C@H](Nc4ccc([N+](=O)[O-])c(C(F)(F)F)c4)CC3)c2)CC1]
44
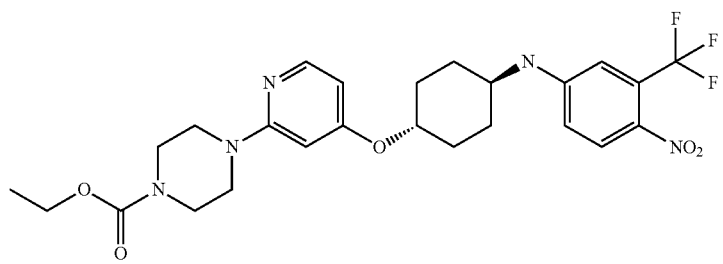
45
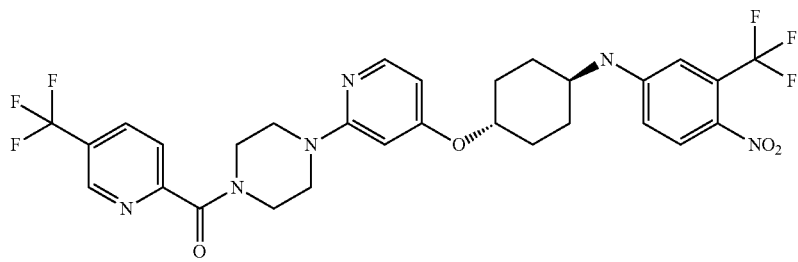 [SMILES: O=C(c1ccc(C(F)(F)F)cn1)N1CCN(c2cc(O[C@H]3CC[C@H](Nc4ccc([N+](=O)[O-])c(C(F)(F)F)c4)CC3)ccn2)CC1]

46 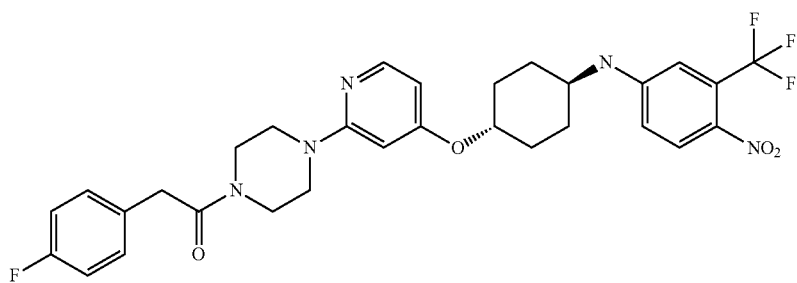 [SMILES: O=C(Cc1ccc(F)cc1)N1CCN(c2cc(O[C@H]3CC[C@H](Nc4ccc([N+](=O)[O-])c(C(F)(F)F)c4)CC3)ccn2)CC1]
47 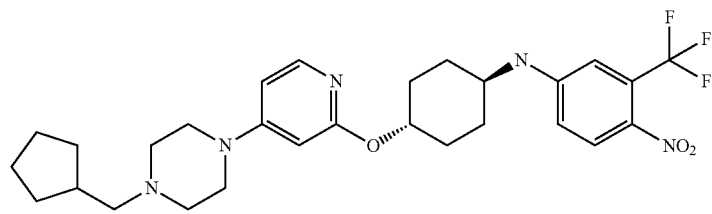
48 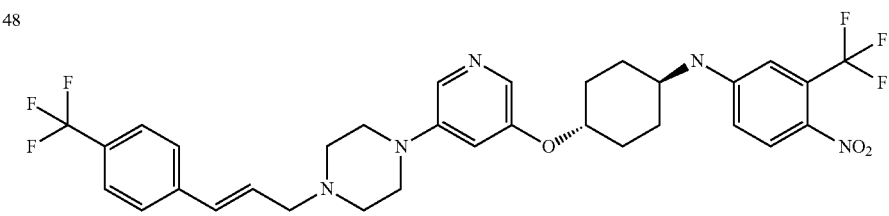
49 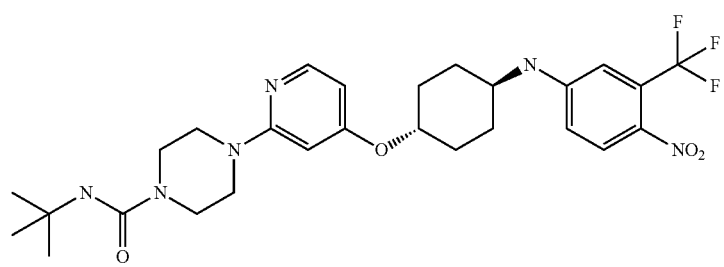
50 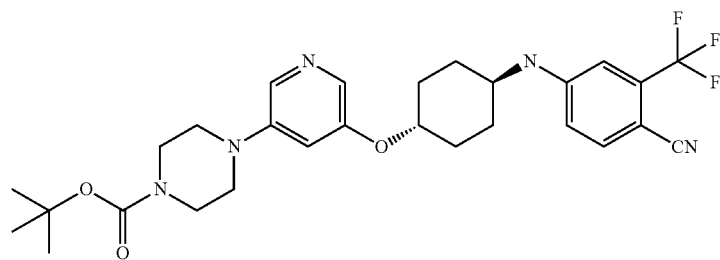
51 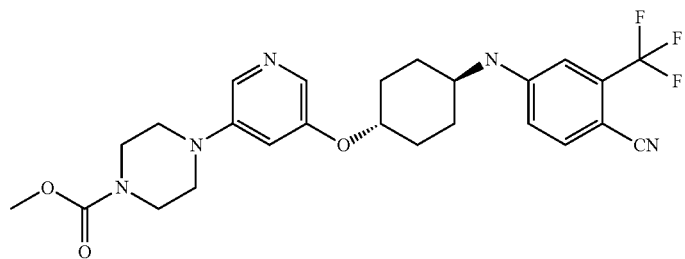 [SMILES: COC(=O)N1CCN(c2cncc(O[C@H]3CC[C@H](Nc4ccc(C#N)c(C(F)(F)F)c4)CC3)c2)CC1]

52 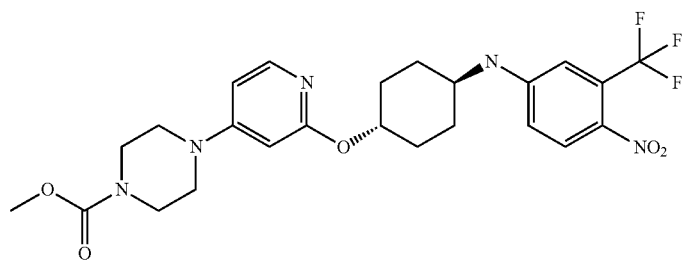
53 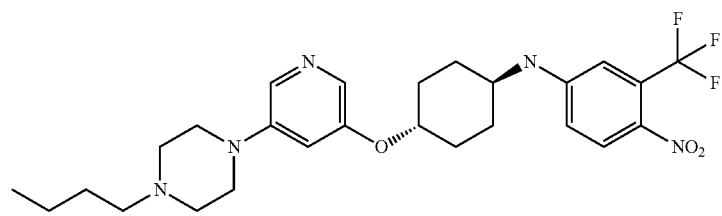
54 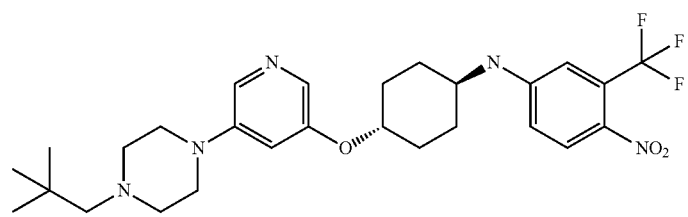 [SMILES: CC(C)(C)CN1CCN(c2cncc(O[C@H]3CC[C@H](Nc4ccc([N+](=O)[O-])c(C(F)(F)F)c4)CC3)c2)CC1]
55 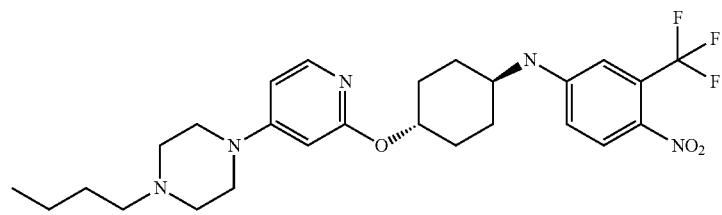 [SMILES: CCCCN1CCN(c2ccnc(O[C@H]3CC[C@H](Nc4ccc([N+](=O)[O-])c(C(F)(F)F)c4)CC3)c2)CC1]
56 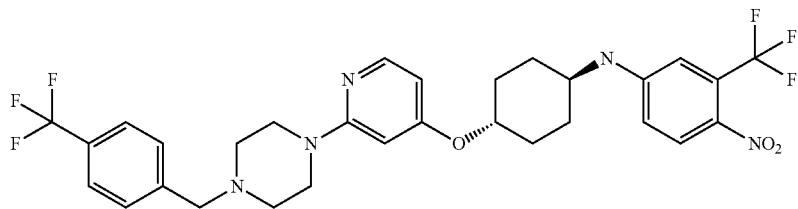
57 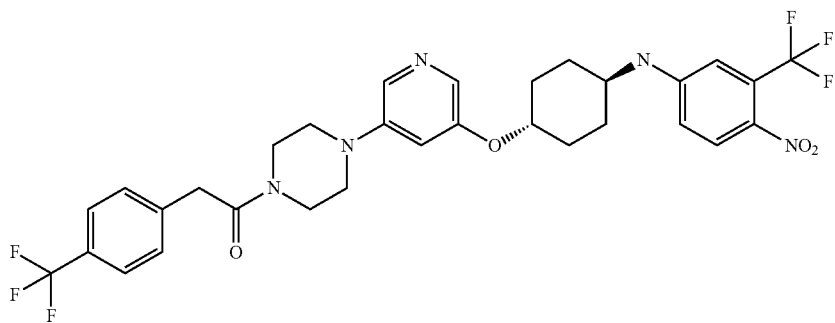 [SMILES: O=C(Cc1ccc(C(F)(F)F)cc1)N1CCN(c2cncc(O[C@H]3CC[C@H](Nc4ccc([N+](=O)[O-])c(C(F)(F)F)c4)CC3)c2)CC1]

-continued
58 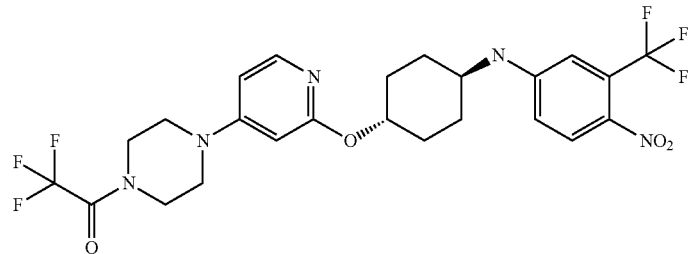 [SMILES: O=C(N1CCN(c2ccnc(O[C@H]3CC[C@H](Nc4ccc([N+](=O)[O-])c(C(F)(F)F)c4)CC3)c2)CC1)C(F)(F)F]
59 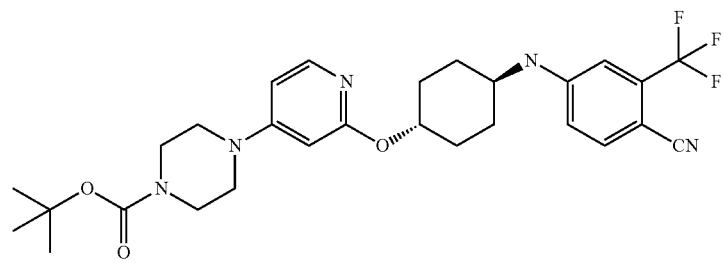 [SMILES: CC(C)(C)OC(=O)N1CCN(c2ccnc(O[C@H]3CC[C@H](Nc4ccc(C#N)c(C(F)(F)F)c4)CC3)c2)CC1]
60 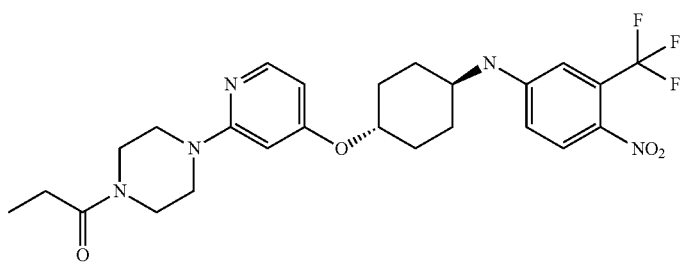
61 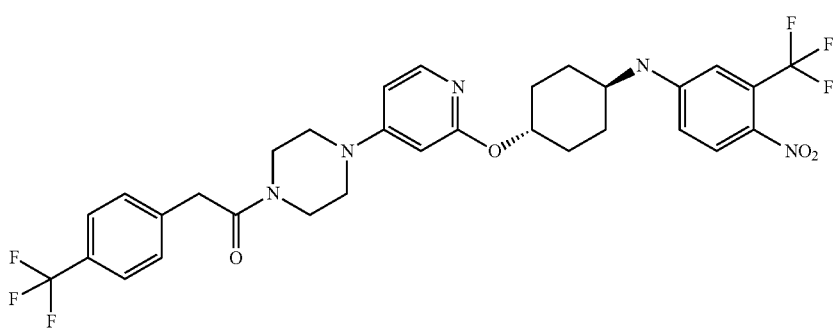
62 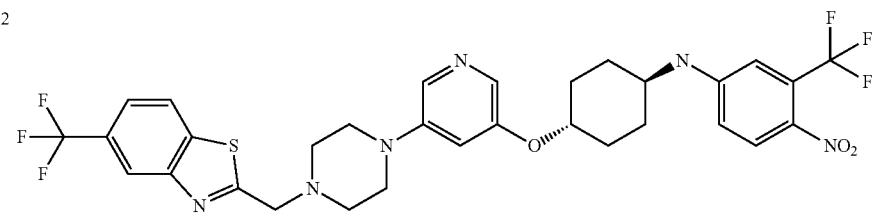
63 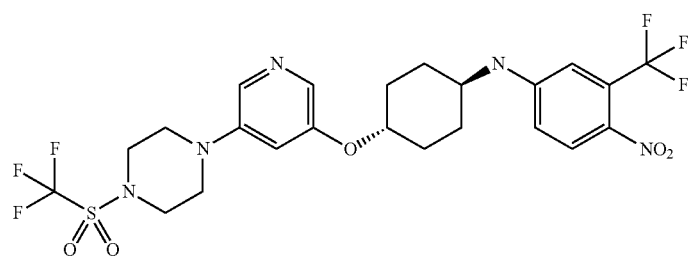 [SMILES: O=[N+]([O-])c1ccc(N[C@H]2CC[C@H](Oc3cncc(N4CCN(S(=O)(=O)C(F)(F)F)CC4)c3)CC2)cc1C(F)(F)F]

-continued
64
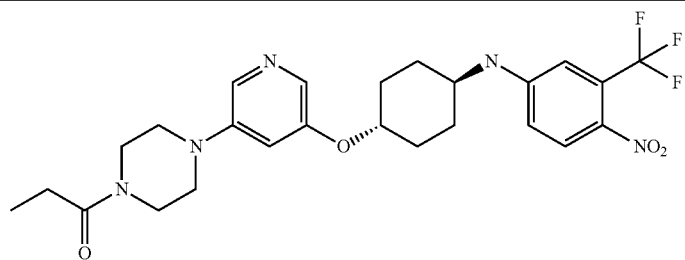
65
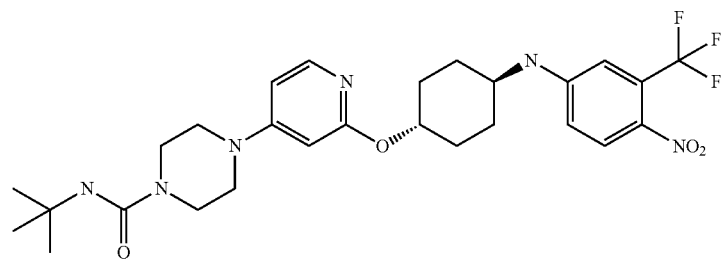
66
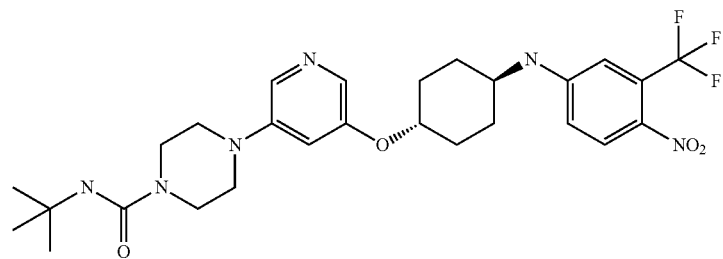
67
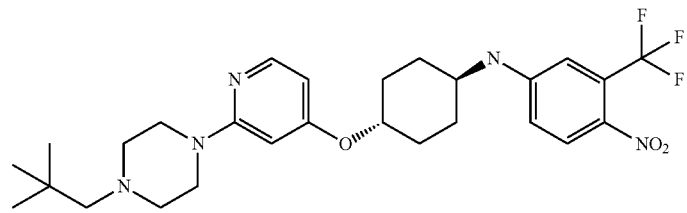 [SMILES: CC(C)(C)CN1CCN(c2cc(O[C@H]3CC[C@H](Nc4ccc([N+](=O)[O-])c(C(F)(F)F)c4)CC3)ccn2)CC1]
68
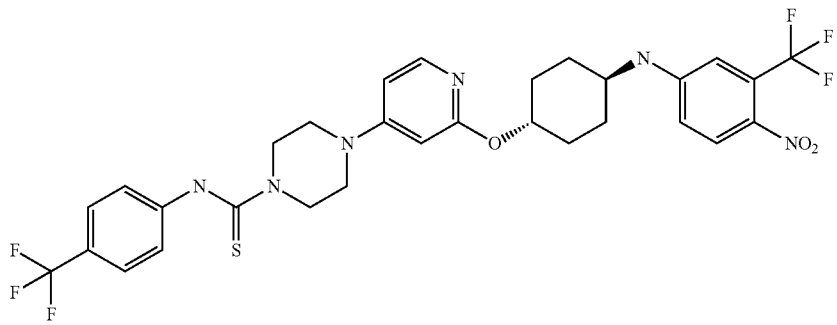
69
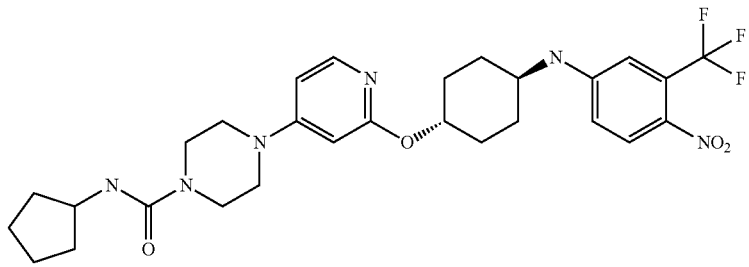

-continued
70
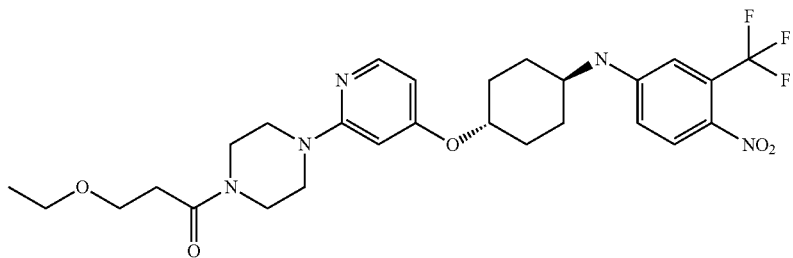 [SMILES: CCOCCC(=O)N1CCN(c2cc(O[C@H]3CC[C@H](Nc4ccc([N+](=O)[O-])c(C(F)(F)F)c4)CC3)ccn2)CC1]
71
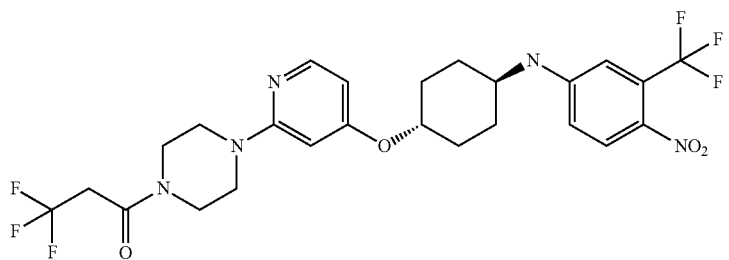 [SMILES: O=C(CC(F)(F)F)N1CCN(c2cc(O[C@H]3CC[C@H](Nc4ccc([N+](=O)[O-])c(C(F)(F)F)c4)CC3)ccn2)CC1]
72
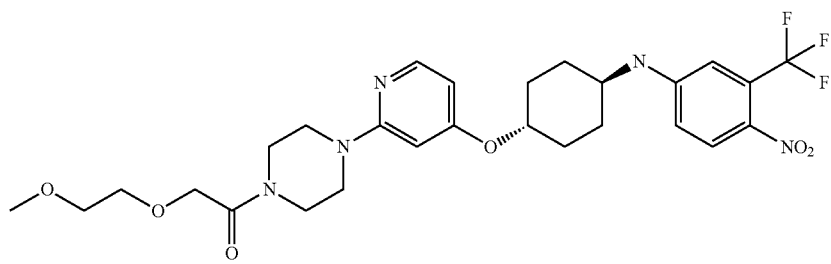 [SMILES: COCCOCC(=O)N1CCN(c2cc(O[C@H]3CC[C@H](Nc4ccc([N+](=O)[O-])c(C(F)(F)F)c4)CC3)ccn2)CC1]
73
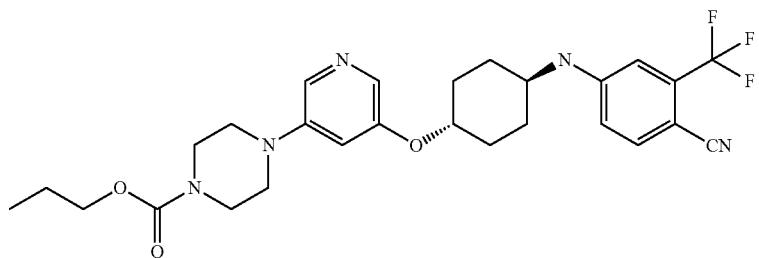
74
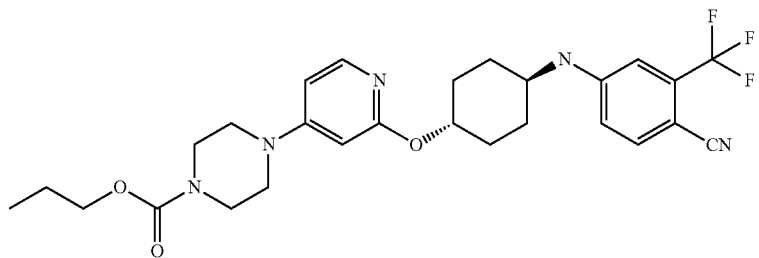 [SMILES: CCCOC(=O)N1CCN(c2ccnc(O[C@H]3CC[C@H](Nc4ccc(C#N)c(C(F)(F)F)c4)CC3)c2)CC1]
75
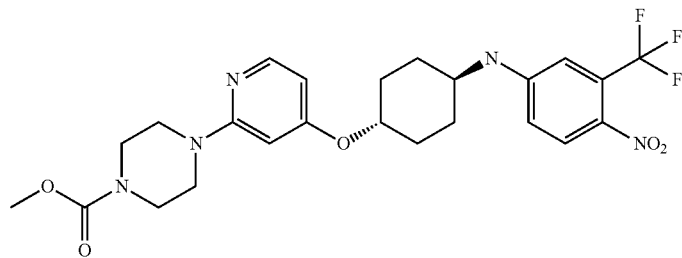 [SMILES: COC(=O)N1CCN(c2cc(O[C@H]3CC[C@H](Nc4ccc([N+](=O)[O-])c(C(F)(F)F)c4)CC3)ccn2)CC1]

-continued
| | |
|---|---|
| 76 | 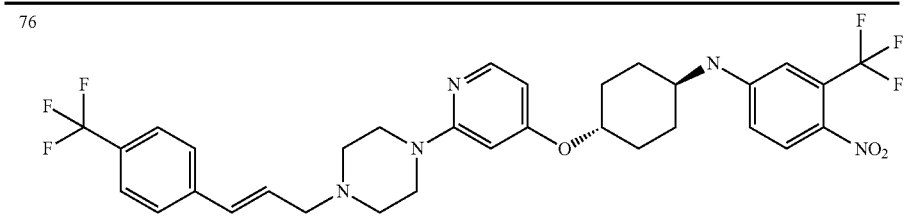 |
| 77 | 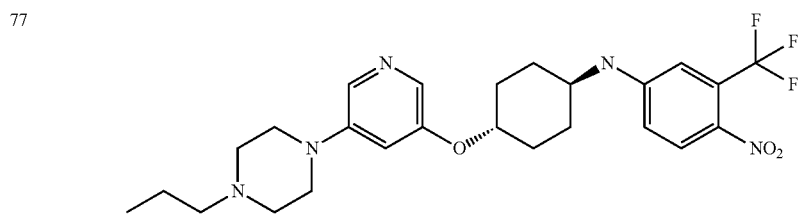 |
| 78 | 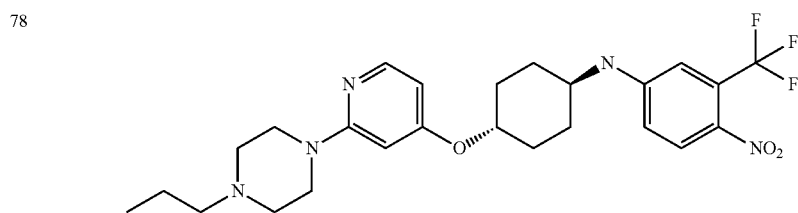 |
| 79 | 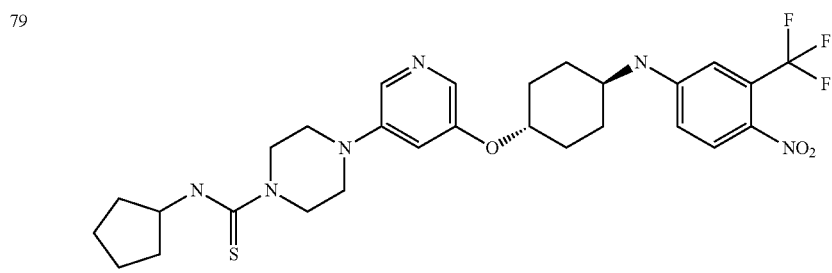 |
| 80 | 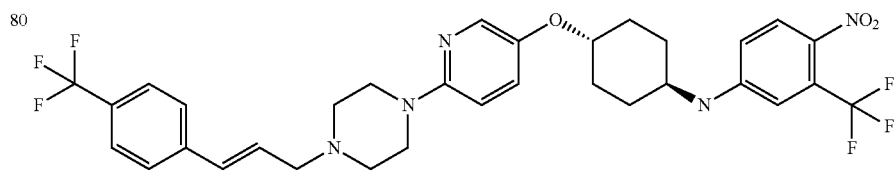 |
| 81 | 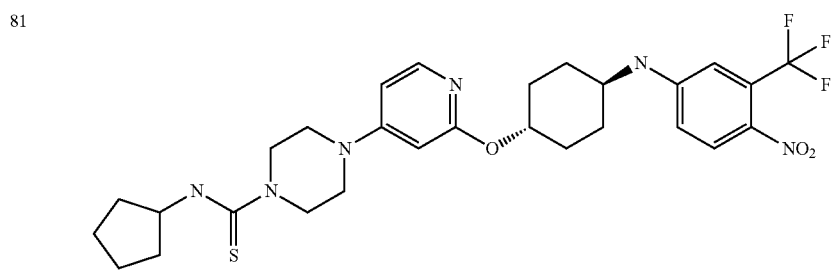 |
| 82 | 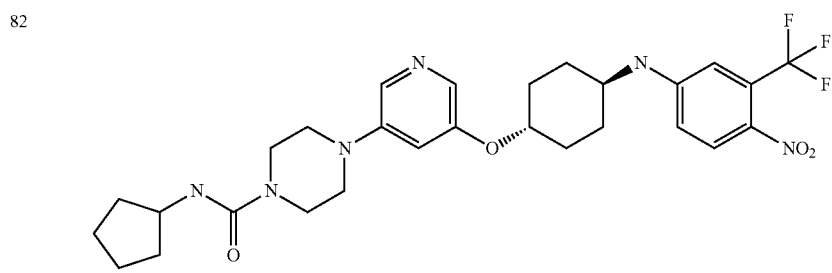 |

83 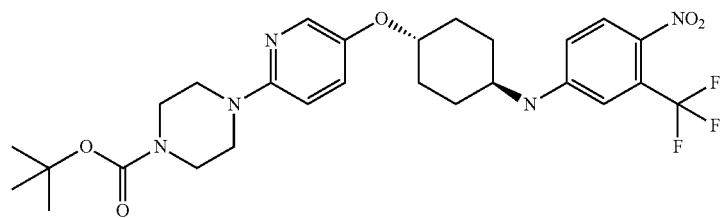 [SMILES: CC(C)(C)OC(=O)N1CCN(c2ccc(O[C@H]3CC[C@H](Nc4ccc([N+](=O)[O-])c(C(F)(F)F)c4)CC3)cn2)CC1]
84 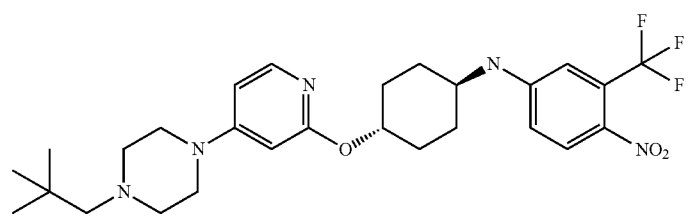 [SMILES: CC(C)(C)CN1CCN(c2ccnc(O[C@H]3CC[C@H](Nc4ccc([N+](=O)[O-])c(C(F)(F)F)c4)CC3)c2)CC1]
85 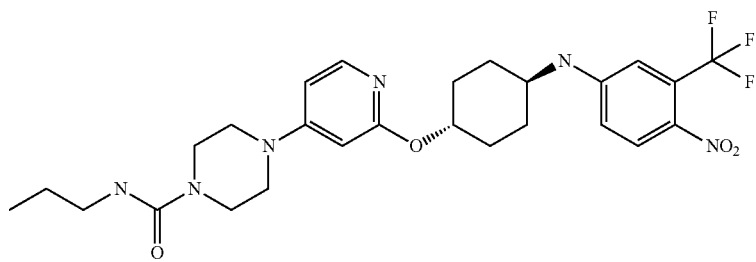
86 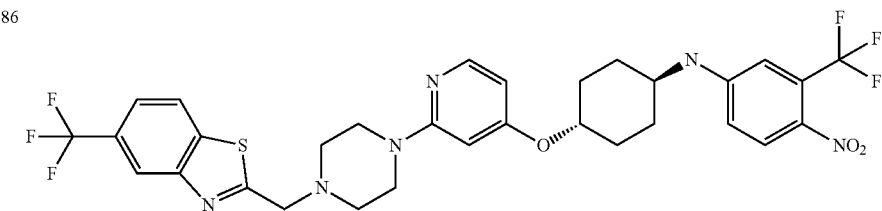
87 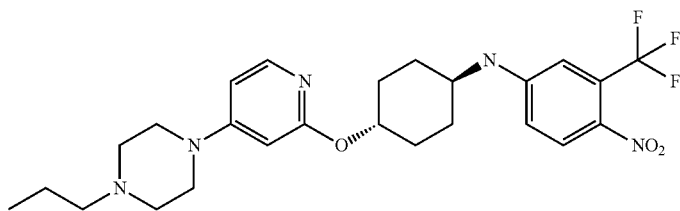 [SMILES: CCCN1CCN(c2ccnc(O[C@H]3CC[C@H](Nc4ccc([N+](=O)[O-])c(C(F)(F)F)c4)CC3)c2)CC1]
88 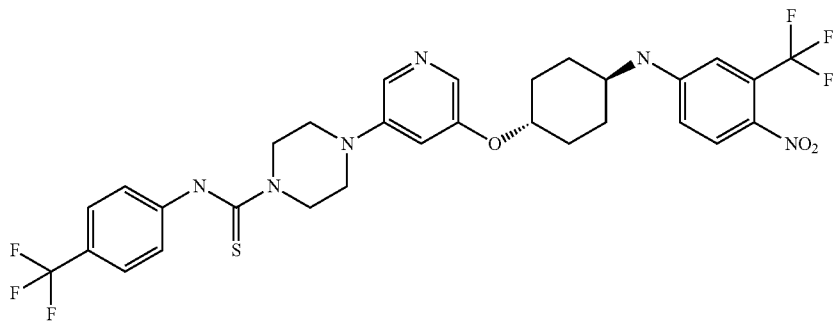 [SMILES: O=[N+]([O-])c1ccc(N[C@H]2CC[C@H](Oc3cncc(N4CCN(C(=S)Nc5ccc(C(F)(F)F)cc5)CC4)c3)CC2)cc1C(F)(F)F]

89
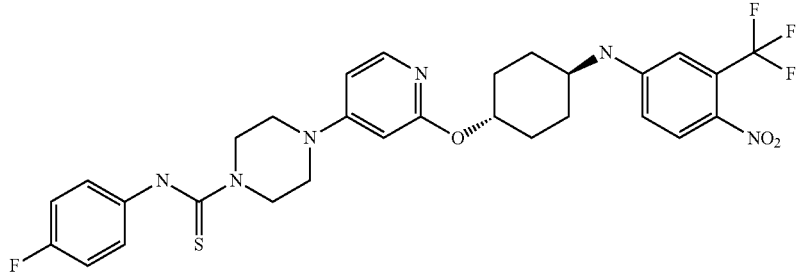 [SMILES: O=[N+]([O-])c1ccc(N[C@H]2CC[C@H](Oc3cc(N4CCN(C(=S)Nc5ccc(F)cc5)CC4)ccn3)CC2)cc1C(F)(F)F]
90
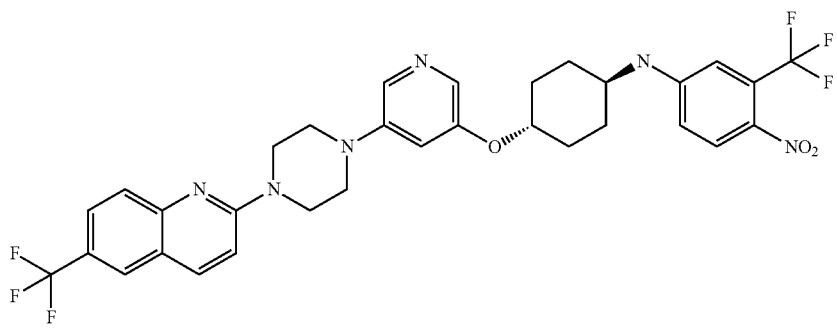 [SMILES: O=[N+]([O-])c1ccc(N[C@H]2CC[C@H](Oc3cncc(N4CCN(c5ccc6cc(C(F)(F)F)ccc6n5)CC4)c3)CC2)cc1C(F)(F)F]
91
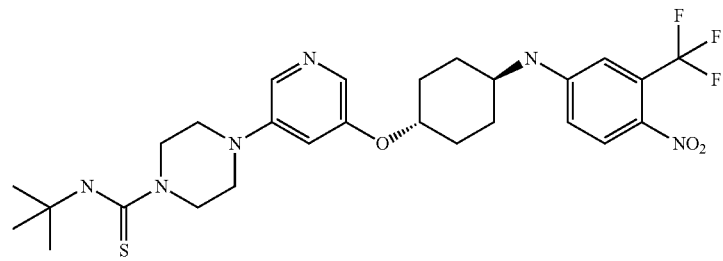
92
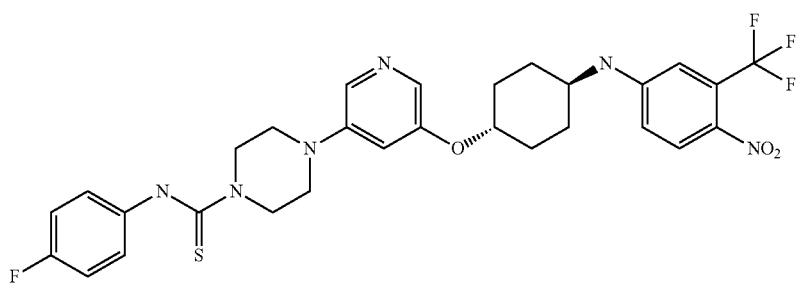
93
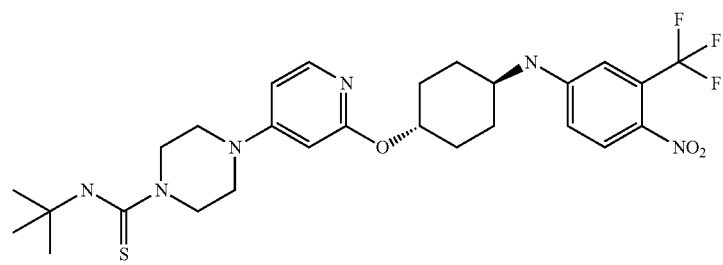

-continued
| | |
|---|---|
| 94 | 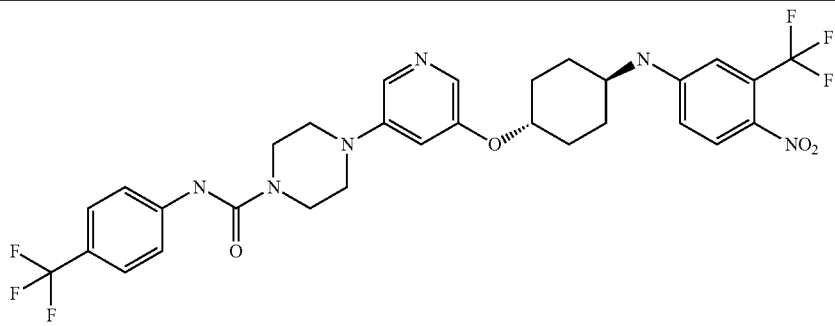 |
| 95 | 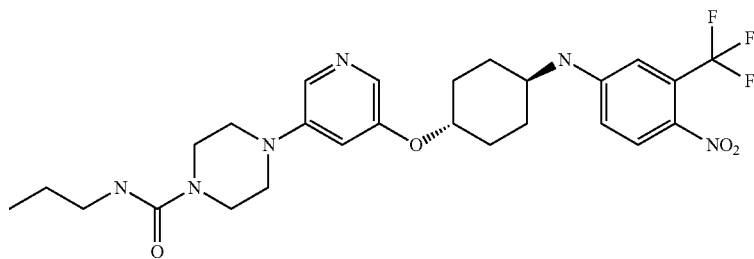 |
| 96 | 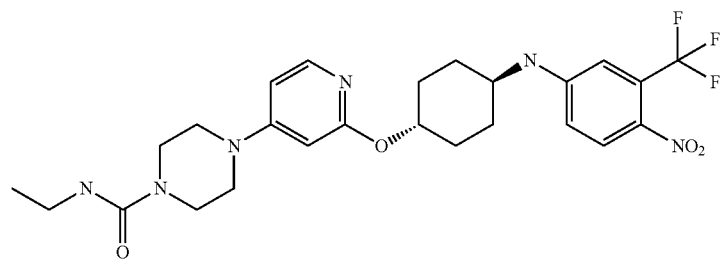 |
| 97 | 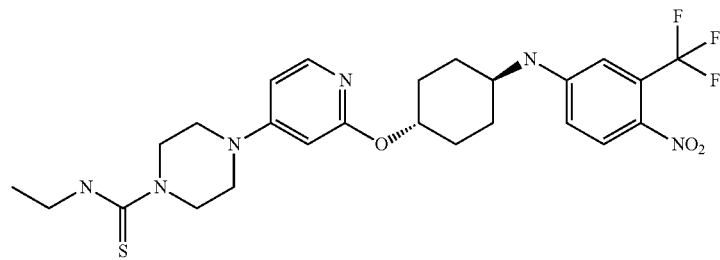 [SMILES: CCNC(=O)N1CCN(c2ccnc(O[C@H]3CC[C@H](Nc4ccc([N+](=O)[O-])c(C(F)(F)F)c4)CC3)c2)CC1] |
| 98 | 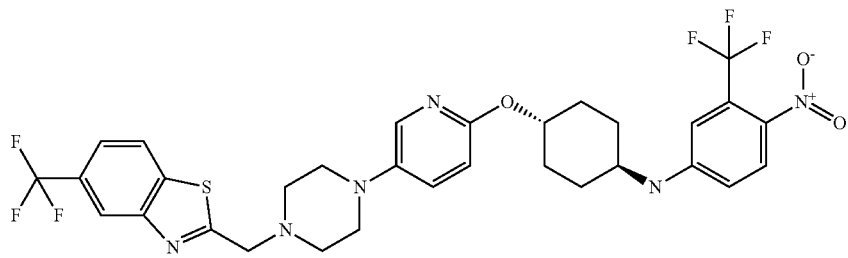 [SMILES: O=[N+]([O-])c1ccc(N[C@H]2CC[C@H](Oc3ccc(N4CCN(Cc5nc6cc(C(F)(F)F)ccc6s5)CC4)cn3)CC2)cc1C(F)(F)F] |
| 99 | 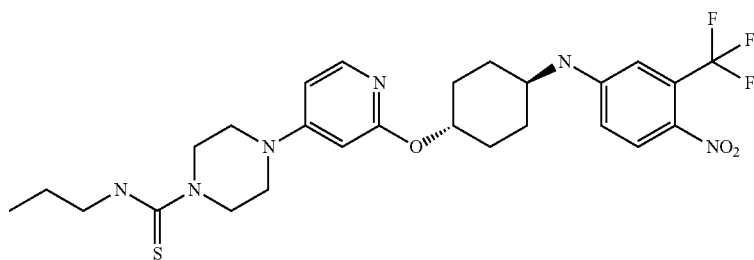 |

100 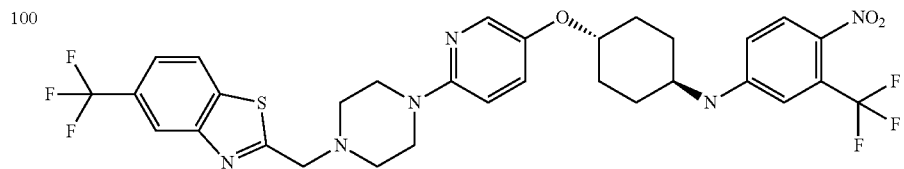
101 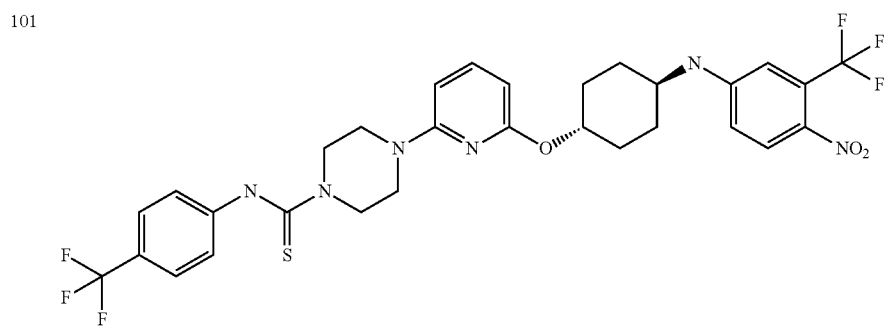
102 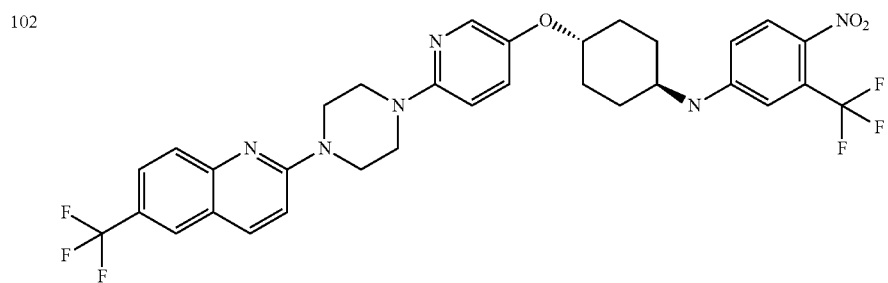
103 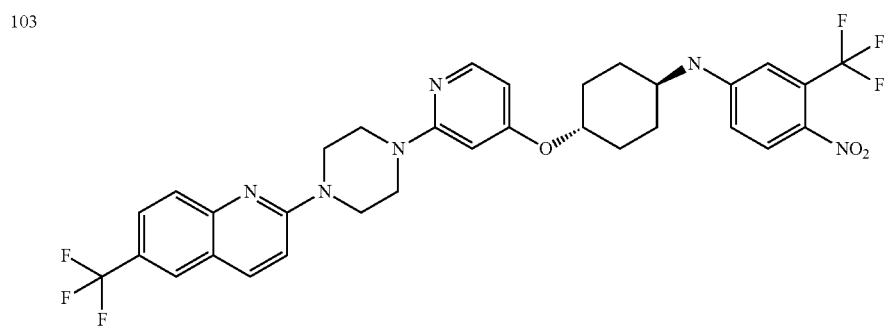
104 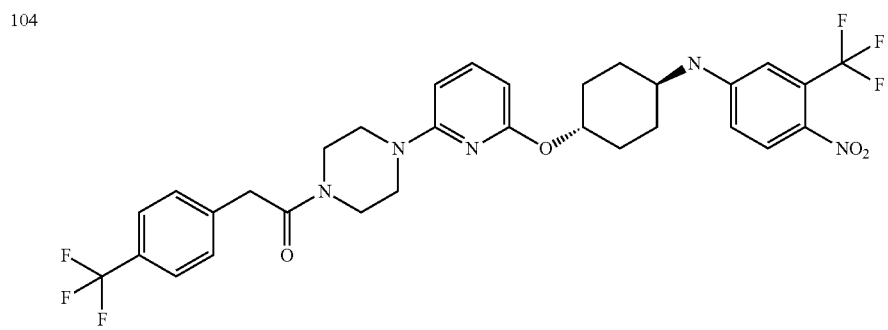

-continued
| 105 | 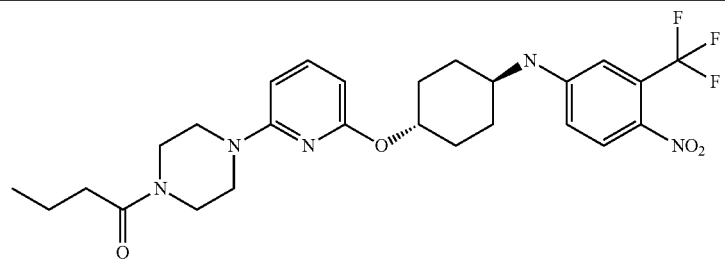 |
| 106 | 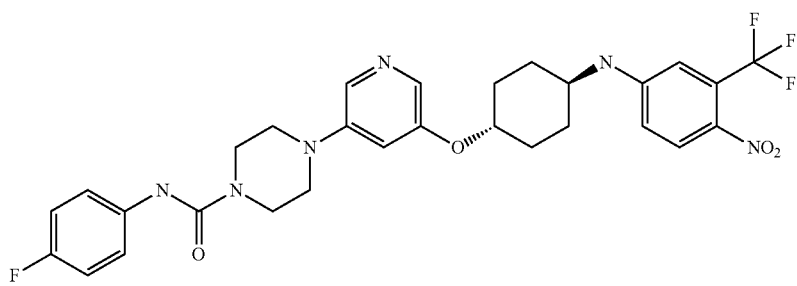 |
| 107 | 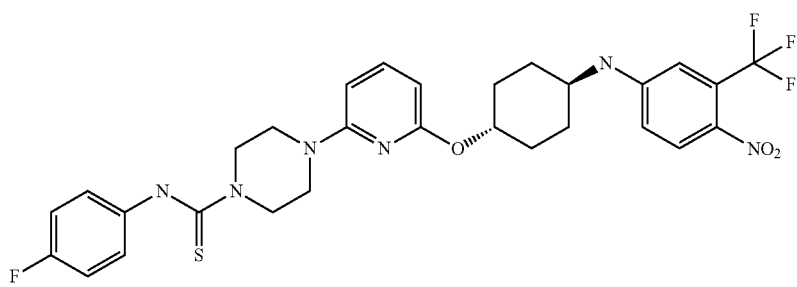 |
| 108 | 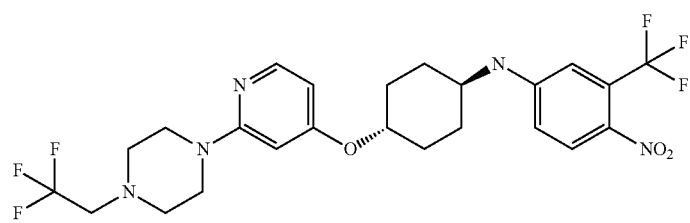 [SMILES: O=[N+]([O-])c1ccc(N[C@H]2CC[C@H](Oc3ccnc(N4CCN(CC(F)(F)F)CC4)c3)CC2)cc1C(F)(F)F] |
| 109 | 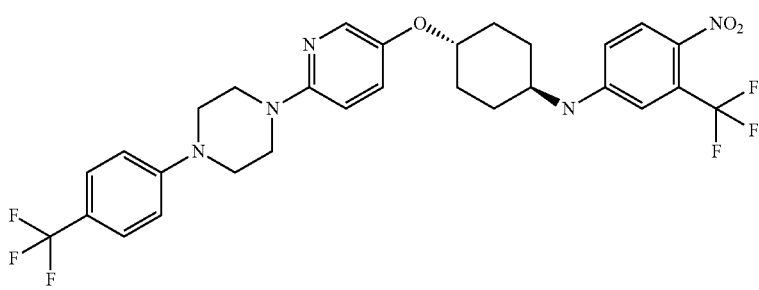 [SMILES: O=[N+]([O-])c1ccc(N[C@H]2CC[C@H](Oc3ccc(N4CCN(c5ccc(C(F)(F)F)cc5)CC4)nc3)CC2)cc1C(F)(F)F] |
| 110 | 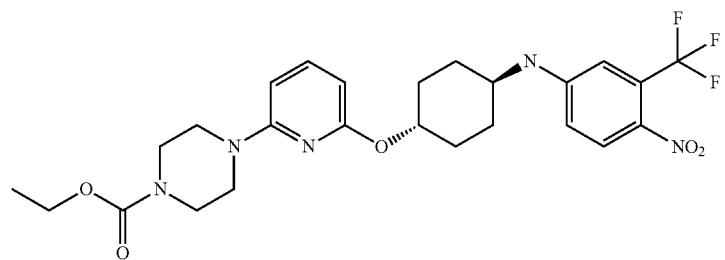 |

111
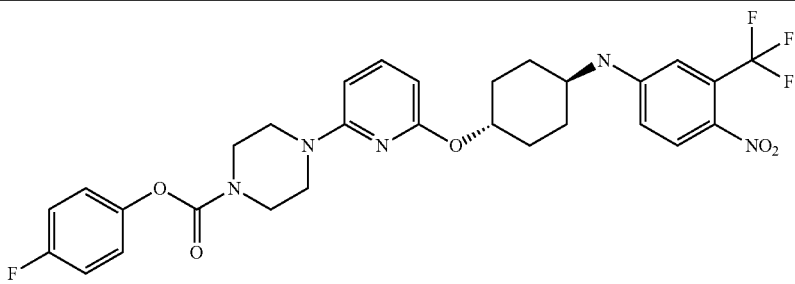
112
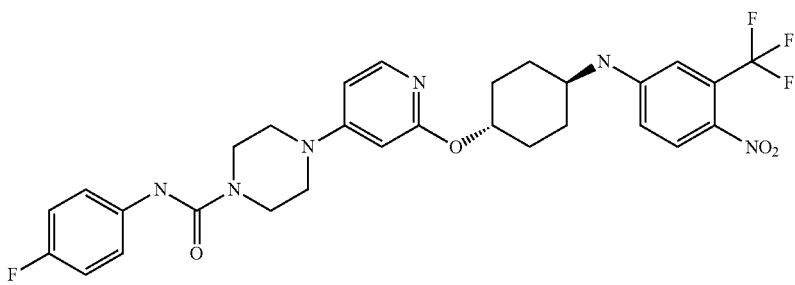
113
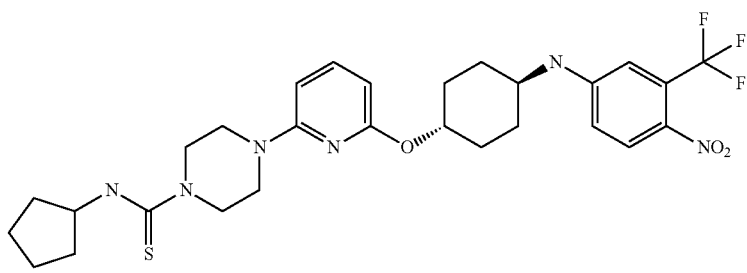 [SMILES: O=[N+]([O-])c1ccc(N[C@H]2CC[C@H](Oc3cccc(N4CCN(C(=S)NC5CCCC5)CC4)n3)CC2)cc1C(F)(F)F]
114
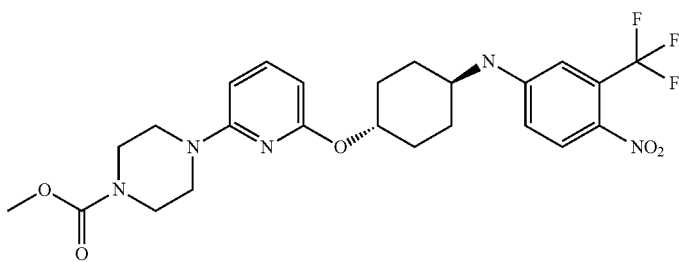 [SMILES: COC(=O)N1CCN(c2cccc(O[C@H]3CC[C@H](Nc4ccc([N+](=O)[O-])c(C(F)(F)F)c4)CC3)n2)CC1]
115
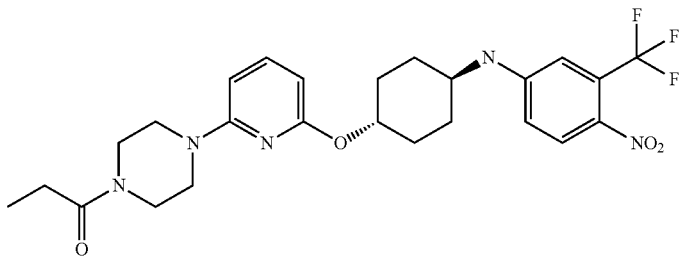 [SMILES: CCC(=O)N1CCN(c2cccc(O[C@H]3CC[C@H](Nc4ccc([N+](=O)[O-])c(C(F)(F)F)c4)CC3)n2)CC1]
116
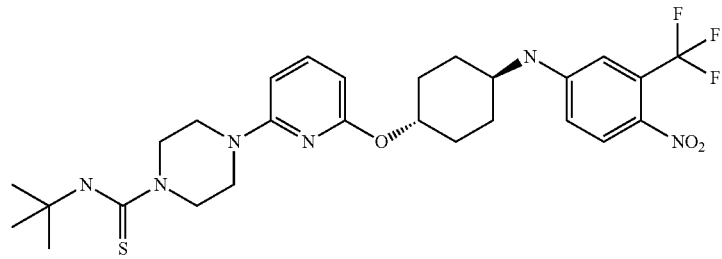

117
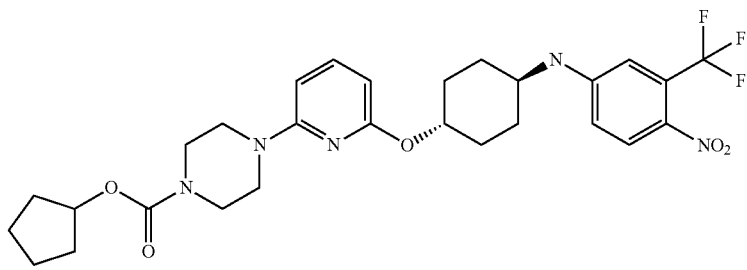 [SMILES: O=C(OC1CCCC1)N1CCN(c2cccc(O[C@H]3CC[C@H](Nc4ccc([N+](=O)[O-])c(C(F)(F)F)c4)CC3)n2)CC1]
118
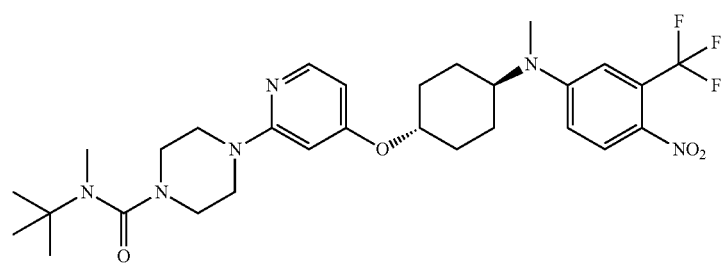 [SMILES: CN(C(=O)N1CCN(c2cc(O[C@H]3CC[C@H](N(C)c4ccc([N+](=O)[O-])c(C(F)(F)F)c4)CC3)ccn2)CC1)C(C)(C)C]
119
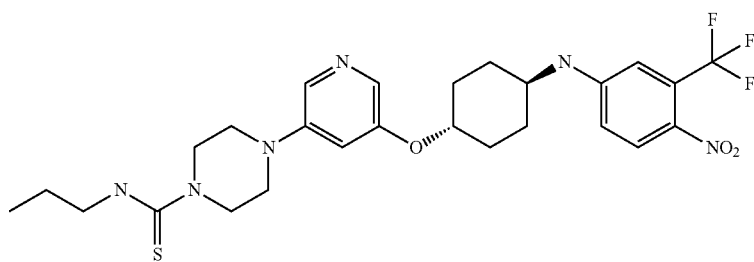
120
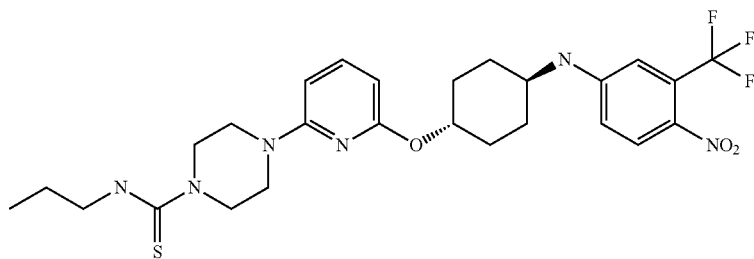
121
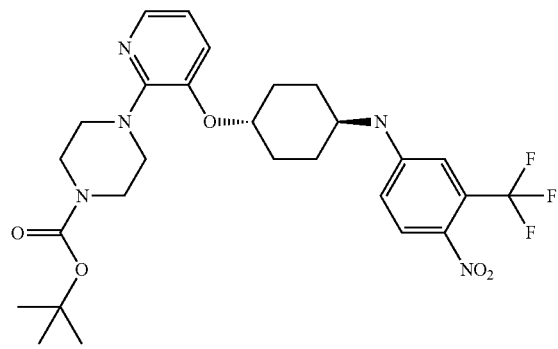 [SMILES: CC(C)(C)OC(=O)N1CCN(c2ncccc2O[C@H]2CC[C@H](Nc3ccc([N+](=O)[O-])c(C(F)(F)F)c3)CC2)CC1]

122
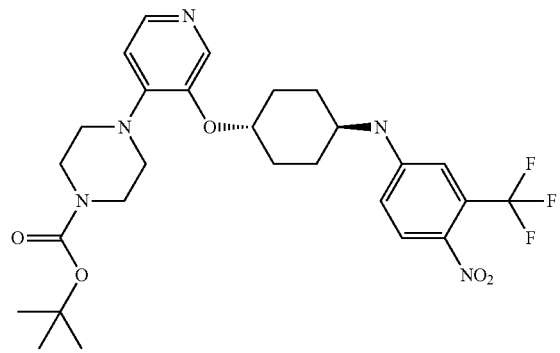 [SMILES: CC(C)(C)OC(=O)N1CCN(c2ccncc2O[C@H]2CC[C@H](Nc3ccc([N+](=O)[O-])c(C(F)(F)F)c3)CC2)CC1]
123
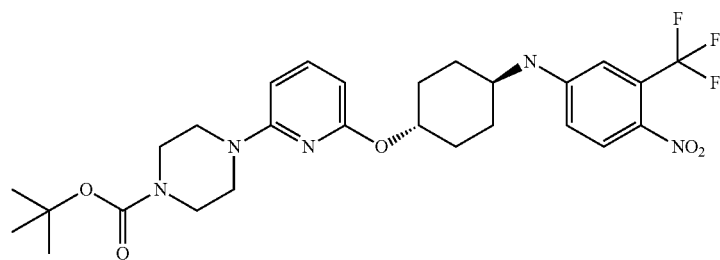
124
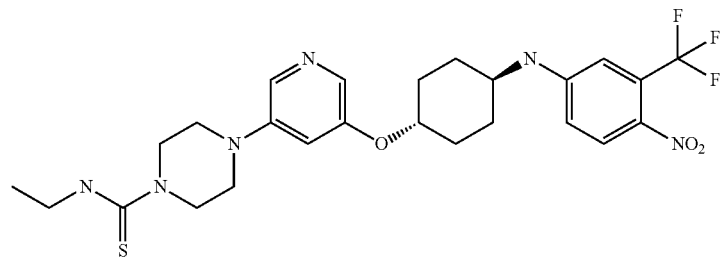 [SMILES: CCNC(=S)N1CCN(c2cncc(O[C@H]3CC[C@H](Nc4ccc([N+](=O)[O-])c(C(F)(F)F)c4)CC3)c2)CC1]
125
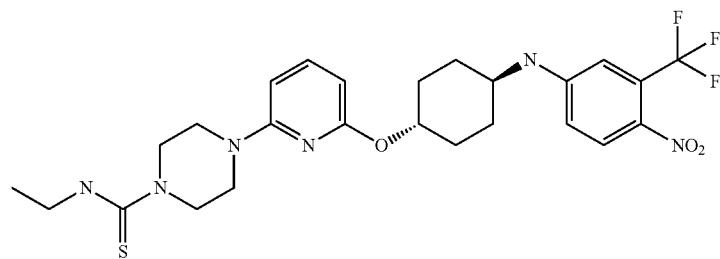
126
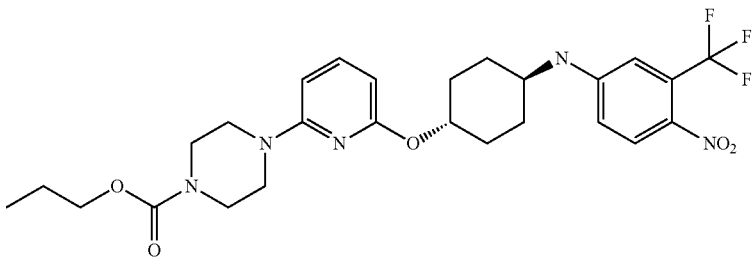

-continued
127
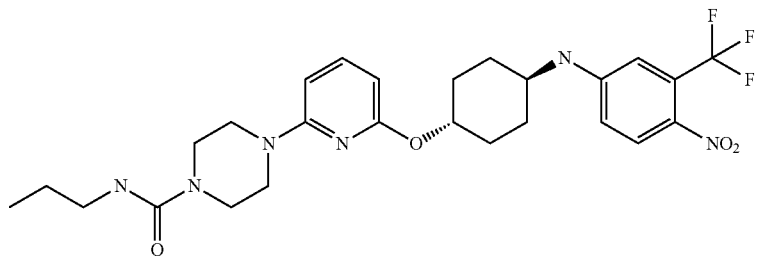
128
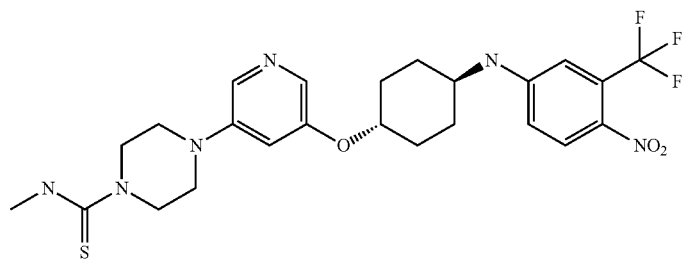
129
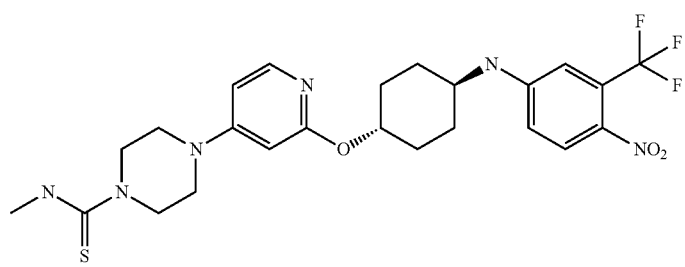 [SMILES: CNC(=S)N1CCN(c2ccnc(O[C@H]3CC[C@H](Nc4ccc([N+](=O)[O-])c(C(F)(F)F)c4)CC3)c2)CC1]
130
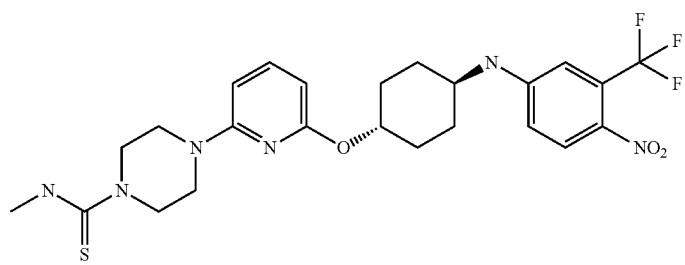
131
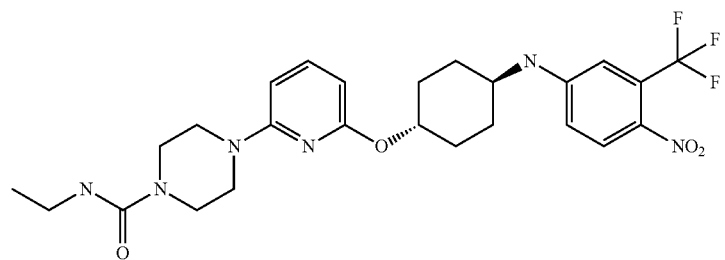 [SMILES: CCNC(=O)N1CCN(c2cccc(O[C@H]3CC[C@H](Nc4ccc([N+](=O)[O-])c(C(F)(F)F)c4)CC3)n2)CC1]
132
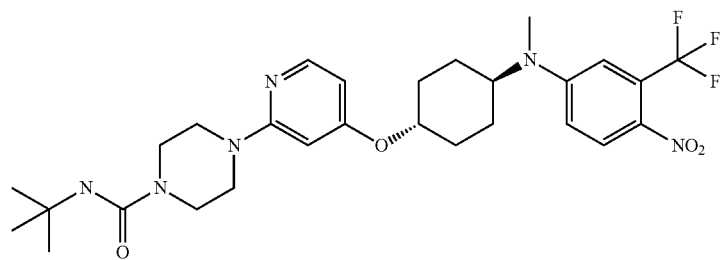

-continued
133 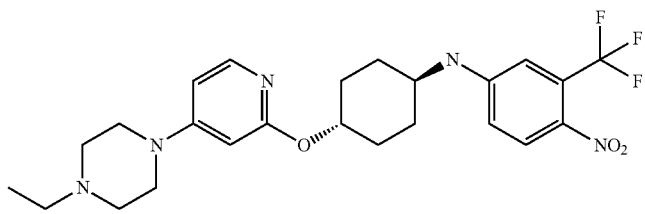 [SMILES: CCN1CCN(c2ccnc(O[C@H]3CC[C@H](Nc4ccc([N+](=O)[O-])c(C(F)(F)F)c4)CC3)c2)CC1]
134 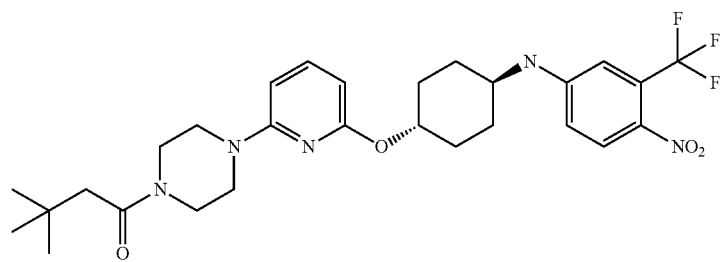 [SMILES: CC(C)(C)CC(=O)N1CCN(c2cccc(O[C@H]3CC[C@H](Nc4ccc([N+](=O)[O-])c(C(F)(F)F)c4)CC3)n2)CC1]
135 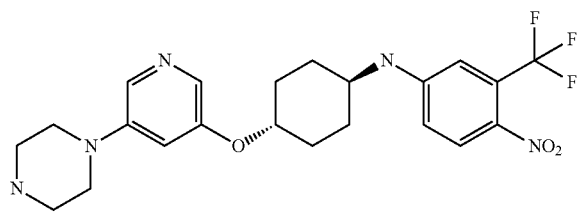 [SMILES: O=[N+]([O-])c1ccc(N[C@H]2CC[C@H](Oc3cncc(N4CCNCC4)c3)CC2)cc1C(F)(F)F]
136 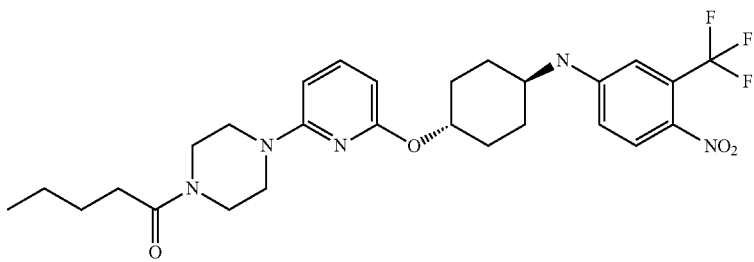
137 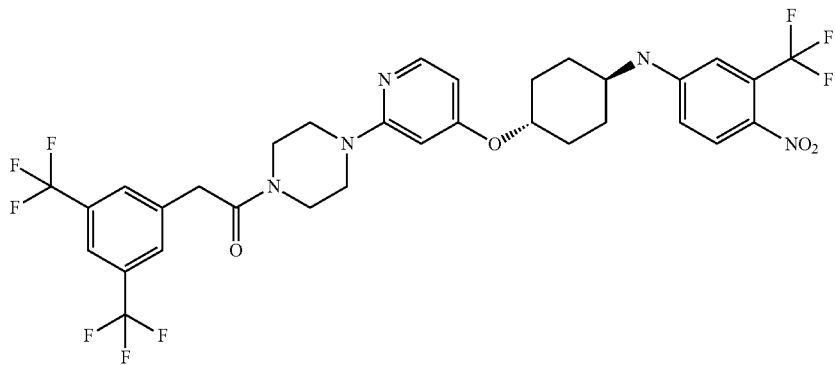 [SMILES: O=C(Cc1cc(C(F)(F)F)cc(C(F)(F)F)c1)N1CCN(c2cc(O[C@H]3CC[C@H](Nc4ccc([N+](=O)[O-])c(C(F)(F)F)c4)CC3)ccn2)CC1]

138
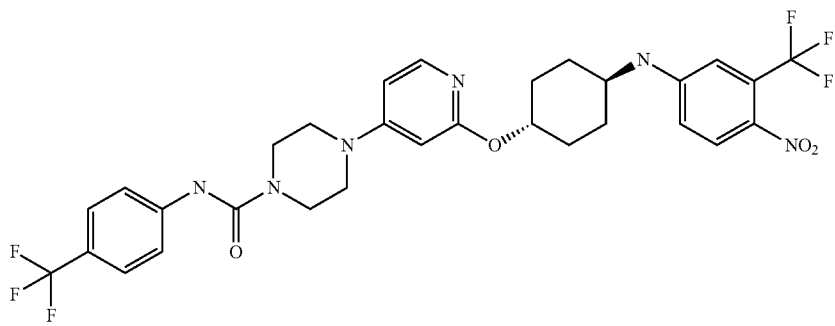
139
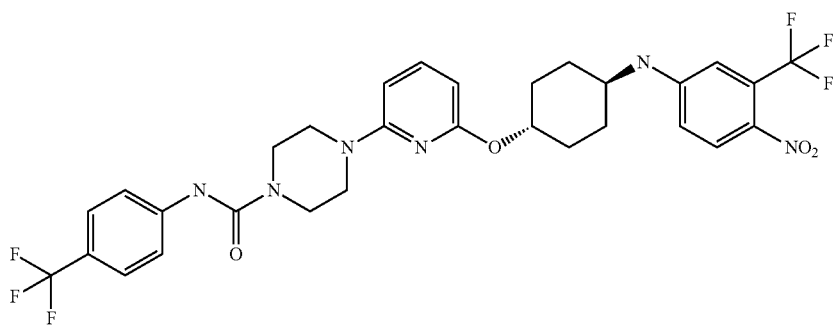
140
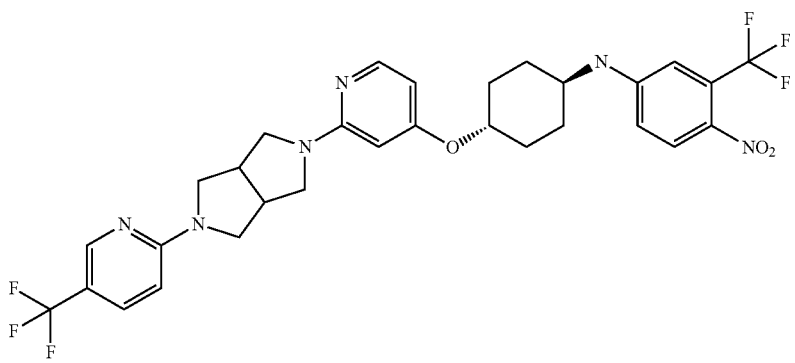 [SMILES: O=[N+]([O-])c1ccc(N[C@H]2CC[C@H](Oc3ccnc(N4CC5CN(c6ccc(C(F)(F)F)cn6)CC5C4)c3)CC2)cc1C(F)(F)F]
141
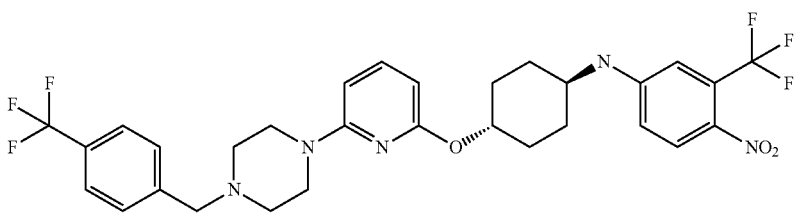 [SMILES: O=[N+]([O-])c1ccc(N[C@H]2CC[C@H](Oc3cccc(N4CCN(Cc5ccc(C(F)(F)F)cc5)CC4)n3)CC2)cc1C(F)(F)F]
142
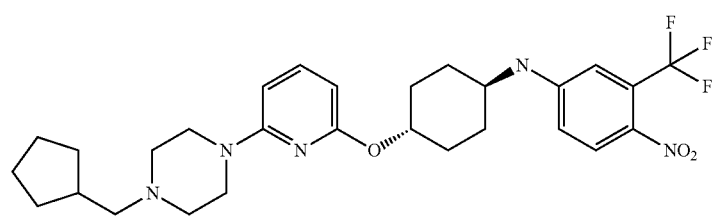 [SMILES: O=[N+]([O-])c1ccc(N[C@H]2CC[C@H](Oc3cccc(N4CCN(CC5CCCC5)CC4)n3)CC2)cc1C(F)(F)F]

143
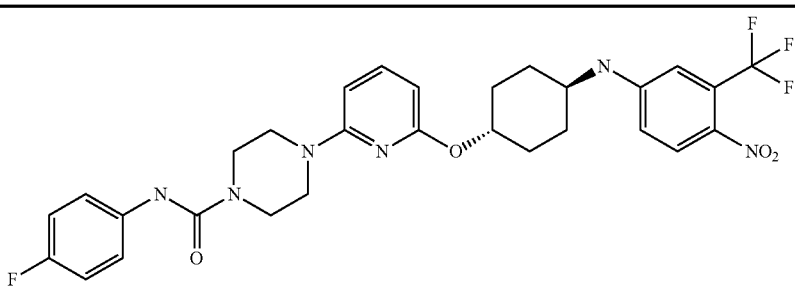
144
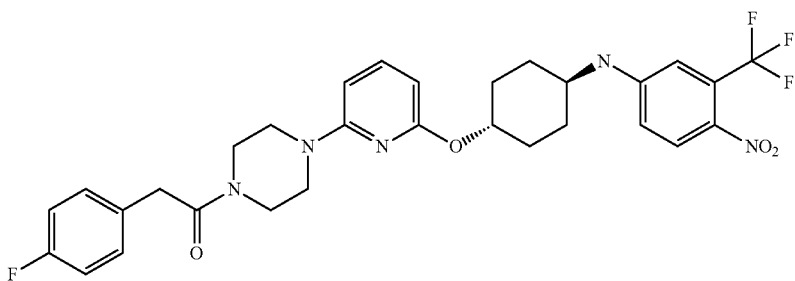
145
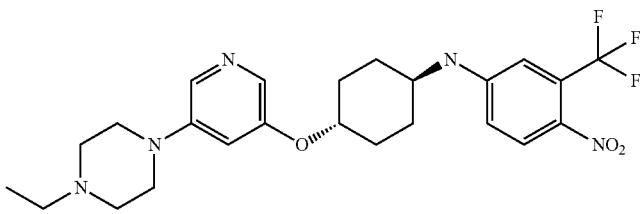
146
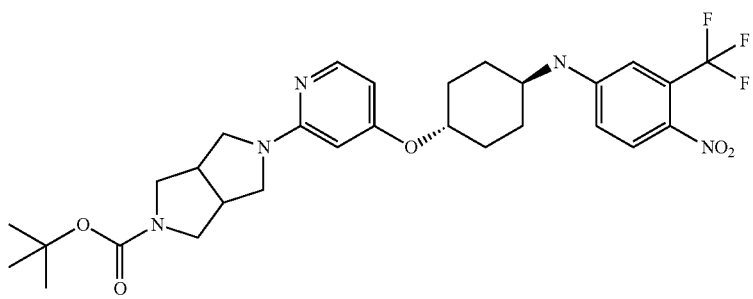 [SMILES: CC(C)(C)OC(=O)N1CC2CN(c3cc(O[C@H]4CC[C@H](Nc5ccc([N+](=O)[O-])c(C(F)(F)F)c5)CC4)ccn3)CC2C1]
147
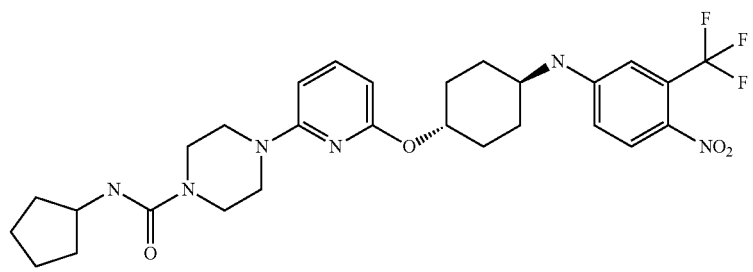
148
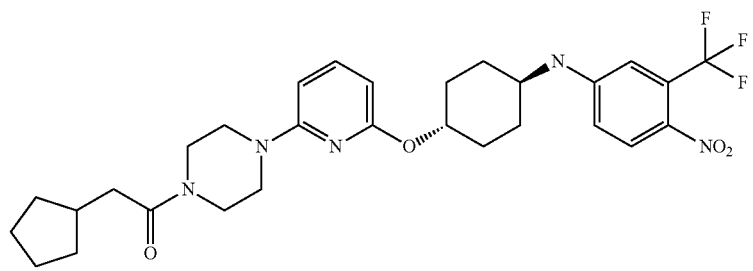

149 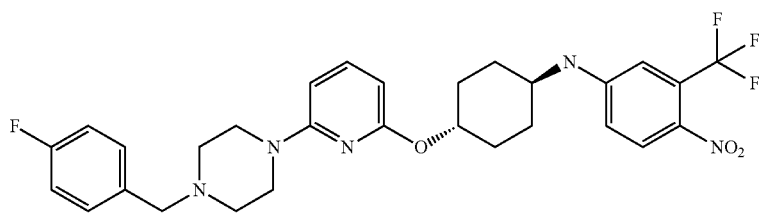 [SMILES: O=[N+]([O-])c1ccc(N[C@H]2CC[C@H](Oc3cccc(N4CCN(Cc5ccc(F)cc5)CC4)n3)CC2)cc1C(F)(F)F]
150 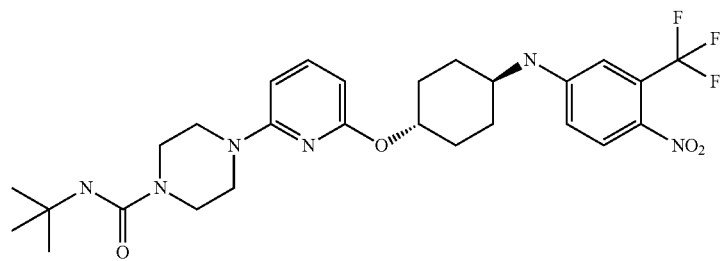
151 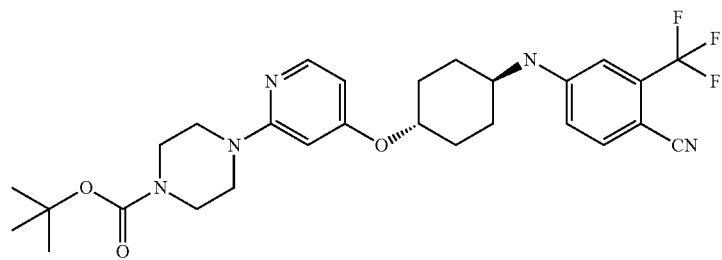
152 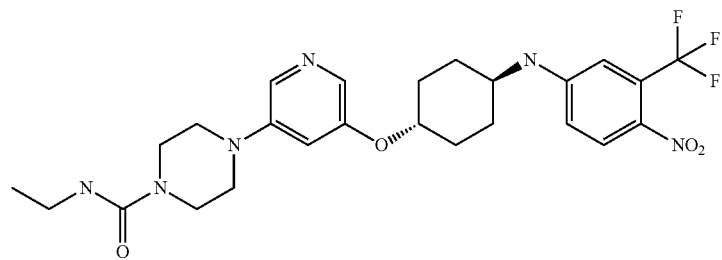
153 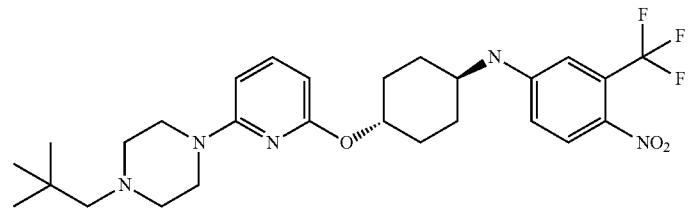
154 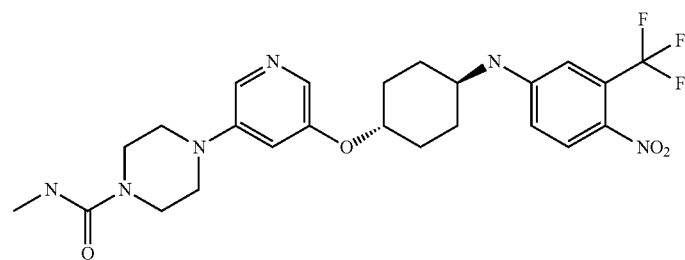 [SMILES: CNC(=O)N1CCN(c2cncc(O[C@H]3CC[C@H](Nc4ccc([N+](=O)[O-])c(C(F)(F)F)c4)CC3)c2)CC1]

-continued
| | |
|---|---|
| 155 | 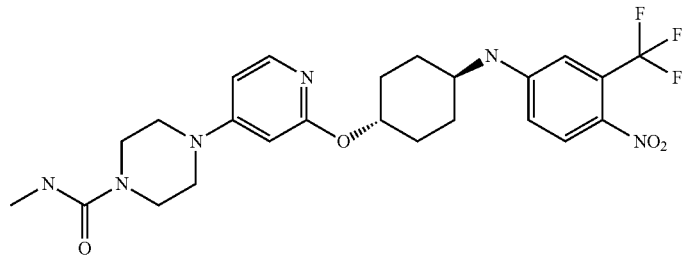 |
| 156 | 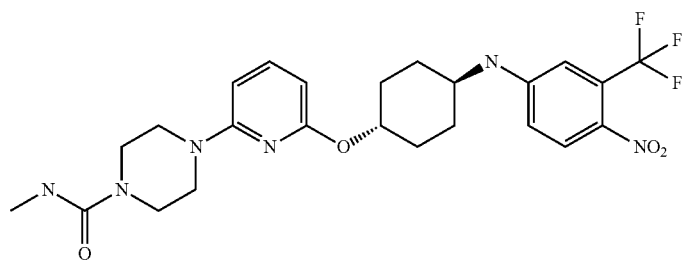 [SMILES: CNC(=O)N1CCN(c2cccc(O[C@H]3CC[C@H](Nc4ccc([N+](=O)[O-])c(C(F)(F)F)c4)CC3)n2)CC1] |
| 157 | 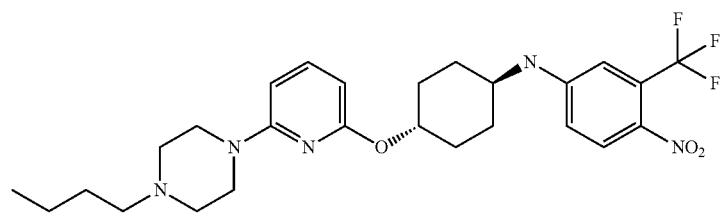 [SMILES: CCCCN1CCN(c2cccc(O[C@H]3CC[C@H](Nc4ccc([N+](=O)[O-])c(C(F)(F)F)c4)CC3)n2)CC1] |
| 158 | 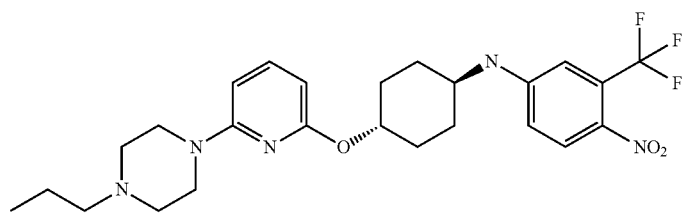 [SMILES: CCCN1CCN(c2cccc(O[C@H]3CC[C@H](Nc4ccc([N+](=O)[O-])c(C(F)(F)F)c4)CC3)n2)CC1] |
| 159 | 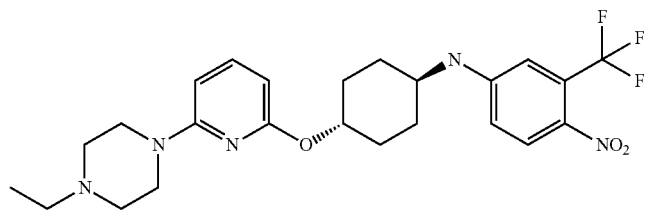 [SMILES: CCN1CCN(c2cccc(O[C@H]3CC[C@H](Nc4ccc([N+](=O)[O-])c(C(F)(F)F)c4)CC3)n2)CC1] |
| 160 | 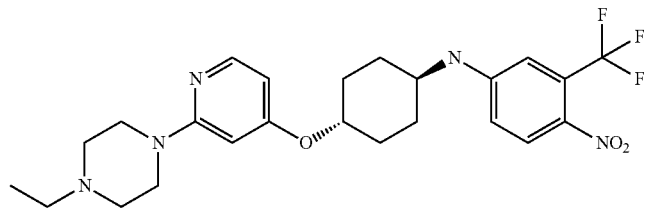 [SMILES: CCN1CCN(c2cc(O[C@H]3CC[C@H](Nc4ccc([N+](=O)[O-])c(C(F)(F)F)c4)CC3)ccn2)CC1] |

161 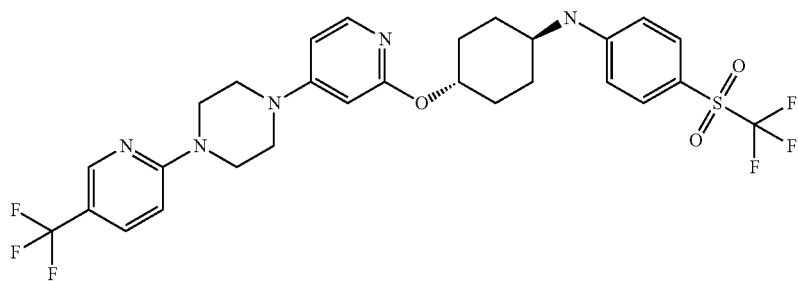 [SMILES: O=S(=O)(c1ccc(N[C@H]2CC[C@H](Oc3cc(N4CCN(c5ccc(C(F)(F)F)cn5)CC4)ccn3)CC2)cc1)C(F)(F)F]
162 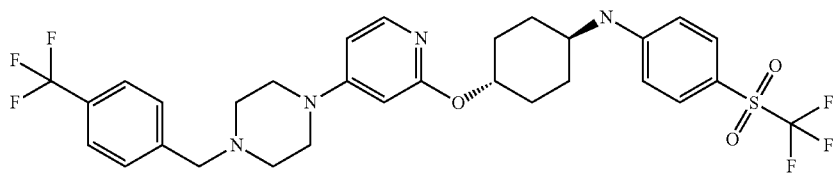 [SMILES: O=S(=O)(c1ccc(N[C@H]2CC[C@H](Oc3cc(N4CCN(Cc5ccc(C(F)(F)F)cc5)CC4)ccn3)CC2)cc1)C(F)(F)F]
163 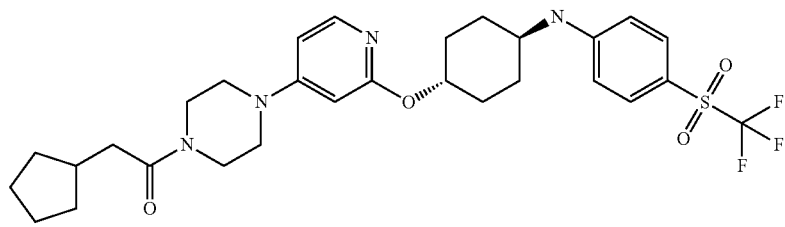 [SMILES: O=C(CC1CCCC1)N1CCN(c2ccnc(O[C@H]3CC[C@H](Nc4ccc(S(=O)(=O)C(F)(F)F)cc4)CC3)c2)CC1]
164 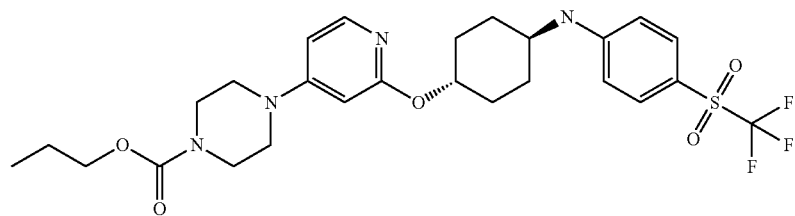 [SMILES: CCCOC(=O)N1CCN(c2ccnc(O[C@H]3CC[C@H](Nc4ccc(S(=O)(=O)C(F)(F)F)cc4)CC3)c2)CC1]
165 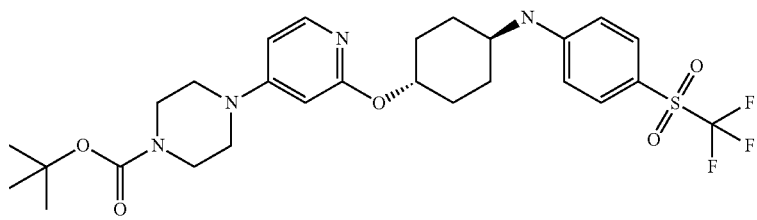 [SMILES: CC(C)(C)OC(=O)N1CCN(c2ccnc(O[C@H]3CC[C@H](Nc4ccc(S(=O)(=O)C(F)(F)F)cc4)CC3)c2)CC1]
166 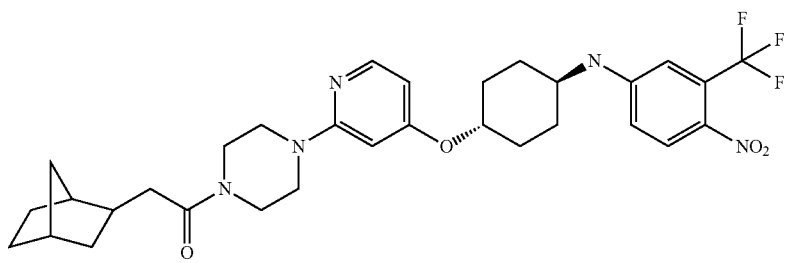 [SMILES: O=C(CC1CC2CCC1C2)N1CCN(c2cc(O[C@H]3CC[C@H](Nc4ccc([N+](=O)[O-])c(C(F)(F)F)c4)CC3)ccn2)CC1]

167
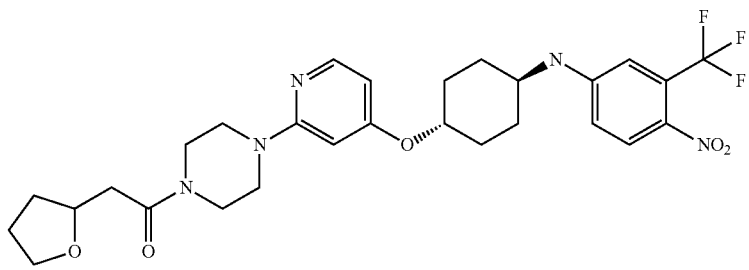
168
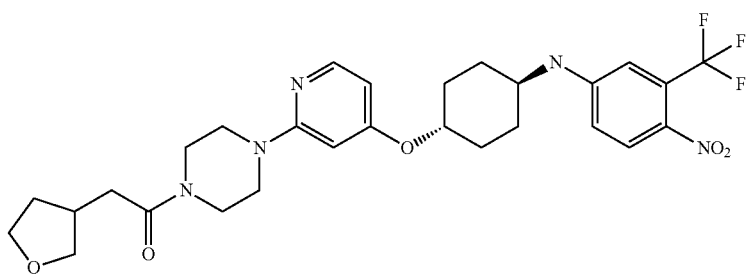 [SMILES: O=C(CC1CCOC1)N1CCN(c2cc(O[C@H]3CC[C@H](Nc4ccc([N+](=O)[O-])c(C(F)(F)F)c4)CC3)ccn2)CC1]
169
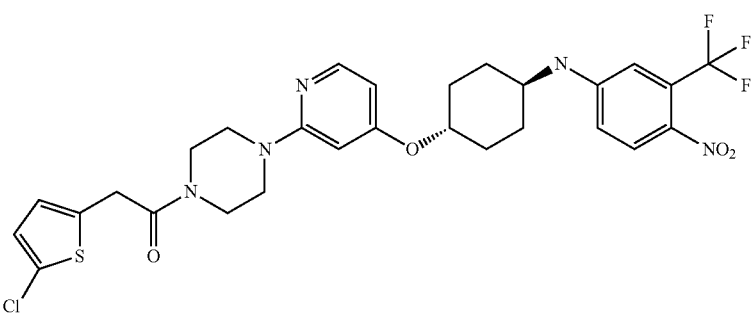 [SMILES: O=C(Cc1ccc(Cl)s1)N1CCN(c2cc(O[C@H]3CC[C@H](Nc4ccc([N+](=O)[O-])c(C(F)(F)F)c4)CC3)ccn2)CC1]
170
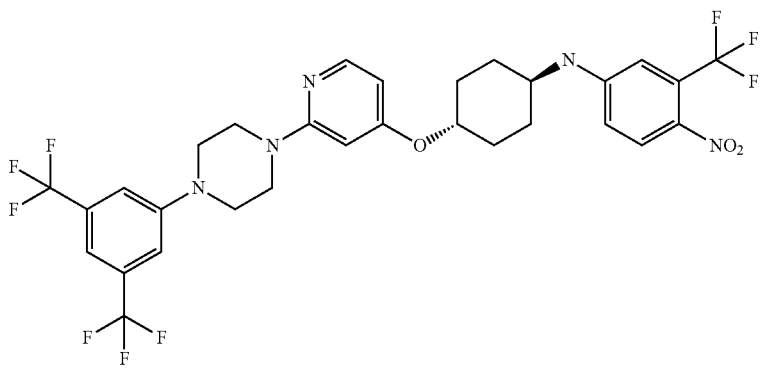 [SMILES: O=[N+]([O-])c1ccc(N[C@H]2CC[C@H](Oc3ccnc(N4CCN(c5cc(C(F)(F)F)cc(C(F)(F)F)c5)CC4)c3)CC2)cc1C(F)(F)F]
171
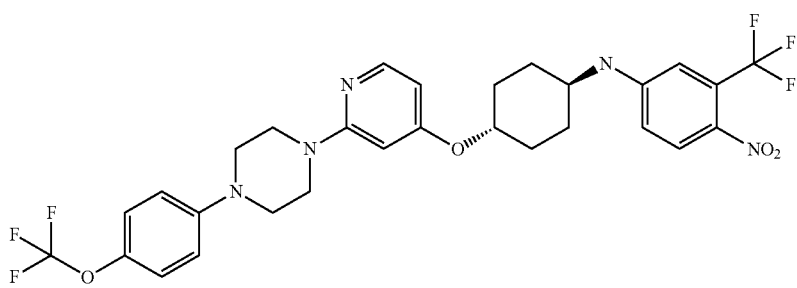 [SMILES: O=[N+]([O-])c1ccc(N[C@H]2CC[C@H](Oc3ccnc(N4CCN(c5ccc(OC(F)(F)F)cc5)CC4)c3)CC2)cc1C(F)(F)F]

172
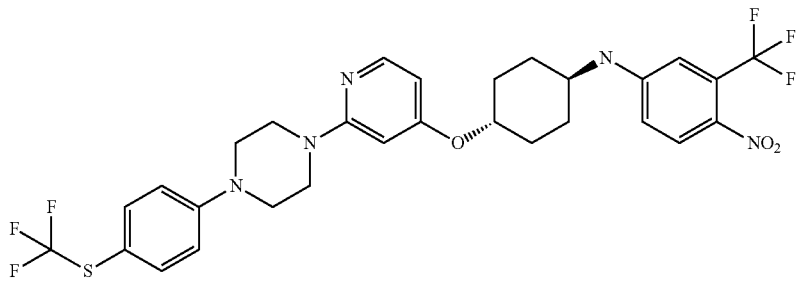 [SMILES: O=[N+]([O-])c1ccc(N[C@H]2CC[C@H](Oc3ccnc(N4CCN(c5ccc(SC(F)(F)F)cc5)CC4)c3)CC2)cc1C(F)(F)F]
173
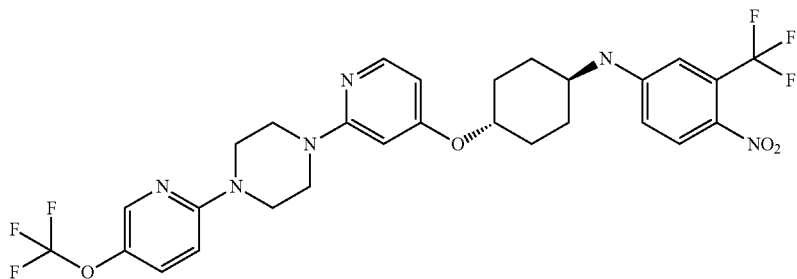 [SMILES: O=[N+]([O-])c1ccc(N[C@H]2CC[C@H](Oc3ccnc(N4CCN(c5ccc(OC(F)(F)F)cn5)CC4)c3)CC2)cc1C(F)(F)F]
174
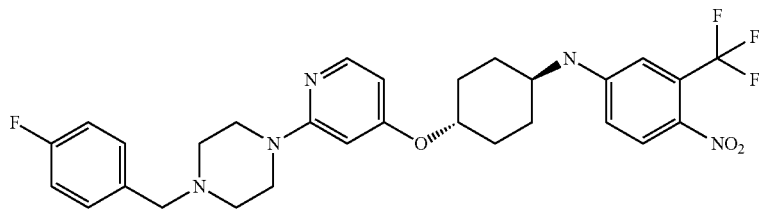 [SMILES: O=[N+]([O-])c1ccc(N[C@H]2CC[C@H](Oc3ccnc(N4CCN(Cc5ccc(F)cc5)CC4)c3)CC2)cc1C(F)(F)F]
175
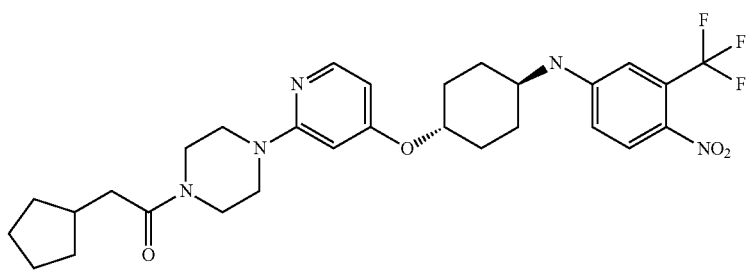
176
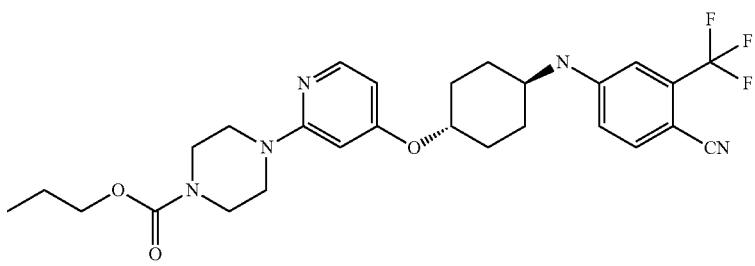
177
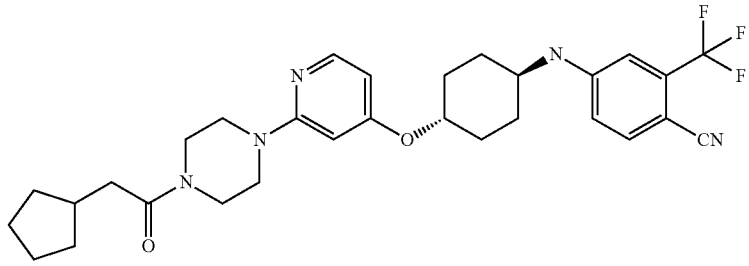 [SMILES: N#Cc1ccc(N[C@H]2CC[C@H](Oc3ccnc(N4CCN(C(=O)CC5CCCC5)CC4)c3)CC2)cc1C(F)(F)F]

-continued
| 178 | 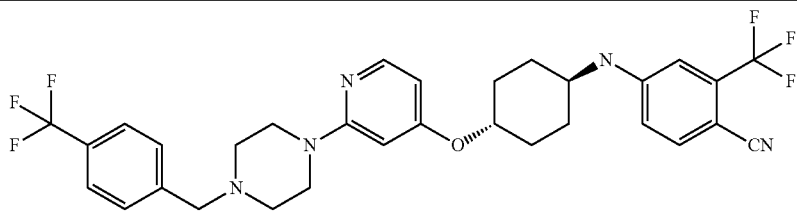 |
| 179 | 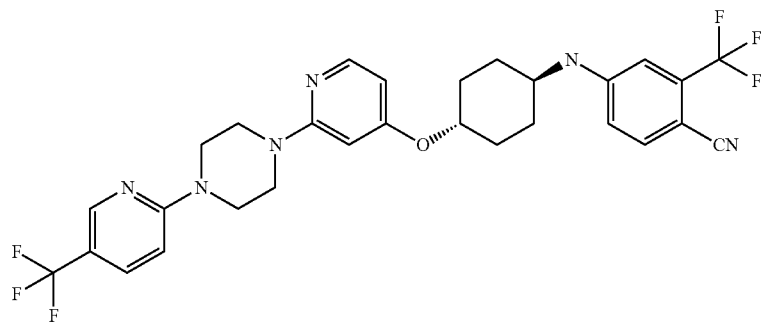 [SMILES: N#Cc1ccc(N[C@H]2CC[C@H](Oc3ccnc(N4CCN(c5ccc(C(F)(F)F)cn5)CC4)c3)CC2)cc1C(F)(F)F] |
| 180 | 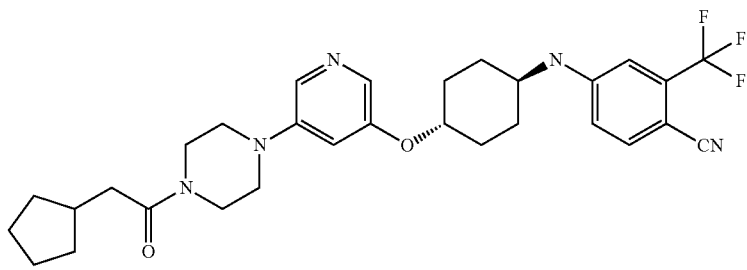 [SMILES: N#Cc1ccc(N[C@H]2CC[C@H](Oc3cncc(N4CCN(C(=O)CC5CCCC5)CC4)c3)CC2)cc1C(F)(F)F] |
| 181 | 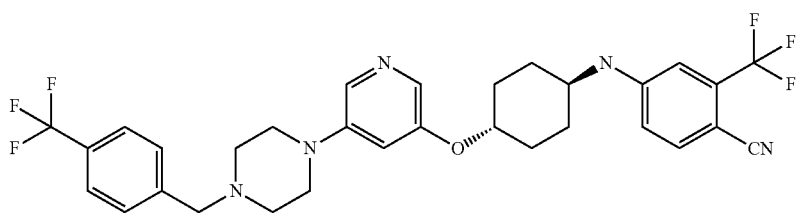 [SMILES: N#Cc1ccc(N[C@H]2CC[C@H](Oc3cncc(N4CCN(Cc5ccc(C(F)(F)F)cc5)CC4)c3)CC2)cc1C(F)(F)F] |
| 182 | 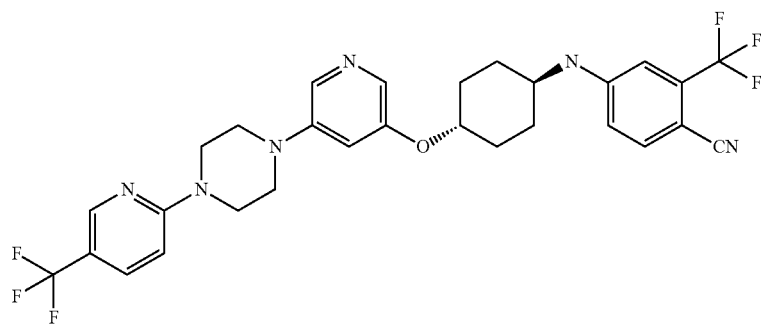 |
| 183 | 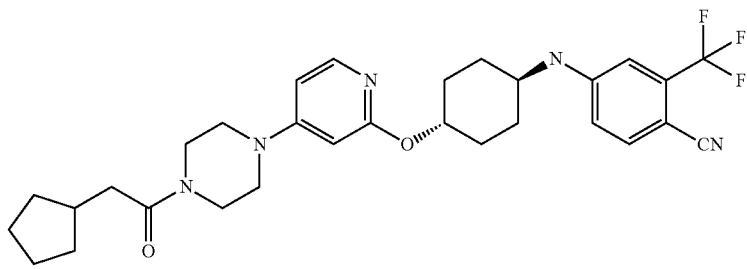 |

184
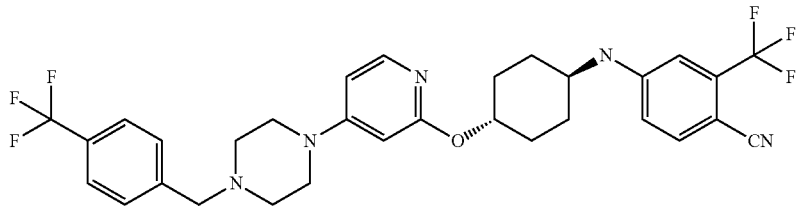 [SMILES: N#Cc1ccc(N[C@H]2CC[C@H](Oc3cc(N4CCN(Cc5ccc(C(F)(F)F)cc5)CC4)ccn3)CC2)cc1C(F)(F)F]
185
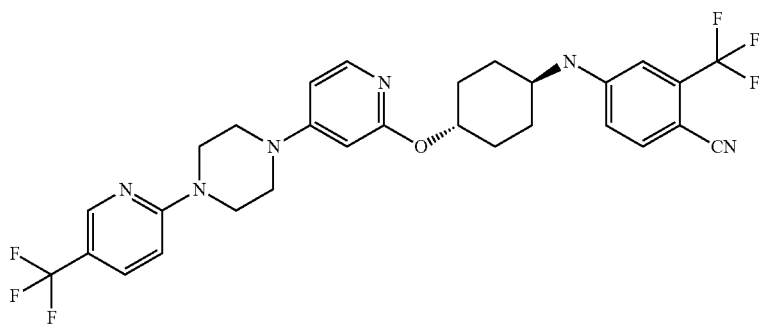 [SMILES: N#Cc1ccc(N[C@H]2CC[C@H](Oc3cc(N4CCN(c5ccc(C(F)(F)F)cn5)CC4)ccn3)CC2)cc1C(F)(F)F]
186
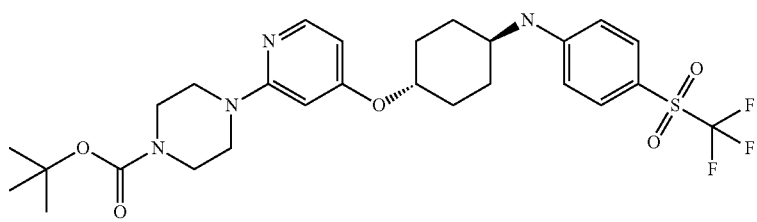 [SMILES: CC(C)(C)OC(=O)N1CCN(c2cc(O[C@H]3CC[C@H](Nc4ccc(S(=O)(=O)C(F)(F)F)cc4)CC3)ccn2)CC1]
187
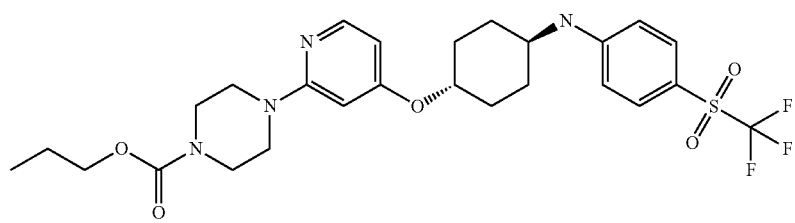 [SMILES: CCCOC(=O)N1CCN(c2cc(O[C@H]3CC[C@H](Nc4ccc(S(=O)(=O)C(F)(F)F)cc4)CC3)ccn2)CC1]
188
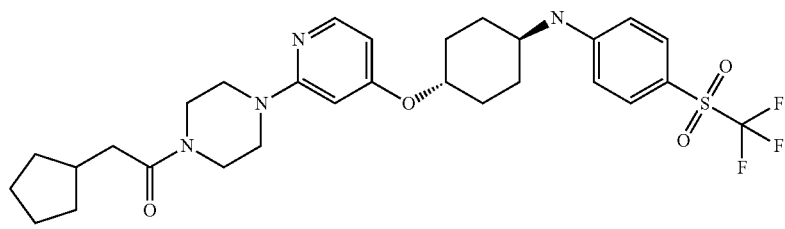
189
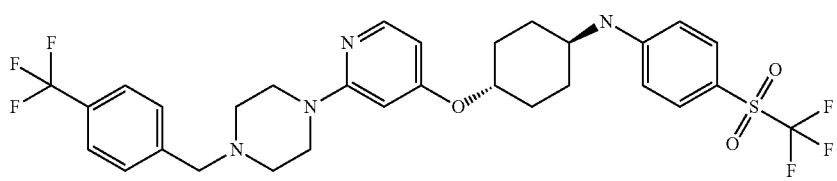 [SMILES: O=S(=O)(c1ccc(N[C@H]2CC[C@H](Oc3ccnc(N4CCN(Cc5ccc(C(F)(F)F)cc5)CC4)c3)CC2)cc1)C(F)(F)F]

190 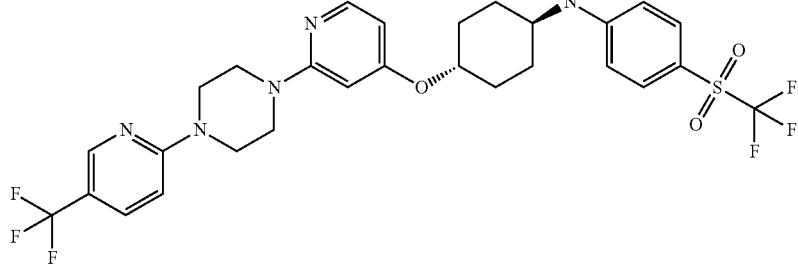
191 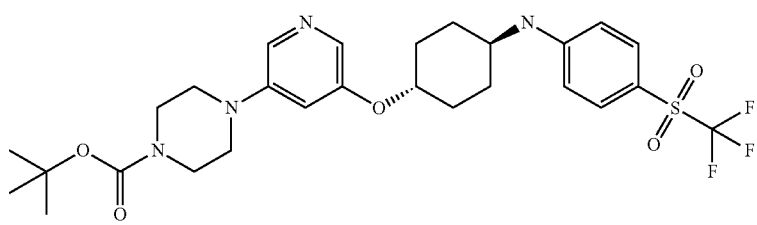 [SMILES: CC(C)(C)OC(=O)N1CCN(c2cncc(O[C@H]3CC[C@H](Nc4ccc(S(=O)(=O)C(F)(F)F)cc4)CC3)c2)CC1]
192 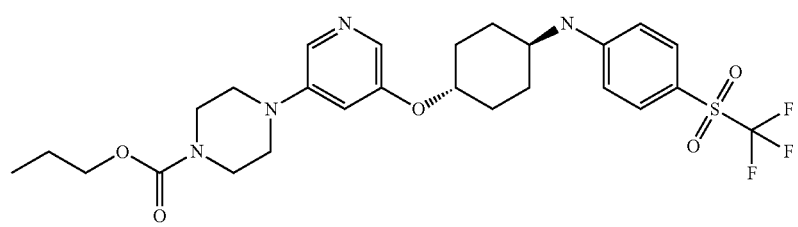 [SMILES: CCCOC(=O)N1CCN(c2cncc(O[C@H]3CC[C@H](Nc4ccc(S(=O)(=O)C(F)(F)F)cc4)CC3)c2)CC1]
193 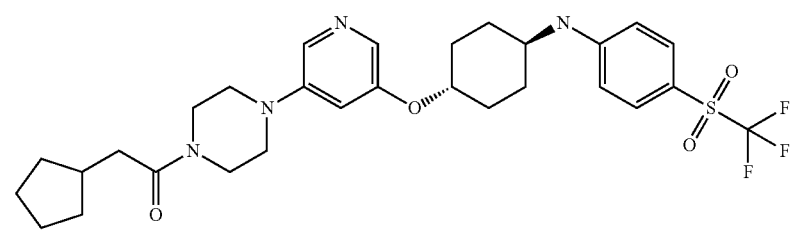 [SMILES: O=C(CC1CCCC1)N1CCN(c2cncc(O[C@H]3CC[C@H](Nc4ccc(S(=O)(=O)C(F)(F)F)cc4)CC3)c2)CC1]
194 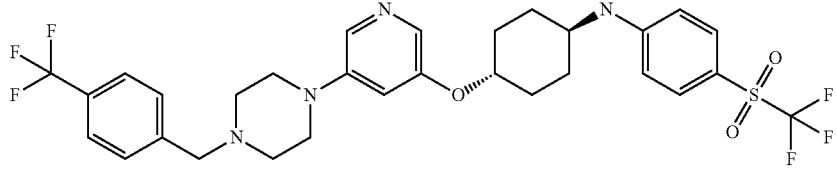 [SMILES: O=S(=O)(c1ccc(N[C@H]2CC[C@H](Oc3cncc(N4CCN(Cc5ccc(C(F)(F)F)cc5)CC4)c3)CC2)cc1)C(F)(F)F]
195 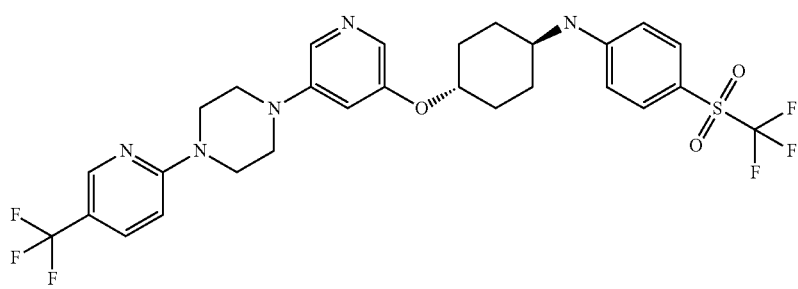 [SMILES: O=S(=O)(c1ccc(N[C@H]2CC[C@H](Oc3cncc(N4CCN(c5ccc(C(F)(F)F)cn5)CC4)c3)CC2)cc1)C(F)(F)F]

Another preferred embodiment of the invention is an anthelmintic compound of Formula (IA), (IA-1), (IA-2), or (IA-3), provided that when Ring C is pyrimidinyl, then Ring B is not $C_3$-$C_6$ monocyclic cycloakylene, or $C_4$-$C_6$ monocyclic heterocyclylene.

Another preferred embodiment of the invention is an anthelmintic compound of Formula (IA), (IA-1), (IA-2), or (IA-3), provided that that when Ring C is pyrimidinyl, then Ring B is not cyclohexylene, cyclobutylene, cyclopropylene, piperidin-diyl, pyrrolidin-diyl, piperazin-diyl, azetidin-diyl, or morpholin-diyl.

Another preferred embodiment of the invention is an anthelmintic compound of Formula (IA), (IA-1), (IA-2), or (IA-3), provided that when Ring C is pyrimidinyl, then Ring B is not 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, or morpholin-2,4-diyl.

Another preferred embodiment of the invention is an anthelmintic compound of Formula (IA), (IA-1), (IA-2), or (IA-3), provided that when Ring C is pyrimidinyl; and Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, or morpholin-2,4-diyl, then X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, or —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl; and Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, or morpholin-2,4-diyl; then X8 is not a bond, —N(R$^1$)(CH$_2$)$_n$— where n is 0 to 2, —(CH$_2$)— where n is 1 to 3, —C(O)—, —S(O)$_2$—, —O—, or —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;

X6 is a bond, —O—, —N(R$^1$)(CH$_2$)$_n$— where n is 0 to 2; and

Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl, X6 is a bond, —O—, —N(R$^1$)(CH$_2$)$_n$— where n is 0 to 2; and Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;

Z is substituted phenyl, then

Ring B is not C3-C6 monocyclic cycloakylene, or C4-C6 monocyclic heterocyclylene.

Another preferred embodiment of the invention is an anthelmintic compound of Formula (IA), (IA-1), (IA-2), or (IA-3), provided that when Ring C is pyrimidinyl; and Z is substituted phenyl, then Ring B is not cyclohexylene, cyclobutylene, cyclopropylene, piperidin-diyl, pyrrolidin-diyl, piperazin-diyl, azetidin-diyl, morpholin-diyl.

Another preferred embodiment of the invention is an anthelmintic compound of Formula (IA), (IA-1), (IA-2), or (IA-3), provided that when Ring C is pyrimidinyl; and Z is substituted phenyl, then Ring B is not 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl.

Another preferred embodiment of the invention is an anthelmintic compound of Formula (IA), (IA-1), (IA-2), or (IA-3), provided that when Ring C is pyrimidinyl;

Z is substituted phenyl; and

Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;

Z is substituted phenyl; and

Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;

Z is substituted phenyl;

X6 is a bond, —O—, —N(R$^1$)(CH$_2$)$_n$— where n is 0 to 2; and

Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;
Z is substituted phenyl;
X6 is a bond, —O—, —N(R$^1$)(CH$_2$)$_n$— where n is 0 to 2, and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl; and
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl;
Ring B is not C3-C6 monocyclic cycloakylene, or C4-C6 monocyclic heterocyclylene.

Another preferred embodiment of the invention is an anthelmintic compound of Formula (IA), (IA-1), (IA-2), or (IA-3), provided that when Ring C is pyrimidinyl; and
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl, then
Ring B is not cyclohexylene, cyclobutylene, cyclopropylene, piperidin-diyl, pyrrolidin-diyl, piperazin-diyl, azetidin-diyl, morpholin-diyl.

Another preferred embodiment of the invention is an anthelmintic compound of Formula (IA), (IA-1), (IA-2), or (IA-3), provided that when Ring C is pyrimidinyl; and
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl, then
Ring B is not 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl.

Another preferred embodiment of the invention is an anthelmintic compound of Formula (IA), (IA-1), (IA-2), or (IA-3), provided that when Ring C is pyrimidinyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl; and Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyrimidinyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is substituted phenyl;
X6 is —O—;
Ring B is piperidin-1,4-diyl or cyclohexane-diyl; and
X8 is —N(R$^1$)(CH$_2$)$_n$— where n is 0 to 2, then
then Z is not substituted phenyl.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is substituted phenyl;
X6 is —O—;
Ring B is piperidin-1,4-diyl or cyclohexane-diyl; and
X8 is —N(R$^1$)(CH$_2$)$_n$— where n is 0 to 2, then
Z is not phenyl substituted with haloalkyl and nitro groups.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is phenyl substituted with haloalkyl;
X6 is —O—;
Ring B is piperidin-1,4-diyl or cyclohexylene; and
X8 is —N(R$^1$)(CH$_2$)$_n$— where n is 0 to 2, then
then Z not substituted phenyl.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is phenyl substituted with haloalkyl;
X6 is —O—;
Ring B is piperidin-1,4-diyl or cyclohexylene; and
X8 is —N(R$^1$)(CH$_2$)$_n$— where n is 0 to 2, then
then Z is not phenyl substituted with haloalkyl and nitro groups.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is substituted phenyl or pyridyl;
X6 is —O—;
Ring B is piperidin-1,4-diyl or cyclohexane-diyl; and
X8 is —N(R$^1$)(CH$_2$)$_n$— where n is 0 to 2, then
then Z is not substituted phenyl.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is substituted phenyl or pyridyl;
X6 is —O—;
Ring B is piperidin-1,4-diyl or cyclohexane-diyl; and
X8 is —N(R$^1$)(CH$_2$)$_n$— where n is 0 to 2, then
then Z is not phenyl substituted with haloalkyl and nitro groups.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is phenyl substituted with haloalkyl or pyridyl substituted with haloalkyl;
X6 is —O—;
Ring B is piperidin-1,4-diyl or cyclohexylene; and
X8 is —N(R$^1$)(CH$_2$)$_n$— where n is 0 to 2, then
then Z not substituted phenyl.

Another preferred embodiment of the invention is an anthelmintic compound of Formula (IA), (IA-1), (IA-2), or (IA-3), provided that when Ring C is pyridine-diyl;
Ring A is piperidin-2,4-diyl;
X1 is a bond;
Y is phenyl substituted with haloalkyl or pyridyl substituted with haloalkyl;
X6 is —O—;
Ring B is piperidin-1,4-diyl or cyclohexylene; and
X8 is —N(R$^1$)(CH$_2$)$_n$— where n is 0 to 2, then
then Z is not phenyl substituted with haloalkyl and nitro groups.

Another preferred embodiment of the invention is an anthelmintic compound of Formula (IA), (IA-1), (IA-2), or (IA-3), provided that when Ring C is pyridine-diyl, then
Ring B is not C3-C6 monocyclic cycloakylene, or C4-C6 monocyclic heterocyclylene.

Another preferred embodiment of the invention is an anthelmintic compound of Formula (IA), (IA-1), (IA-2), or (IA-3), provided that when Ring C is pyridine-diyl, then
Ring B is not cyclohexylene, cyclobutylene, cyclopropylene, piperidin-diyl, pyrrolidin-diyl, piperazin-diyl, azetidin-diyl, morpholin-diyl.

Another preferred embodiment of the invention is an anthelmintic compound of Formula (IA), (IA-1), (IA-2), or (IA-3), provided that when Ring C is pyridine-diyl, then
Ring B is not 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl.

Another preferred embodiment of the invention is an anthelmintic compound of Formula (IA), (IA-1), (IA-2), or (IA-3), provided that when Ring C is pyridine-diyl; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl; and
Z is substituted phenyl, then
Ring B is not C3-C6 monocyclic cycloakylene, or C4-C6 monocyclic heterocyclylene.

Another preferred embodiment of the invention is an anthelmintic compound of Formula (IA), (IA-1), (IA-2), or (IA-3), provided that when Ring C is pyridine-diyl; and
Z is substituted phenyl, then
Ring B is not cyclohexylene, cyclobutylene, cyclopropylene, piperidin-diyl, pyrrolidin-diyl, piperazin-diyl, azetidin-diyl, morpholin-diyl, Another preferred embodiment of the invention is an anthelmintic compound of Formula (IA), (IA-1), (IA-2), or (IA-3), provided that when Ring C is pyridine-diyl; and
Z is substituted phenyl, then
Ring B is not 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, Another preferred embodiment of the invention is an anthelmintic compound of Formula (IA), (IA-1), (IA-2), or (IA-3), provided that when Ring C is pyrimidinyl;
Z is substituted phenyl; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
Z is substituted phenyl; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
Z is substituted phenyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
Z is substituted phenyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl; and
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl, then
Ring B is not C3-C6 monocyclic cycloakylene, or C4-C6 monocyclic heterocyclylene.

Another preferred embodiment of the invention is an anthelmintic compound of Formula (IA), (IA-1), (IA-2), or (IA-3), provided that when Ring C is pyridine-diyl; and
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl, then
Ring B is not cyclohexylene, cyclobutylene, cyclopropylene, piperidin-diyl, pyrrolidin-diyl, piperazin-diyl, azetidin-diyl, morpholin-diyl.

Another preferred embodiment of the invention is an anthelmintic compound of Formula (IA), (IA-1), (IA-2), or (IA-3), provided that when Ring C is pyridine-diyl; and
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl, then
Ring B is not 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl.

Another preferred embodiment of the invention is an anthelmintic compound of Formula (IA), (IA-1), (IA-2), or (IA-3), provided that when Ring C is pyridine-diyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S—, —S(O)—, —S(O)$_2$—, —O—, —(CH$_2$)$_n$—N(R$^1$)— where n is 0 to 2.

Another preferred embodiment of the invention is an anthelmintic compound of Formula (IA), (IA-1), (IA-2), or (IA-3), provided that when Ring C is pyridine-diyl;
Z is phenyl substituted by one or more groups selected from halogen, nitro, cyano, amino, alkylamino, dialkylamino, aminoalkyl, alkyl, haloalkyl, alkoxy, haloalkylthio, alkylsulfinyl, and haloalkylsulfinyl;
X6 is a bond, —O—, —N(R$^1$)(CH$_2$)$_n$— where n is 0 to 2; and
Ring B is 1,4-cyclohexylene, 1,3-cyclobutylene, 1,1-cyclopropylene, piperidin-1,4-diyl, pyrrolidin-1,3-diyl, piperazin-1,4-diyl, azetidin-1,3-diyl, morpholin-2,4-diyl, then
X8 is not a bond, —N(R$^1$)(CH$_2$)$_n$— where n is 0 to 2, —(CH$_2$)$_n$ where n is 1 to 3, —C(O)—, —S(O)$_2$—, —O—, —(CH$_2$)$_n$—N(R$^1$)— where n is 0 to 2.

Another preferred embodiment of the invention is an anthelmintic compound
as shown in any one of the Examples.

Another preferred embodiment of the invention is a composition for the treatment and prevention of a parasitic infection or infestation in an animal, comprising a therapeutically effective amount of at least one anthelmintic compound of Formula (IA), (IA-1), (IA-2), or (IA-3), in combination with a pharmaceutically acceptable carrier.

Another preferred embodiment of the invention is a composition for the treatment and prevention of a parasitic infection or infestation in an animal, comprising a therapeutically effective amount of at least one anthelmintic compound of Formula (IA), (IA-1), (IA-2), or (IA-3), in combination with a pharmaceutically acceptable carrier and which comprises an additional parasiticidal active agent.

A method for the treatment and prevention of a parasitic infection or infestation in an animal, comprising administering a therapeutically effective amount of the compound of any one of claims of Formula (IA), (IA-1), (IA-2), or (IA-3), to the animal.

Use of a compound of Formula (IA), (IA-1), (IA-2), or (IA-3), in the manufacture of a medicament for the treatment of a parasitic infestation or infection in an animal.

Another embodiment of formulations of the present invention may further comprise one or more additional anti-parasitic agent such as morantel, monepantel, pyrantel, febrantel, thiabendazole cambendazole, abamectin, dimadectin, doramectin, emamectin, eprinomectin, ivermectin, latidectin, lepimectin, milbemectin, milbemycin D, milbemycin oxime, moxidectin, nemadectin, selamectin, albendazole, fenbenzazole, mebendazole, methoprene, pyriproxyfen, oxibendazole, triclobendazole, pyrantel, praziquantel levamisole, fipronil, nodulisporic acid, hydroprene, cyromazine, fluazuron, lufenuron, novaluron, or novaluron.

The compounds of the invention were found to exhibit superior permeability compared with prior art compounds. For an orally-dosed compound the permeability of a compound across the epithelium cells along the gastrointestinal tract is an important limiting factor for the oral absorption and systemic availability of the compound. Thus, the permeability of a systemically-acting compound is a feature that can significantly impact the efficacy of a compound against internal and/or external parasites when administered orally or topically.

In one embodiment, the compounds of the invention exhibit surprisingly improved permeability compared with the compounds of the prior art having only monocyclic rings at the position corresponding to Y and/or Z (for example compounds of WO 2009/077527 and EP 2468096). The significantly higher permeability of the compounds of the invention is expected to result in higher in vivo efficacy against internal parasites such as nematodes and external parasites that consume blood meals. This is because the increased permeability across the mammalian gut enhances the amount of the active compounds present in the blood circulation for delivery and uptake at the required sites. Furthermore, the increased permeability of the compounds is likely to result in increased permeability across the nematode tissue. In addition, increased permeability of the active compounds may result in improved transdermal passage of the compounds into the bloodstream following topical administration.

In one embodiment, the compounds of the invention exhibit about 20% to about 30% higher permeability than the prior art compounds. In another embodiment, the compounds of the invention exhibit about 40% to about 60% or about 50% to about 70% higher permeability than the prior art compounds. In still other embodiments, the compounds of the invention exhibit about 60% to about 100% higher permeability. In yet other embodiments, the compounds of the invention exhibit about about 20% to about 50% or about 30% to about 75% higher permeability compared with the prior art compounds. In yet other embodiments, the compounds of the invention exhibit about 50% to about 100% higher permeability compared with the prior art compounds.

In other embodiments, the compounds of the invention exhibit about 50% to about 500% greater permeability than the prior art compounds. In other embodiments, the compounds of the invention exhibit about 100% to about 500% greater permeability than the prior art compounds. In yet other embodiments, the compounds of the invention exhibit about 200% to about 400% greater permeability. In other embodiments, the compounds of the invention exhibit In yet other embodiments, the compounds of the invention exhibit about 100% to about 300% higher permeability or about 200% to about 300% greater permeability than the prior art compounds. In yet other embodiments, the compounds of the invention exhibit about 100% to about 200% higher permeability compared with the prior art compounds. In other embodiments, the compounds of the invention exhibit about 300% to about 500% higher permeability or about 400% to about 500% higher permeability compared with the prior art compounds.

Compositions of the Invention

In another aspect, the invention provides parasiticidal compositions which comprise at least one anthelmintic compound of formula (IA) of the invention and a pharmaceutically acceptable carrier. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolized $C_8$-$C_{10}$ glycerides or polyglyceryl-6 dioleate.

In addition to these surfactants, the co-surfactants include short-chain alcohols, such as ethanol and propanol.

Some compounds are common to the three components discussed above, i.e., aqueous phase, surfactant and co-surfactant. However, it is well within the skill level of the practitioner to use different compounds for each component of the same formulation. In one embodiment for the amount of surfactant/co-surfactant, the co-surfactant to surfactant ratio will be from about 1/7 to about 1/2. In another embodiment for the amount of co-surfactant, there will be from about 25 to about 75% v/v of surfactant and from about 10 to about 55% v/v of co-surfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the anthelmintic compounds of the invention, the paste can also contain fumed silica; a viscosity modifier; a carrier; optionally, an absorbent; and optionally, a colorant, stabilizer, surfactant, or preservative.

The process for preparing a paste formulation comprises the steps of:

(a) dissolving or dispersing the anthelmintic compound into the carrier by mixing;

(b) adding the fumed silica to the carrier containing the dissolved anthelmintic compound and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste.

The above steps are illustrative, but not limiting. For example, step (a) can be the last step.

In one embodiment of the formulation, the formulation is a paste containing at least one anthelmintic compound of formula (IA), fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (POLYSORBATE 80 or TWEEN 80), and poloxomers (e.g., PLURONIC L 81); an absorbent selected from the group consisting of magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable compositions.

Topical, dermal and subdermal formulations can include emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, a spot-on or pour-on composition, can allow for the inventive compound to be absorbed through the skin to achieve systemic levels, distributed through the sebaceous glands or on the surface of the skin achieving levels throughout the hair coat. When the compound is distributed through the sebaceous glands, they can act as a reservoir, whereby there can be a long-lasting effect (up to several months) effect. Spot-on formulations are typically applied in a localized region which refers to an area other than the entire animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. The pour-on formulations may be advantageously oily, and generally comprise a diluent or vehicle and also a solvent (e.g. an organic solvent) for the active ingredient if the latter is not soluble in the diluent.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. One embodiment of the emollient and/or spreading and/or film-forming agent are those agents selected from the group consisting of:

(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulfosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulfate and sulfonate anions; cetyltrimethylammonium bromide is among the cationic surfactants which can be used, (d) amine salts of formula $N^+HR'R''R'''$ in which the radicals R, R', R" and R'" are optionally independently hydroxylated hydrocarbon radicals; octadecylamine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the anthelmintic compound of formula (I) and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume.

In another embodiment of the invention, the composition can be in ready-to-use solution form as is described in U.S. Pat. No. 6,395,765, incorporated herein by reference. In addition to the anthelmintic compound of the invention, the ready-to-use solution can contain a crystallization inhibitor, an organic solvent and an organic co-solvent.

In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by a the test in which 0.3 ml of a solution comprising 10% (w/v) of an anthelmintic compound of the invention in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystal.

In one embodiment, the organic solvent has a dielectric constant of a range selected from the group consisting of between about 2 to about 35, about 10 to about 35 or about 20 to about 30. In other embodiments, the solvent will have a dielectric constant of between about 2 and about 20, or between about 2 and about 10. The content of this organic solvent in the overall composition represents the complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, this co-solvent may be present in the composition in an organic co-solvent/organic solvent weight/weight (W/W) ratio of about 1/15 to about 1/2. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:

(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsulfoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulfosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and Y is an anion of a strong acid, such as halide, sulfate and sulfonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. POLYSORBATE 80, or polyoxyethylenated alkyl ethers; poly ethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulfate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference), which in one embodiment of the spot-on formulation comprises a solvent and a co-solvent wherein the solvent is selected from the group consisting of acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents and the co-solvent is selected from the group consisting of absolute ethanol, isopropanol or methanol.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

In a particular advantageous embodiment of the invention, the dose of the inventive compounds is about 0.1 mg/kg to about 100 mg/kg. In other embodiments, the dose of the inventive compounds is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the active compounds is about 0.1 mg/kg to 5 mg/kg, 0.1 mg/kg to about 3 mg/kg, or about 0.1 mg/kg to 1.5 mg/kg. In still other embodiments of the invention, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

Another embodiment of the invention is directed toward a method of treating endoparasitic infestation or infection in an animal, comprising administering a therapeutically effective amount of the compound of the invention to the animal in need thereof. The compounds of the invention have been shown to have superior efficacy against endoparasites, and in particular against parasites that are resistant to active agents of the macrocyclic lactone class. For example, a compound of the invention has been shown to have superior efficacy against ivermectin-resistant endoparasites in sheep. FIG. 2 shows that a compound of the invention (compound 3.024) administered at a dosage of 1.5 mg/kg or 3 mg/kg orally had greater than 95% efficacy against ivermectin-resistant strains of *Haemonchus contortus, Ostertagia circumcincta* and *Trichostrongylus columbriformis*. In contrast, ivermectin administered orally at a dose of 0.2 mg/kg was almost completely inactive against *Haemonchus contortus*, less than 30% effective against *Ostertagia circumcincta* and less than 60% effective against *Trichostrongylus columbriformis*. It is surprising that the compounds of the invention have superior efficacy against endoparasites that are resistant to ivermectin, which is one of the most potent active agents known against endo- and ectoparasites.

Accordingly, in another embodiment, the invention provides a method for treating an endoparasitic infestation or infection in an animal, comprising administering a therapeutically effective amount of an anthelmintic compound of the invention in combination with a therapeutically effective amount of activators of invertebrate GABA receptors including an avermectin or milbemycin to the animal in need thereof. Avermectins that may be used in combination with the compounds of the invention include, but are not limited to abamectin, dimadectin, doramectin, emamectin, eprinomectin, ivermectin, latidectin, lepimectin, and selamectin Milbemycins compounds that may be used in combination with the compounds of the invention include, but are not limited to, milbemectin, milbemycin D, moxidectin and nemadectin. Also included are the 5-oxo and 5-oxime derivatives of said avermectins and milbemycins.

In one embodiment, the compounds and compositions of the invention may be used for treating endoparasiticidal infection or infestation an endoparasite including, but not limited to, *Anaplocephala (Anoplocephala), Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria*, and combinations thereof.

In a particularly preferred embodiment of the invention, the compounds and compositions of the invention are used to treat or prevent an infection by *Dirofilaria immitis*. In another embodiment the compounds and compositions of the invention are used to treat or prevent an infection by *Dirofilaria repens*.

In another embodiment of the invention, the helminth is *Haemonchus contortus, Ostertagia circumcincta, Trichostrongylus axei, Trichostrongylus colubriformis, Cooperia curticei, Nematodirus battus* and combinations thereof.

Another embodiment of the invention is directed toward a method of treating ectoparasitic infestation or infection in an animal in need thereof which comprises administering a therapeutically effective amount of the compound of the invention to the animal in need thereof.

In one embodiment, the infection or infestation is caused by fleas, ticks, mites, mosquitoes, flies, lice, blowfly and combinations thereof.

In still another embodiment, invention provides a method for treating an ectoparasitic infestation or infection in an animal, comprising administering a therapeutically effective amount of an anthelmintic compound of the invention in combination with a therapeutically effective amount of an avermectin or milbemycin active agent to the animal in need thereof.

In certain embodiments, the compounds of the invention may be used to protect plants and crops. In other embodiments, the compounds may be used to treat environmental surfaces and structures.

The compounds of formula (IA) or their salts can be employed as such or in the form of their preparations (formulations) as combinations with other active substances, such as, for example, insecticides, attractants, sterilants, acaricides, nematicides, and with growth regulators.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001,903, U.S. Patent publication 2008/0234331, each incorporated herein by reference, the literature known to the person skilled in the art, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

The compounds of formula (IA) can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (IA) can be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologic" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflächenaktive Äthylenoxiddukte" [Surface-active ethylene oxide adducts], Wiss. Verlagsgesell., Stuttgart 1976; Winnacker-Küchler, "Chemische Technologic" [Chemical Technology], Volume 7, C. Hauser Verlag, Munich, 4th Ed. 1986.

Wettable powders are preparations which are uniformly dispersible in water and which, besides the compounds of formula (IA), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (IA) are, for example, ground finely in conventional apparatuses such as hammer mills, blower mills and air jet mills and mixed with the formulation auxiliaries, either concomitantly or thereafter.

Emulsifiable concentrates are prepared, for example, by dissolving the compounds of formula (IA) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (IA) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula (IA).

The concentration of compounds of formula (IA) in wettable powders is, for example, about 10 to about 90% by weight, the remainder to 100% by weight being composed of customary formulation components. In the case of emulsifiable concentrates, the concentration of compounds of formula (IA) can amount to ranges selected from the group consisting of about 1% to about 90% and about 5% to about 80% by weight. Formulations in the form of dusts usually comprise in the range selected from the group consisting of about 1% to about 30% by weight of compounds of formula (IA) and about 5% to about 20% by weight of compounds of formula (IA). For sprayable solutions comprise a range selected from the group consisting of about 0.05% to about 80% by weight of compounds of formula (IA) and about 2% to about 50% by weight of compounds of formula (IA). In the case of water-dispersible granules, the content of compounds of formula (IA) depends partly on whether the compounds of formula (IA) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (IA) mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

Additional pharmaceutically or veterinarily active ingredients may also be added to the compositions of the invention. In some embodiments, the additional active agents may be one or more parasiticidal compounds including acaricides, anthelmintics, endectocides and insecticides. Antiparasitic agents can include both ectoparasiticisal and endoparasiticidal agents.

Additional pharmaceutical agents that may be included in the compositions of the invention with the inventive anthelmintic compounds are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, de slorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan poly sulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, poly sulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, known in the art may be combined with the anthelmintic compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.). On particularly preferred arylpyrazole compound is fipronil.

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, Ga.).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia, all incorporated herein by reference. Naturally occurring milbemycins are described in U.S. Pat. No. 3,950,360 (incorporated herein by reference) as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In another embodiment of the invention, the compositions may include a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR that may be included in the composition is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2 (2-chloro-2-methyl-propyl)-5-(6-iodo-3-pyridylmethoxy) pyridazine-3 (2H)-one. In a particularly preferred embodiment, the compositions of the invention comprise methoprene or pyriproxyfen.

In another embodiment, the compositions of the invention may include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the compositions of the invention may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, □-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethyl-hexyl)-3a,4,7,7a-tetrahydro-4,7-methano-1H-isoindole-1,3 (2H)dione (MGK-264), dipropyl-2,5-pyridinedicarboxylate (MGK-326) and 2-(octylthio)ethanol (MGK-874). In a particularly preferred embodiment, the compositions of the invention will include permethrin in combination with the anthelmintic compounds of the invention.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

In another embodiment, the compositions of the invention may comprise an active agent from the neonicotinoid class of pesticides. The neonicotinoids bind and inhibit insect specific nicotinic acetylcholine receptors. In one embodiment, the neonicotinoid insecticidal agent that may be included in a composition of the invention is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060.

In another embodiment, the compositions of the invention may comprise nitenpyram, another active agent of the neonicotinoid class of pesticides. Nitenpyram has the following chemical structure and is the active ingredient in the oral product CAPSTAR™ Tablets sold by Novartis Animal Health.

In certain embodiments, an insecticidal agent that can be combined with the compositions of the invention is a semicarbazone, such as metaflumizone.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the compositions of the invention. These compounds are described, for example, in WO 2004/024704 and U.S. Pat. No. 7,084,280 (both incorporated by reference); Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964,621, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In another particularly preferred embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, U.S. Pat. No. 7,662,972, WO 2008/122375, WO 2010/003877, WO 2010/003923, WO 2009/025983, WO 2008/150393, WO 2008/154528, WO 2009/045999, WO 2009/051956, WO 2009/126668, WO 2009/0259832, WO 2008/109760, US 2009/0156643, US 2010/0144797, US 2010/0137612, US 2011/009438 and WO 2011/075591, all of which are incorporated herein by reference in their entirety.

Where appropriate the anthelmintic, parasiticidal and insecticidal agent may also be selected from the group of compounds described above as suitable for agrochemical use.

In general, the additional active agent is included in a dose of between about 0.1 µg and about 500 mg. In some embodiments, the additional active agent may be present in a dose of about 1 mg to about 500 mg, about 1 mg to about 300 mg, or about 1 mg to about 100 mg. In other embodiments, the additional active agent may be present in a dose of about 1 mg to about 50 mg or about 1 mg to about 20 mg. In other embodiment of the invention, the additional active agent is included in a dose of about 1 µg to about 10 mg.

In another embodiment of the invention, the additional active agent is included in a dose of about 5 µg/kg to about 50 mg/kg. In other embodiments, the additional active agent may be included in a dose of about 5 µg/kg to about 30 mg/kg, about 5 µg/kg to about 20 mg/kg or about 5 µg/kg to about 10 mg/kg. In still other embodiments, the additional active agent may be included in a dose of about 10 µg/kg to about 1 mg/kg or about 50 µg/kg to about 500 µg/kg of weight of the animal. In yet another embodiment of the invention, the additional active agent is included in a dose between about 0.1 mg/kg to about 10 mg/kg of weight of animal. In still another embodiment of the invention, the additional active agent is included in a dose between about 0.5 mg/kg to 50 mg/kg.

The proportions, by weight, of the aryloazol-2-yl-cyanoethylamino compound and the additional active agent are for example between about 5/1 and about 10,000/1. However, one of ordinary skill in the art would be able to select the appropriate ratio of aryloazol-2-yl-cyanoethylamino compound and the additional active agent for the intended host and use thereof.

Processes of Preparation

Another aspect of the invention is the process of making the novel anthelmintic compounds of the invention. The compounds of the invention may be prepared according to the processes described herein or by the application or adaptation of known methods (i.e. methods heretofore used or described in the chemical literature). For example, in some embodiments, the compounds of the invention may be prepared by methods described in WO 2009/077527 A1, WO 2010/115688 A1, WO 2010/146083 A1, EP 2 468 096 A1 and WO2014/081697 (all incorporated herein by reference), or by adaptation of methods described in these publications.

Example A: Synthesis of Acid Intermediate

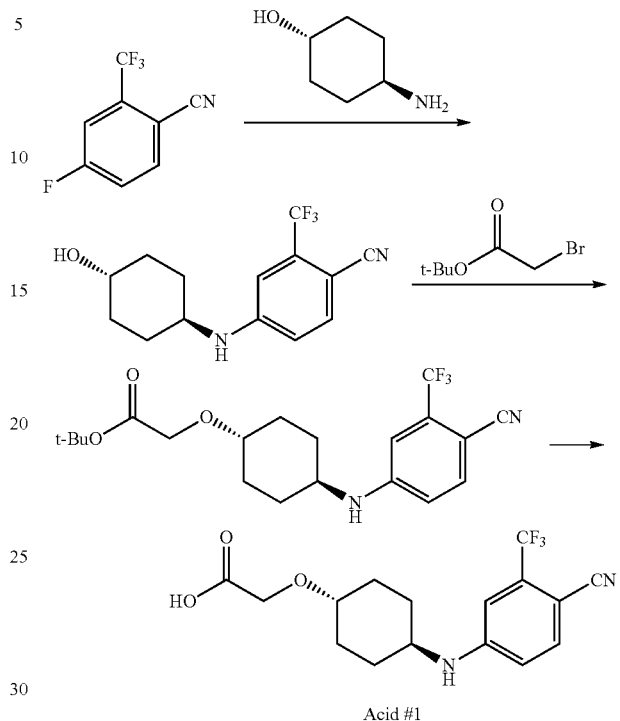

Acid #1

Step 1. Formation of 4-(4-cyano-3-trifluoromethyl-phenylamino)-cyclohexanol

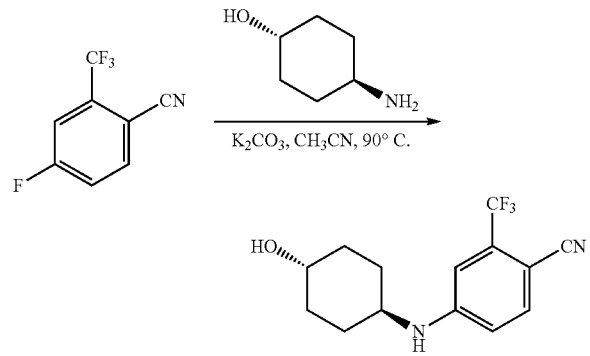

The aryl fluoride (2 g, 10.6 mmol) was placed in a 100 ml round-bottomed flask and stirred in 20 ml acetonitrile at room temperature. Potassium carbonate (3.3 g, 23.9 mmol, 2.2 eq) and 1,4-trans-amino-cyclohexanol (1.34 g, 11.6 mmol, 1.1 eq) were added and the mixture was then heated at 90° C. overnight. The mixture was cooled to room temperature and then concentrated under vacuum. The crude material was purified by silica gel chromatography using 20-40% ethyl acetate in petroleum ether to elute. The product-containing fractions were combined and concentrated under vacuum to provide 1 g (33%) of the desired aniline as a yellow oil. (ES, m/z): [M+H]$^+$ 285.0; $^1$H NMR (300 MHz, DMSO): δ 8.04 (d, J=9.3 Hz, 1H), 7.42 (d, J=7.8

Hz, 1H), 7.06 (d, J=1.8 Hz, 1H), 6.82-6.86 (m, 1H), 4.59 (d, J=4.2 Hz, 1H), 3.39-3.49 (m, 2H), 1.78-1.94 (m, 4H), 1.18-1.32 (m, 4H).

Step 2. Formation of [4-(4-cyano-3-trifluoromethyl-phenylamino)-cyclohexyloxy]-acetic Acid Tert-Butyl Ester

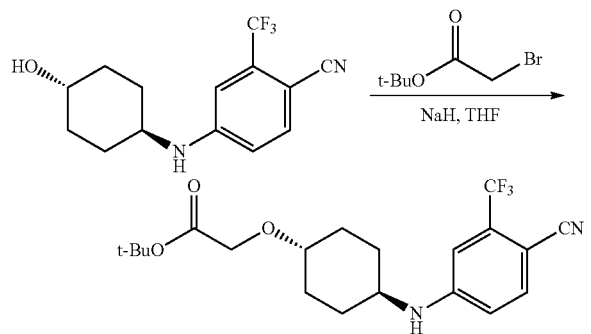

In a 250 ml round-bottomed flask under nitrogen, a solution of 4-(4-nitro-3-trifluoromethyl-phenylamino)-cyclohexanol (1 g, 3.5 mmol) in 20 ml of THF was cooled using an external ice bath. Sodium hydride (254 mg, 10.6 mmol, 3 eq) was then added and the mixture was stirred at ~0-5° C. for 20 minutes before adding the tert-butyl-2-bromoacetate (700 mg, 3.6 mmol, 1 eq). The solution was allowed to warm to room temperature while stirring for 2 hours. The reaction was then diluted using 50 ml of water. The mixture was then extracted with 3×50 ml of ethyl acetate. The organic layers were combined, dried over sodium sulfate, filtered, and concentrated under vacuum. The crude material was purified by silica gel chromatography using 10-20% ethyl acetate in petroleum ether to elute. The product-containing fractions were combined and concentrated under vacuum to provide 0.5 g (36%) of the desired ester as an off-white powder. (ES, m/z): [M+H]$^+$ 399.0. $^1$H NMR (300 MHz, CDCl$_3$): δ 7.53 (d, J=8.7 Hz, 1H), 6.83 (s, 1H), 6.65-6.83 (t, J=6.9 Hz, 1H), 4.01 (s, 2H), 3.36-3.42 (m, 2H), 2.12-2.15 (m, 4H), 1.49 (s, 9H), 1.24-1.32 (m, 4H).

Step 3. Formation of [4-(4-cyano-3-trifluoromethyl-phenylamino)-cyclohexyloxy]-acetic Acid

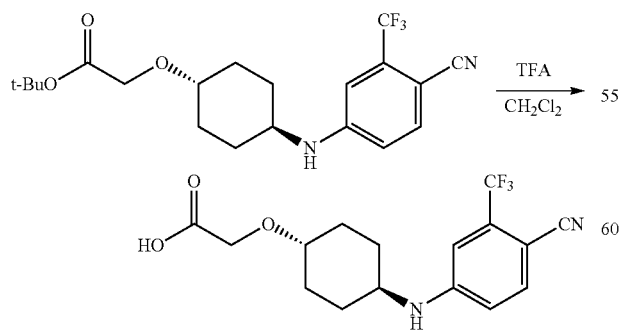

To a solution of tert-butyl 2-(4-(4-nitro-3-(trifluoromethyl)phenylamino)cyclohexyloxy)acetate (150 mg, 0.38 mmol) in dichloromethane (20 ml) was added trifluoroacetic acid (500 mg, 4.4 mmol, 2.6 eq). The resulting solution was stirred for 2 hours at room temperature and then concentrated under vacuum. The residue was dissolved in water (10 ml) and then extracted with n-butanol (2×50 ml). The organic layers were combined, dried over sodium sulfate, filtered, and concentrated under vacuum. The crude material was purified by silica gel chromatography using 3% methanol in dichloromethane to elute. The product-containing fractions were combined and concentrated under vacuum to afford 41.7 mg (32%) of 2-(4-(4-cyano-3-(trifluoromethyl)phenylamino)cyclohexyloxy)acetic acid as a light yellow oil. (ES, m/z): [M+H]$^+$ 343.1; $^1$H NMR (300 MHz, CD$_3$OD): δ 7.58 (d, J=8.7 Hz, 1H), 6.94 (d, J=2.1 Hz, 1H), 6.79-6.83 (dd, J=2.1 Hz, 8.7 Hz, 1H), 4.12 (s, 2H), 3.35-3.51 (m, 2H), 2.04-2.20 (m, 4H), 1.24-1.53 (m, 4H).

Example B: Synthesis of Acid Intermediate

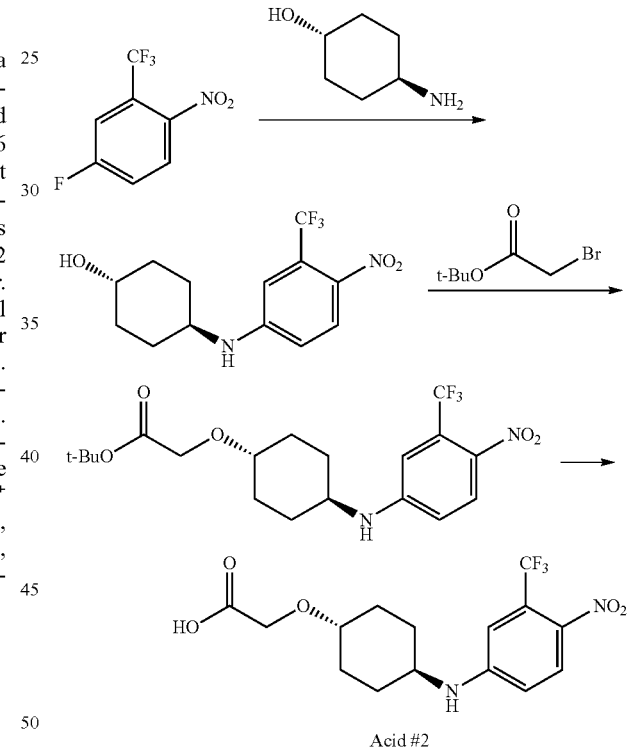

Acid #2

Step 1. Formation of 4-(4-nitro-3-trifluoromethyl-phenylamino)-cyclohexanol

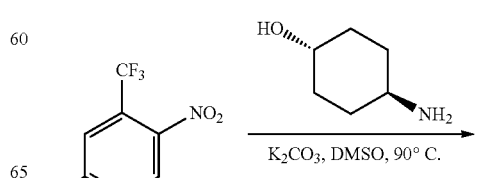

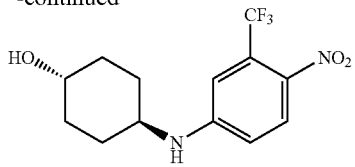

The aryl fluoride (500 mg, 2.4 mmol) was placed in a 100 ml round-bottomed flask and stirred in 10 ml DMSO at room temperature. Potassium carbonate (661 mg, 4.75 mmol, 2 eq) and 1,4-trans-amino-cyclohexanol (413 mg, 3.59 mmol, 1.5 eq) were added and the mixture was then heated at 90° C. overnight. The mixture was cooled to room temperature and then partitioned between water and ethyl acetate (3×80 ml). The organic layers were combined, washed with saturated aqueous sodium chloride, dried over sodium sulfate, filtered, and concentrated under vacuum to provide 400 mg (55%) of the desired aniline as a yellow solid. On both the 10 g and 50 g scale, similar reaction conditions (using acetonitrile as the solvent) provided a 76% yield of the desired product.

Step 2. Formation of [4-(4-nitro-3-trifluoromethyl-phenylamino)-cyclohexyloxy]-acetic Acid Tert-Butyl Ester

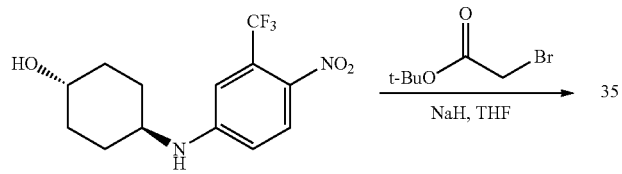

In a 250 ml round-bottomed flask under nitrogen, a solution of 4-(4-nitro-3-trifluoromethyl-phenylamino)-cyclohexanol (10 g, 33 mmol) in 150 ml of THF was cooled using an external ice bath. Sodium hydride (3.65 g, 152 mmol, 3 eq) was then added and the mixture was stirred at ~0° C. for 30 minutes before adding the tert-butyl-2-bromoacetate (9.6 g, 49.2 mmol, 1.5 eq). The solution was allowed to warm to room temperature while stirring overnight. The reaction was then diluted using 500 ml of ice-water. The mixture was then extracted with 3×200 ml of ethyl acetate. The organic layers were combined, dried over sodium sulfate, filtered, and concentrated under vacuum. The crude material was purified by silica gel chromatography using 10% ethyl acetate in petroleum ether to elute. The product-containing fractions were combined and concentrated under vacuum to provide 5 g (36%) of the desired ester as a yellow oil. Repeating this reaction on a larger scale yielded 51% of the desired product.

Step 3. Formation of [4-(4-nitro-3-trifluoromethyl-phenylamino)-cyclohexyloxy]-acetic Acid

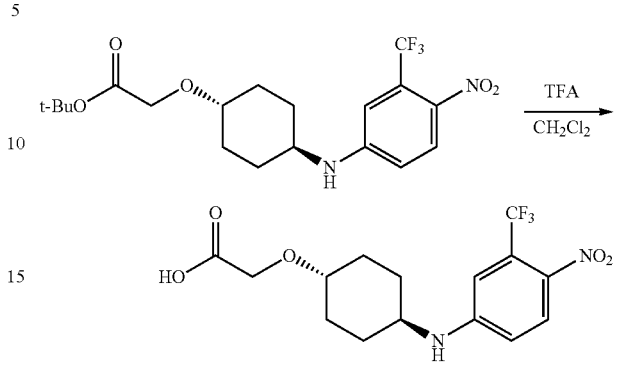

To a solution of tert-butyl 2-(4-(4-nitro-3-(trifluoromethyl)phenylamino)cyclohexyloxy)acetate (1 g, 2.39 mmol) in dichloromethane (30 ml) was added trifluoroacetic acid (5 ml). The resulting solution was stirred for 2 hours at room temperature and then concentrated under vacuum. The resulting solution was diluted with dichloromethane (200 ml), washed with water (100 ml), dried over anhydrous sodium sulfate, filtered, and then concentrated under vacuum to afford 800 mg (92%) of 2-(4-(4-nitro-3-(trifluoromethyl)phenylamino)cyclohexyloxy)acetic acid as yellow oil. $^1$H NMR (300 MHz, DMSO): δ 12.5 (broad s, 1H), 8.07 (d, J=9.3 Hz, 1H), 7.45 (d, J=7.8 Hz, 1H), 7.07 (s, 1H), 6.87 (dd, J=2.4 Hz, 9.3 Hz, 1H), 4.03 (s, 2H), 3.32-3.46 (m, 2H), 1.91-2.03 (m, 4H), 1.17-1.41 (m, 4H).

Example C: Synthesis of Amine Intermediate

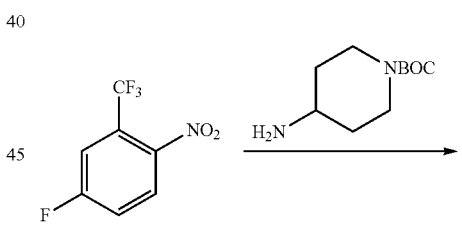

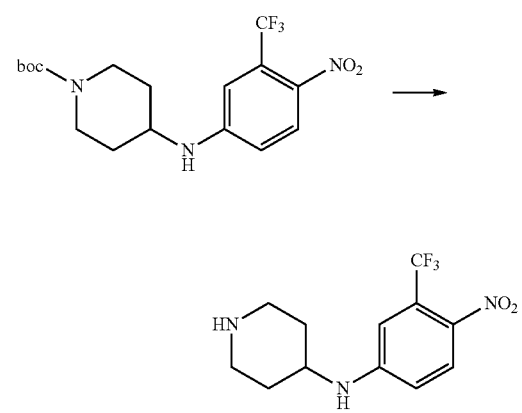

Step 1. Formation of tert-butyl 4-[[4-nitro-3-(trifluoromethyl)phenyl]amino]piperidine-1-carboxylate

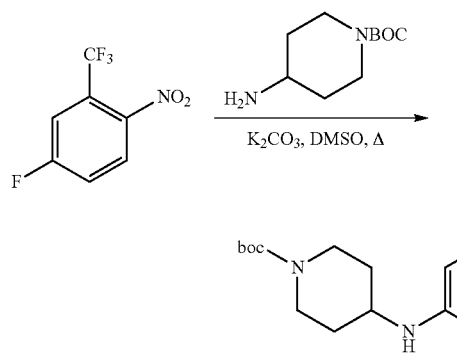

To a solution of 4-fluoro-1-nitro-2-(trifluoromethyl)benzene (5 g, 24 mmol) in DMSO (50 ml) was added tert-butyl 4-aminopiperidine-1-carboxylate (4.78 g, 23.9 mmol, 1 eq.) and potassium carbonate (9.9 g, 72 mmol, 3 eq.). The resulting mixture was stirred with heating overnight at 100° C. (oil bath) and then diluted with water (300 ml). The solids were collected by filtration to afford tert-butyl 4-[[4-nitro-3-(trifluoromethyl)phenyl]amino]piperidine-1-carboxylate as a yellow powder (8 g, 86%); (ES, m/z): [M+H]$^+$ 390.0; $^1$H NMR (300 MHz, DMSO-d6): δ 8.06 (d, J=9.3 Hz, 1H), 7.47 (d, J=7.8 Hz, 1H), 7.08 (d, J=2.1 Hz, 1H), 6.89 (dd, J=2.4, 9.3 Hz, 1H), 3.87 (d, J=13.5 Hz, 2H), 3.68 (m, 1H), 2.95 (m, 2H), 2.54 (s, 0.6H), 1.89 (m, 2H), 1.39 (s, 9H), 1.28 (m, 2H).

Step 2. Formation of N-[4-nitro-3-(trifluoromethyl)phenyl]piperidin-4-amine (Amine #1)

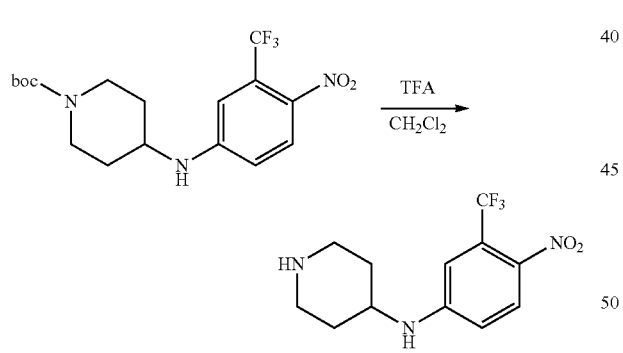

To a solution of tert-butyl 4-[[4-nitro-3-(trifluoromethyl)phenyl]amino]piperidine-1-carboxylate (1 g, 2.6 mmol) in dichloromethane (10 mL) was added trifluoroacetic acid (3 ml). The solution was stirred for 2 hours at room temperature and then concentrated under vacuum. The crude material was diluted with water (50 ml), adjusted pH to 9 with sodium bicarbonate (saturated aqueous), and extracted with dichloromethane (3×100 ml). The organic layers were combined and dried over anhydrous sodium sulfate, filtered, and concentrated under vacuum to afford N-[4-nitro-3-(trifluoromethyl)phenyl]piperidin-4-amine as a yellow powder (800 mg, crude); (ES, m/z): [M+H]$^+$ 290.1; $^1$H NMR (300 MHz, DMSO-d6): δ 8.08 (d, J=9.0 Hz, 1H), 7.20-7.80 (br s), 7.60 (d, J=7.8 Hz, 1H), 7.11 (d, J=2.4 Hz, 1H), 6.91 (dd, J=2.4, 9.0 Hz, 1H), 3.70 (m, 1H), 3.22 (d, J=12.6 Hz, 2H), 2.91 (dd, J=10.5, 11.4 Hz, 2H), 1.99 (d, J=11.4 Hz, 2H), 1.52 (m, 2H).

Example D: Synthesis of Amine Intermediate

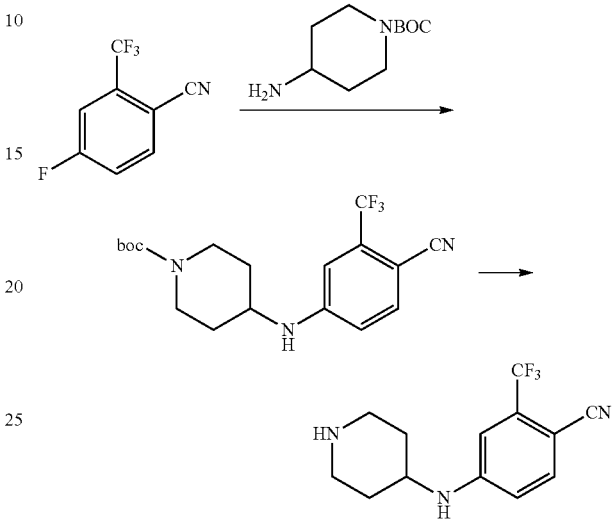

Step 1. Formation of tert-butyl 4-[[4-cyano-3-trifluoromethyl)phenyl]amino]piperidine-1-carboxylate

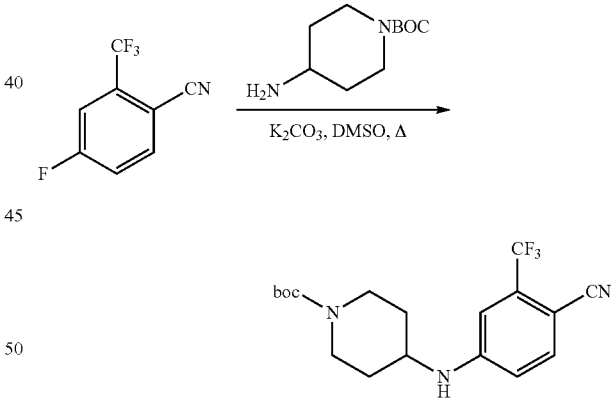

To a solution of 4-fluoro-2-(trifluoromethyl)benzonitrile (5 g, 26 mmol) in DMSO (50 ml) was added tert-butyl 4-aminopiperidine-1-carboxylate (5.3 g, 26.5 mmol, 1 eq.) and potassium carbonate (7.3 g, 52.8 mmol, 2 eq.). The resulting solution was stirred with heating overnight at 100° C. (oil bath). The resulting solution was diluted with of ethyl acetate (300 ml) and washed with sodium chloride (sat., 300 ml). The organic layer was dried over anhydrous sodium sulfate, filtered, and concentrated under vacuum to give a residue, which was applied onto a silica gel column and eluted with ethyl acetate to afford tert-butyl 4-[[4-cyano-3-(trifluoromethyl)phenyl]amino]piperidine-1-carboxylate as a white powder (5 g, 51%). (ES, m/z): [M+H]$^+$ 370.1.

Step 2. Formation of N-[4-cyano-3-(trifluoromethyl)phenyl]piperidin-4-amine (Amine #2)

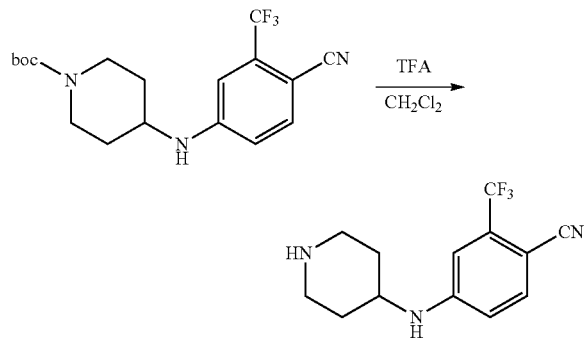

To a solution of tert-butyl 4-[[4-cyano-3-(trifluoromethyl)phenyl]amino]piperidine-1-carboxylate (150 mg, 0.41 mmol) in dichloromethane (4 mL) was added trifluoroacetic acid (1 ml). The solution was stirred for 2 hours at room temperature and then concentrated under vacuum. The crude material was diluted with 100 ml of EtOAc and washed with sodium bicarbonate (saturated aqueous) and then brine. The organic layer was dried over anhydrous sodium sulfate, filtered, and concentrated under vacuum. The crude solids were recrystallized from EtOAc/PE to afford N-[4-cyano-3-(trifluoromethyl)phenyl]piperidin-4-amine as a yellow powder (93.1 mg, 85% yield); (ES, m/z): [M+H]$^+$ 270.1; $^1$H NMR (300 MHz, CDCl$_3$): δ 7.69 (d, J=8.7 Hz, 1H), 7.16 (d, J=7.8 Hz, 1H), 7.03 (d, J=1.2 Hz, 1H), 6.85 (dd, J=2.1, 8.7 Hz, 1H), 3.42 (m, 1H), 2.94 (m, 2H), 2.53 (m, 2H), 1.82 (d, J=10.2 Hz, 2H), 1.27 (m, 2H).

Example 1—Synthesis of Compound 004

Synthesis of 4-nitro-N-[4-[(5-[4-[(4-fluorophenyl)methyl]piperazin-1-yl]pyridin-3-yl)oxy]cyclohexyl]-3-(trifluoromethyl)aniline (Compound 4)

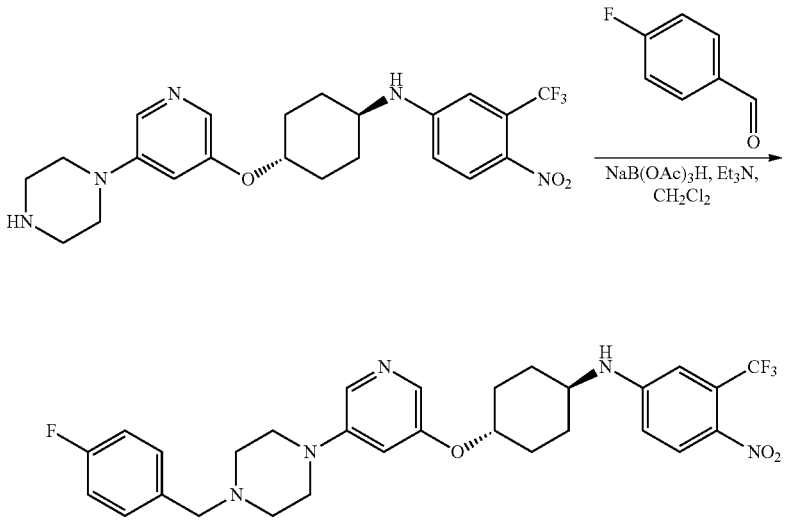

To a solution of 4-nitro-N-[4-[[5-(piperazin-1-yl)pyridin-3-yl]oxy]cyclohexyl]-3-(trifluoromethyl)aniline (200 mg, 0.43 mmol) in dichloromethane (20 mL) was added triethylamine (0.2 mL) and 4-fluorobenzaldehyde (59 mg, 0.48 mmol, 1.1 eq.). This was followed by the addition of sodium triacetoxyborohydride (136 mg, 0.64 mmol, 1.50 eq.) and the contents were stirred at room temperature for 12 hours. The reaction was then quenched by the addition of 20 mL of saturated ammonium chloride. The resulting mixture was extracted with 3×20 mL of dichloromethane. The organic layers were combined, dried over anhydrous sodium sulfate, and concentrated under vacuum to give a residue which was purified by a silica gel column eluting with ethyl acetate/petroleum ether (1:1) to afford 4-nitro-N-[4-[(5-[4-[(4-fluorophenyl)methyl]piperazin-1-yl]pyridin-3-yl)oxy]cyclohexyl]-3-(trifluoromethyl)aniline (70.3 mg, 29%) of as a yellow solid. (ES, m/z): [M+H]$^+$ 574; NMR (300 MHz, DMSO): δ 8.08 (d, J=9.3 Hz, 1H), 7.89 (d, J=2.4 Hz, 1H), 7.76 (d, J=2.1 Hz, 1H), 7.52 (d, J=7.5 Hz, 1H), 7.38-7.34 (m, 2H), 7.18-7.10 (m, 3H), 6.89-6.85 (m, 2H), 4.49-4.42 (m, 1H), 3.51 (m & s, 3H), 3.20-3.17 (m, 4H), 2.51-2.47 (m, 4H), 2.09-2.02 (m, 4H), 1.59-1.42 (m, 4H).

Example 2—Synthesis of Compound 012

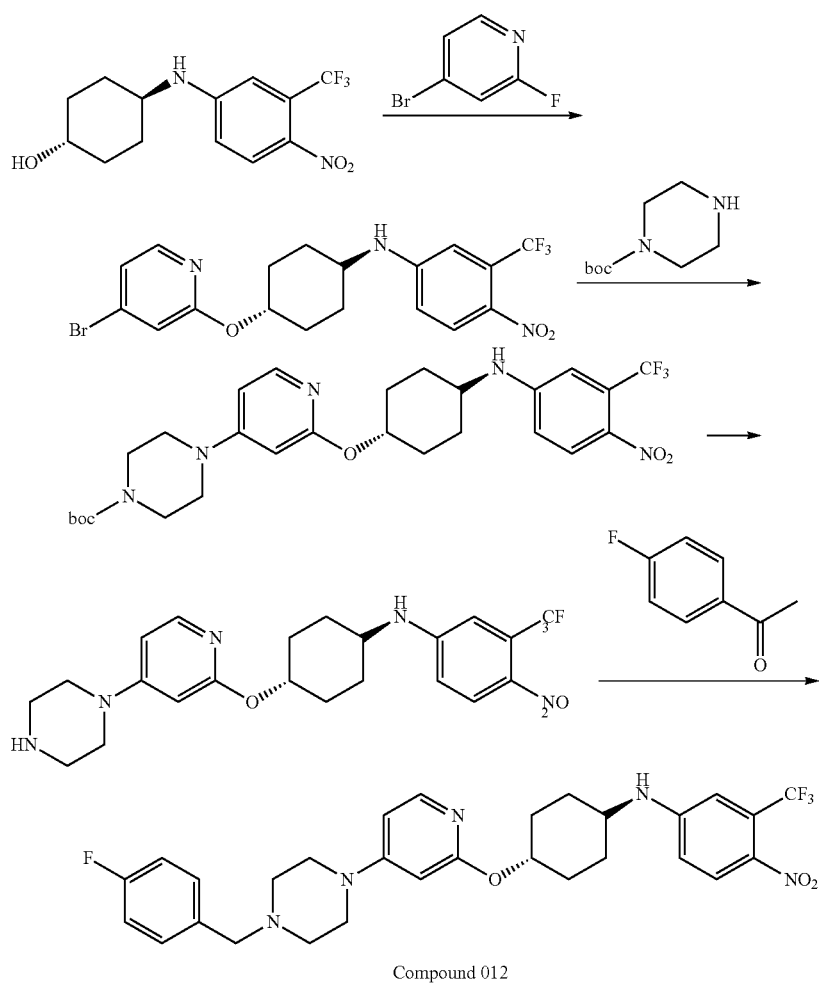

Compound 012

Step 1—Synthesis of N-(4-(4-bromopyridin-2-yloxy)cyclohexyl)-4-nitro-3-(trifluoro-methyl)benzenamine

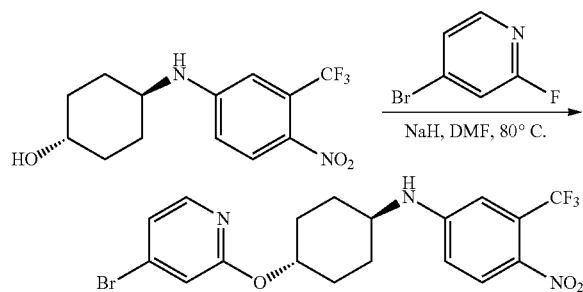

To a solution of 4-[[4-nitro-3-(trifluoromethyl)phenyl]amino]cyclohexan-1-ol (15 g, 49 mmol) in N,N-dimethylformamide (50 mL) was added sodium hydride (5.9 g, 246 mmol) The mixture was stirred for 30 minutes at 0° C. To this was added 4-bromo-2-fluoropyridine (8.7 g, 49 mmol). The resulting solution was stirred for 2 hours at 65° C. The reaction was then quenched by the addition of water. The resulting solution was extracted with ethyl acetate and the organic layers were combined and dried over anhydrous sodium sulfate before concentration under vacuum. The residue was applied onto a silica gel column and eluted with ethyl acetate/petroleum ether (1:20→1:5). Concentration of the product containing fractions provided 15.3 g (67%) of 4-nitro-N-[4-[(4-bromopyridin-2-yl)oxy]cyclohexyl]-3-(trifluoromethyl)aniline as a yellow solid; $^1$H NMR (300 MHz, DMSO): δ 8.08-8.05 (m, 2H), 7.52-7.49 (m, 1H), 7.21-7.09 (m, 3H), 6.90-6.86 (m, 1H), 5.05-4.91 (m, 1H), 3.61-3.51 (m, 1H), 2.10-2.08 (m, 4H), 1.66-1.54 (m, 2H), 1.45-1.33 (m, 2H).

Step 2—Synthesis of tert-butyl 4-(2-(4-(4-nitro-3-(trifluoromethyl)phenylamino) cyclohexyloxy)pyridin-4-yl)piperazine-1-carboxylate

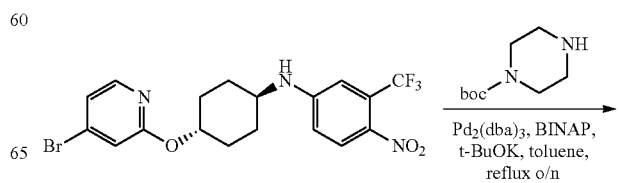

145

-continued

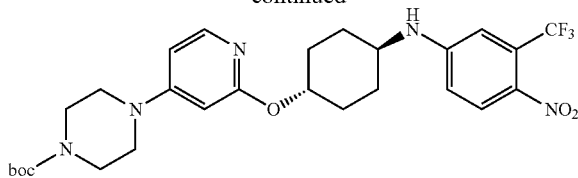

146

-continued

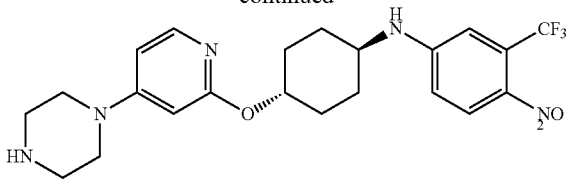

To a solution of 4-nitro-N-[4-[(4-bromopyridin-2-yl)oxy] cyclohexyl]-3-(trifluoromethyl) aniline (10 g, 22 mmol) in toluene (100 mL) was added tert-butyl piperazine-1-carboxylate (8.07 g, 43.3 mmol), BINAP (2.7 g, 4.3 mmol), potassium tert-butoxide (4.87 g, 43.4 mmol), and $Pd_2(dba)_3$ (2.2 g, 2.2 mmol). The resulting solution was heated at reflux overnight. The solids were filtered out. The filter cake was washed with ethyl acetate. The resulting filtrate was concentrated under vacuum. The residue was applied onto a silica gel column and eluted with ethyl acetate/petroleum ether (1:10→1:1) and the product containing fractions were combined and concentrated under vacuum. The crude product was purified by re-crystallization from methanol. The product containing fractions were combined and concentrated under vacuum to provide 10 g (81%) of tert-butyl 4-(2-[[4-[[4-nitro-3-(trifluoromethyl)phenyl]amino]cyclohexyl]oxy]pyridin-4-yl)piperazine-1-carboxylate as a yellow solid; $^1$H NMR (300 MHz, $CDCl_3$): δ 8.04 (d, J=9.0 Hz, 1H), 7.88 (d, J=6.3 Hz, 1H), 6.89 (d, J=2.4 Hz, 1H), 6.69-6.40 (m, 1H), 6.39-6.37 (m, 1H), 6.04 (d, J=2.1 Hz, 1H), 5.08-5.06 (m, 1H), 4.59 (d, J=7.8 Hz, 1H), 3.58-3.56 (m, 4H), 3.49-3.45 (m, 1H), 3.33-3.29 (m, 4H), 2.26-2.18 (m, 4H), 1.64-1.60 (m, 2H), 1.57-1.45 (m, 11H).

Step 3—Synthesis of 4-nitro-N-(4-(4-(piperazin-1-yl)pyridin-2-yloxy)cyclohexyl)-3-(trifluoromethyl) benzenamine

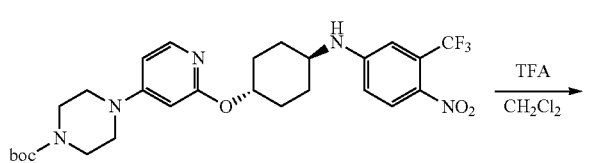

To a solution of tert-butyl 4-[2-[(4-[[4-nitro-3-(trifluoromethyl)phenyl]amino]cyclohexyl) oxy]pyridin-4-yl]piperazine-1-carboxylate (8.8 g, 16 mmol) in dichloromethane (40 mL) was added trifluoroacetic acid (10 mL). The resulting solution was stirred for 3 hours at room temperature and then concentrated under vacuum. The residue was diluted with dichloromethane (100 mL). The pH value of the solution was adjusted to 8-9 with saturated sodium bicarbonate. The solids were collected by filtration. The product containing fractions were combined and concentrated under vacuum to provide 8.2 g (91%) of 4-nitro-N-(4-[[4-(piperazin-1-yl)pyridin-2-yl]oxy]cyclohexyl)-3-(trifluoromethyl) aniline (TFA salt) as a yellow solid; $^1$H NMR (300 MHz, DMSO): δ 8.07 (d, J=9.0 Hz, 1H), 7.85 (d, J=6.3 Hz, 1H), 7.53 (d, J=7.8 Hz, 1H), 7.10 (s, 1H), 6.90-6.85 (m, 1H), 6.59-6.57 (m, 1H), 6.18 (d, J=1.8 Hz, 1H), 4.50-4.93 (m, 1H), 3.53-3.50 (m, 5H), 3.19-3.15 (m, 4H), 2.11-2.00 (m, 4H), 1.60-1.33 (m, 4H).

Step 4—Synthesis of N-[4-[(4-[4-[(4-fluorophenyl) methyl]piperazin-1-yl]pyridin-2-yl)oxy]cyclohexyl]-4-nitro-3-(trifluoromethyl)aniline (Compound 12)

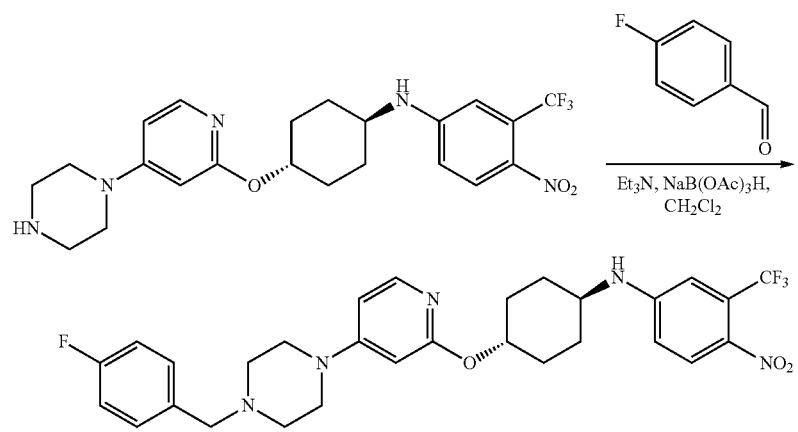

Into a 25-mL round-bottom flask, was placed 4-nitro-N-(4-[[4-(piperazin-1-yl)pyridin-2-yl]oxy]cyclohexyl)-3-(trifluoromethyl)aniline (TFA salt, 100 mg, 0.17 mmol), dichloromethane (10 mL), triethylamine (0.2 mL), and 4-fluorobenzaldehyde (26 mg, 0.21 mmol, 1.2 eq.). The mixture was stirred for 3 hours. To this was added sodium triacetoxyborohydride (134 mg, 3.6 eq.). The resulting solution was stirred for 1 hour at room temperature. The reaction was then quenched by the addition of 20 mL of water. The resulting solution was extracted with 10 mL of dichloromethane. The organic layers were combined and concentrated under vacuum. The residue was applied onto a silica gel column and eluted with ethyl acetate/petroleum ether (2:1). The product containing fractions were combined to provide 72.5 mg (73%) as a yellow solid; (ES, m/z): $[M+H]^+$ 573.24; NMR (300 MHz, DMSO): δ 8.07 (d, J=9.0 Hz, 1H), 7.77 (d, J=6.0 Hz, 1H), 7.52-7.36 (m, 1H), 7.38-7.33 (m, 2H), 7.19-7.09 (m, 3H), 6.89-6.85 (m, 1H), 6.52-6.49 (m, 1H), 6.06 (d, J=2.4 Hz, 1H), 4.97-4.90 (m, 1H), 3.54-3.49

(m, 3H), 3.26-3.25 (m, 4H), 2.44-2.41 (m, 4H), 2.09-1.98 (m, 4H), 1.58-1.51 (m, 2H), 1.47-1.43 (m, 2H).

Example 3—Synthesis of Compound 141

Synthesis of 4-nitro-N-[4-[[6-(4-[[4-(trifluoromethyl)phenyl]methyl]piperazin-1-yl)pyridin-2-yl]oxy]cyclohexyl]-3-(trifluoromethyl)aniline (Compound 141)

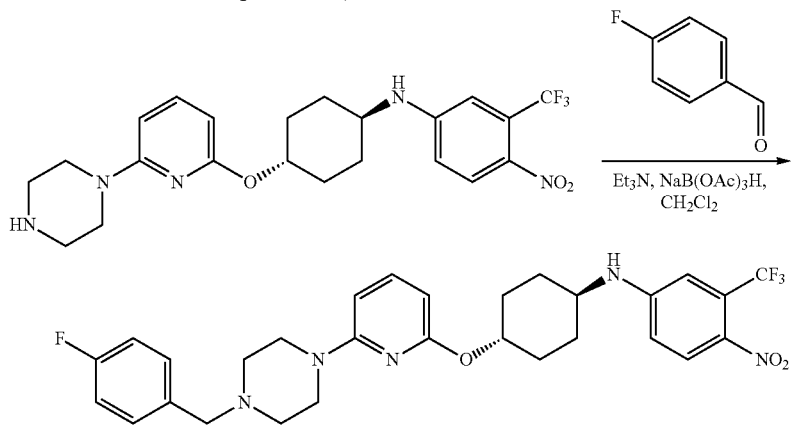

Into a 40-mL round-bottom flask, was placed a solution of 4-nitro-N-[4-[[6-(piperazin-1-yl)pyridin-2-yl]oxy]cyclohexyl]-3-(trifluoromethyl)aniline (100 mg, 0.21 mmol) in dichloromethane (10 mL), 4-(trifluoromethyl)benzaldehyde (45 mg, 0.26 mmol, 1.2 eq.), and triethylamine (0.2 mL). The mixture was stirred for 1 hour at room temperature. To the mixture was added sodium triacetoxyborohydride (164 mg, 3.7 eq.). The resulting solution was stirred for 30 minutes at room temperature and then quenched by the addition of 10 mL of water. The resulting mixture was concentrated under vacuum. The residue was purified by thin layer chromatography developed with ethyl acetate/petroleum ether (1/5). The product containing fractions were combined and concentrated under vacuum to provide 132.4 mg (99%) as a yellow solid. (ES, m/z): 624; NMR (DMSO, 300 MHz) δ: 8.07 (d, J=9.3 Hz, 1H), 7.72-7.69 (d, J=8.1 Hz, 2H), 7.59-7.56 (d, J=8.1 Hz, 2H), 7.45-7.40 (m, 2H), 7.07 (s, 1H), 6.89-6.85 (m, 1H), 6.28 (d, J=8.1 Hz, 1H), 6.01 (d, J=7.8 Hz, 1H), 4.85-4.82 (m, 1H), 3.62 (s, 3H), 3.46-3.32 (m, 5H), 2.49-2.47 (m, 4H), 2.12-1.99 (m, 4H), 1.57-1.36 (m, 4H).

Example 4—Synthesis of Compound 019

Synthesis of 1-[4-(5-[[4-[[4-nitro-3-(trifluoromethyl)phenyl]amino]cyclohexyl]oxy]pyridin-3-yl)piperazin-1-yl]pentan-1-one (Compound 19)

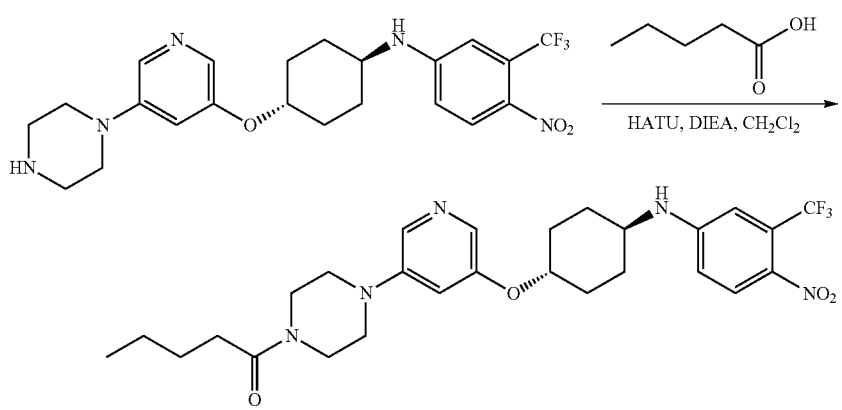

To a solution of 4-nitro-N-[4-[[5-(piperazin-1-yl)pyridin-3-yl]oxy]cyclohexyl]-3-(trifluoromethyl)aniline (200 mg, 0.43 mmol) in dichloromethane (20 mL) was added HATU (327 mg, 0.86 mmol, 2 eq.), pentanoic acid (44 mg, 0.43 mmol, 1 eq.) and DIEA (0.5 mL, 3 eq.). The resulting solution was stirred for 2 h at room temperature, the solids were filtered off, and the filtrate was concentrated under vacuum. The residue was purified with a silica gel column eluting with ethyl acetate/petroleum ether (1:1) to afford 1-[4-(5-[[4-[[4-nitro-3-(trifluoromethyl)phenyl]amino]cyclohexyl]oxy]pyridin-3-yl)piperazin-1-yl]pentan-1-one (59.8 mg, 25%) as a yellow solid. (ES, m/z): [M+H]+ 550; 1H NMR (300 MHz, DMSO): δ 8.08 (d, J=9.3 Hz, 1H), 7.91 (d, J=2.1 Hz, 1H), 7.79 (d, J=2.1 Hz, 1H), 7.53 (d, J=7.8 Hz, 1H), 7.11 (s, 1H), 6.92-6.86 (m, 2H), 4.51-4.44 (m, 1H), 3.60-3.53 (m, 5H), 3.21-3.16 (m, 4H), 2.37-2.32 (m, 2H), 2.14-1.94 (m, 4H), 1.60-1.20 (m, 8H), 0.90 (m, 3H).

Example 5—Synthesis of Compound 005

Synthesis of 2-cyclopentyl-1-(4-(2-(4-(4-nitro-3-(trifluoromethyl)phenylamino) cyclohexyl oxy) pyridin-4-yl)piperazin-1-yl)ethanone (Compound 5)

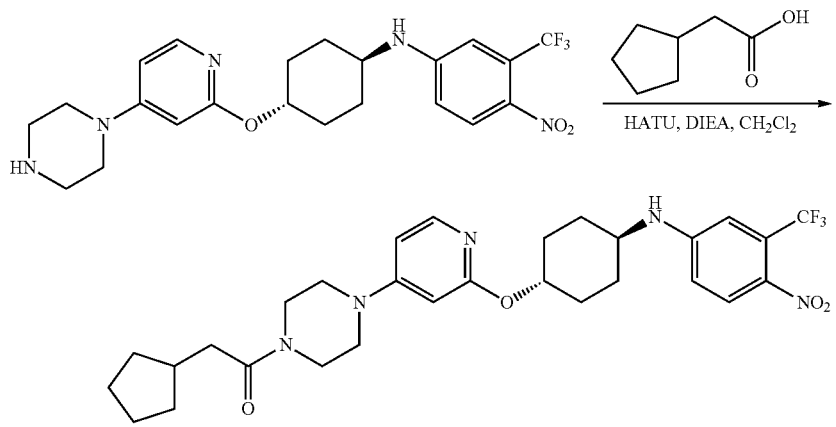

To a solution of 2-cyclopentylacetic acid (40 mg, 0.31 mmol) in dichloromethane (10 mL) was added DIEA (268 mg, 2.07 mmol), HATU (197 mg, 0.52 mmol), and 4-nitro-N-(4-[[4-(piperazin-1-yl)pyridin-2-yl]oxy]cyclohexyl)-3-(trifluoromethyl)aniline (TFA salt, 150 mg, 0.26 mmol). The resulting solution was stirred overnight at room temperature. The reaction was then quenched by the addition of water (20 mL) and extracted with dichloromethane (10 mL). The organic layers were combined and concentrated under vacuum. The residue was applied onto a silica gel column and eluted with ethyl acetate/petroleum ether (2:1). The product containing fractions were combined and concentrated under vacuum to provide 93.3 mg (63%) of 2-cyclopentyl-1-(4-(2-(4-(4-nitro-3-(trifluoromethyl)phenylamino) cyclohexyloxy)pyridin-4-yl)piperazin-1-yl) ethanone as a yellow solid. (ES, m/z): [M+H]+ 576; 1H NMR (300 MHz, DMSO): δ 8.07 (d, J=9.3 Hz, 1H), 7.80 (d, J=6.0 Hz, 1H), 7.51 (d, J=7.5 Hz, 1H), 7.10 (d, J=2.1 Hz, 1H), 6.90-6.86 (m, 1H), 6.54-6.52 (m, 1H), 6.09 (d, J=1.8 Hz, 1H), 5.09-4.85 (m, 1H), 3.61-3.52 (m, 5H), 3.38-3.20 (m, 3H), 2.13 (d, J=7.8 Hz, 2H), 2.10-1.99 (m, 5H), 1.98-1.88 (m, 2H), 1.78-1.36 (m, 9H), 1.16-1.09 (m, 2H).

Example 6—Synthesis of Compound 029

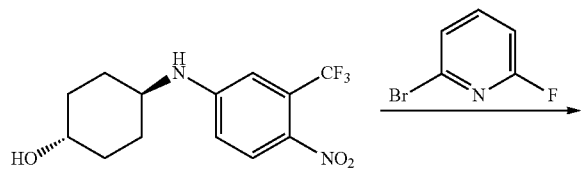

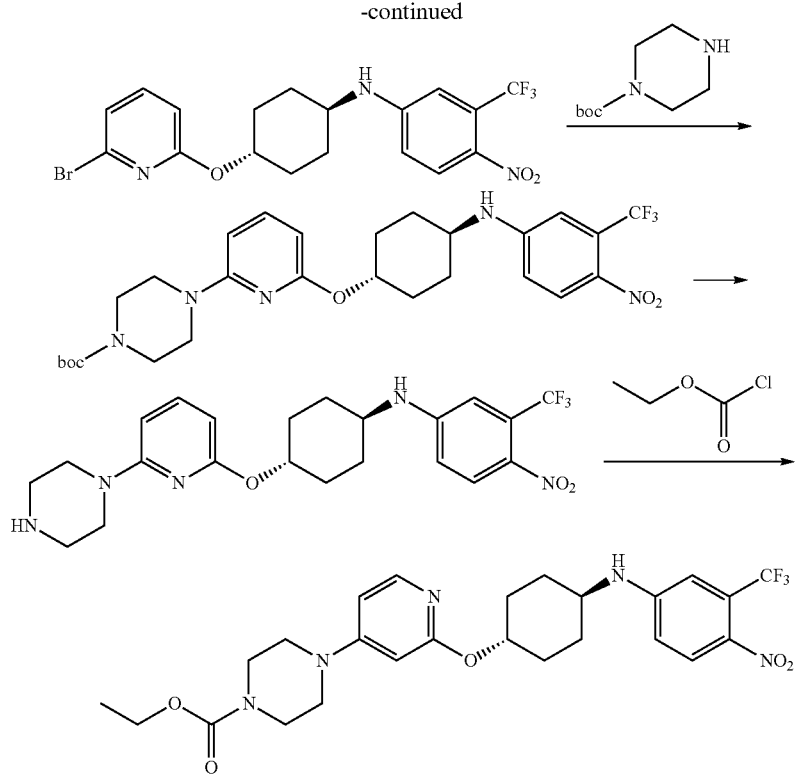

Compound 29

Step 1—Synthesis of 4-nitro-N-[4-[(6-bromopyridin-2-yl)oxy]cyclohexyl]-3-(trifluoromethyl)aniline

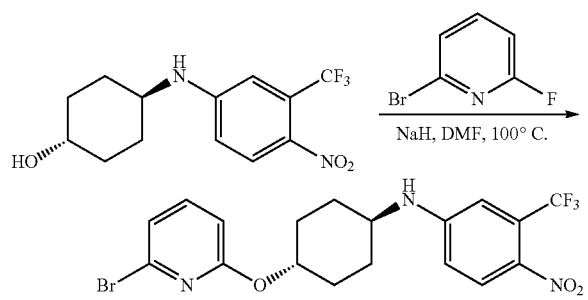

Into a 100-mL round-bottom flask purged and maintained with an inert atmosphere of nitrogen, was placed a solution of 4-[[4-nitro-3-(trifluoromethyl)phenyl]amino]cyclohexan-1-ol (1.0 g, 3.3 mmol) in N,N-dimethylformamide (10 mL). This was followed by the addition of sodium hydride (60%, 400 mg, 10 mmol, 3 eq.) at 0° C. over a 30 minute period. To this mixture was added 2-bromo-6-fluoropyridine (697 mg, 3.96 mmol, 1.2 eq.). The resulting solution was stirred for 2 hours at 100° C. and then cooled to room temperature before quenching with 100 mL of water. The resulting solution was extracted with 2×100 mL of ethyl acetate and the organic layers were combined. The resulting mixture was washed with 1×100 mL of brine. The organic layer was dried over anhydrous sodium sulfate and concentrated under vacuum. The residue was purified by preparative TLC eluting with ethyl acetate:petroleum ether (1:5). The product containing fractions were combined and concentrated under vacuum to provide 78.2 mg (51%) of 4-nitro-N-[4-[(6-bromopyridin-2-yl)oxy]cyclohexyl]-3-(trifluoromethyl) aniline as a yellow solid. (ES, m/z): 460; $^1$H NMR (DMSO, 300 MHz) δ: 8.08 (d, J=9.0 Hz, 1H), 7.68-7.63 (m, 1H), 7.51 (d, J=7.8 Hz, 1H), 7.21-7.19 (m, 1H), 7.10 (s, 1H), 6.91-6.83 (m, 2H), 4.95-4.88 (m, 1H), 3.58-3.56 (m, 1H), 2.14-2.00 (m, 4H), 1.67-1.63 (m, 2H), 1.58-1.47 (m, 2H).

Step 2—Synthesis of tert-butyl 4-(6-[[4-[[4-nitro-3-(trifluoromethyl)phenyl]amino]cyclohexyl]oxy]pyridin-2-yl)piperazine-1-carboxylate

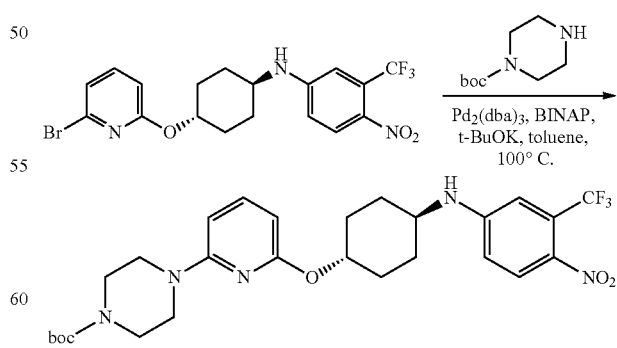

Into a 50-mL round-bottom flask purged and maintained with an inert atmosphere of nitrogen, was placed 4-nitro-N-[4-[(6-bromopyridin-2-yl)oxy]cyclohexyl]-3-(trifluoromethyl)aniline (500 mg, 1.09 mmol), tert-butylpiperazine-1- carboxylate (810 mg, 4.35 mmol, 4 eq.), Pd$_2$(dba)$_3$·CHCl$_3$ (80 mg, 0.08 mmol, 0.07 equiv), toluene (5 mL), BINAP (80 mg, 0.13 mmol, 0.12 eq.), and potassium tert-butoxide (370 mg, 3.30 mmol, 3 eq.). The resulting solution was stirred overnight at 100° C. The reaction mixture was cooled to room temperature. The solids were filtered out. The resulting mixture was concentrated under vacuum. The residue was purified by preparative TLC (ethyl acetate:petroleum ether=1:5). The product containing fractions were combined and concentrated under vacuum to provide 1.066 g (87%) of tert-butyl 4-(6-[[4-[[4-nitro-3-(trifluoromethyl) phenyl]amino]cyclohexyl]oxy]pyridin-2-yl)piperazine-1-carboxylate as a yellow solid. (ES, m/z): 566; NMR (DMSO, 300 MHz) δ: 8.07 (d, J=9.3 Hz, 1H), 7.49-7.43 (m, 2H), 7.10 (d, J=2.1 Hz, 1H), 6.90-6.89 (m, 1H), 6.32 (d, J=8.1 Hz, 1H), 6.04 (d, J=7.8 Hz, 1H), 4.88-4.85 (m, 1H), 3.56-3.55 (m, 1H), 3.43-3.38 (m, 8H), 2.06-2.00 (m, 4H), 1.58-1.54 (m, 2H), 1.47-1.45 (m, 11H).

Step 3—Synthesis of 4-nitro-N-[4-[[6-(piperazin-1-yl)pyridin-2-yl]oxy]cyclohexyl]-3-(trifluoromethyl)aniline

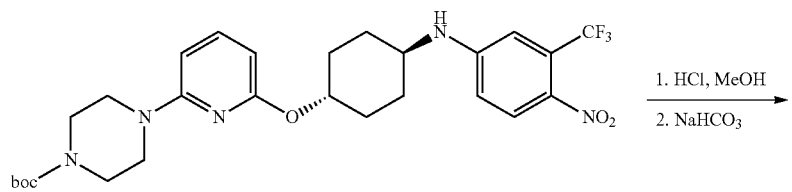

Into a 100-mL round-bottom flask, was placed tert-butyl 4-(6-[[4-[[4-nitro-3-(trifluoromethyl)phenyl]amino]cyclohexyl]oxy]pyridin-2-yl)piperazine-1-carboxylate (1.0 g, 1.8 mmol) and methanol/HCl (50 mL). The resulting solution was stirred for 1 hour at room temperature and then concentrated under vacuum. The residue was stirred in 50 mL of water and the solids were collected by filtration to provide 650 mg (79%) as a yellow solid.

Step 4—Synthesis of ethyl 4-(6-[[4-[[4-nitro-3-(trifluoromethyl)phenyl]amino]cyclohexyl]oxy]pyridin-2-yl)piperazine-1-carboxylate (Compound 29)

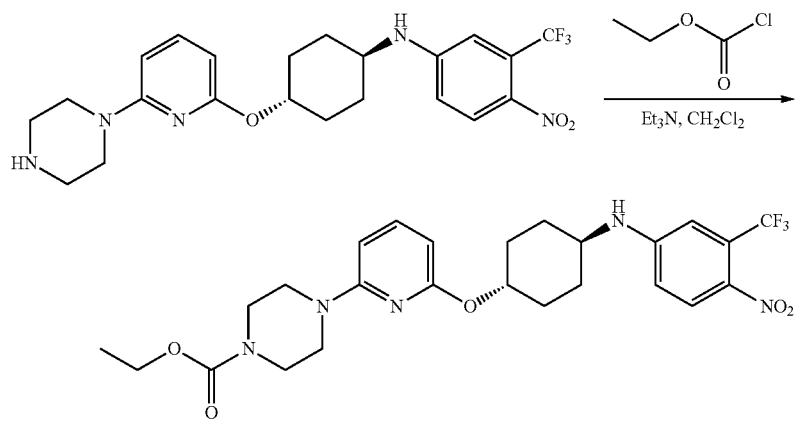

Into a 40-mL round-bottom flask, was placed 4-nitro-N-[4-[[6-(piperazin-1-yl)pyridin-2-yl]oxy]cyclohexyl]-3-(trifluoromethyl)aniline (100 mg, 0.21 mmol), dichloromethane (10 mL), triethylamine (0.2 mL), and ethyl chloroformate (28 mg, 0.26 mmol, 1.20 eq.). The resulting solution was stirred for 30 minutes at room temperature. The reaction was then quenched by the addition of 20 mL of water. The resulting mixture was concentrated under vacuum. The residue was purified by preparative TLC (ethyl acetate:petroleum ether=1:5). The product containing fractions were combined and concentrated under vacuum to provide 90.3 mg (78%) as a yellow solid. (ES, m/z): 538; $^1$H NMR (CDCl$_3$, 300 MHz) δ: 8.08 (d, J=9.0 Hz, 1H), 7.49-7.43 (m, 2H), 7.09 (s, 1H), 6.90-6.86 (m, 1H), 6.33 (d, J=8.1 Hz, 1H), 6.04 (d, J=7.8 Hz, 1H), 4.87 (brs, 1H), 4.10-4.03 (m, 2H), 3.57-3.55 (m, 1H), 3.46 (s, 8H), 2.12-2.01 (m, 4H), 1.58-1.39 (m, 4H), 1.24-1.20 (m, 3H).

Example 7—Synthesis of Compound 196

Synthesis of cyclopentyl 4-(5-[[4-[[4-nitro-3-(trifluoromethyl)phenyl]amino]cyclohexyl]oxy]pyridin-3-yl)piperazine-1-carboxylate (Compound 196)

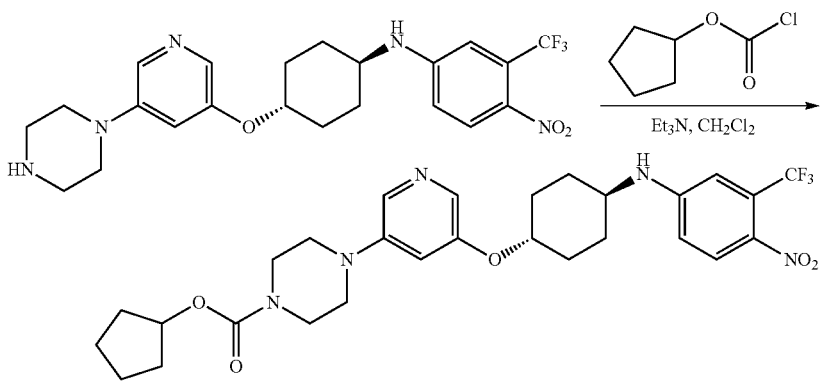

Into a 40-mL round-bottom flask, was placed a solution of 4-nitro-N-(4-[[5-(piperazin-1-yl)pyridin-3-yl]oxy]cyclohexyl)-3-(trifluoromethyl)aniline (100 mg, 0.21 mmol) in dichloromethane (10 mL). This was followed by the addition of triethylamine (65 mg, 0.64 mmol, 3 eq.) dropwise with stirring at room temperature. The resulting solution was stirred for 10 minutes at room temperature in a water bath. To this was added cyclopentyl chloroformate (32 mg, 0.22 mmol, 1 eq.). The solution was stirred for 1 hour at room temperature then concentrated under vacuum. The residue was applied onto a silica gel column and eluted with ethyl acetate:petroleum ether (1:1). The product containing fractions were combined and concentrated under vacuum to provide 83.9 mg (68%) of cyclopentyl 4-(5-[[4-[[4-nitro-3-(trifluoromethyl)phenyl]amino]cyclohexyl]oxy]pyridin-3-yl)piperazine-1-carboxylate as a yellow solid. (ES, m/z): [M+H]$^+$ 578; NMR (300 MHz, CDCl3): δ 8.06 (d, J=9.0 Hz, 1H), 7.96 (d, J=2.4 Hz, 1H), 7.84 (d, J=2.1 Hz, 1H), 6.92 (s, 1H), 6.82 (s, 1H), 6.70 (dd, J=2.7, 9.0 Hz, 1H), 5.19-5.15 (m, 1H), 4.59 (d, J=7.8 Hz, 1H), 4.41-4.30 (m, 1H), 3.66-3.63 (m, 4H), 3.53-3.51 (m, 1H), 3.25-3.22 (m, 4H), 2.26-2.23 (m, 4H), 1.95-1.89 (m, 2H), 1.77-1.63 (m, 8H), 1.49-1.27 (m, 2H).

Example 8—Synthesis of Compound 009

Synthesis of 4-[2-[(4-[[4-nitro-3-(trifluoromethyl)phenyl]amino]cyclohexyl)oxy]pyridin-4-yl]piperazine-1-carboxylate (Compound 9)

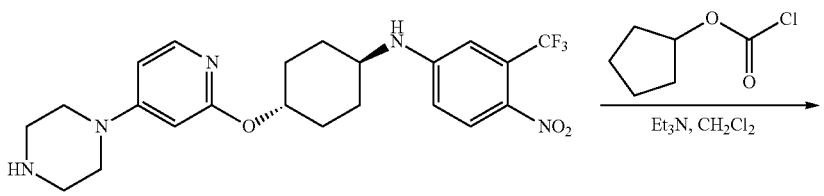

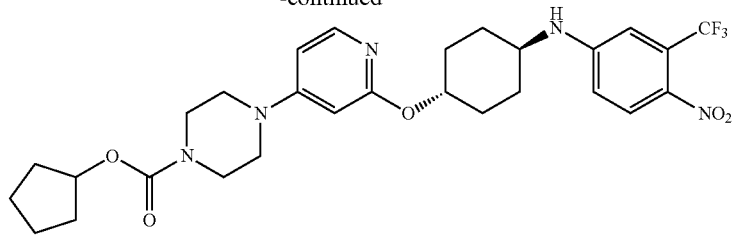

To a solution of 4-nitro-N-(4-[[4-(piperazin-1-yl)pyridin-2-yl]oxy]cyclohexyl)-3-(trifluoromethyl)aniline (TFA salt, 100 mg, 0.17 mmol) in dichloromethane (10 mL) was added triethylamine (0.2 mL) and cyclopentyl chloroformate (31 mg, 0.21 mmol). The resulting solution was stirred for 1 hour at room temperature. The reaction was then quenched by the addition of water (20 mL). The resulting solution was extracted with dichloromethane (10 mL) and the organic layers were combined and concentrated under vacuum. The residue was applied onto a silica gel column and eluted with ethyl acetate/petroleum ether (2:1). The product containing fractions were combined and concentrated under vacuum to provide 85.3 mg (86%) of cyclopentyl 4-[2-[(4-[[4-nitro-3-(trifluoromethyl)phenyl]amino]cyclohexyl)oxy]pyridin-4-yl]piperazine-1-carboxylate as a yellow solid. (ES, m/z): [M+H]+ 578; NMR (300 MHz, DMSO): δ 8.07 (d, J=9.3 Hz, 1H), 7.79 (d, J=6.3 Hz, 1H), 7.50 (d, J=7.8 Hz, 1H), 7.10 (s, 1H), 6.89-6.86 (m, 1H), 6.53-6.51 (m, 1H), 6.09 (d, J=1.8 Hz, 1H), 5.03-4.95 (m, 1H), 3.52-3.41 (m, 5H), 3.31-3.28 (m, 4H), 1.81-1.76 (m, 4H), 1.81-1.74 (m, 2H), 1.65-1.34 (m, 10H).

Example 9—Synthesis of Compound 068

Synthesis of 4-[2-[(4-[[4-nitro-3-(trifluoromethyl)phenyl]amino]cyclohexyl)oxy]pyridin-4-yl]-N-[4-(trifluoromethyl)phenyl]piperazine-1-carbothioamide (Compound 68)

Into a 25-mL round-bottom flask, was placed 4-nitro-N-(4-[[4-(piperazin-1-yl)pyridin-2-yl]oxy]cyclohexyl)-3-(trifluoromethyl)aniline (TFA salt, 100 mg, 0.17 mmol), dichloromethane (10 mL), triethylamine (0.2 mL), and 1-isothiocyanato-4-(trifluoromethyl)benzene (42 mg, 0.21 mmol, 1.2 eq.). The resulting solution was stirred for 1 hour at room temperature. The reaction was then quenched by the addition of 20 mL of water and extracted with 10 mL of dichloromethane. The organic layers were combined and concentrated under vacuum. The residue was applied onto a silica gel column and eluted with ethyl acetate/petroleum ether (2:1). The product containing fractions were combined and concentrated under vacuum to provide 88.8 mg (77%) of as a yellow solid; (ES, m/z): [M+H]+ 668.20; NMR (300 MHz, DMSO): δ 9.64 (s, 1H), 8.07 (d, J=9.0 Hz, 1H), 7.82 (d, J=6.0 Hz, 1H), 7.67-7.56 (m, 4H), 7.52 (d, J=7.8 Hz, 1H), 7.10 (s, 1H), 6.90-6.86 (m, 1H), 6.56-6.53 (m, 1H), 6.11 (s, 1H), 5.00-4.93 (m, 1H), 4.04 (m, 4H), 3.56-3.49 (m, 5H), 2.11-2.00 (m, 4H), 1.60-1.24 (m, 4H).

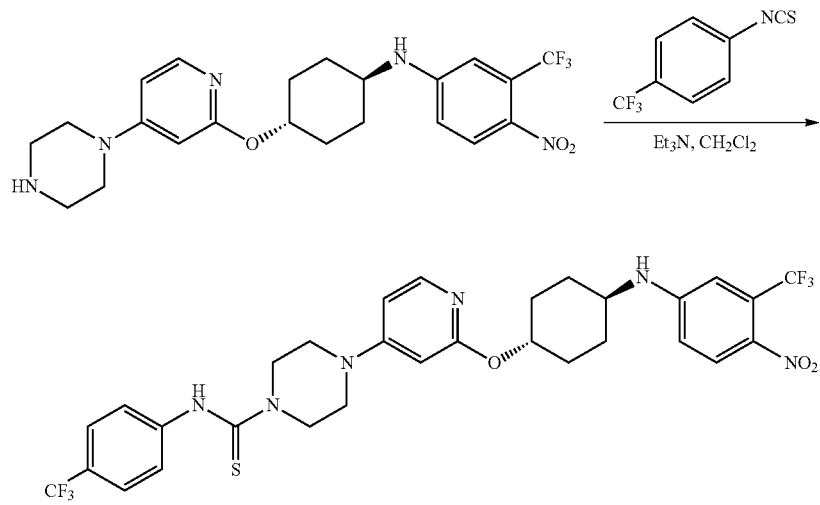

Example 10—Synthesis of Compound 101

Synthesis of 4-(6-[[4-[[4-nitro-3-(trifluoromethyl)phenyl]amino]cyclohexyl]oxy]pyridin-2-yl)-N-[4-(trifluoromethyl)phenyl]piperazine-1-carbothioamide (Compound 101)

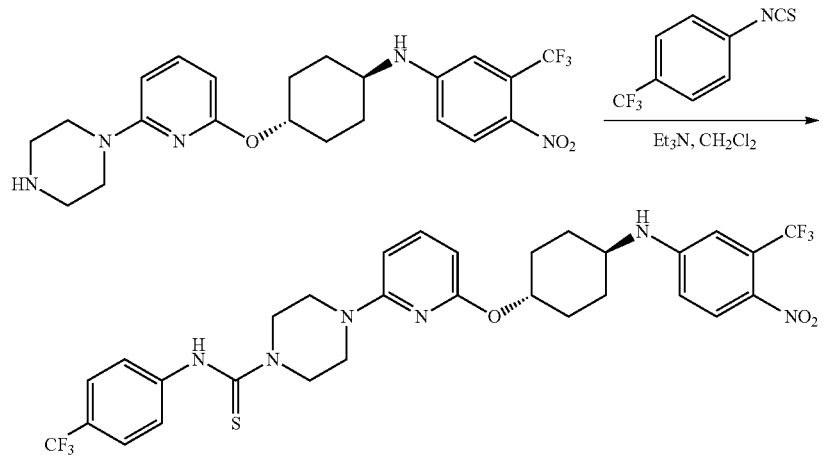

Into a 40-mL round-bottom flask, was placed a solution of 4-nitro-N-[4-[[6-(piperazin-1-yl)pyridin-2-yl]oxy]cyclohexyl]-3-(trifluoromethyl)aniline (100 mg, 0.21 mmol) in dichloromethane (20 mL), triethylamine (0.2 mL), and 1-isothiocyanato-4-(trifluoromethyl)benzene (52 mg, 0.26 mmol, 1.2 eq.). The resulting mixture was stirred for 30 minutes at room temperature. The solids were collected by filtration. The filter cake was washed with 1×10 mL of water and 2×10 mL of hexane. The product was dried under vacuum to provide 120.5 mg (84%) as a yellow solid. (ES, m/z): 669; $^1$H NMR (DMSO, 300 MHz) δ: 9.63 (s, 1H), 8.07 (d, J=9.3 Hz, 1H), 7.67-7.64 (d, J=8.7 Hz, 2H), 7.59-7.56 (d, J=9.3 Hz, 2H), 7.51-7.45 (m, 2H), 7.09 (s, 1H), 6.90-6.86 (m, 1H), 6.34 (d, J=7.8 Hz, 1H), 6.06 (d, J=7.8 Hz, 1H), 4.91 (m, 1H), 4.05 (br s, 4H), 3.62-3.59 (m, 5H), 2.11-2.02 (m, 4H), 1.59-1.39 (m, 4H).

Example 11—Synthesis of Compound 127

Synthesis N-propyl-4-(6-[[4-[[4-nitro-3-(trifluoromethyl)phenyl]amino]cyclohexyl]oxy]pyridin-2-yl)piperazine-1-carboxamide (Compound 127)

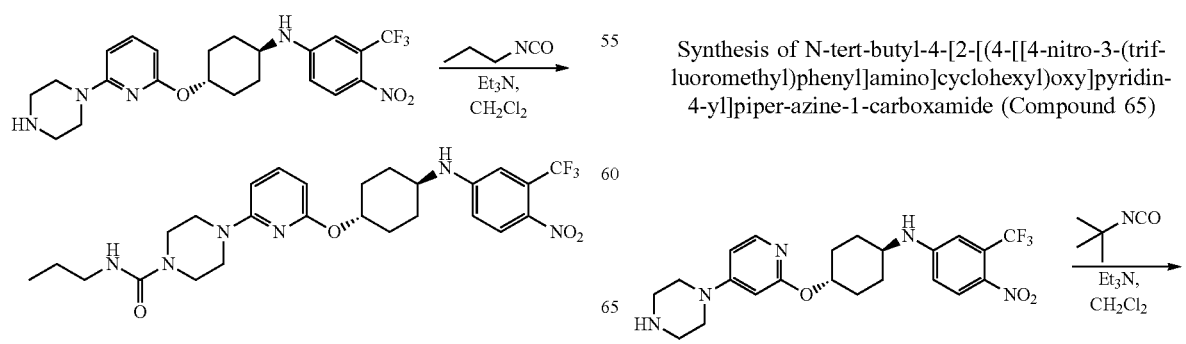

Into a 25-mL round-bottom flask purged and maintained with an inert atmosphere of nitrogen, was placed 4-nitro-N-[4-[[6-(piperazin-1-yl)pyridin-2-yl]oxy]cyclohexyl]-3-(trifluoromethyl)aniline (100 mg, 0.21 mmol), dichloromethane (10 mL), 1-isocyanatopropane (20.1 mg, 0.24 mmol, 1.1 eq.), and triethylamine (65 mg, 0.64 mmol, 3 eq.). The resulting solution was stirred for 1 hour at room temperature. The resulting mixture was concentrated under vacuum. The residue was applied onto a silica gel column and eluted with ethyl acetate/petroleum ether (0:100→100:0). The product containing fractions were combined and concentrated under vacuum to provide 76.1 mg (64%) as a yellow solid. (ES, m/z): 550; NMR (CDCl$_3$, 300 MHz) δ: 8.05 (d, J=9.0 Hz, 1H), 7.52-7.47 (dd, J=8.1, 11.7 Hz, 1H), 6.90 (d, J=2.1 Hz, 1H), 6.70-6.67 (dd, J=2.4, 9.0 Hz 1H), 6.34 (d, J=8.1 Hz, 1H), 6.18 (d, J=7.8 Hz, 1H), 4.96-4.92 (m, 1H), 4.55 (br s, 1H), 3.58-3.51 (m, 9H), 3.27-3.22 (m, 2H), 2.26-2.23 (m, 4H), 1.74-1.40 (m, 8H), 0.99-0.98 (t, J=7.2 Hz, 3H).

Example 12—Synthesis of Compound 065

Synthesis of N-tert-butyl-4-[2-[(4-[[4-nitro-3-(trifluoromethyl)phenyl]amino]cyclohexyl)oxy]pyridin-4-yl]piper-azine-1-carboxamide (Compound 65)

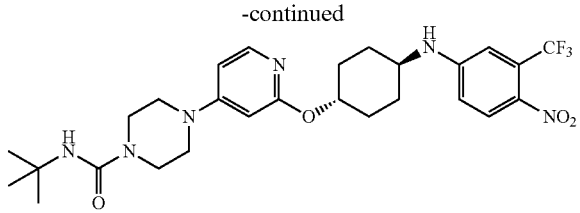

To a solution of 4-nitro-N-(4-[[4-(piperazin-1-yl)pyridin-2-yl]oxy]cyclohexyl)-3-(trifluoromethyl)aniline (TFA salt, 150 mg, 0.26 mmol) in dichloromethane (10 mL) was added triethylamine (0.5 mL), and 2-isocyanato-2-methylpropane (31 mg, 0.31 mmol). The resulting solution was stirred for 1 hour at room temperature. The reaction was then quenched by the addition of water (20 mL) and extracted with dichloromethane (10 mL). The organic layers were combined and concentrated under vacuum. The residue was applied onto a silica gel column and eluted with ethyl acetate/petroleum ether (2:1). The product containing fractions were combined and concentrated under vacuum to provide 74.9 mg (54%) of N-ethyl-4-[2-[(4-[[4-nitro-3-(trifluoromethyl) phenyl]amino]cyclo-hexyl)oxy]pyridin-4-yl]piperazine-1-carboxamide as a yellow solid. (ES, m/z): [M+H]$^+$ 565; $^1$H NMR (300 MHz, DMSO): δ 8.07 (d, J=9.3 Hz, 1H), 7.79 (d, J=6.0 Hz, 1H), 7.51 (d, J=7.2 Hz, 1H), 7.10 (s, 1H), 6.90-6.86 (m, 1H), 6.55-6.53 (m, 1H), 6.09 (d, J=2.1 Hz, 1H), 5.90 (s, 1H), 4.98-4.92 (m, 1H), 3.55-3.54 (m, 1H), 3.36-3.32 (m, 4H), 3.26-3.25 (m, 4H), 2.10-2.04 (m, 4H), 1.56-1.36 (m, 4H), 1.26 (s, 9H).

Example 13—Synthesis of Compound 003

Synthesis of 2-Cyclopentyl-1-[4-(4-[[4-[[4-nitro-3-(trifluoromethyl)phenyl]amino]cyclohexyl]oxy]pyridin-2-yl)piperazin-1-yl]ethan-1-one (Compound 3)

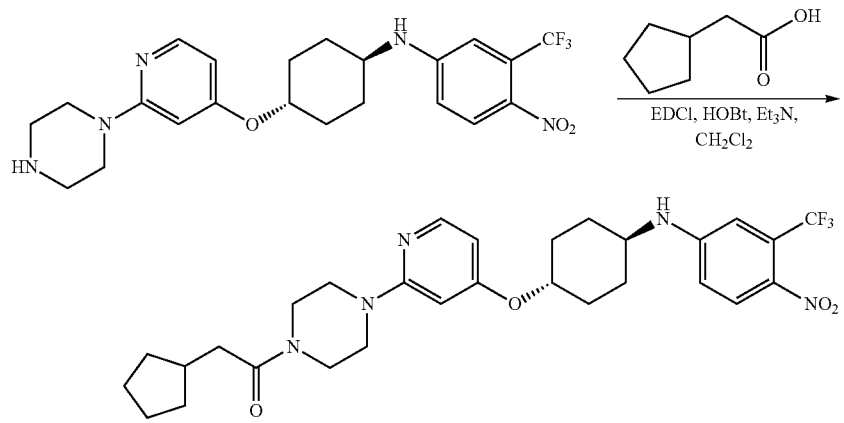

Into a 50-mL round-bottom flask purged and maintained with an inert atmosphere of nitrogen, was placed a solution of 2-cyclopentylacetic acid (50 mg, 0.39 mmol) in dichloromethane (10 mL), HOBt (105 mg, 0.78 mmol, 2 eq.), EDCI (149 mg, 0.78 mmol, 2 eq.), triethylamine (118 mg, 1.17 mmol, 3 eq.), and 4-nitro-N-[4-[[2-(piperazin-1-yl)pyridin-4-yl]oxy]cyclohexyl]-3-(trifluoromethyl)aniline (181 mg, 0.39 mmol, 1 eq.). The resulting solution was stirred overnight at room temperature and then diluted with 20 mL of dichloromethane. The crude solution was washed with water and then with brine. The organic fraction was dried over anhydrous sodium sulfate and the solids were filtered off. The residue was applied onto a silica gel column and eluted with dichloromethane:methanol (30:1). The product containing fractions were combined and concentrated under vacuum to provide 49.7 mg (22%) of as a yellow solid. (ES, m/z): [M+H]$^+$ 576; $^1$H NMR (300 MHz, CDCl$_3$): δ 8.08-8.01 (m, 2H), 6.91-6.87 (d, J=2.7 Hz, 1H), 6.68-6.65 (dd, J=2.4, 9.0 Hz, 1H), 6.35-6.33 (m, 1H), 6.13 (s, 1H), 4.53 (d, J=7.5 Hz, 1H), 4.39 (br s, 1H), 3.77-3.65 (overlapping m, 6H), 3.48 (br s, 4H), 2.41-2.38 (leaning d, J=7.2 Hz, 2H), 2.27-2.22 (m, 5H), 1.89-1.80 (m, 2H), 1.67-1.55 (m, 4H), 1.46-1.42 (m, 2H), 1.20-1.09 (m, 2H).

Example 14—Synthesis of Compound 37

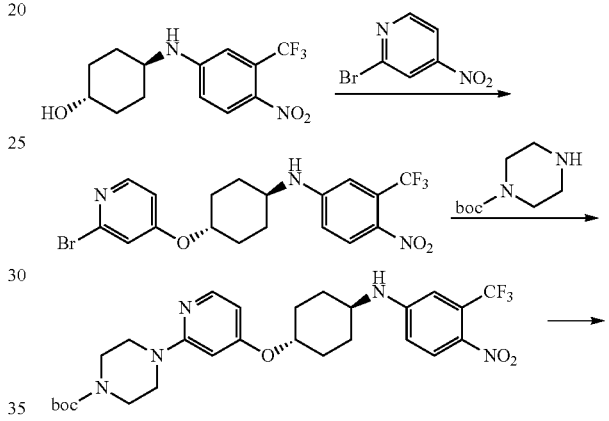

-continued

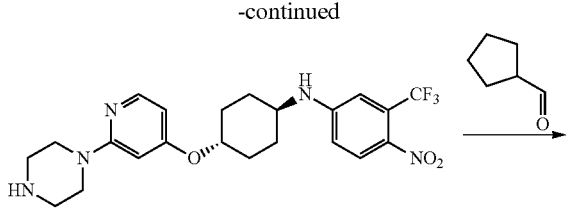

-continued

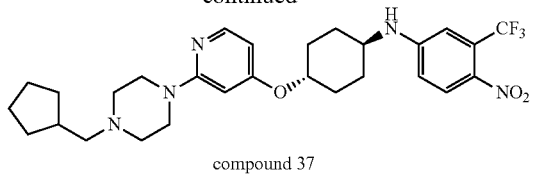

compound 37

Step 1—Synthesis of 4-nitro-N-[4-[(2-bromopyridin-4-yl)oxy]cyclohexyl]-3-(trifluoromethyl)

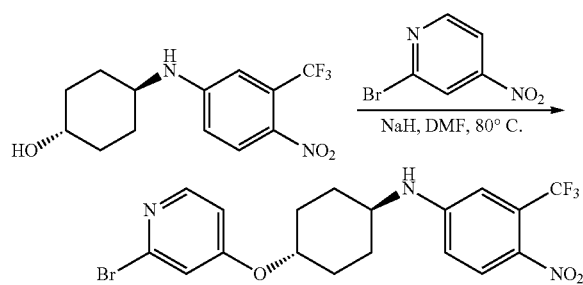

Into a 250-mL 3-necked round-bottom flask purged and maintained with an inert atmosphere of nitrogen, was placed a mixture of 4-[[4-nitro-3-(trifluoromethyl)phenyl]amino] cyclohexan-1-ol (12 g, 39 mmol, 1.3 eq.) in N,N-dimethylformamide (100 mL), sodium hydride (1.9 g, 79 mmol, 2 eq.), and 2-bromo-4-nitropyridine (6.2 g, 31 mmol). The resulting solution was stirred for 1.5 hours at room temperature in an oil bath. The reaction was then quenched by the addition of 200 mL of water. The resulting solution was diluted with 200 mL of ethyl acetate. The resulting mixture was washed with water and then brine. The organic layer was dried over anhydrous sodium sulfate. The solids were filtered out and the solution was concentrated under vacuum to provide 10 g (56%) of aniline as a yellow solid.

Step 2—Synthesis of tert-butyl 4-(4-[[4-[[4-nitro-3-(trifluoromethyl)phenyl]amino]cyclohexyl]oxy]pyridine-2-yl) piperazine-1-carboxylate

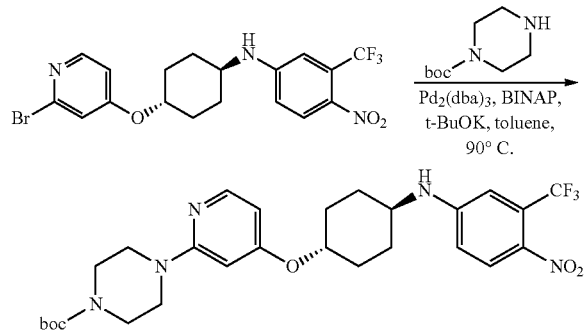

Into a 100-mL 3-necked round-bottom flask purged and maintained with an inert atmosphere of nitrogen, was placed a solution of 4-nitro-N-[4-[(2-bromopyridin-4-yl)oxy]cyclohexyl]-3-(trifluoromethyl)aniline (10 g, 22 mmol) in toluene (100 mL), tert-butyl piperazine-1-carboxylate (12 g, 64 mmol, 3 eq.), potassium tert-butoxide (7.3 g, 65 mmol, 3 eq.), BINAP (1.4 g, 2.2 mmol, 0.1 eq.), and Pd$_2$(dba)$_3$·CHCl$_3$ (2.3 g, 0.10 eq.). The resulting solution was stirred overnight at 90° C. using an oil bath to heat. The solids were filtered off and the resulting solution was diluted with 200 mL of ethyl acetate. The solution was washed with water and then brine. The organic layer was dried over anhydrous sodium sulfate and the solids were filtered off. The residue was applied onto a silica gel column and eluted with ethyl acetate/petroleum ether (1:1-10:1). The product containing fractions were combined and concentrated under vacuum to provide 4 g (33%) of tert-butyl 4-(4-[[4-[[4-nitro-3-(trifluoromethyl)phenyl]amino]cyclohexyl]oxy]pyridine-2-yl) piperazine-1-carboxylate as a yellow solid.

Step 3—Synthesis of 4-nitro-N-[4-[[2-(piperazin-1-yl)pyridin-4-yl]oxy]cyclohexyl]-3-(trifluoromethyl)

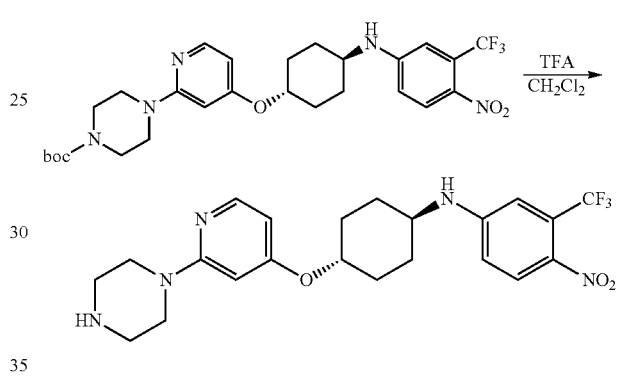

Into a 50-mL round-bottom flask purged and maintained with an inert atmosphere of nitrogen, was placed tert-butyl 4-(4-[[4-[[4-nitro-3-(trifluoromethyl)phenyl]amino]cyclohexyl]oxy]pyridin-2-yl)piperazine-1-carboxylate (4 g, 7.07 mmol) along with dichloromethane (30 mL) and triethylamine (5 mL). The resulting solution was stirred for 1 hour at room temperature and then concentrated under vacuum. The reissue was diluted with 30 mL of ethyl acetate. The pH value of the solution was adjusted to 8 with sodium bicarbonate. The organic layer was washed with water and then brine. The organic fraction was dried over anhydrous sodium sulfate and the solids were filtered off. The resulting solution was concentrated under vacuum to provide 3.0 g (91%) of the amine as a yellow solid.

Step 4—Synthesis of 4-nitro-N-[4-([2-[4-(cyclopentylmethyl)piperazin-1-yl]pyridin-4-yl]oxy)cyclohexyl]-3-(trifluoromethyl) (Compound 37)

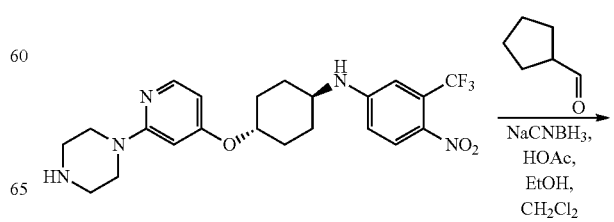

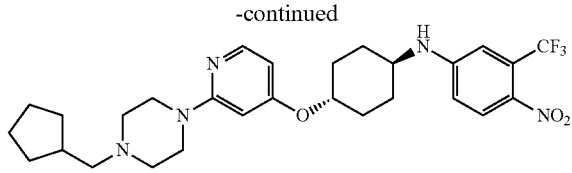

Into a 50-mL round-bottom flask purged and maintained with an inert atmosphere of nitrogen, was placed a solution of 4-nitro-N-[4-[[2-(piperazin-1-yl)pyridin-4-yl]oxy]cyclohexyl]-3-(trifluoromethyl)aniline (100 mg, 0.21 mmol) in ethanol (10 mL), acetic acid (0.2 mL, 1.00 eq.), cyclopentanecarbaldehyde (21 mg, 0.21 mmol, 1 eq.), and sodium cyanoborohydride (14 mg, 0.22 mmol, 1 eq.). The resulting solution was stirred overnight at room temperature and then concentrated under vacuum. The residue was diluted with 20 mL of ethyl acetate and washed with water and then brine. The organic fraction was dried over anhydrous sodium sulfate and the solids were filtered off. The filtrate was concentrated under vacuum. The residue was applied onto a silica gel column and eluted with ethyl acetate:petroleum ether (1:1). The product containing fractions were combined and concentrated under vacuum to provide 76.6 mg (65%) of 4-nitro-N-[4-([2-[4-(cyclopentylmethyl)piperazin-1-yl]pyridin-4-yl]oxy)cyclohexyl]-3-(trifluoromethyl) as a light yellow solid. (ES, m/z): [M+H]$^+$ 548; NMR (300 MHz, CDCl$_3$): δ 8.04 (d, J=6.0 Hz, 1H), 8.02 (d, J=6.4 Hz, 1H), 6.88 (d, J=2.4 Hz, 1H), 6.66 (dd, J=2.4, 8.8 Hz, 1H), 6.27 (dd, J=2.0, 6.0 Hz, 1H), 6.12 (d, J=2.0 Hz, 1H), 4.54 (d, J=7.2 Hz, 1H), 4.37-4.31 (m, 1H), 3.70 (br s, 4H), 3.49 (br s, 1H), 2.83 (br s, 4H), 2.60 (br s, 2H), 2.20 (br m, 6H), 1.86 (d, J=6.8 Hz, 2H), 1.71-1.52 (overlapping m, 7H), 1.49-1.38 (m, 2H), 1.30-1.20 (m, 2H), impurity (observed w/ UV @ 220 nm) causing integration to be high.

Example 15—Synthesis of Compound 007

Synthesis of 4-(4-[[4-[[4-nitro-3-(trifluoromethyl)phenyl]amino]cyclohexyl]oxy]pyridin-2-yl)piperazine-1-carboxylate (Compound 7)

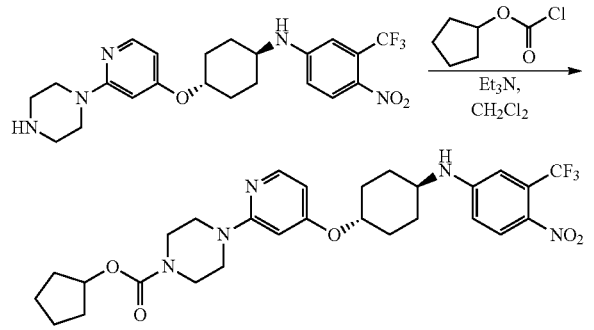

Into a 50-mL round-bottom flask purged and maintained with an inert atmosphere of nitrogen, was placed a solution of 4-nitro-N-[4-[[2-(piperazin-1-yl)pyridin-4-yl]oxy]cyclohexyl]-3-(trifluoromethyl)aniline (100 mg, 0.21 mmol) in dichloromethane (10 mL), triethylamine (65 mg, 0.64 mmol, 3 eq.), and cyclopentyl chloroformate (32 mg, 0.22 mmol, 1 eq.). The resulting solution was stirred for 2 hours at room temperature. The crude material was diluted with 30 mL of ethyl acetate and then washed with water and then with brine. The organic layer was dried over anhydrous sodium sulfate and the solids were filtered off. The filtrate was concentrated under vacuum. The residue was applied onto a silica gel column and eluted with ethyl acetate:petroleum ether (1:1). The product containing fractions were combined and concentrated under vacuum to provide 52.5 mg (42%) of 4-(4-[[4-[[4-nitro-3-(trifluoromethyl)phenyl]amino]cyclohexyl]oxy]pyridin-2-yl) piperazine-1-carboxylate as a yellow solid. (ES, m/z): [M+H]$^+$ 578; $^1$H NMR (300 MHz, CDCl$_3$): δ 8.08-8.03 (m, 2H), 6.90 (d, J=2.4 Hz, 1H), 6.70-6.66 (dd, J=2.4, 9.0 Hz, 1H), 6.32 (br s, 1H), 6.13 (s, 1H), 5.17-5.13 (m, 1H), 4.59 (d, J=7.5 Hz, 1H), 4.38 (br s, 1H), 3.66-3.48 (m, 9H), 2.29-2.18 (m, 4H), 2.06-1.84 (m, 2H), 1.76-1.64 (m, 8H), 1.63-1.39 (m, 2H).

Example 16—Synthesis of Compound 06

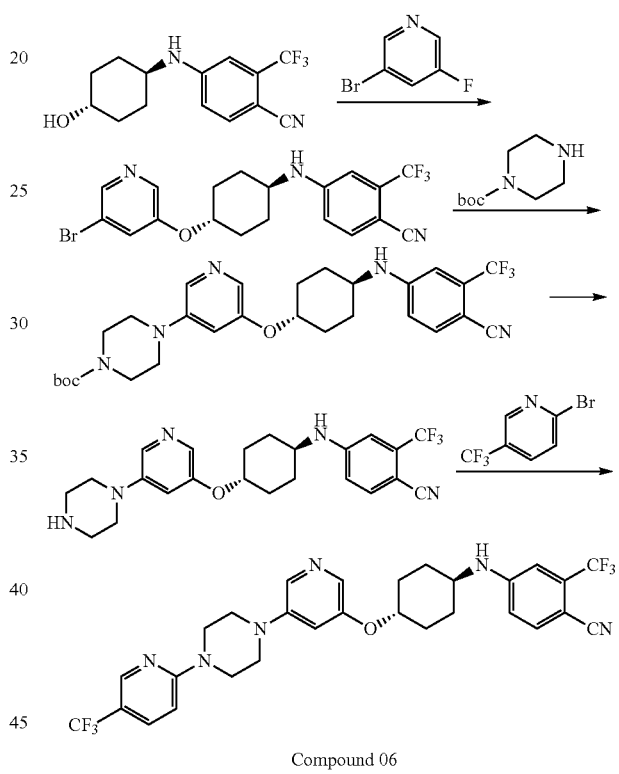

Compound 06

Step 1—Synthesis of 4-[[4-[(5-bromopyridin-3-yl)oxy]cyclohexyl]amino]-2-(trifluoromethyl)benzonitrile

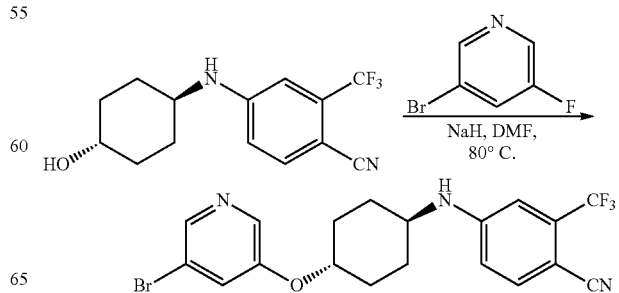

Into a 250-mL 3-necked round-bottom flask purged and maintained with an inert atmosphere of nitrogen, was placed a solution of 4-[[4-hydroxycyclohexyl]amino]-2-(trifluoromethyl)benzonitrile (3 g, 10.5 mmol) in N,N-dimethylformamide (20 mL), sodium hydride (60%, 850 mg, 21 mmol, 2 eq.), and 3-bromo-5-fluoropyridine (1.85 g, 10.5 mmol, 1 eq.). The resulting mixture was stirred overnight at 80° C. using an oil bath to heat. The reaction was then quenched by the addition of 100 mL of water. The resulting mixture was diluted with 100 mL of ethyl acetate and washed with of water and then with brine. The organic fraction was dried over anhydrous sodium sulfate and the solids were filtered off. The mixture was concentrated under vacuum to provide 2.48 g (55%) of 4-[[4-[(5-bromopyridin-3-yl)oxy]cyclohexyl]amino]-2-(trifluoromethyl) benzonitrile as a white solid.

Step 2—Synthesis of tert-butyl 4-(5-[[4-[[4-cyano-3-(trifluoromethyl)phenyl]amino]cyclohexyl]oxy]pyridin-3-yl)piperazine-1-carboxylate

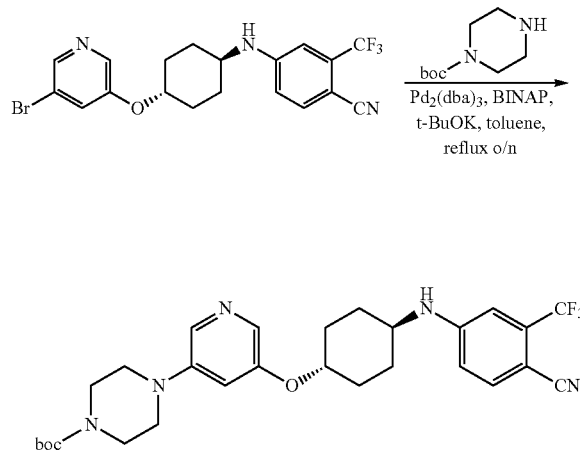

Into a 250-mL 3-necked round-bottom flask purged and maintained with an inert atmosphere of nitrogen, was placed a solution of 4-[[4-[(5-bromo-5,6-dihydropyridin-3-yl)oxy]cyclohexyl]amino]-2-(trifluoromethyl)benzonitrile (2.48 g, 5.61 mmol) in toluene (50 mL), tert-butyl piperazine-1-carboxylate (2.5 g, 13.4 mmol, 2.4 eq.), potassium tert-butoxide (1.5 g, 13.4 mmol, 2.4 eq.), BINAP (280 mg, 0.45 mmol, 0.1 eq.), and Pd(dba)₃-CHCl₃ (0.47 g, 0.1 eq.). The resulting solution was stirred overnight at 90° C. using an oil bath to heat. The resulting solution was then diluted with 100 mL of ethyl acetate and washed with water and then brine. The organic layer was dried over anhydrous sodium sulfate and the solids were filtered off. The filtrate was concentrated under vacuum. The residue was applied onto a silica gel column and eluted with ethyl acetate:petroleum ether (1:1). The product containing fractions were combined and concentrated under vacuum to provide 1.1 g (36%) of tert-butyl 4-(5-[[4-[[4-cyano-3-(trifluoromethyl)phenyl]amino]cyclohexyl]oxy]pyridin-3-yl)piperazine-1-carboxylate as a off-white solid.

Step 3—Synthesis of 4-[[4-[[5-(piperazin-1-yl)pyridin-3-yl]oxy]cyclohexyl]amino]-2-(trifluoromethyl)benzonitrile

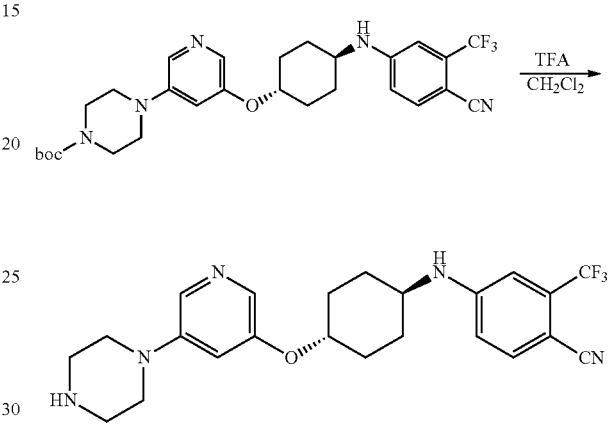

Into a 50-mL round-bottom flask purged and maintained with an inert atmosphere of nitrogen, was placed a solution of tert-butyl 4-(5-[[4-[[4-cyano-3-(trifluoromethyl)phenyl]amino]cyclohexyl]oxy]pyridin-3-yl)piperazine-1-carboxylate (1.0 g, 1.8 mmol) in dichloromethane (20 mL) with trifluoroacetic acid (3 mL). The resulting solution was stirred for 1 hour at room temperature and then concentrated under vacuum. The residue was diluted with 20 mL of ethyl acetate and made slightly basic with sodium bicarbonate. The resulting mixture was washed with water and then brine. The organic layer was dried over anhydrous sodium sulfate and the solids were filtered off. The filtrate was concentrated under vacuum to provide 0.74 g (91%) of 4-[[4-[[5-(piperazin-1-yl)pyridin-3-yl]oxy]cyclohexyl]amino]-2-(trifluoromethyl)benzonitrile as a off-white solid.

Step 4—Synthesis of 4-[[4-[(5-[4-[5-(trifluoromethyl)pyridin-2-yl]piperazin-1-yl]pyridin-3-yl)oxy]cyclohexyl]amino]-2-(trifluoromethyl)benzonitrile (Compound 6)

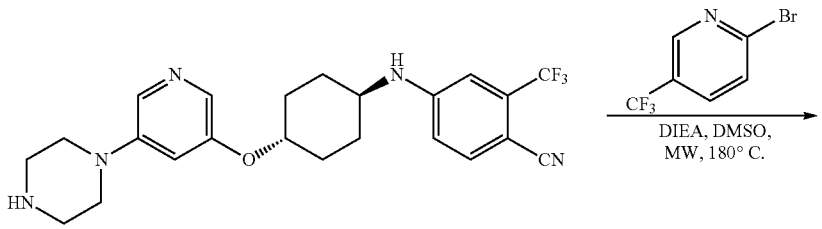

-continued

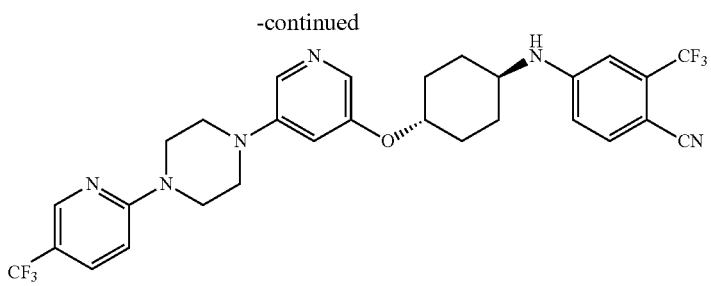

Into a 10-mL wavetube, was placed a solution of 4-[[4-[[5-(piperazin-1-yl)pyridin-3-yl]oxy]cyclohexyl]amino]-2-(trifluoromethyl)benzonitrile (100 mg, 0.22 mmol) in DMSO (3 mL) with 2-bromo-5-(trifluoromethyl)pyridine (51 mg, 0.23 mmol, 1 eq.) and DIEA (84 mg, 0.65 mmol, 3 eq.). The resulting solution was heated for 30 min at 180° C. The resulting solution was diluted with 20 mL of ethyl acetate and washed with water and then with brine. The organic fraction was dried over anhydrous sodium sulfate and the solids were filtered off. The resulting mixture was concentrated under vacuum. The residue was applied onto a silica gel column and eluted with ethyl acetate:petroleum ether (1:1). The product containing fractions were combined and concentrated under vacuum to provide 26.3 mg (20%) of 4-[[4-[(5-[4-[5-(trifluoromethyl)pyridin-2-yl]piperazin-1-yl]pyridin-3-yl)oxy]cyclohexyl]amino]-2-(trifluoromethyl)benzonitrile as a light brown solid. (ES, m/z): [M+H]+ 591; $^1$H NMR (300 MHz, CDCl$_3$): δ 8.44 (s, 1H), 7.92 (s, 1H), 7.76 (s, 1H), 7.72-7.69 (dd, J=2.7, 9.3 Hz, 1H), 7.58-7.55 (d, J=5.4 Hz, 1H), 7.06 (s, 1H), 6.85 (s, 1H), 6.71-6.68 (m, 2H), 4.48-4.31 (m, 2H), 3.90-3.86 (m, 4H), 3.50-3.47 (m, 5H), 2.25-2.21 (m, 4H), 1.80-1.59 (m, 2H), 1.50-1.25 (m, 2H).

Biological Activity Examples

Method A:

Screening method to test activity of compounds against *Haemonchus contortus*.

Twenty L1 *Haemonchus contortus* larvae were added to wells of a microtitre plate containing a nutrient medium and the test compound in DMSO. An analysis was conducted at 4 days to determine the extent of development of the larvae. Larvae exposed to DMSO alone served as controls. Compounds numbers 34, 5, 6, 7, 8, 9, 10, 11, 13, 14, 15, 17, 18, 19, 20, 21, 22, 23, 24, 25, 26, 27, 28, 29, 30, 31, 33, 34, 35, 36, 37, 38, 39, 40, 41, 46, 47, 48, 49, 50, 53, 54, 58, 59, 60, 61, 62, 63, 64, 65, 66, 67, 68, 69, 70, 71, 72, 74, 75, 76, 77, 78, 79, 80, 81, 82, 83, 84, 85, 86, 87, 88, 89, 90, 94, 95, 96, 106, 163, 176, 177, 180, 181, 183, 188, 193, & 196 gave at least 90% motility inhibition at a test concentration of less than or equal to 5 μM when assessed at the 4 day time point.

Method B:

Screening method to test activity of compounds against an anthelmintic-resistant isolate of *Haemonchus contortus*.

The conditions described in method A were used against an isolate of *H. contortus* found to be functionally resistant against the benzimidazole class of anthelmintics (e.g. 127-fold resistance to thiabendazole). Analogs 5, 6, 9, 11, 13, 14, 15, 17, 18, 21, 25, 27, 30, 31, 34, 35, & 196 were evaluated and found to be of similar efficacy to that observed against the wild-type strain of *H. contortus*.

Method C:

Screening method to test activity of compounds against microfilaria of *Dirofilaria immitis*.

Microfilaria of *Dirofilaria immitis* were added to the wells of a microtitre plate containing buffer and the test compounds in DMSO. An assessment was conducted at 24 hours to determine survival of the microfilaria. Microfilaria exposed to DMSO alone served as controls. Compounds 3, 4, 7, 8, 14, 18, 22, 23, 24, 25, 26, 27, 28, 29, 33, 36, 37, 40, 41, 46, 47, 49, 53, 54, 59, 60, 67, 69, 70, 71, 72, 75, 77, 78, 82, 87, 95, 96, 106, 112, 132, 136, 137, 138, 139, 140, 142, 147, 150, 151, 154, 155, 157, 158, 160, 177, 181, 183, 186, 187, 188, & 195 were found to inhibit ≥90% of the microfilaria's motility when screened at a dosage of 10 μM. Compound 4 was found to inhibit ≥90% of the microfilaria's motility when screened at a dosage of 1 μM. Compounds 5, 13, 17, 21, 30, 34, 35, 38, 39, 48, 56, 58, 61, 64, 65, 66, 68, 76, 79, 80, 81, 83, 85, 86, 89, 91, 92, 93, 99, 108, 110, 115, 116, 119, 120, 121, 124, 125, 127, 128, 129, 130, 131, & 196 were found to inhibit ≥90% of the microfilaria's motility when screened at a dosage of 5 ppm. Compounds 56, 80, 81, & 99 were found to inhibit ≥90% of the microfilaria's motility when screened at a dosage of 1 ppm.

Method D:

Permeability of Compounds.

Permeability of a compound across the epithelium cells along the gastrointestinal tract is an important limiting factor for the oral absorption and systemic availability of the compound. An in vitro model utilizing Caco-2/TC7 cells is employed to assess the permeability characteristics of new chemical entities (NCEs). For orally administered compounds, absorption depends on the intrinsic permeability across the intestinal epithelium and whether the active agent is a substrate or inhibitor of uptake or efflux transporters.

The permeability studies were performed under standard conditions in the apical to basolateral (A→B) direction with a pH gradient and a BSA gradient (standard apical medium (0.5% BSA at pH 6.5)/standard basal medium (5% BSA at pH 7.4)); conditions that most closely reflect the conditions in the in vivo situation. Samples were deproteinized by the addition of 400 μl acetonitrile to 200 μl sample, followed by a 20-minute centrifugation at 1730 g. Compound solubilisation: compound solutions at final concentrations of 20 μM were prepared following dilutions of stock solutions (starting from 10 mM in DMSO) in HBSS. Final concentration of DMSO was adjusted to 1%. Analytical conditions: Supernatants recovered following centrifugation were analysed by LC/MS/MS using a reverse phase column and the mobile phases delivered at 0.3 ml/minute in a gradient: water (A) and acetonitrile (B) (each with 0.1% formic acid).

The permeability of standard compounds in the CACO-2/TC7 in vitro model for permeability is shown in table 9. Every experiment (n) represents the mean of 3 filters per experiment.

TABLE 9

Permeability as measured in the CACO-2/TC7 model.

| Compound # | Permeability (A-B) [×10$^{-7}$ cm/sec] |
|---|---|
| 3 | 26.4 |
| 4 | 18.4 |
| 6 | 6.4 |
| 8 | 40.1 |
| 9 | 10.8 |
| 10 | 58.1 |
| 11 | 5.5 |
| 13 | 7.8 |
| 14 | 22.8 |
| 15 | 20.7 |
| 17 | 39.9 |
| 18 | 5.3 |
| 21 | 34.5 |
| 22 | 15.7 |
| 23 | 10.9 |
| 24 | 44.6 |
| 27 | 23.3 |
| 31 | 107.2 |
| 34 | 17.7 |
| 35 | 49.9 |
| 36 | 24.1 |
| 37 | 25.5 |
| 102 | 0.1 |

Method E:

Method to test activity of compounds against *Haemonchus contortus* in vivo in Mongolian jirds (*Meriones unguiculatus*).

Mongolian jirds, at least five weeks old, that have been immunosuppressed were artificially infected with ensheathed *Haemonchus contortus* third instar larvae. Six days after infection, the jirds were treated by oral gavage with the test compounds, dissolved in a mixture of DMSO/corn oil, at doses of 5 mg/kg. Jirds treated only with the placebo (DMSO/corn oil carrier) served as controls. On day 9 (3 days after treatment) the jirds were euthanized and necropsied for recovery of parasites from the stomach. Efficacy was calculated as the average % reduction in the number of worms in each test group compared with the average number of worms from the control group. Compound 6 provided a 100% reduction in nematode infestation in Mongolian jirds treated by oral gavage with the test article at a dose of 5 mg/kg.

Method F:

Method to test activity of compounds against *Trichostrongylus colubriformis* in vivo in Mongolian jirds (*Meriones unguiculatus*). Mongolian jirds, at least five weeks old, that have been immunosuppressed were artificially infected with ensheathed *Trichostrongylus colubriformis* third instar larvae. Six days after infection, the jirds were treated by oral gavage with the test compounds, dissolved in a mixture of DMSO/corn oil, at doses of 30 mg/kg. Jirds treated only with the placebo (DMSO/corn oil carrier) served as controls. On day 9 (3 days after treatment) the jirds were euthanized and necropsied for recovery of parasites from the stomach. Efficacy was calculated as the average % reduction in the number of worms in each test group compared with the average number of worms from the control group. Compound 6 provided a 99% reduction in nematode infestation in Mongolian jirds treated by oral gavage with the test article at a dose of 5 mg/kg.

Relative to the prior art compound CC-1 (described in WO2014/023723) compounds 11 & 18 were 100-200% more permeable, compounds 6 & 13 were 200-300% more permeable, and compounds 4, 8, 9, 10, 14, 15, 17, 21, 22, 23, 24, 27, 31, 34, 35, 36, & 37 were over 300% more permeable in the intestinal cell model.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

It is further noted that it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO ((35 U.S.C.) 112, first paragraph) or the EPO (Article 83 of the EPC), such that Applicants reserve the right and hereby disclose a disclaimer terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

What is claimed is:

1. An anthelmintic compound of formula (IA):

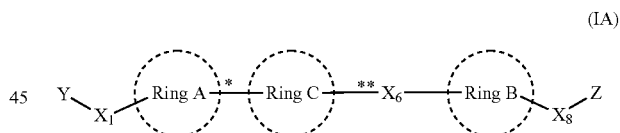

wherein:

Ring A is piperazinyl;

Ring C is pyridine-2,4-diyl, pyridine-2,3-diyl, pyridine-2,5-diyl, pyridine-3,5-diyl, or pyridine-2,6-diyl;

Y is $C_1$-$C_4$ alkyl, $C_6$-$C_{10}$-aryl, $C_3$-$C_{10}$-cycloalkyl, or 5-10 membered heteroaryl, or 3-8 membered heterocyclyl, each optionally substituted by one or more of halogen, alkyl, haloalkyl, alkoxy, haloalkoxy, alkylthio, halothio, haloalkylthio, alkylsulfinyl, haloalkylsulfinyl, alkylsulfonyl, or haloalkylsulfonyl;

$X_1$ is, $C_2$-$C_4$ alkenylene, —O—, —S—, —C(O)—, —S(O)$_2$—, —O—C(O)—, —C(O)—O—, —C(O)—N(R$^1$)—, N(R$^1$)—C(O)—, —C(S)—N(R$^1$)—, N(R$^1$)—C(S)—, —N(R$^1$)SO$_2$—, —(CH$_2$)$_n$—, —C(O)—(CH$_2$)$_n$—, —(CH$_2$)$_n$—C(O)—, or —O—(CH$_2$)$_n$—C(O)—, where
n is independently 1 to 3;
$R^1$ is independently H, or $C_1$-$C_3$ alkyl; and
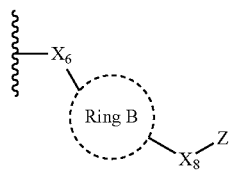
is selected from the group consisting of:
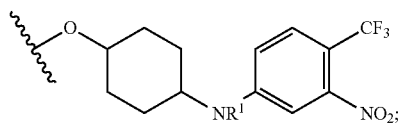
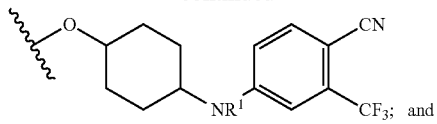
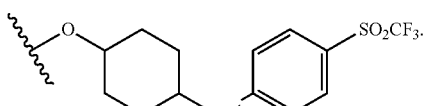
2. A compound according to claim 1, which is selected from the group consisting of:
3
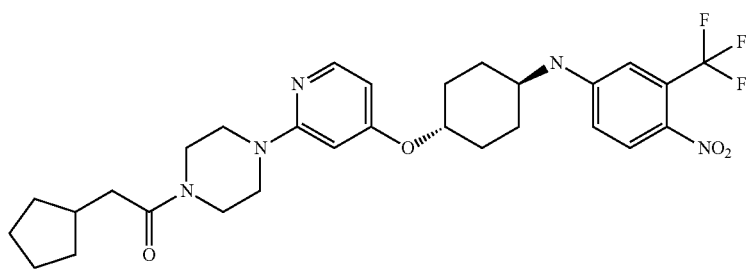
4
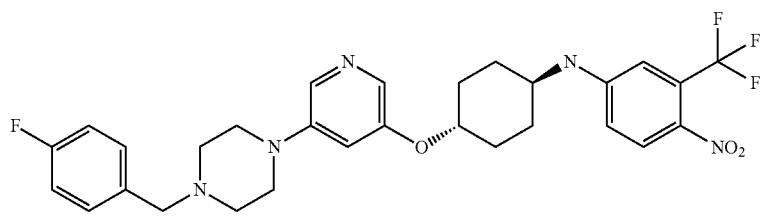 [SMILES: O=[N+]([O-])c1ccc(N[C@H]2CC[C@H](Oc3cncc(N4CCN(Cc5ccc(F)cc5)CC4)c3)CC2)cc1C(F)(F)F]
5
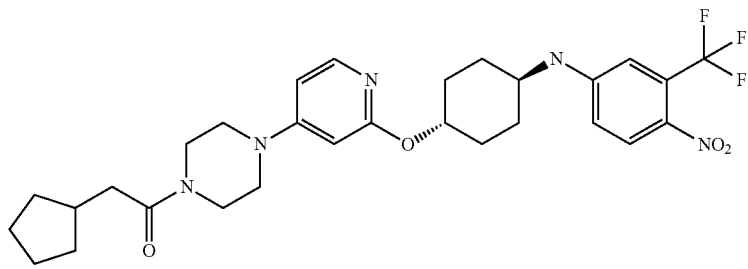 [SMILES: O=C(CC1CCCC1)N1CCN(c2ccnc(O[C@H]3CC[C@H](Nc4ccc([N+](=O)[O-])c(C(F)(F)F)c4)CC3)c2)CC1]
7
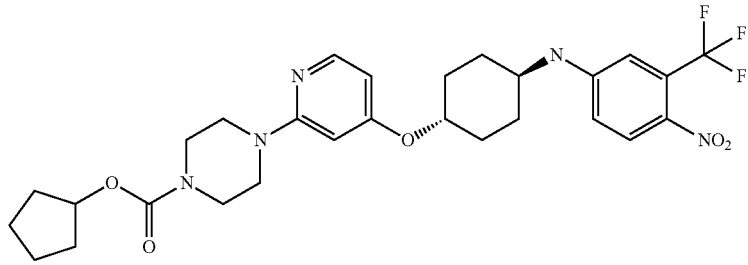 [SMILES: O=C(OC1CCCC1)N1CCN(c2cc(O[C@H]3CC[C@H](Nc4ccc([N+](=O)[O-])c(C(F)(F)F)c4)CC3)ccn2)CC1]

8
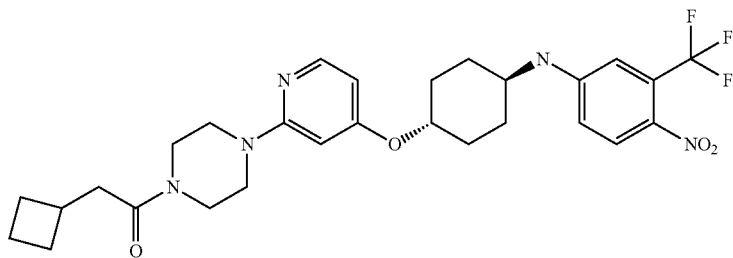 [SMILES: O=C(CC1CCC1)N1CCN(c2cc(O[C@H]3CC[C@H](Nc4ccc([N+](=O)[O-])c(C(F)(F)F)c4)CC3)ccn2)CC1]
9
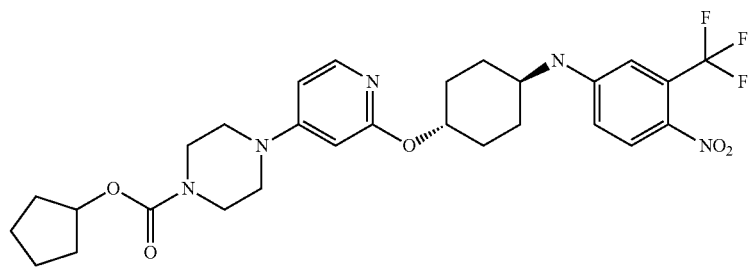
10
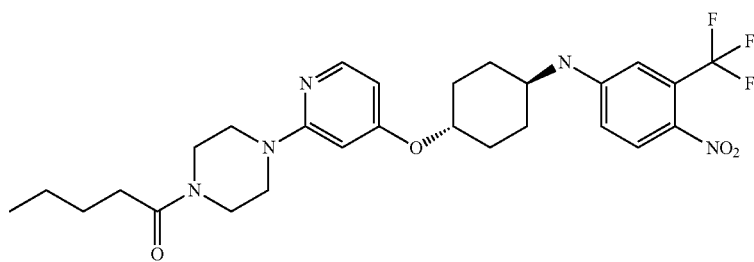
11
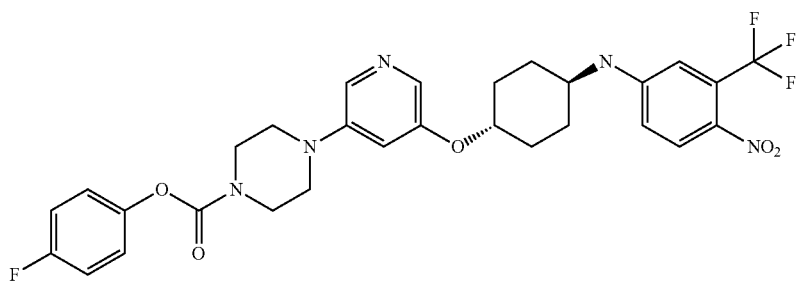
13
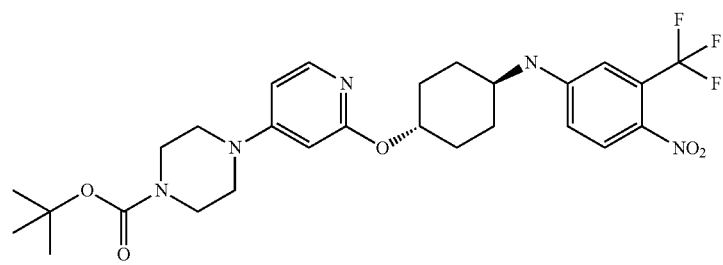
14
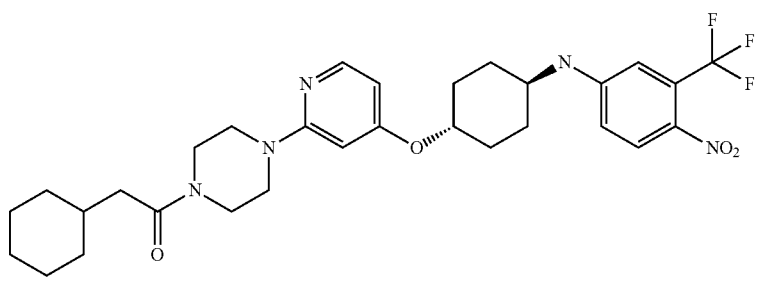 [SMILES: O=C(CC1CCCCC1)N1CCN(c2cc(O[C@H]3CC[C@H](Nc4ccc([N+](=O)[O-])c(C(F)(F)F)c4)CC3)ccn2)CC1]

15 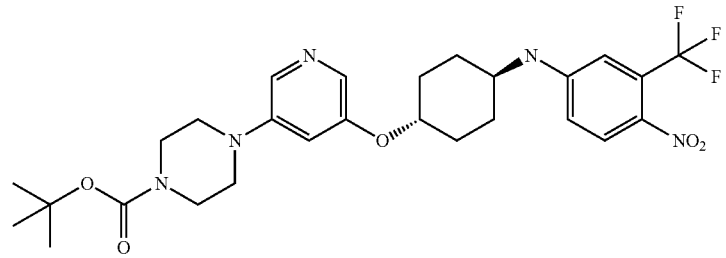
16 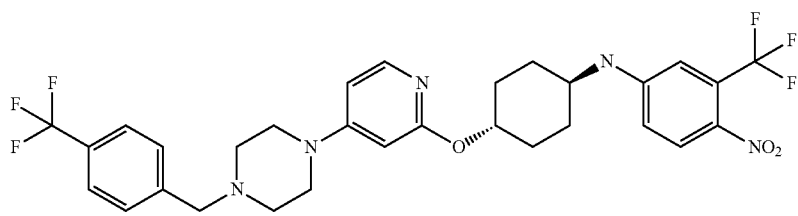
17 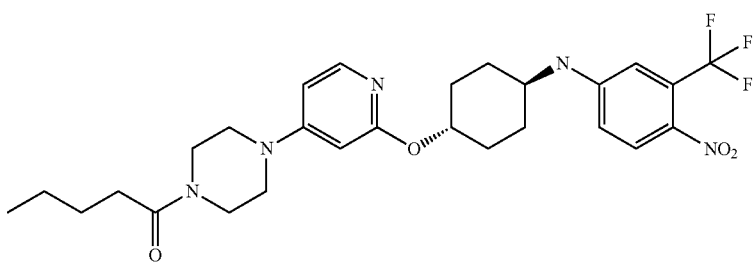
18 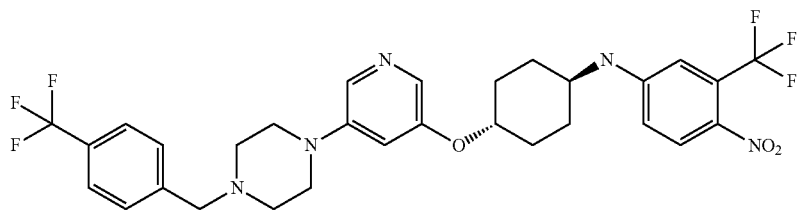
19 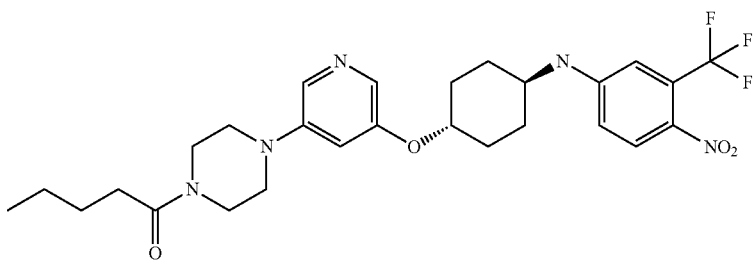 [SMILES: CCCCC(=O)N1CCN(c2cncc(O[C@H]3CC[C@H](Nc4ccc([N+](=O)[O-])c(C(F)(F)F)c4)CC3)c2)CC1]
20 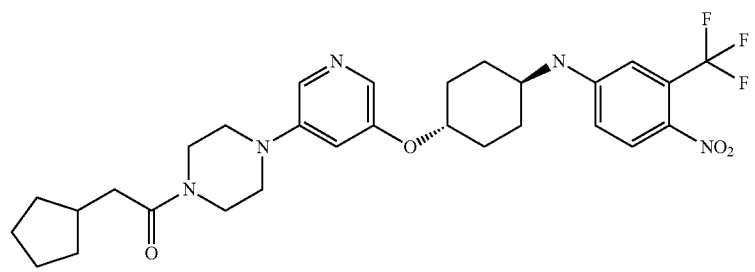

-continued
21
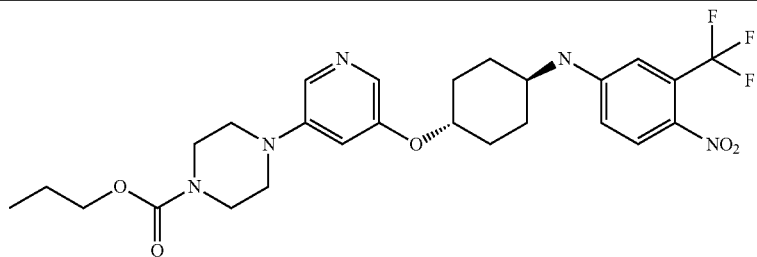
22
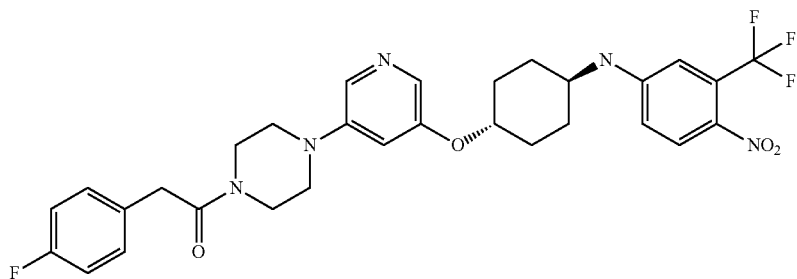 [SMILES: O=C(Cc1ccc(F)cc1)N1CCN(c2cncc(O[C@H]3CC[C@H](Nc4ccc([N+](=O)[O-])c(C(F)(F)F)c4)CC3)c2)CC1]
23
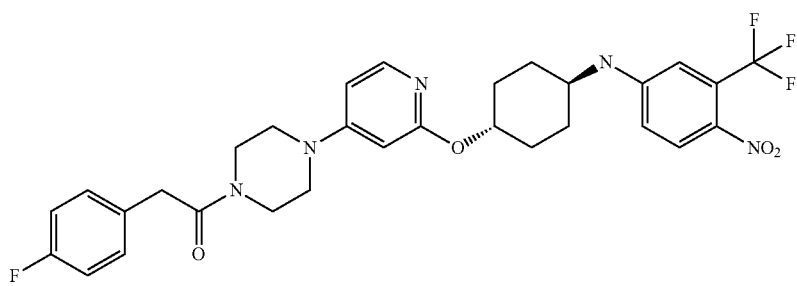 [SMILES: O=C(Cc1ccc(F)cc1)N1CCN(c2ccnc(O[C@H]3CC[C@H](Nc4ccc([N+](=O)[O-])c(C(F)(F)F)c4)CC3)c2)CC1]
24
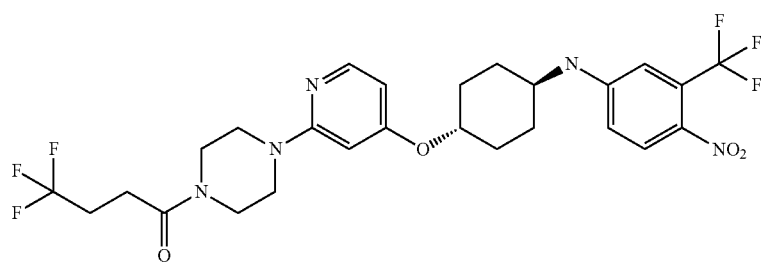 [SMILES: O=C(CCC(F)(F)F)N1CCN(c2cc(O[C@H]3CC[C@H](Nc4ccc([N+](=O)[O-])c(C(F)(F)F)c4)CC3)ccn2)CC1]
25
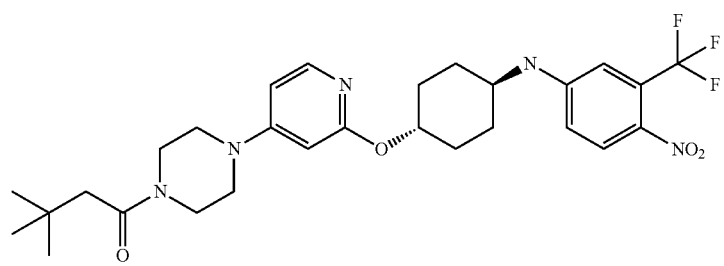 [SMILES: CC(C)(C)CC(=O)N1CCN(c2ccnc(O[C@H]3CC[C@H](Nc4ccc([N+](=O)[O-])c(C(F)(F)F)c4)CC3)c2)CC1]
26
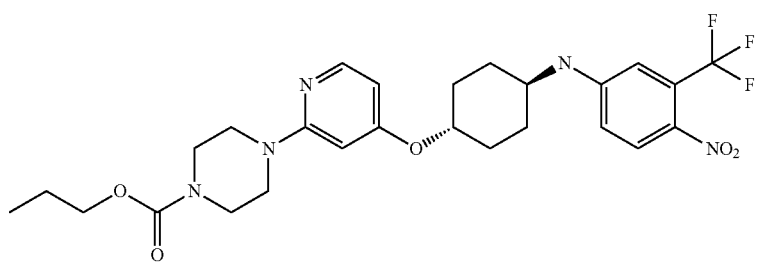 [SMILES: CCCOC(=O)N1CCN(c2cc(O[C@H]3CC[C@H](Nc4ccc([N+](=O)[O-])c(C(F)(F)F)c4)CC3)ccn2)CC1]

27
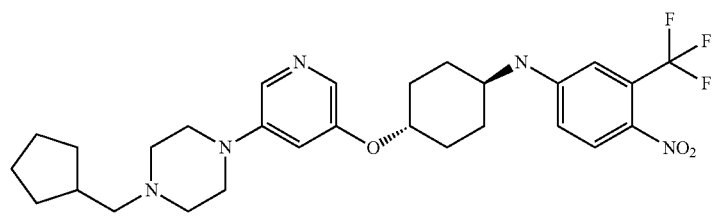 [SMILES: O=[N+]([O-])c1ccc(N[C@H]2CC[C@H](Oc3cncc(N4CCN(CC5CCCC5)CC4)c3)CC2)cc1C(F)(F)F]
28
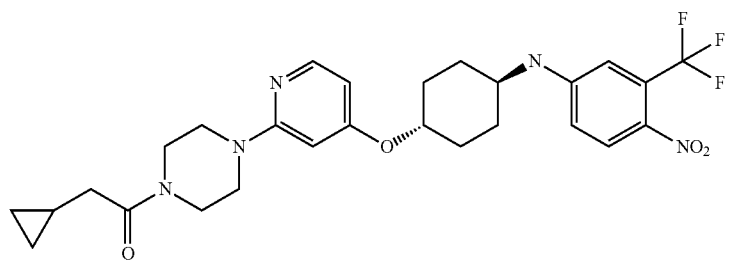 [SMILES: O=C(CC1CC1)N1CCN(c2cc(O[C@H]3CC[C@H](Nc4ccc([N+](=O)[O-])c(C(F)(F)F)c4)CC3)ccn2)CC1]
29
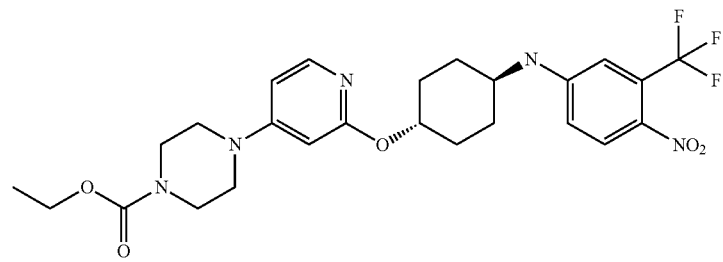
30
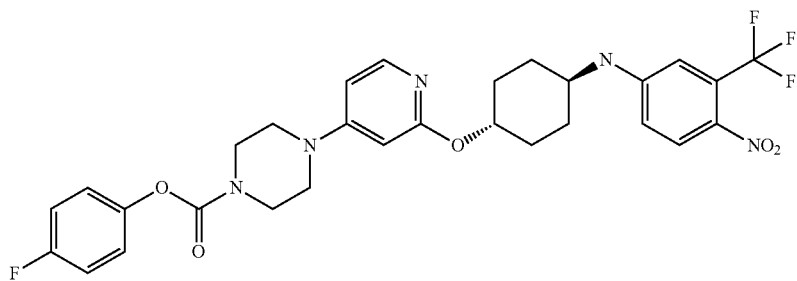
31
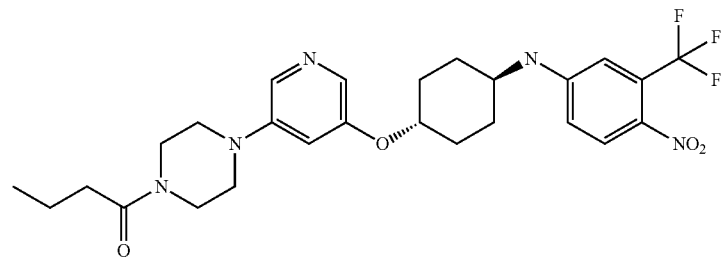 [SMILES: CCCC(=O)N1CCN(c2cncc(O[C@H]3CC[C@H](Nc4ccc([N+](=O)[O-])c(C(F)(F)F)c4)CC3)c2)CC1]
32
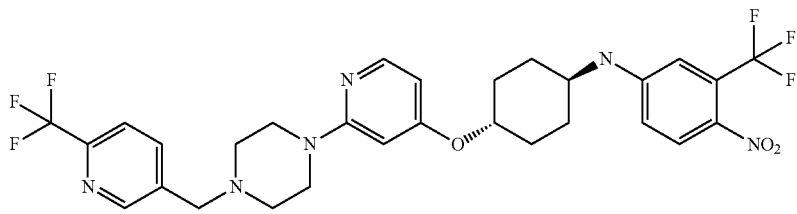 [SMILES: O=[N+]([O-])c1ccc(N[C@H]2CC[C@H](Oc3ccnc(N4CCN(Cc5ccc(C(F)(F)F)nc5)CC4)c3)CC2)cc1C(F)(F)F]

-continued
33
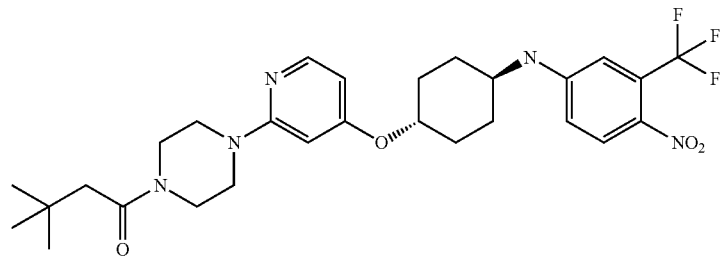
34
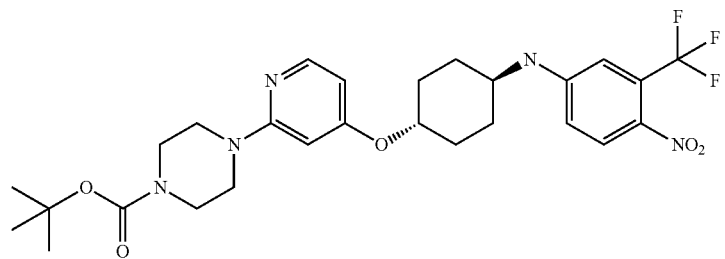
35
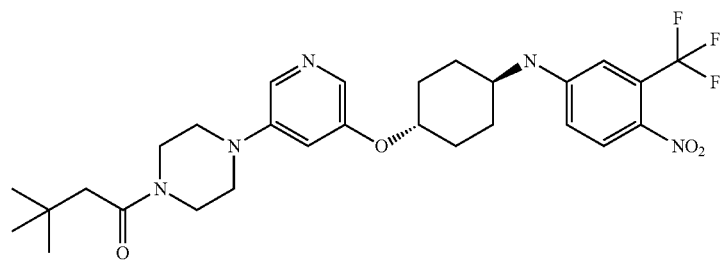 [SMILES: CC(C)(C)CC(=O)N1CCN(c2cncc(O[C@H]3CC[C@H](Nc4ccc([N+](=O)[O-])c(C(F)(F)F)c4)CC3)c2)CC1]
36
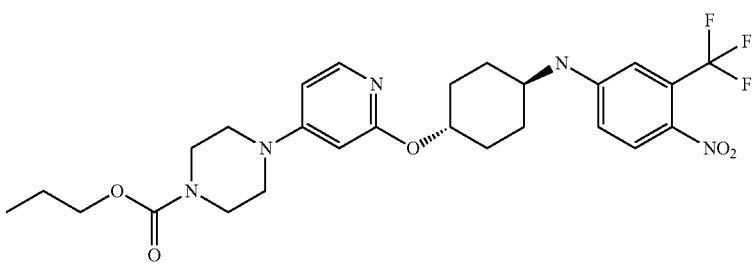 [SMILES: CCCOC(=O)N1CCN(c2ccnc(O[C@H]3CC[C@H](Nc4ccc([N+](=O)[O-])c(C(F)(F)F)c4)CC3)c2)CC1]
37
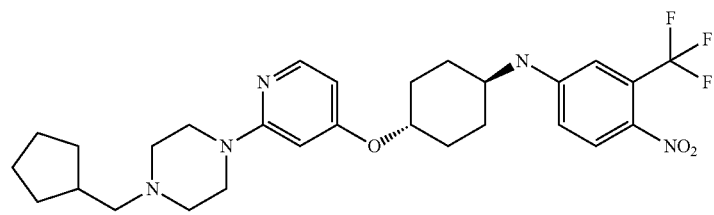 [SMILES: O=[N+]([O-])c1ccc(N[C@H]2CC[C@H](Oc3ccnc(N4CCN(CC5CCCC5)CC4)c3)CC2)cc1C(F)(F)F]
38
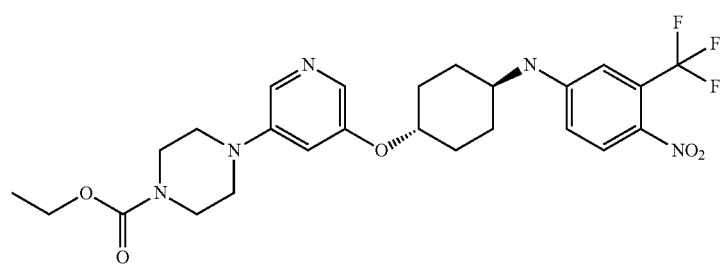

39
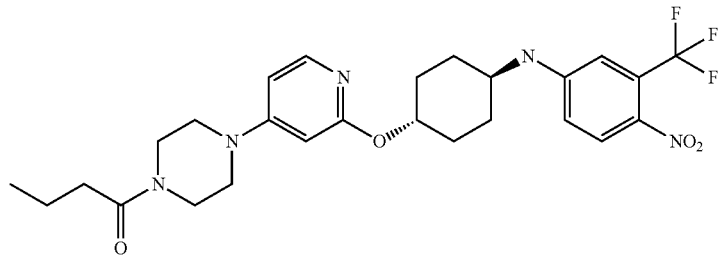 [SMILES: CCCC(=O)N1CCN(c2ccnc(O[C@H]3CC[C@H](Nc4ccc([N+](=O)[O-])c(C(F)(F)F)c4)CC3)c2)CC1]
40
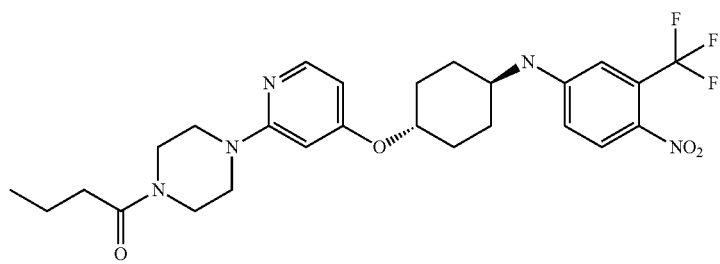 [SMILES: CCCC(=O)N1CCN(c2cc(O[C@H]3CC[C@H](Nc4ccc([N+](=O)[O-])c(C(F)(F)F)c4)CC3)ccn2)CC1]
41
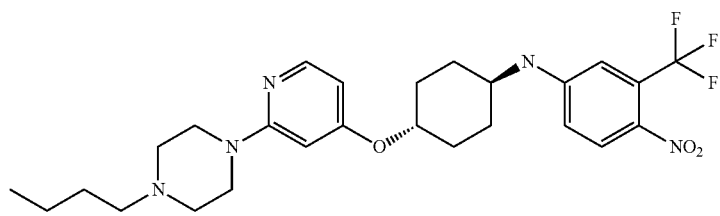 [SMILES: CCCCN1CCN(c2cc(O[C@H]3CC[C@H](Nc4ccc([N+](=O)[O-])c(C(F)(F)F)c4)CC3)ccn2)CC1]
43
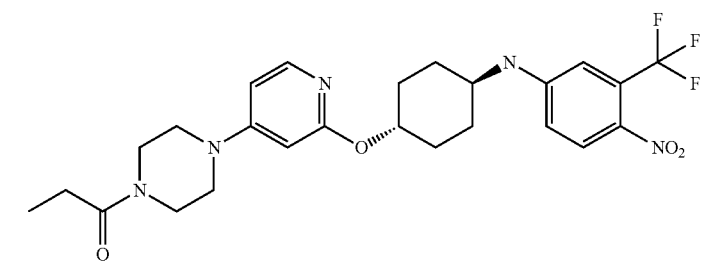 [SMILES: CCC(=O)N1CCN(c2ccnc(O[C@H]3CC[C@H](Nc4ccc([N+](=O)[O-])c(C(F)(F)F)c4)CC3)c2)CC1]
44
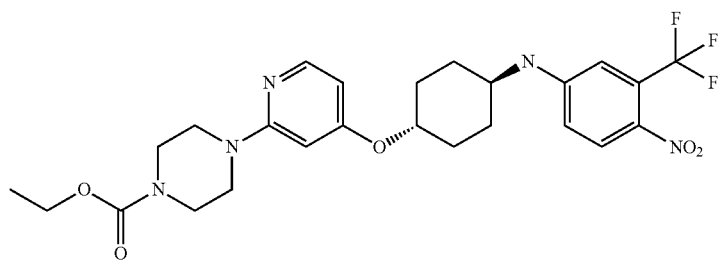
45
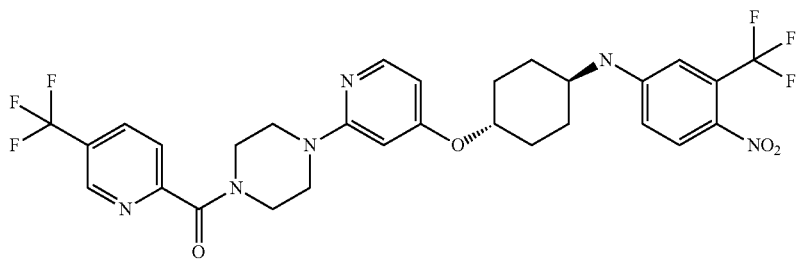 [SMILES: O=C(c1ccc(C(F)(F)F)cn1)N1CCN(c2cc(O[C@H]3CC[C@H](Nc4ccc([N+](=O)[O-])c(C(F)(F)F)c4)CC3)ccn2)CC1]

46
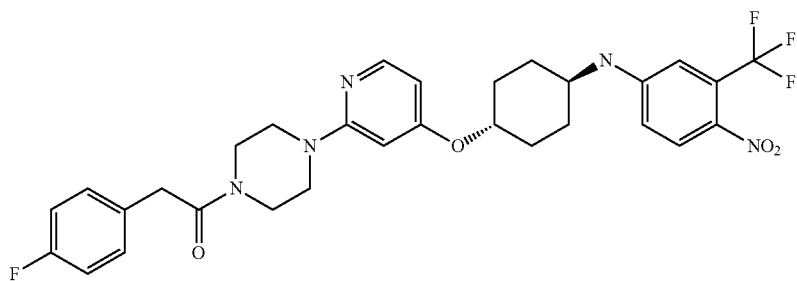 [SMILES: O=C(Cc1ccc(F)cc1)N1CCN(c2cc(O[C@H]3CC[C@H](Nc4ccc([N+](=O)[O-])c(C(F)(F)F)c4)CC3)ccn2)CC1]
47
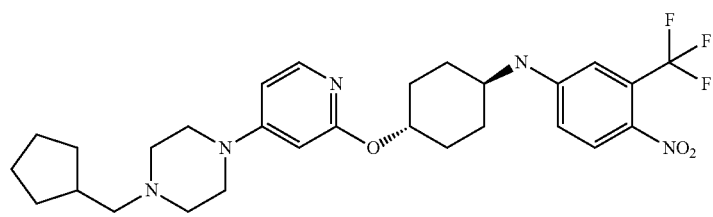 [SMILES: O=[N+]([O-])c1ccc(N[C@H]2CC[C@H](Oc3cc(N4CCN(CC5CCCC5)CC4)ccn3)CC2)cc1C(F)(F)F]
48
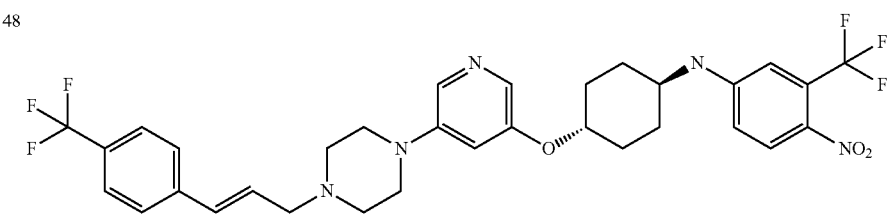
49
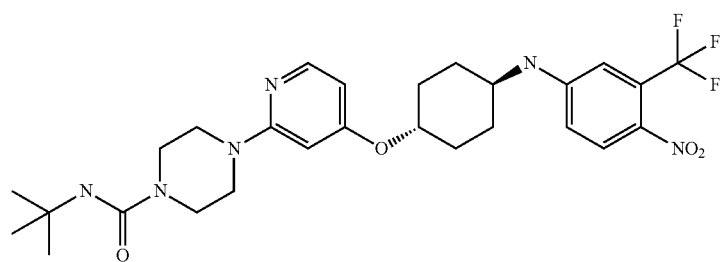
50
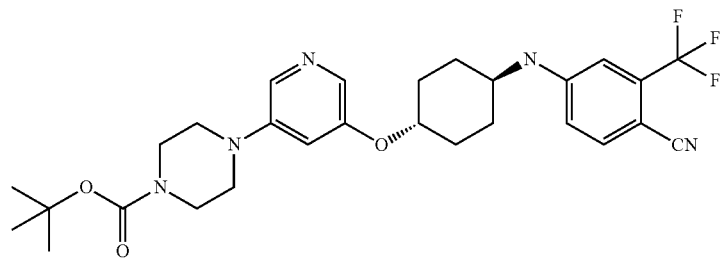
51
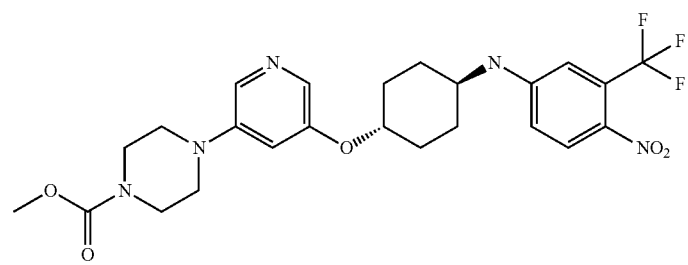

52  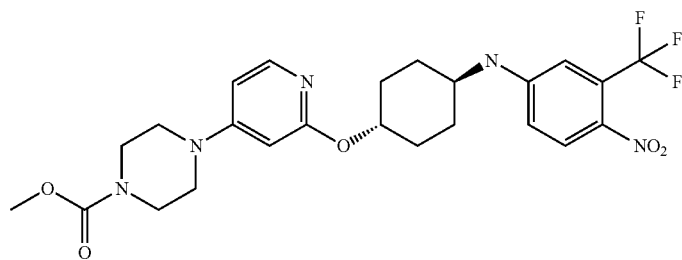 [SMILES: COC(=O)N1CCN(c2ccnc(O[C@H]3CC[C@H](Nc4ccc([N+](=O)[O-])c(C(F)(F)F)c4)CC3)c2)CC1]
53  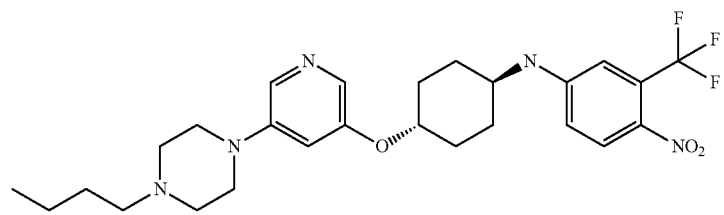 [SMILES: CCCCN1CCN(c2cncc(O[C@H]3CC[C@H](Nc4ccc([N+](=O)[O-])c(C(F)(F)F)c4)CC3)c2)CC1]
54  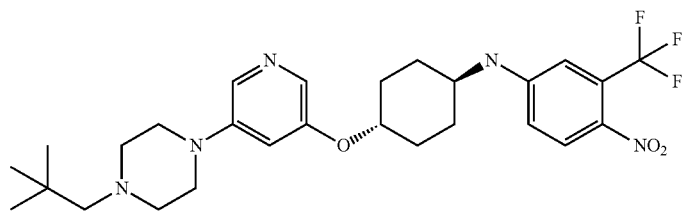 [SMILES: CC(C)(C)CN1CCN(c2cncc(O[C@H]3CC[C@H](Nc4ccc([N+](=O)[O-])c(C(F)(F)F)c4)CC3)c2)CC1]
55  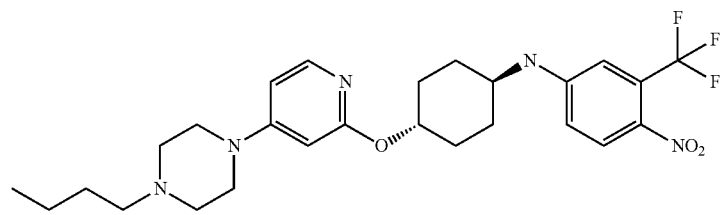 [SMILES: CCCCN1CCN(c2ccnc(O[C@H]3CC[C@H](Nc4ccc([N+](=O)[O-])c(C(F)(F)F)c4)CC3)c2)CC1]
56  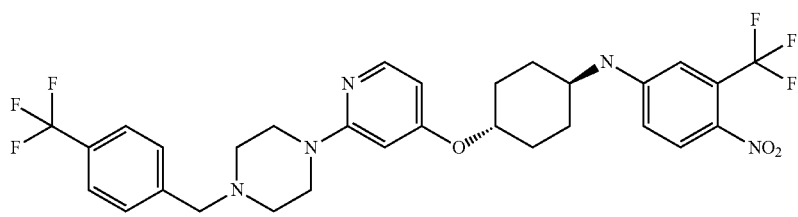
57  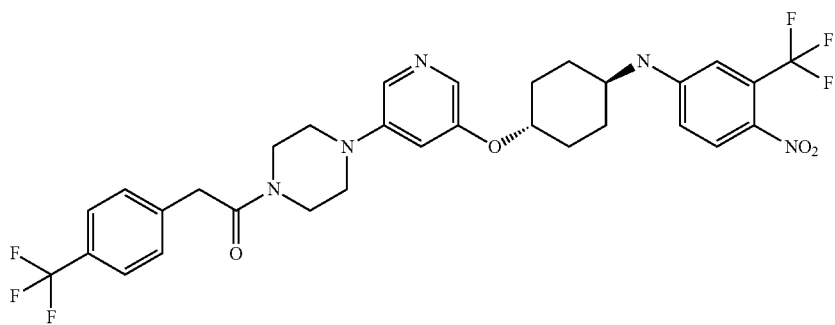 [SMILES: O=C(Cc1ccc(C(F)(F)F)cc1)N1CCN(c2cncc(O[C@H]3CC[C@H](Nc4ccc([N+](=O)[O-])c(C(F)(F)F)c4)CC3)c2)CC1]

58 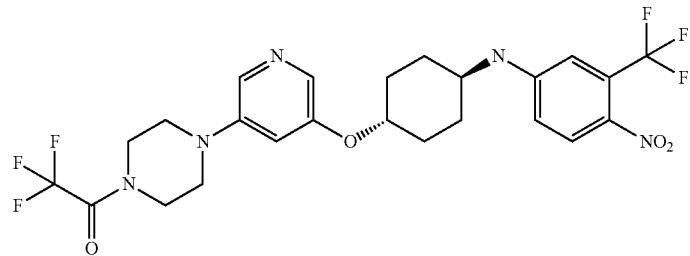 [SMILES: O=C(N1CCN(c2cncc(O[C@H]3CC[C@H](Nc4ccc([N+](=O)[O-])c(C(F)(F)F)c4)CC3)c2)CC1)C(F)(F)F]
59 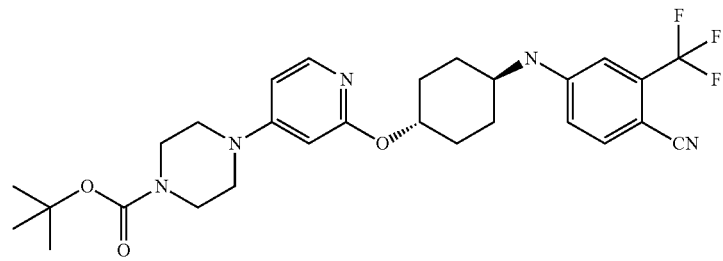 [SMILES: CC(C)(C)OC(=O)N1CCN(c2ccnc(O[C@H]3CC[C@H](Nc4ccc(C#N)c(C(F)(F)F)c4)CC3)c2)CC1]
60 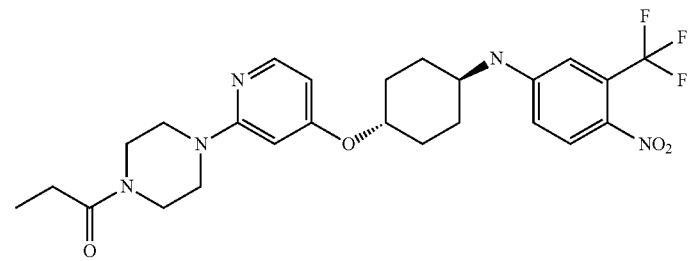 [SMILES: CCC(=O)N1CCN(c2cc(O[C@H]3CC[C@H](Nc4ccc([N+](=O)[O-])c(C(F)(F)F)c4)CC3)ccn2)CC1]
61 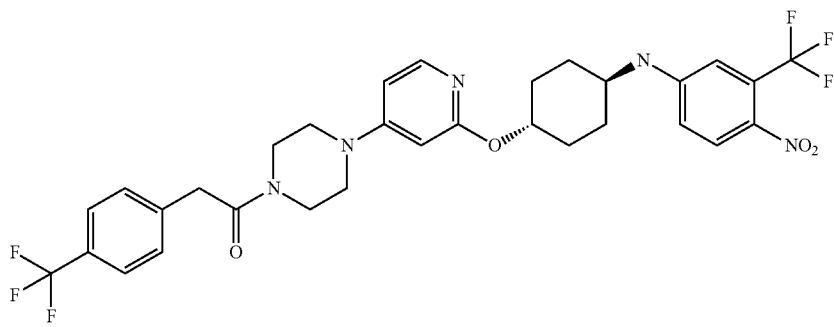 [SMILES: O=C(Cc1ccc(C(F)(F)F)cc1)N1CCN(c2ccnc(O[C@H]3CC[C@H](Nc4ccc([N+](=O)[O-])c(C(F)(F)F)c4)CC3)c2)CC1]
62 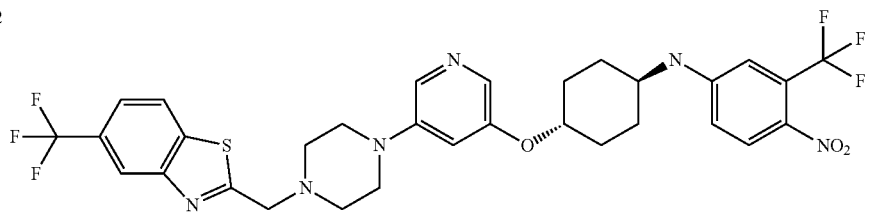
63 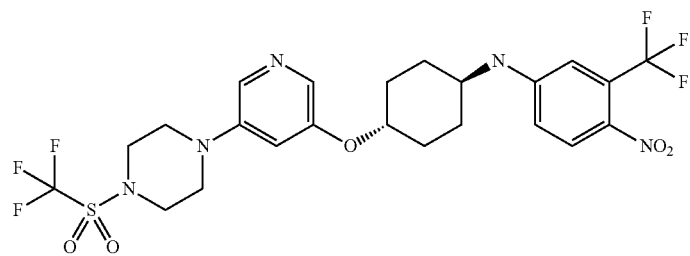 [SMILES: O=[N+]([O-])c1ccc(N[C@H]2CC[C@H](Oc3cncc(N4CCN(S(=O)(=O)C(F)(F)F)CC4)c3)CC2)cc1C(F)(F)F]

-continued
| 64 | 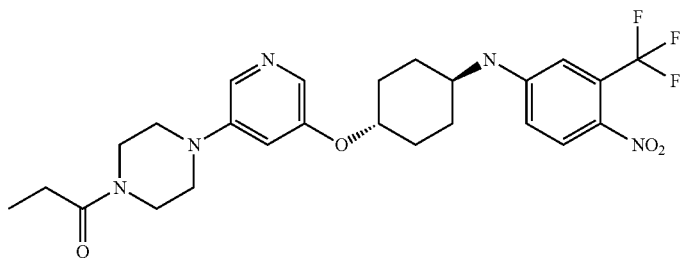 [SMILES: CCC(=O)N1CCN(c2cncc(O[C@H]3CC[C@H](Nc4ccc([N+](=O)[O-])c(C(F)(F)F)c4)CC3)c2)CC1] |
| 65 | 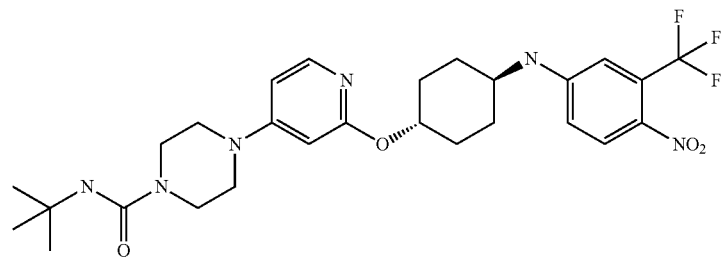 |
| 66 | 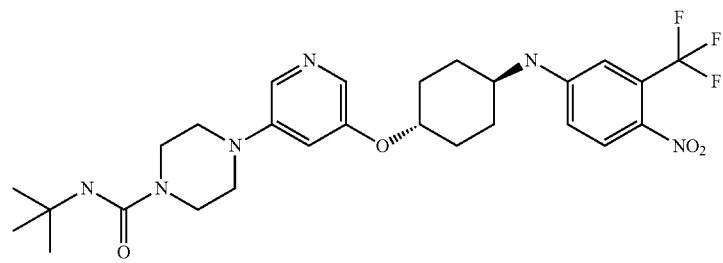 [SMILES: CC(C)(C)NC(=O)N1CCN(c2cncc(O[C@H]3CC[C@H](Nc4ccc([N+](=O)[O-])c(C(F)(F)F)c4)CC3)c2)CC1] |
| 67 | 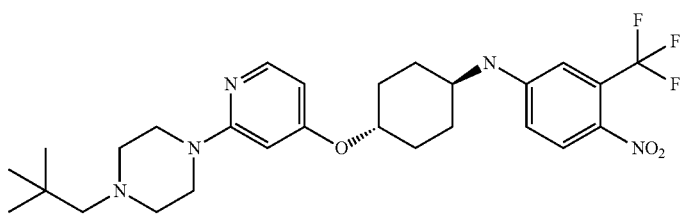 [SMILES: CC(C)(C)CN1CCN(c2cc(O[C@H]3CC[C@H](Nc4ccc([N+](=O)[O-])c(C(F)(F)F)c4)CC3)ccn2)CC1] |
| 68 | 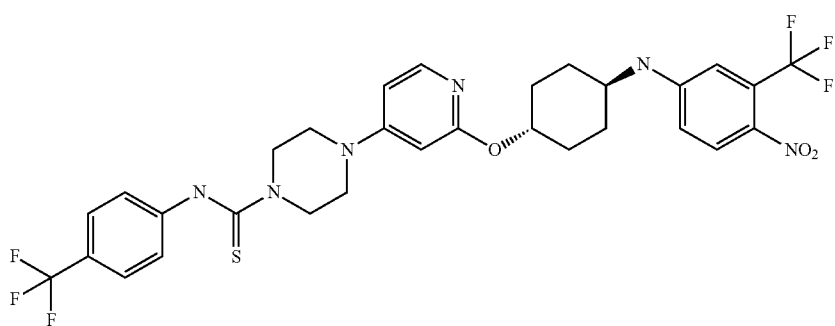 |
| 69 | 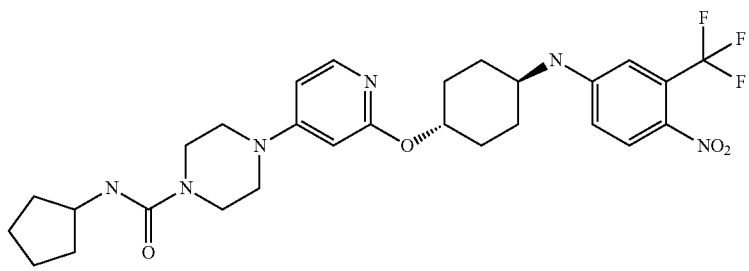 |

-continued
70
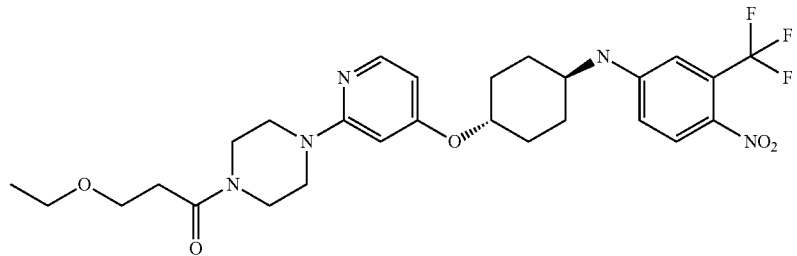 [SMILES: CCOCCC(=O)N1CCN(c2cc(O[C@H]3CC[C@H](Nc4ccc([N+](=O)[O-])c(C(F)(F)F)c4)CC3)ccn2)CC1]
71
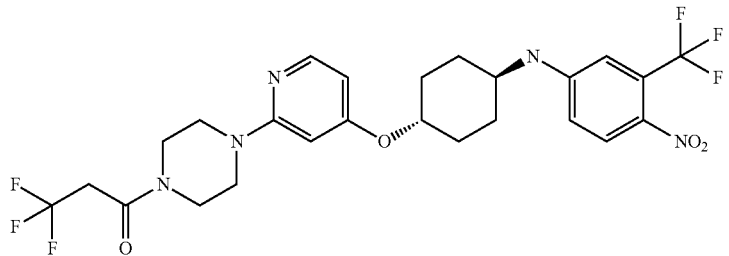 [SMILES: O=C(CC(F)(F)F)N1CCN(c2cc(O[C@H]3CC[C@H](Nc4ccc([N+](=O)[O-])c(C(F)(F)F)c4)CC3)ccn2)CC1]
72
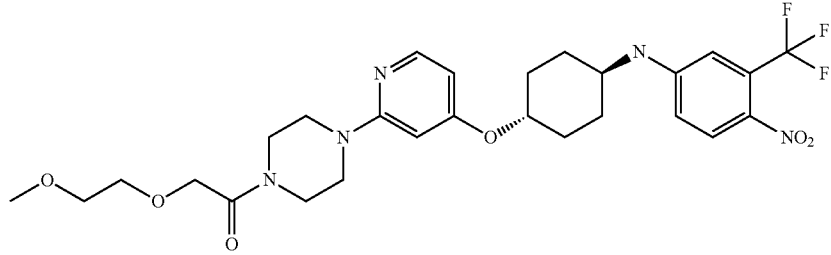 [SMILES: COCCOCC(=O)N1CCN(c2cc(O[C@H]3CC[C@H](Nc4ccc([N+](=O)[O-])c(C(F)(F)F)c4)CC3)ccn2)CC1]
73
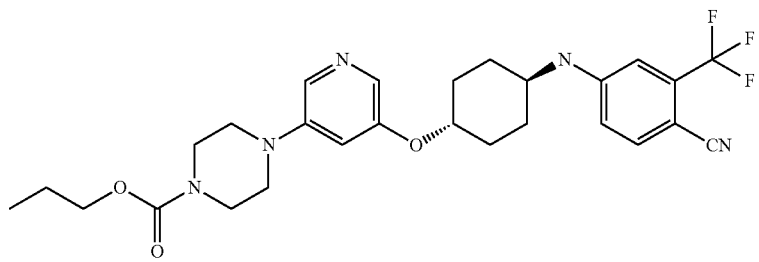 [SMILES: CCCOC(=O)N1CCN(c2cncc(O[C@H]3CC[C@H](Nc4ccc(C#N)c(C(F)(F)F)c4)CC3)c2)CC1]
74
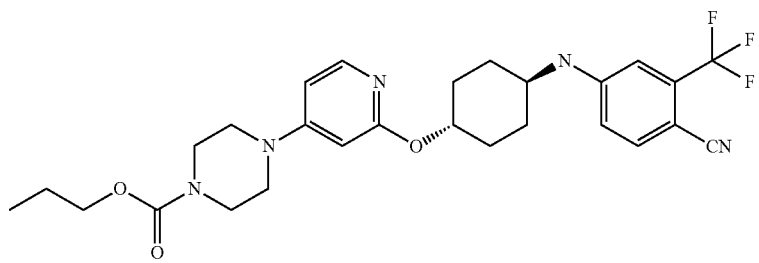 [SMILES: CCCOC(=O)N1CCN(c2ccnc(O[C@H]3CC[C@H](Nc4ccc(C#N)c(C(F)(F)F)c4)CC3)c2)CC1]
75
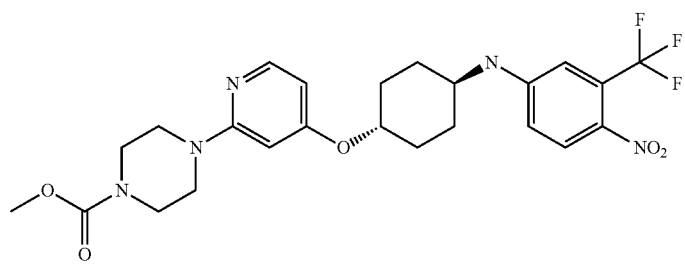 [SMILES: COC(=O)N1CCN(c2cc(O[C@H]3CC[C@H](Nc4ccc([N+](=O)[O-])c(C(F)(F)F)c4)CC3)ccn2)CC1]

76
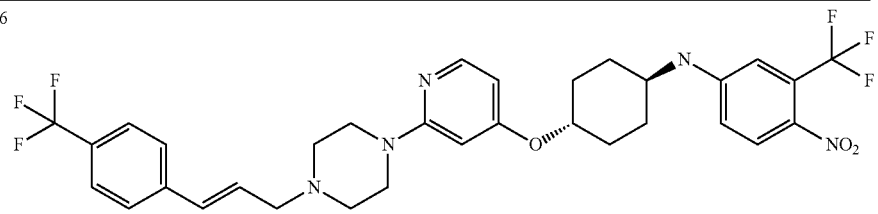
77
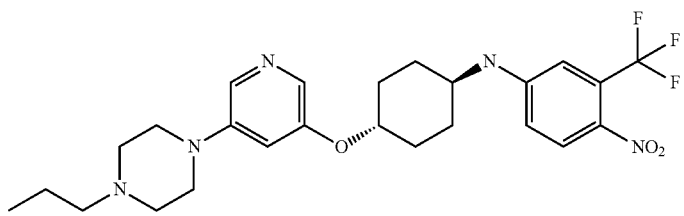 [SMILES: CCCN1CCN(c2cncc(O[C@H]3CC[C@H](Nc4ccc([N+](=O)[O-])c(C(F)(F)F)c4)CC3)c2)CC1]
78
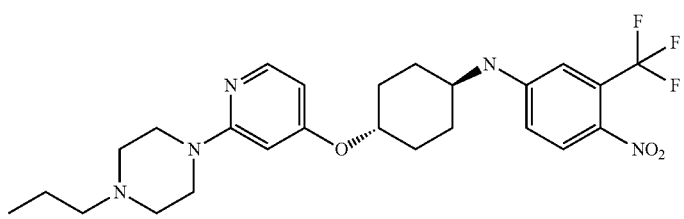 [SMILES: CCCN1CCN(c2cc(O[C@H]3CC[C@H](Nc4ccc([N+](=O)[O-])c(C(F)(F)F)c4)CC3)ccn2)CC1]
79
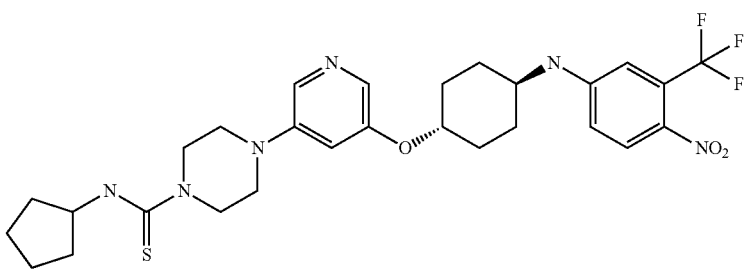
80
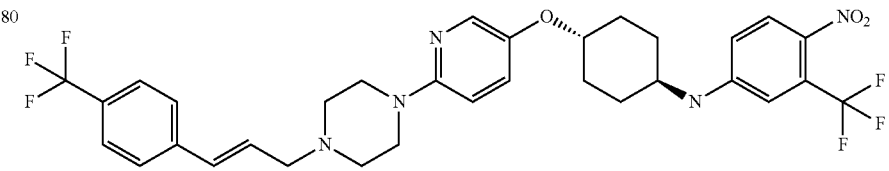
81
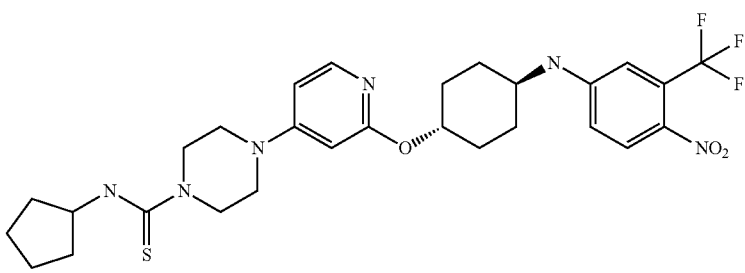
82
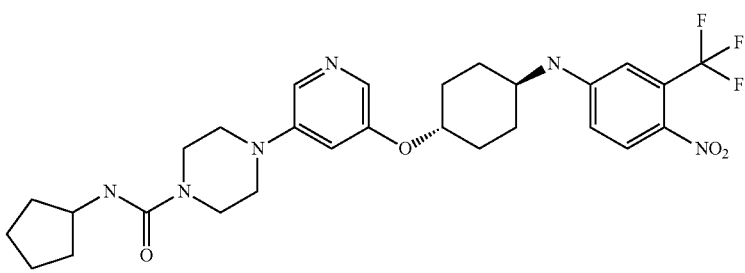

83 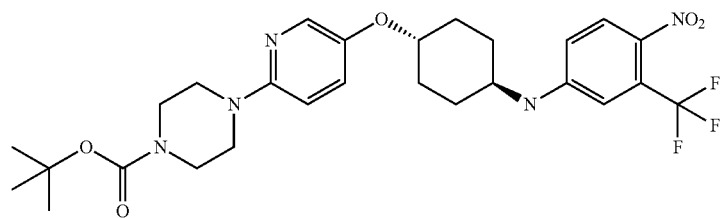 [SMILES: CC(C)(C)OC(=O)N1CCN(c2ccc(O[C@H]3CC[C@H](Nc4ccc([N+](=O)[O-])c(C(F)(F)F)c4)CC3)cn2)CC1]
84 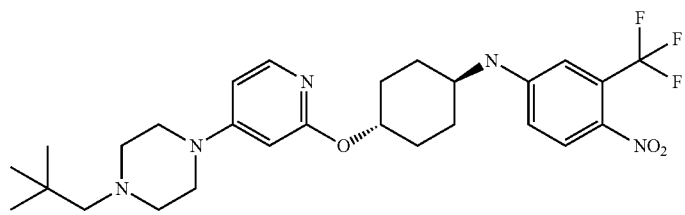 [SMILES: CC(C)(C)CN1CCN(c2ccnc(O[C@H]3CC[C@H](Nc4ccc([N+](=O)[O-])c(C(F)(F)F)c4)CC3)c2)CC1]
85 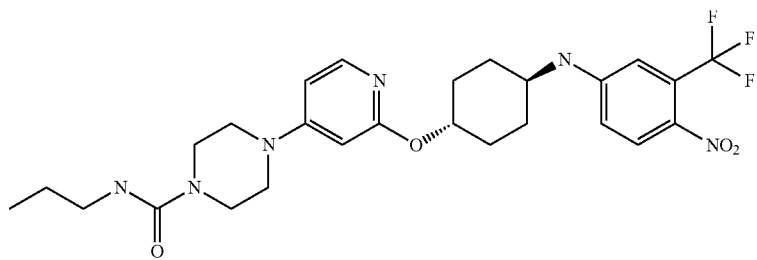
86 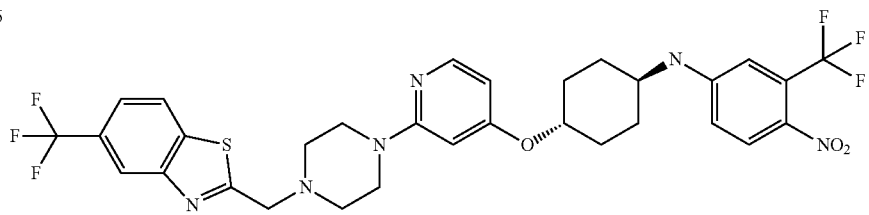
87 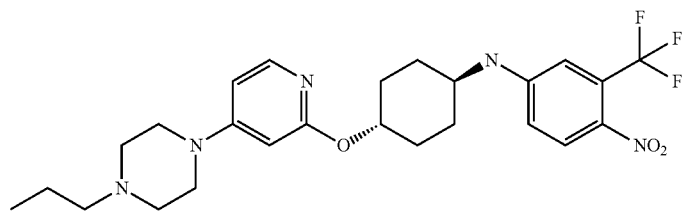 [SMILES: CCCN1CCN(c2ccnc(O[C@H]3CC[C@H](Nc4ccc([N+](=O)[O-])c(C(F)(F)F)c4)CC3)c2)CC1]
88 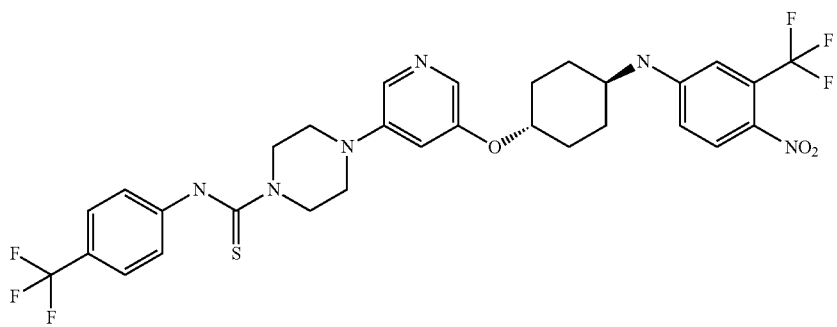

89
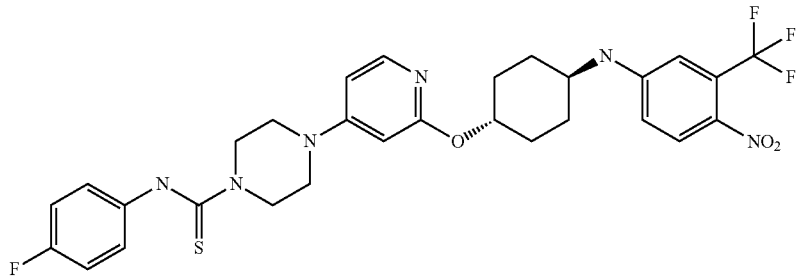 [SMILES: O=[N+]([O-])c1ccc(N[C@H]2CC[C@H](Oc3cc(N4CCN(C(=S)Nc5ccc(F)cc5)CC4)ccn3)CC2)cc1C(F)(F)F]
91
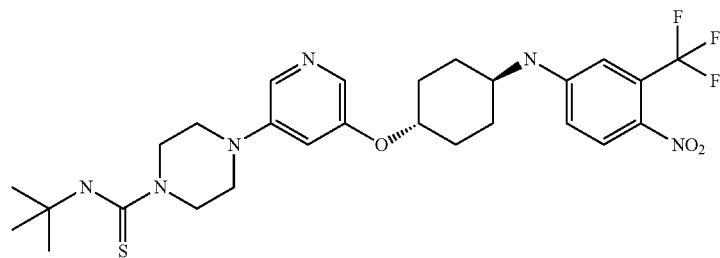 [SMILES: CC(C)(C)NC(=S)N1CCN(c2cncc(O[C@H]3CC[C@H](Nc4ccc([N+](=O)[O-])c(C(F)(F)F)c4)CC3)c2)CC1]
92
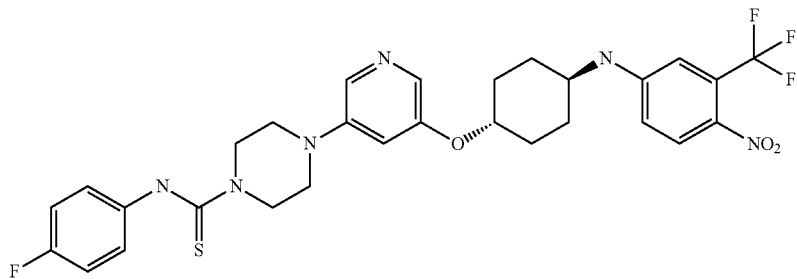
93
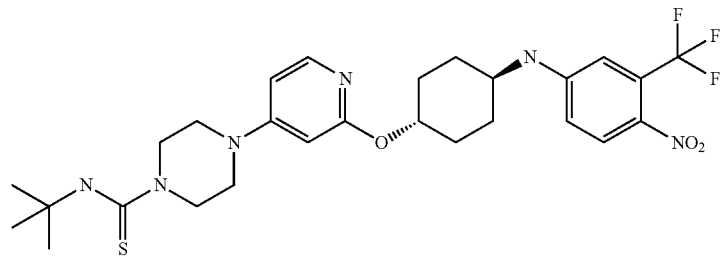
94
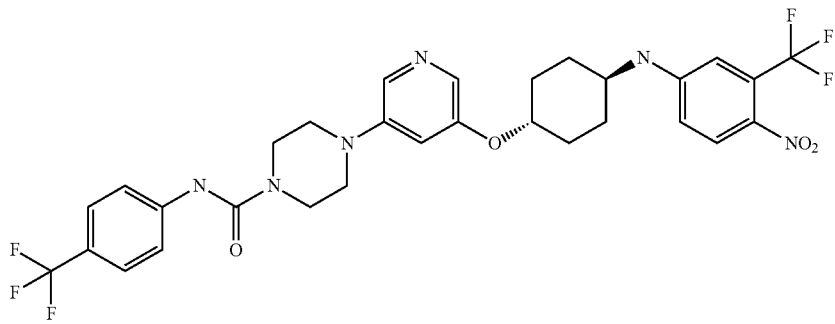 [SMILES: O=C(Nc1ccc(C(F)(F)F)cc1)N1CCN(c2cncc(O[C@H]3CC[C@H](Nc4ccc([N+](=O)[O-])c(C(F)(F)F)c4)CC3)c2)CC1]

-continued
95
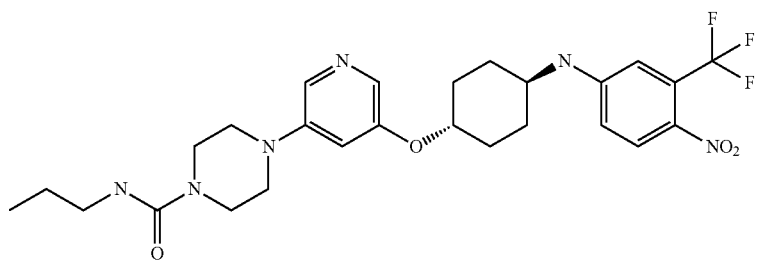
96
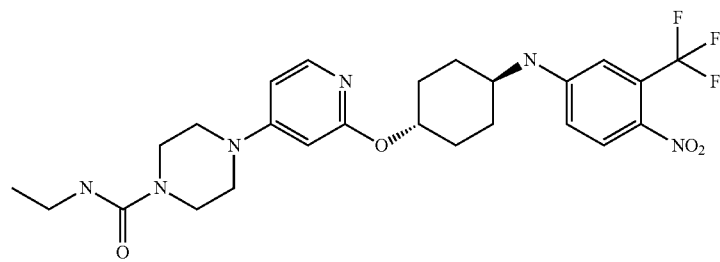
97
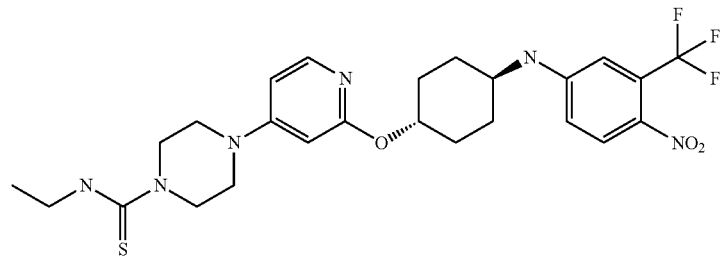 [SMILES: CCNC(=S)N1CCN(c2ccnc(O[C@H]3CC[C@H](Nc4ccc([N+](=O)[O-])c(C(F)(F)F)c4)CC3)c2)CC1]
98
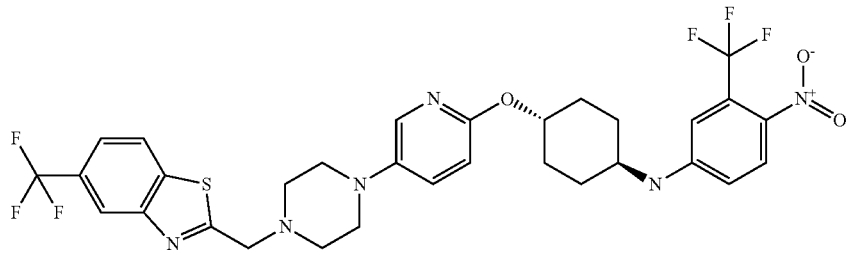 [SMILES: O=[N+]([O-])c1ccc(N[C@H]2CC[C@H](Oc3ccc(N4CCN(Cc5nc6cc(C(F)(F)F)ccc6s5)CC4)cn3)CC2)cc1C(F)(F)F]
99
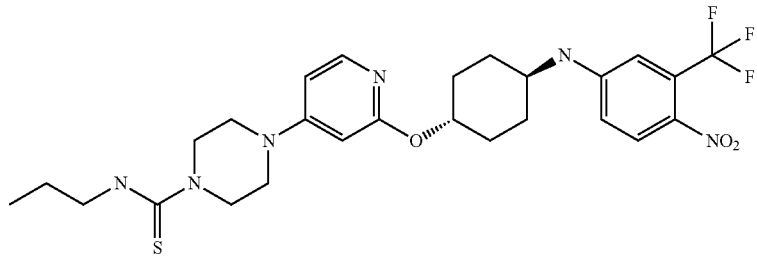 [SMILES: CCCNC(=S)N1CCN(c2ccnc(O[C@H]3CC[C@H](Nc4ccc([N+](=O)[O-])c(C(F)(F)F)c4)CC3)c2)CC1]
100
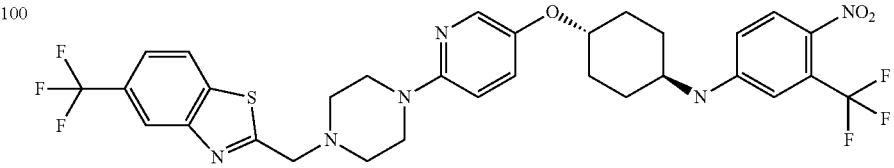

101
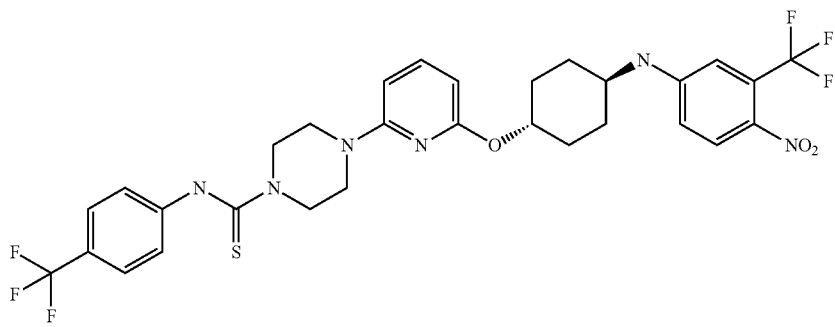
104
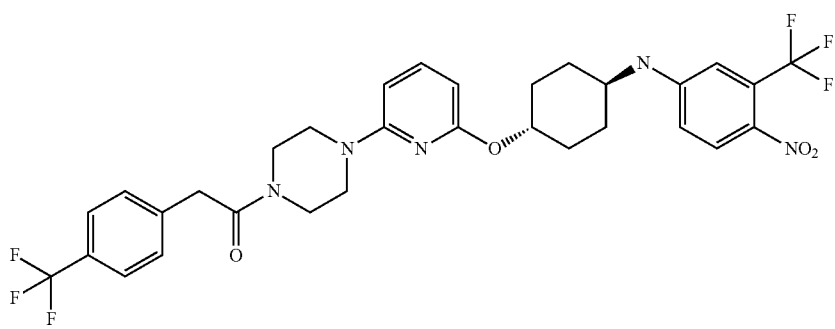 [SMILES: O=C(Cc1ccc(C(F)(F)F)cc1)N1CCN(c2cccc(O[C@H]3CC[C@H](Nc4ccc([N+](=O)[O-])c(C(F)(F)F)c4)CC3)n2)CC1]
105
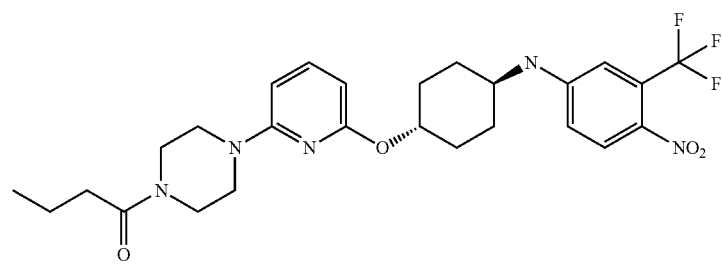 [SMILES: CCCC(=O)N1CCN(c2cccc(O[C@H]3CC[C@H](Nc4ccc([N+](=O)[O-])c(C(F)(F)F)c4)CC3)n2)CC1]
106
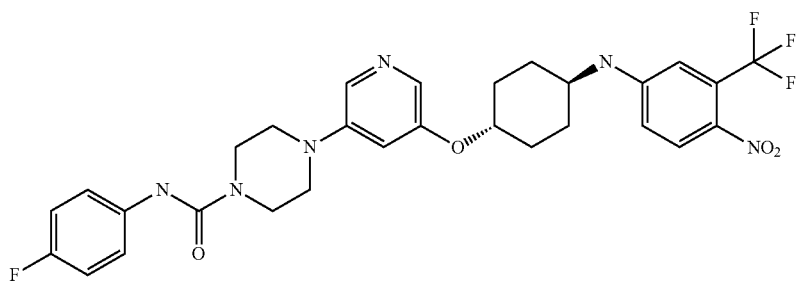
107
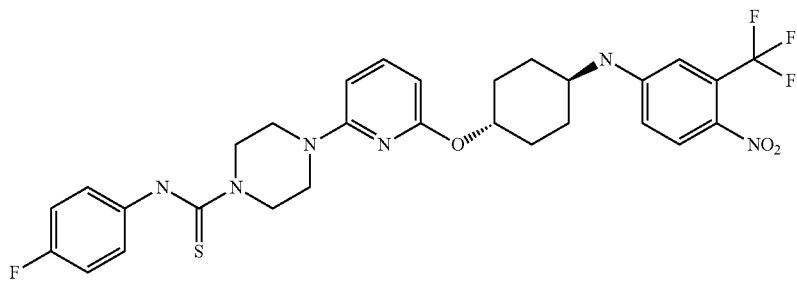

108
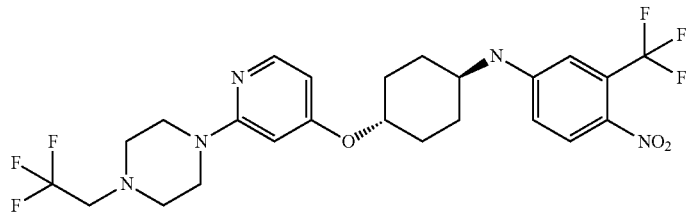 [SMILES: O=[N+]([O-])c1ccc(N[C@H]2CC[C@H](Oc3ccnc(N4CCN(CC(F)(F)F)CC4)c3)CC2)cc1C(F)(F)F]
110
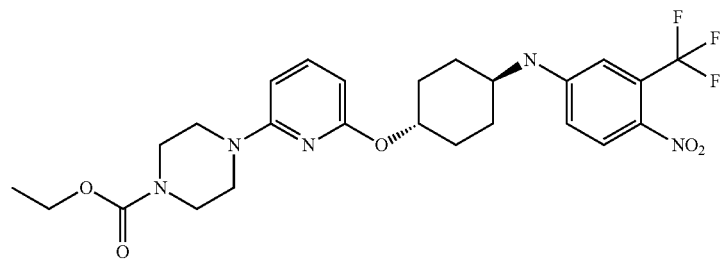
111
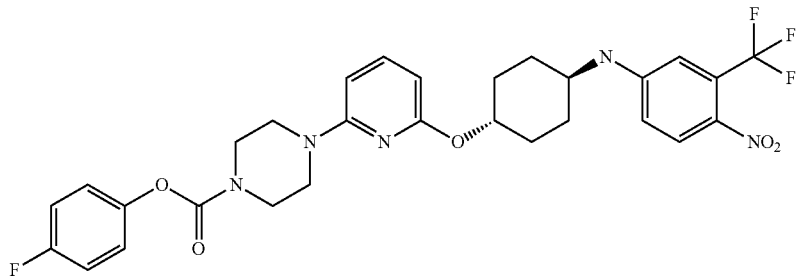
112
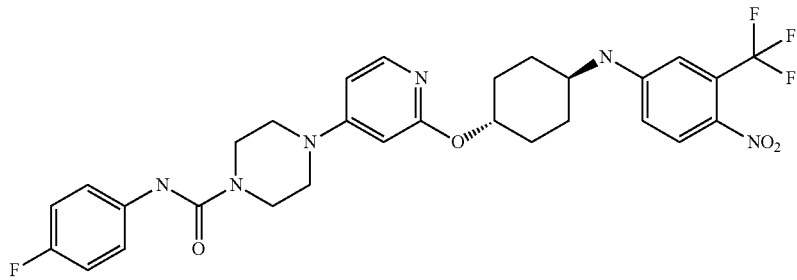
113
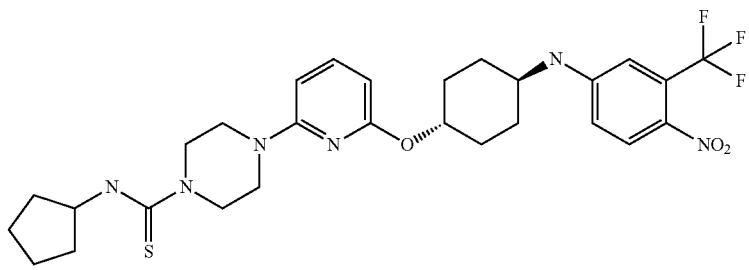
114
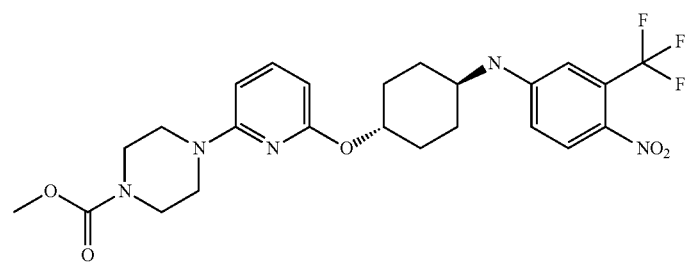

-continued
115
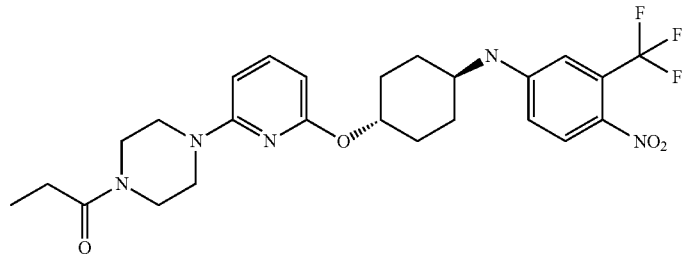 [SMILES: CCC(=O)N1CCN(c2cccc(O[C@H]3CC[C@H](Nc4ccc([N+](=O)[O-])c(C(F)(F)F)c4)CC3)n2)CC1]
116
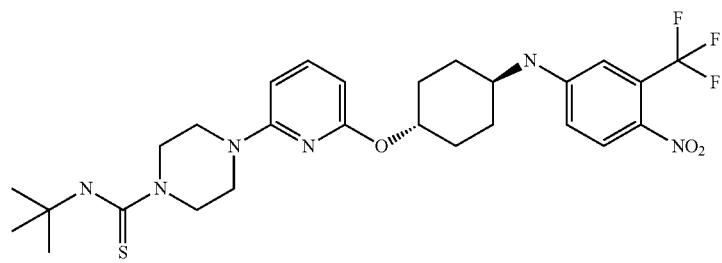
117
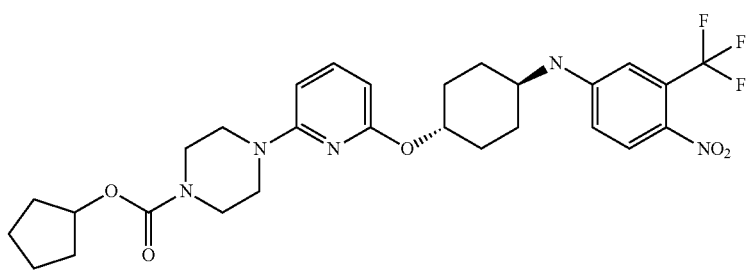
118
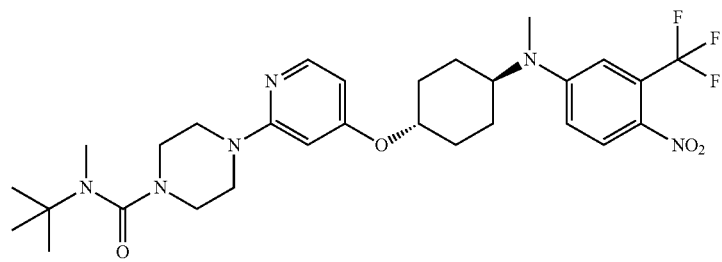 [SMILES: CN(C(=O)N1CCN(c2cc(O[C@H]3CC[C@H](N(C)c4ccc([N+](=O)[O-])c(C(F)(F)F)c4)CC3)ccn2)CC1)C(C)(C)C]
119
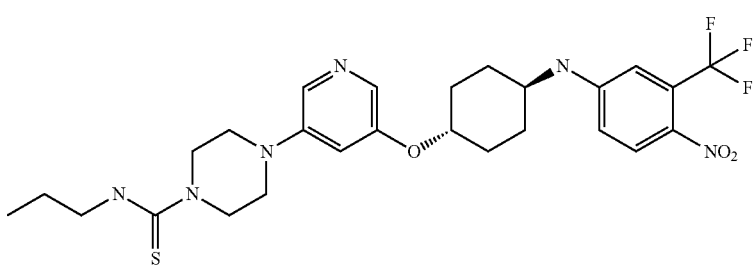
120
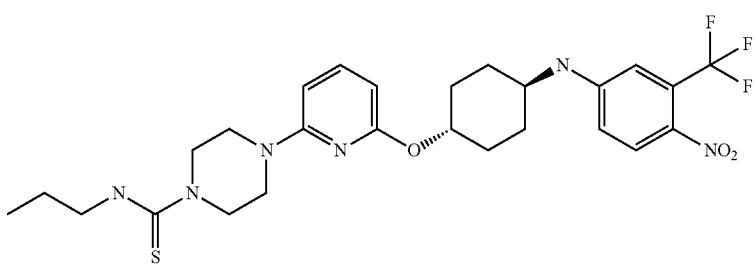

-continued
121
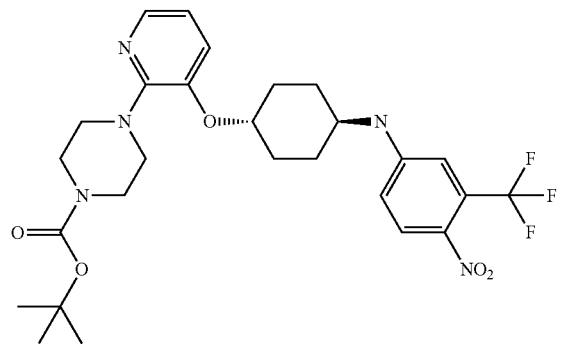 [SMILES: CC(C)(C)OC(=O)N1CCN(c2ncccc2O[C@H]2CC[C@H](Nc3ccc([N+](=O)[O-])c(C(F)(F)F)c3)CC2)CC1]
122
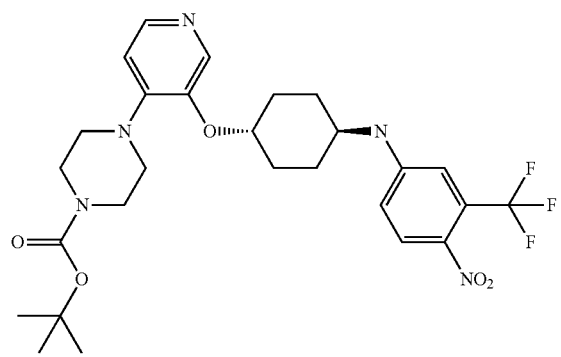 [SMILES: CC(C)(C)OC(=O)N1CCN(c2ccncc2O[C@H]2CC[C@H](Nc3ccc([N+](=O)[O-])c(C(F)(F)F)c3)CC2)CC1]
123
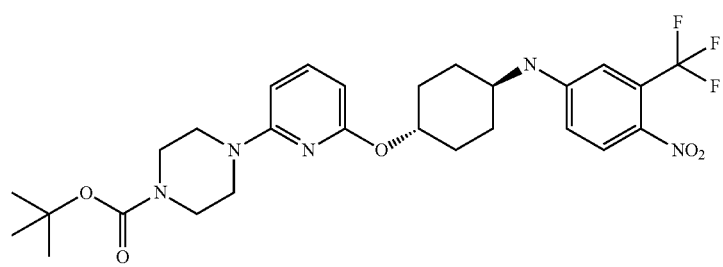
124
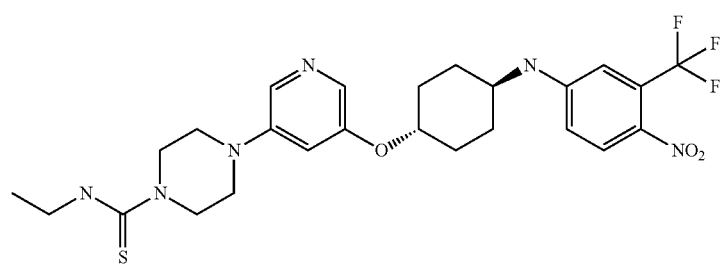
125
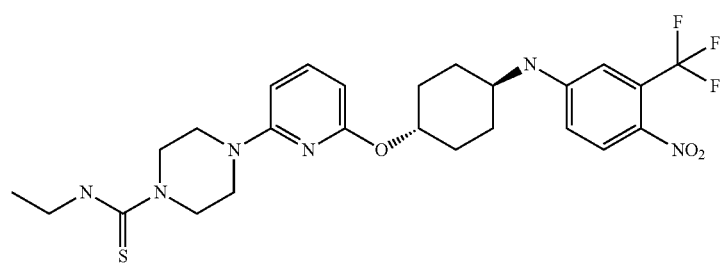

-continued
126
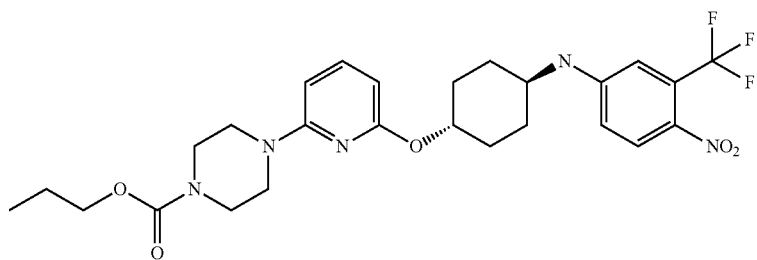 [SMILES: CCCNC(=O)N1CCN(c2cccc(O[C@H]3CC[C@H](Nc4ccc([N+](=O)[O-])c(C(F)(F)F)c4)CC3)n2)CC1]
127
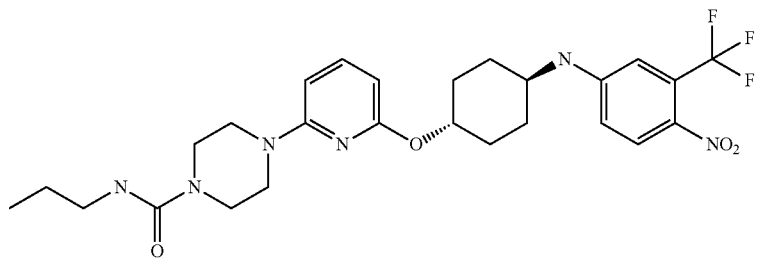
128
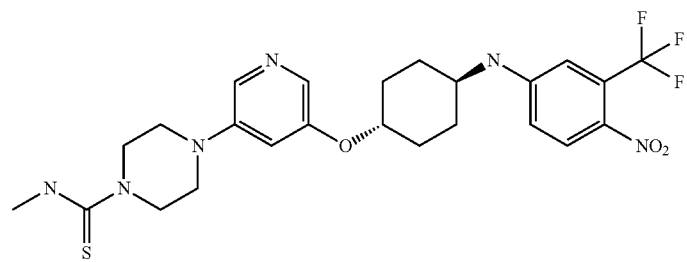
129
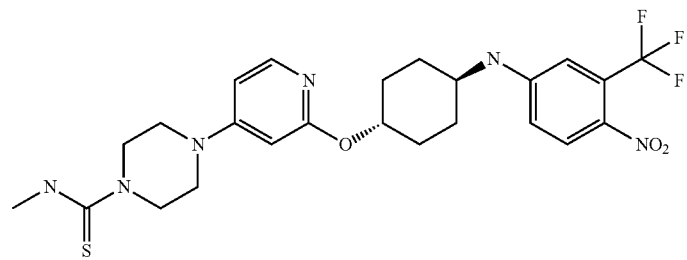
130
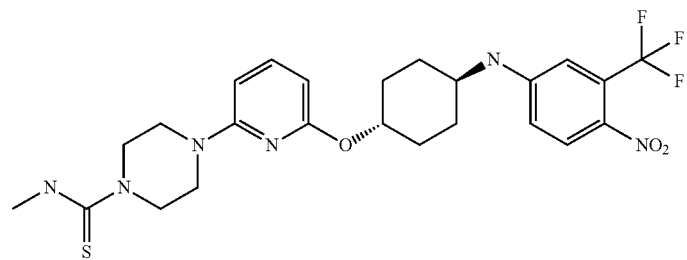
131
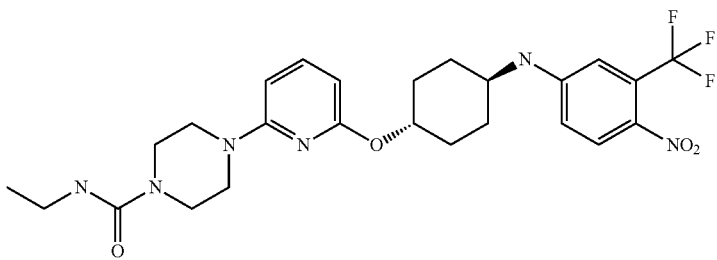

-continued
132
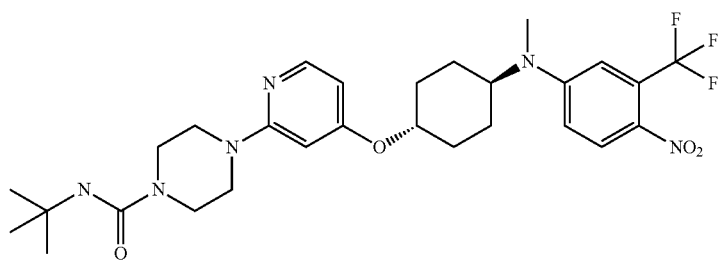 [SMILES: CN(c1ccc([N+](=O)[O-])c(C(F)(F)F)c1)[C@H]1CC[C@H](Oc2ccnc(N3CCN(C(=O)NC(C)(C)C)CC3)c2)CC1]
133
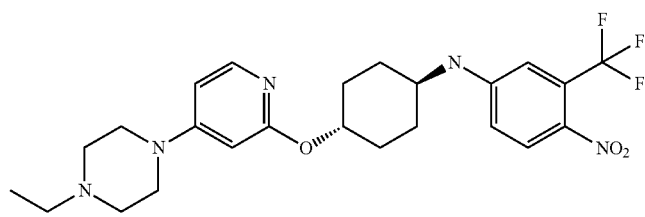 [SMILES: CCN1CCN(c2ccnc(O[C@H]3CC[C@H](Nc4ccc([N+](=O)[O-])c(C(F)(F)F)c4)CC3)c2)CC1]
134
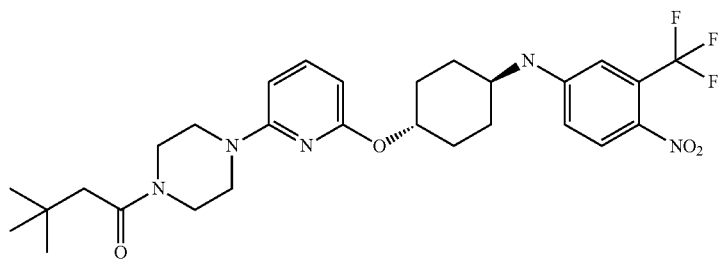 [SMILES: CC(C)(C)CC(=O)N1CCN(c2cccc(O[C@H]3CC[C@H](Nc4ccc([N+](=O)[O-])c(C(F)(F)F)c4)CC3)n2)CC1]
136
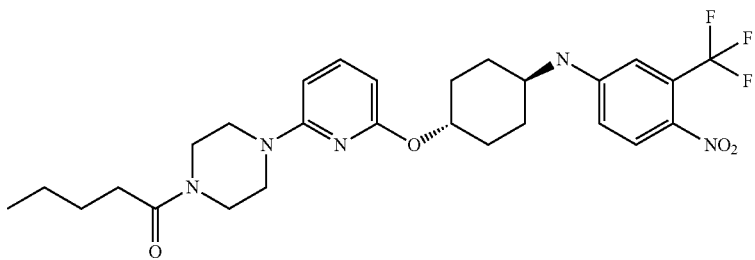 [SMILES: CCCCC(=O)N1CCN(c2cccc(O[C@H]3CC[C@H](Nc4ccc([N+](=O)[O-])c(C(F)(F)F)c4)CC3)n2)CC1]
137
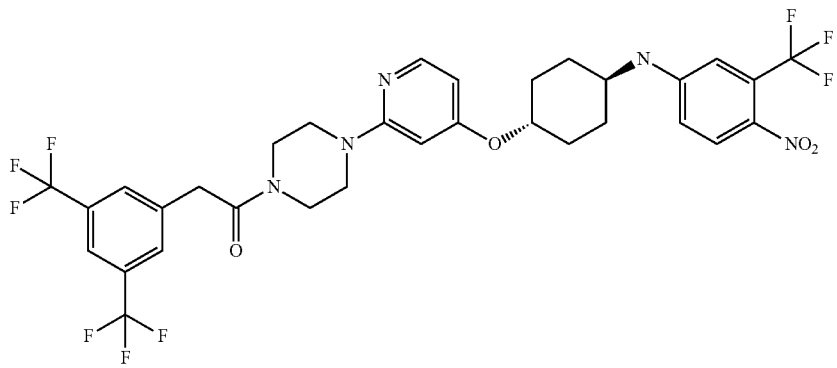 [SMILES: O=C(Cc1cc(C(F)(F)F)cc(C(F)(F)F)c1)N1CCN(c2cc(O[C@H]3CC[C@H](Nc4ccc([N+](=O)[O-])c(C(F)(F)F)c4)CC3)ccn2)CC1]

138
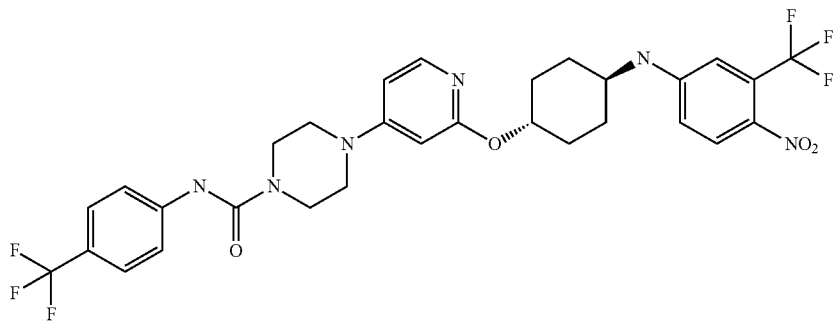
139
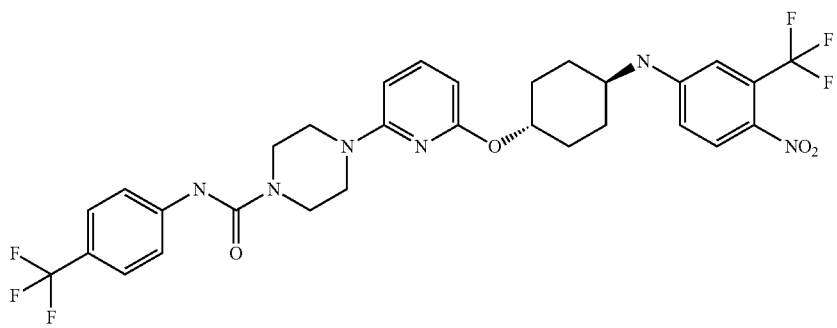
141
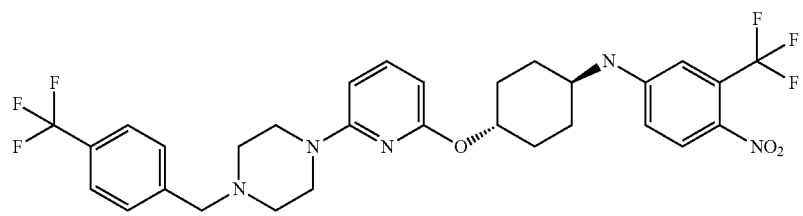 [SMILES: O=[N+]([O-])c1ccc(N[C@H]2CC[C@H](Oc3cccc(N4CCN(Cc5ccc(C(F)(F)F)cc5)CC4)n3)CC2)cc1C(F)(F)F]
142
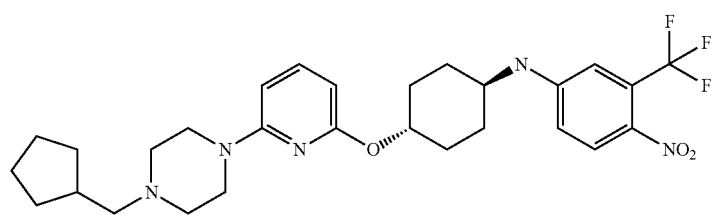
143
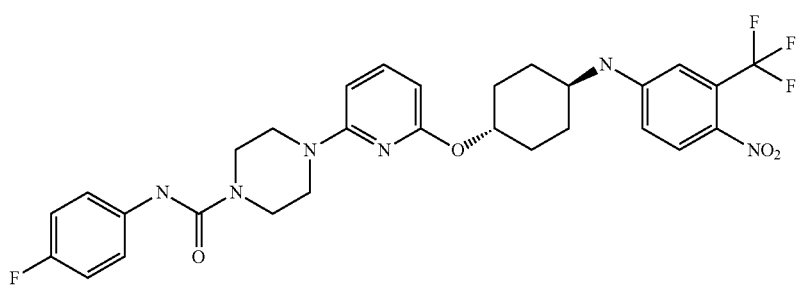 [SMILES: O=C(Nc1ccc(F)cc1)N1CCN(c2cccc(O[C@H]3CC[C@H](Nc4ccc([N+](=O)[O-])c(C(F)(F)F)c4)CC3)n2)CC1]

-continued
144
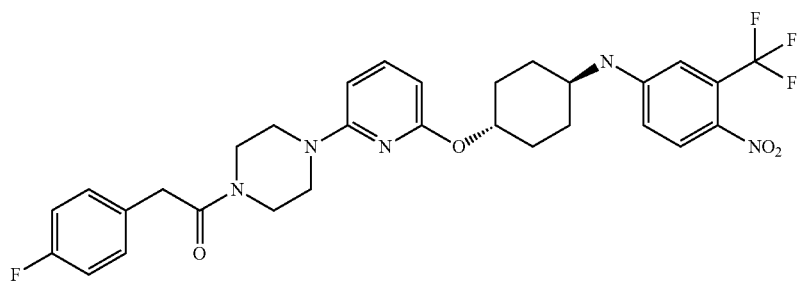 [SMILES: O=C(Cc1ccc(F)cc1)N1CCN(c2cccc(O[C@H]3CC[C@H](Nc4ccc([N+](=O)[O-])c(C(F)(F)F)c4)CC3)n2)CC1]
145
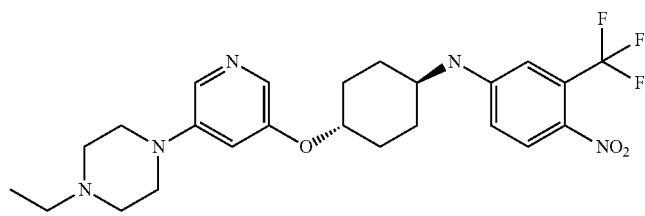 [SMILES: CCN1CCN(c2cncc(O[C@H]3CC[C@H](Nc4ccc([N+](=O)[O-])c(C(F)(F)F)c4)CC3)c2)CC1]
147
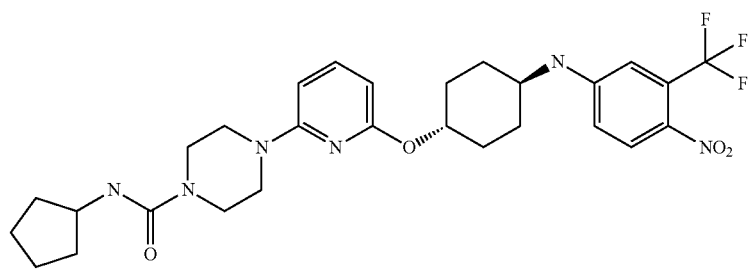
148
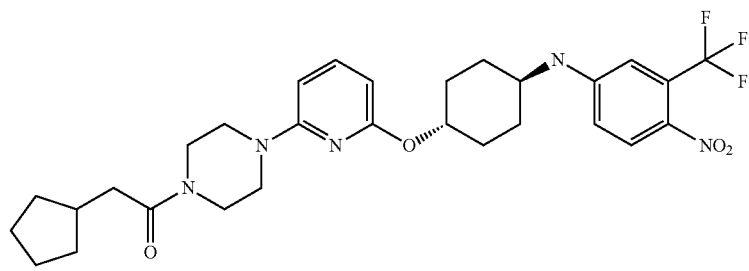
149
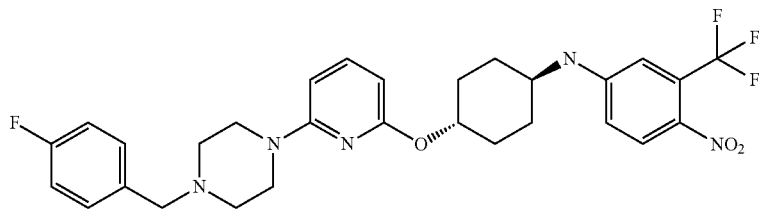 [SMILES: O=[N+]([O-])c1ccc(N[C@H]2CC[C@H](Oc3cccc(N4CCN(Cc5ccc(F)cc5)CC4)n3)CC2)cc1C(F)(F)F]
150
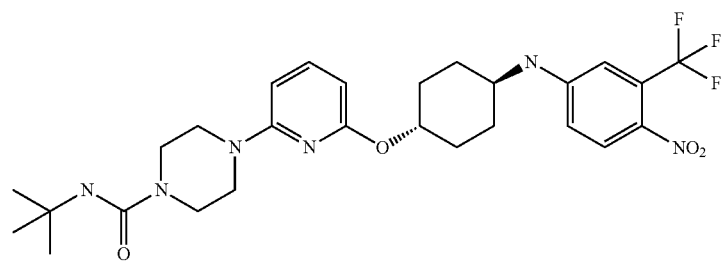 [SMILES: CC(C)(C)NC(=O)N1CCN(c2cccc(O[C@H]3CC[C@H](Nc4ccc([N+](=O)[O-])c(C(F)(F)F)c4)CC3)n2)CC1]

151 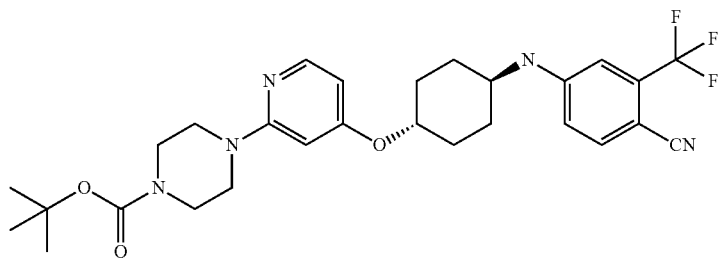 [SMILES: CC(C)(C)OC(=O)N1CCN(c2cc(O[C@H]3CC[C@H](Nc4ccc(C#N)c(C(F)(F)F)c4)CC3)ccn2)CC1]
152 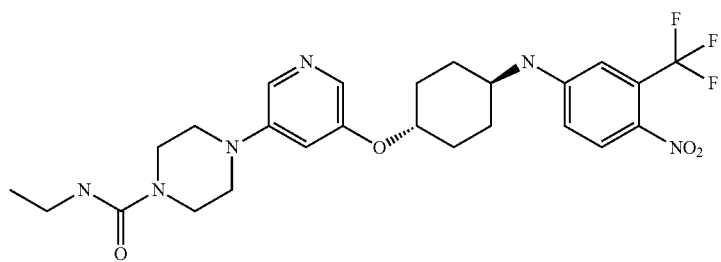
153 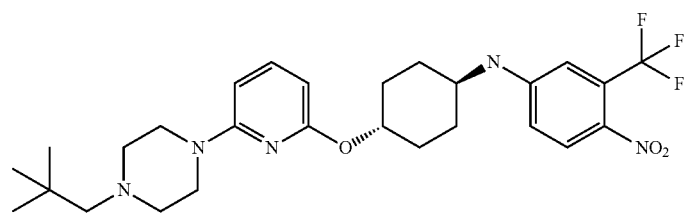 [SMILES: CC(C)(C)CN1CCN(c2cccc(O[C@H]3CC[C@H](Nc4ccc([N+](=O)[O-])c(C(F)(F)F)c4)CC3)n2)CC1]
154 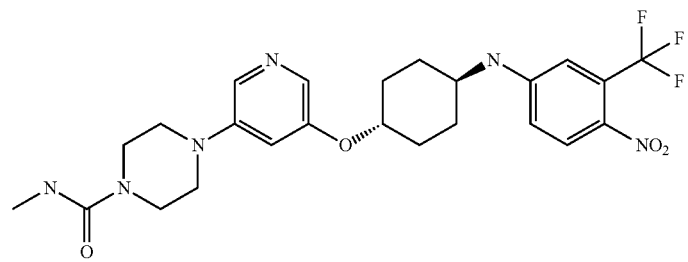
155 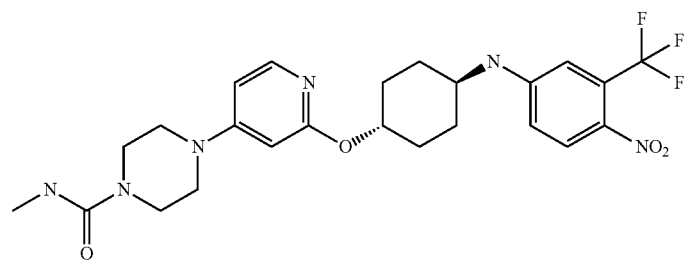
156 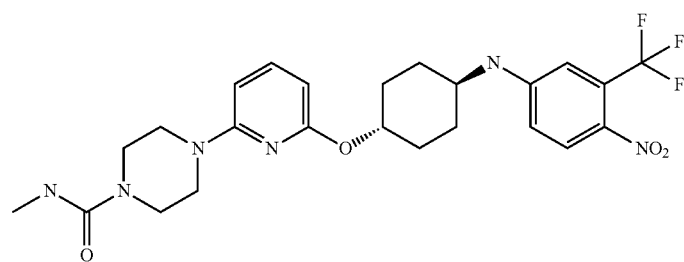 [SMILES: CNC(=O)N1CCN(c2cccc(O[C@H]3CC[C@H](Nc4ccc([N+](=O)[O-])c(C(F)(F)F)c4)CC3)n2)CC1]

-continued
157
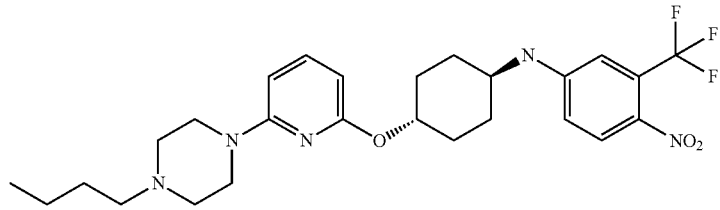 [SMILES: CCCCN1CCN(c2cccc(O[C@H]3CC[C@H](Nc4ccc([N+](=O)[O-])c(C(F)(F)F)c4)CC3)n2)CC1]
158
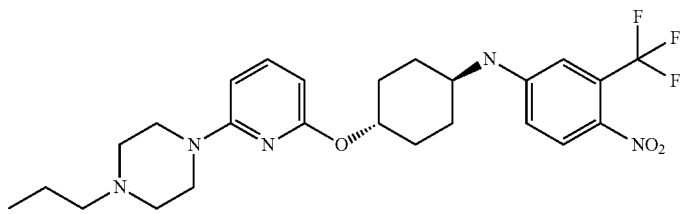 [SMILES: CCCN1CCN(c2cccc(O[C@H]3CC[C@H](Nc4ccc([N+](=O)[O-])c(C(F)(F)F)c4)CC3)n2)CC1]
159
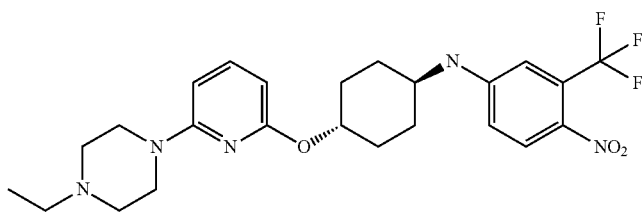 [SMILES: CCN1CCN(c2cccc(O[C@H]3CC[C@H](Nc4ccc([N+](=O)[O-])c(C(F)(F)F)c4)CC3)n2)CC1]
160
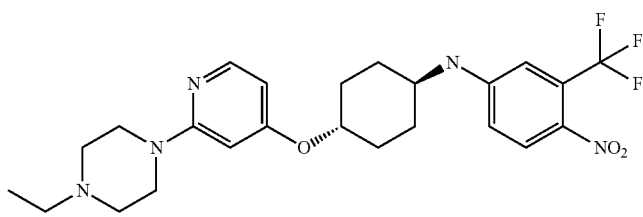
162
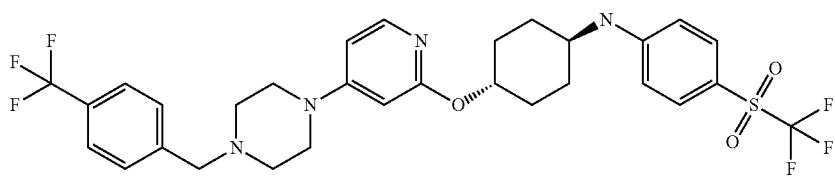 [SMILES: O=S(=O)(c1ccc(N[C@H]2CC[C@H](Oc3cc(N4CCN(Cc5ccc(C(F)(F)F)cc5)CC4)ccn3)CC2)cc1)C(F)(F)F]
163
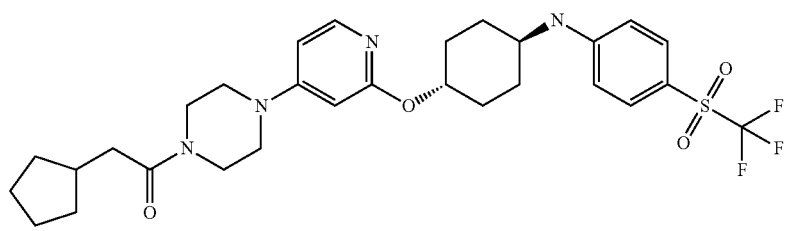 [SMILES: O=C(CC1CCCC1)N1CCN(c2ccnc(O[C@H]3CC[C@H](Nc4ccc(S(=O)(=O)C(F)(F)F)cc4)CC3)c2)CC1]
164
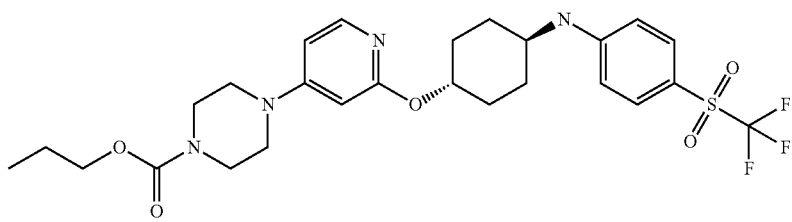 [SMILES: CCCOC(=O)N1CCN(c2ccnc(O[C@H]3CC[C@H](Nc4ccc(S(=O)(=O)C(F)(F)F)cc4)CC3)c2)CC1]

-continued
165
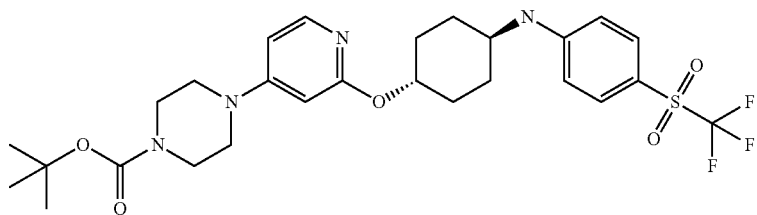 [SMILES: CC(C)(C)OC(=O)N1CCN(c2ccnc(O[C@H]3CC[C@H](Nc4ccc(S(=O)(=O)C(F)(F)F)cc4)CC3)c2)CC1]
166
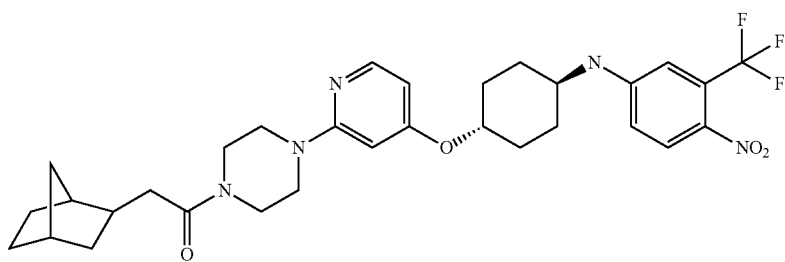 [SMILES: O=C(CC1CC2CCC1C2)N1CCN(c2cc(O[C@H]3CC[C@H](Nc4ccc([N+](=O)[O-])c(C(F)(F)F)c4)CC3)ccn2)CC1]
167
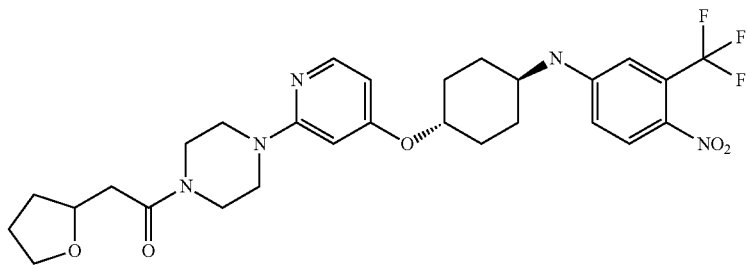 [SMILES: O=C(CC1CCCO1)N1CCN(c2cc(O[C@H]3CC[C@H](Nc4ccc([N+](=O)[O-])c(C(F)(F)F)c4)CC3)ccn2)CC1]
168
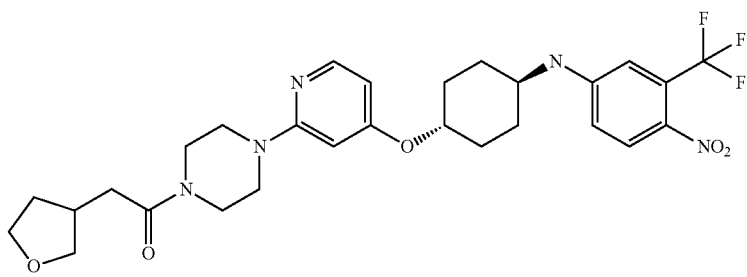 [SMILES: O=C(CC1CCOC1)N1CCN(c2cc(O[C@H]3CC[C@H](Nc4ccc([N+](=O)[O-])c(C(F)(F)F)c4)CC3)ccn2)CC1]
169
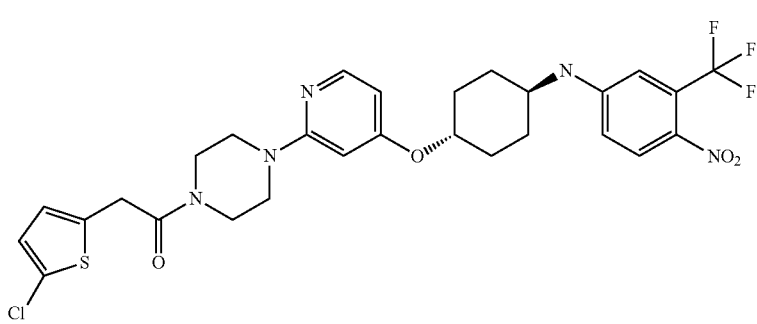 [SMILES: O=C(Cc1ccc(Cl)s1)N1CCN(c2cc(O[C@H]3CC[C@H](Nc4ccc([N+](=O)[O-])c(C(F)(F)F)c4)CC3)ccn2)CC1]
174
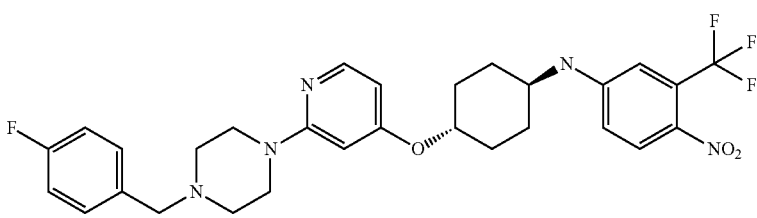 [SMILES: O=[N+]([O-])c1ccc(N[C@H]2CC[C@H](Oc3ccnc(N4CCN(Cc5ccc(F)cc5)CC4)c3)CC2)cc1C(F)(F)F]

-continued
175
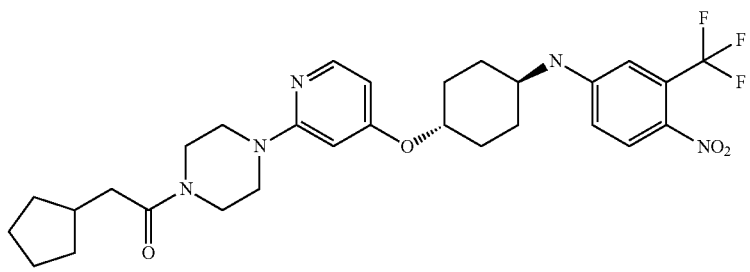
176
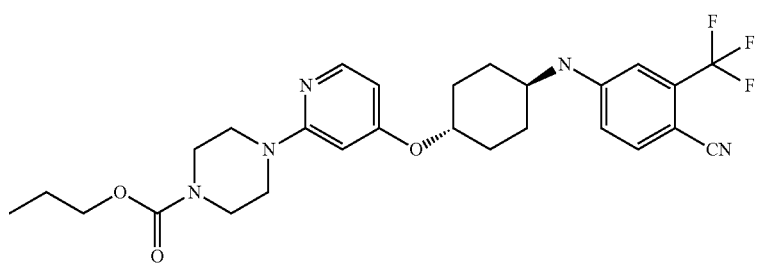
177
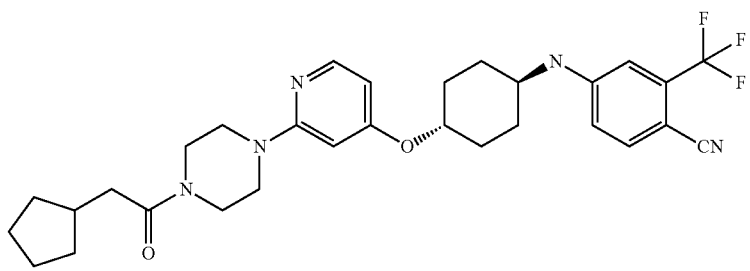 [SMILES: N#Cc1ccc(N[C@H]2CC[C@H](Oc3ccnc(N4CCN(C(=O)CC5CCCC5)CC4)c3)CC2)cc1C(F)(F)F]
178
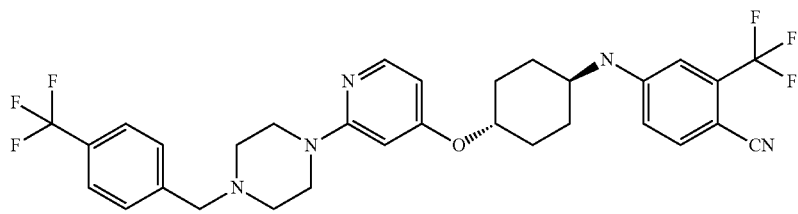 [SMILES: N#Cc1ccc(N[C@H]2CC[C@H](Oc3ccnc(N4CCN(Cc5ccc(C(F)(F)F)cc5)CC4)c3)CC2)cc1C(F)(F)F]
180
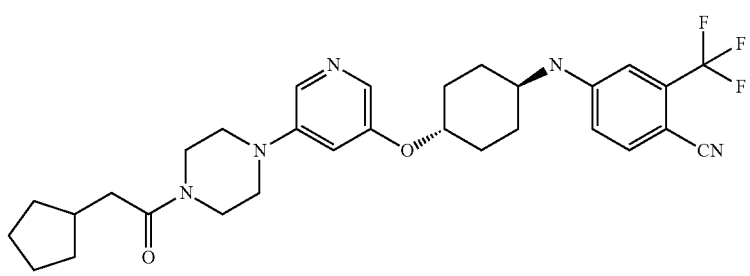 [SMILES: N#Cc1ccc(N[C@H]2CC[C@H](Oc3cncc(N4CCN(C(=O)CC5CCCC5)CC4)c3)CC2)cc1C(F)(F)F]
181
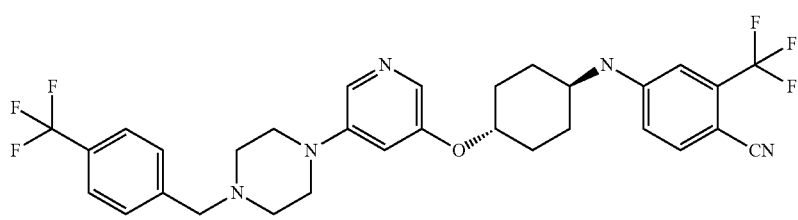 [SMILES: N#Cc1ccc(N[C@H]2CC[C@H](Oc3cncc(N4CCN(Cc5ccc(C(F)(F)F)cc5)CC4)c3)CC2)cc1C(F)(F)F]

183 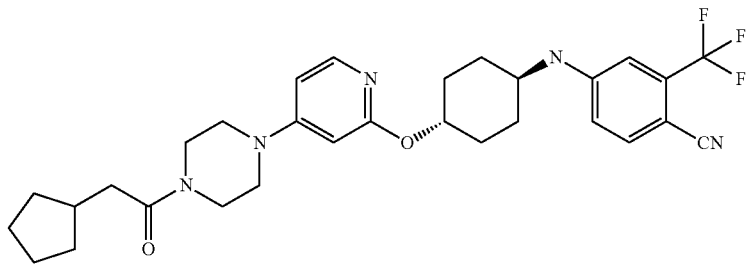
184 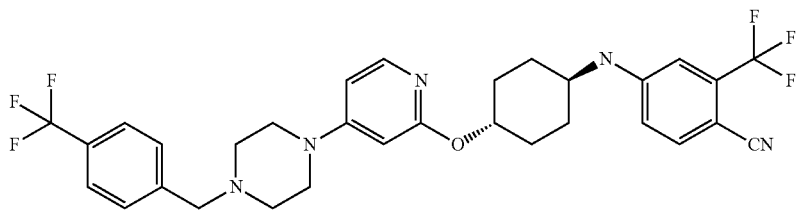
186 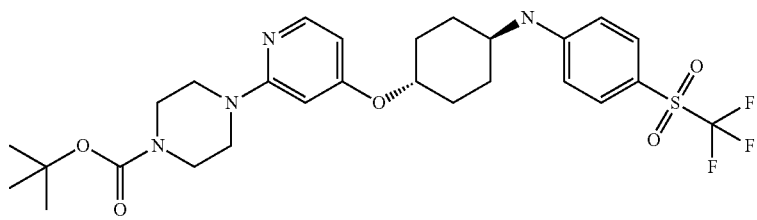 [SMILES: CC(C)(C)OC(=O)N1CCN(c2cc(O[C@H]3CC[C@H](Nc4ccc(S(=O)(=O)C(F)(F)F)cc4)CC3)ccn2)CC1]
187 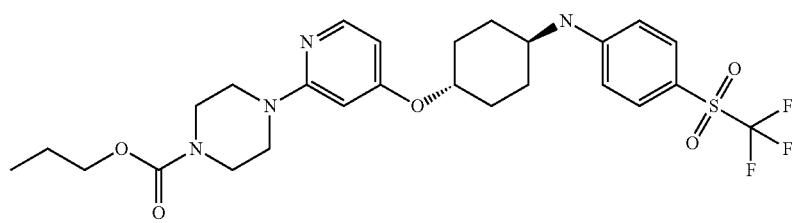 [SMILES: CCCOC(=O)N1CCN(c2cc(O[C@H]3CC[C@H](Nc4ccc(S(=O)(=O)C(F)(F)F)cc4)CC3)ccn2)CC1]
188 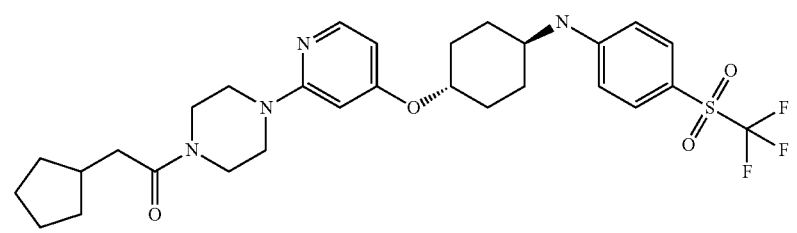
189 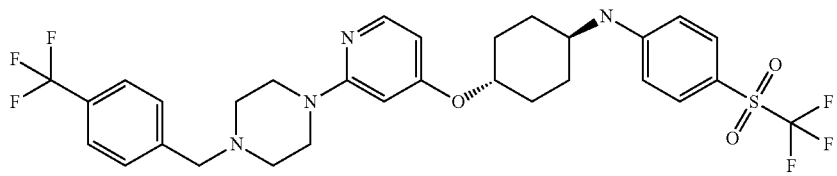 [SMILES: O=S(=O)(c1ccc(N[C@H]2CC[C@H](Oc3ccnc(N4CCN(Cc5ccc(C(F)(F)F)cc5)CC4)c3)CC2)cc1)C(F)(F)F]
191 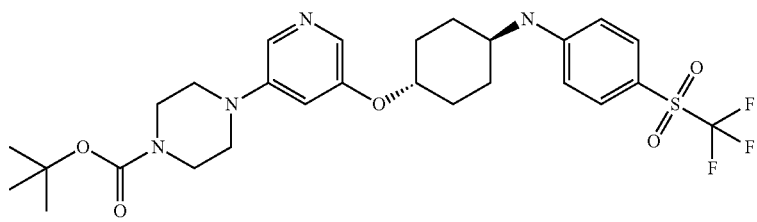 [SMILES: CC(C)(C)OC(=O)N1CCN(c2cncc(O[C@H]3CC[C@H](Nc4ccc(S(=O)(=O)C(F)(F)F)cc4)CC3)c2)CC1]

192 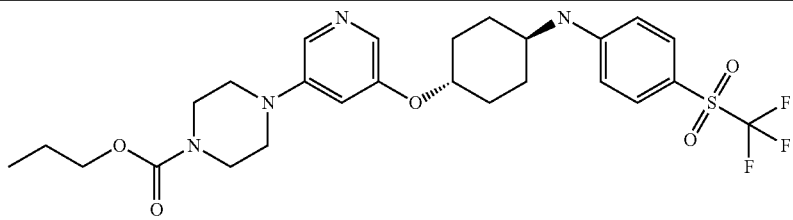

193 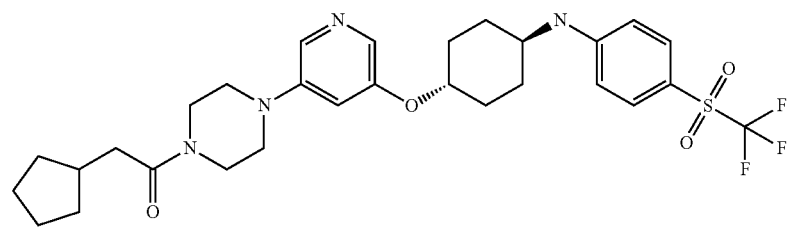 [SMILES: O=C(CC1CCCC1)N1CCN(c2cncc(O[C@H]3CC[C@H](Nc4ccc(S(=O)(=O)C(F)(F)F)cc4)CC3)c2)CC1]

194 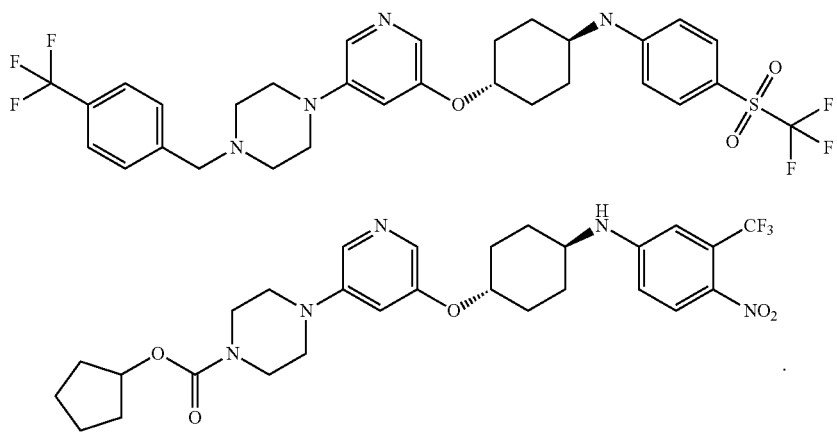

3. A composition for the treatment and prevention of a parasitic infection or infestation in an animal, comprising a therapeutically effective amount of at least one anthelmintic compound of claim 1 in combination with a pharmaceutically acceptable carrier.

4. A method for the treatment and prevention of a parasitic infection or infestation in an animal, comprising administering a therapeutically effective amount of the compound of claim 1 to the animal.

\* \* \* \* \*